United States Patent
Strobel et al.

(10) Patent No.: US 7,759,379 B2
(45) Date of Patent: Jul. 20, 2010

(54) CYCLIC UREA DERIVATIVES, PREPARATION THEREOF AND PHARMACEUTICAL USE THEREOF AS KINASE INHIBITORS

(75) Inventors: Hartmut Strobel, Liederbach (DE); Sven Ruf, Flörsheim (DE); Dominique Lesuisse, Montreuil (FR); Conception Nemecek, Thiais (FR); Youssef El-Ahmad, Creteil (FR); Stefan Guessregen, Wiesbaden (DE); Anne Lebrun, Paris (FR); Kurt Ritter, Frankfurt am Main (DE); Didier Benard, Montsoult (FR); Augustin Hittinger, Igny (FR); Hervé Bouchard, Thiais (FR)

(73) Assignee: Aventis Pharma S.A., Antony (FR)

( * ) Notice: Subject to any disclaimer, the term of this patent is extended or adjusted under 35 U.S.C. 154(b) by 550 days.

(21) Appl. No.: 11/627,518

(22) Filed: Jan. 26, 2007

(65) Prior Publication Data
US 2008/0004300 A1    Jan. 3, 2008

Related U.S. Application Data

(63) Continuation of application No. PCT/EP2005/008720, filed on Jul. 25, 2005.

(30) Foreign Application Priority Data

Jul. 27, 2004   (EP) ................... 04291904

(51) Int. Cl.
C07D 239/02    (2006.01)
A61K 31/505    (2006.01)
A61P 43/00     (2006.01)

(52) U.S. Cl. .................... 514/398; 548/320.1
(58) Field of Classification Search .............. 548/320.1; 514/398
See application file for complete search history.

(56) References Cited

U.S. PATENT DOCUMENTS

| | | | |
|---|---|---|---|
| 4,992,431 A | 2/1991 | Heymes et al. | |
| 5,411,981 A | 5/1995 | Gaillard-Kelly et al. | |
| 6,004,963 A | 12/1999 | Zimmer et al. | |
| 6,022,875 A | 2/2000 | Zimmer et al. | |
| 6,114,365 A | 9/2000 | Pevarello et al. | |
| 6,759,415 B1 | 7/2004 | Poitout et al. | |
| 2004/0248884 A1 | 12/2004 | Patek et al. | |
| 2008/0108654 A1 | 5/2008 | Patek et al. | |

FOREIGN PATENT DOCUMENTS

| | | |
|---|---|---|
| EP | 0 034 536 | 8/1981 |
| EP | 0 494 819 | 7/1992 |
| WO | WO01/09090 | 2/2001 |
| WO | WO 2004/022572 | 3/2004 |
| WO | WO 2004/070050 | 8/2004 |
| WO | WO 2005/049580 A1 | 6/2005 |
| WO | WO2006/010642 | 2/2006 |
| WO | WO2006/010643 | 2/2006 |

OTHER PUBLICATIONS

U.S. Appl. No. 11/627,505, filed Jan. 26, 2007, Strobel et al.
U.S. Appl. No. 11/627,515, filed Jan. 26, 2007, Strobel et al.
Dyer et al, Preparation of Poly(hydrouracils) and Poly(iminoimidazolidinones), Journal of Polymer Science, Polymer Chemistry Edition, 1969, 7(3), pp. 833-849.
Baserga, The IGF-I Receptor in Cancer Research, Exp. Cell. Res., 1999 (253) pp. 1-6.
Bundgaard et al, A Novel Solution-Stable, Water-Soluble Prodrug Type for Drugs Containing a Hydroxyl or an NH-Acidic Group, J. Med. Chem., 1989 (32) 12, pp. 2503-2507.
Cardone et al, Regulation of Cell Death Protease Caspase-9 by Phosphorylation, Science, 1998 (282) pp. 1318-1321.
Cary et al, Stimulation of cell migration by overexpression of focal adhesion kinase and its association with Src and Fyn, Journal of Cell Science, 1996 (109), pp. 1787-1794.
Chan et. al., The Role of Protein Tyrosine Kinases and Protein Tyrosine Phosphatases in T Cell Antigen Receptor Signal Transduction, Annu. Rev. Immunol., 1994 (12), pp. 555-592.
Chen et al, Association of focal adhesion kinase with its potential substrate phosphatidylinositol 3-kinase, Proc. Natl. Acad. Sci. USA, 1994 (91), pp. 10148-10152.
Hanks et al, The Eukaryotic Protein Kinase Superfamily: Kinase (Catalytic) Domain Structure and Classification, FASEB, 1995 (9), pp. 576-596.
Iwashita et al, Signal Transduction System for Growth Factor Receptors Associated with Tyrosine Kinase Activity: Epidermal Growth Factor Receptor Signalling and its Regulation, Cellular Signalling, 1992 (4) 2, pp. 123-132.

(Continued)

Primary Examiner—Kahsay T Habte
(74) Attorney, Agent, or Firm—Kelly L. Bender; Paul R. Darkes

(57) ABSTRACT

The invention relates to compounds of formula (I):

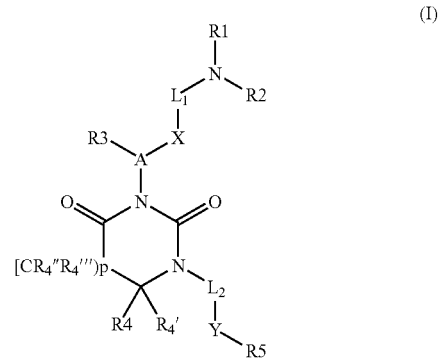

in which R1, R2, $L_1$, X, R3, A, R4, $R_4'$, $R_4''$, $R_4'''$, R5, Y and $L_2$ are as herein defined, salts and prodrugs thereof, to their use as protein kinase inhibitors, and to methods of treating diseases comprising adminstration thereof.

18 Claims, No Drawings

OTHER PUBLICATIONS

Khwaja, Akt is more than just a Bad kinase, Nature, 1999 (401), pp. 33-34.

Kornberg et al, Cell Adhesion or Integrin Clustering Increases Phosphorylation of a Focal Adhesion-associated Tyrosine Kinase, J. Biol. Chem., 1992 (267) 33, pp. 23439-23442.

Ling et al, Malignant Astrocytoma Cell Attachment and Migration to Various Matrix Proteins Is Differentially Sensitive to Phosphoinositide 3-OH Kinase Inhibitors, J. Cell. Biochemistry, 1999 (73), pp. 533-544.

Maung et al, Requirement for focal adhesion kinase in tumor cell adhesion, Oncogene, 1999 (18), pp. 6824-6828.

Mazure et al, Induction of Vascular Endothelial Growth Factor by Hypoxia Is Modulated by a Phosphatidylinositol 3-Kinase/Akt Signaling Pathway in Ha-ras-Transformed Cells Through a Hypoxia Inducible Factor-1 Transcriptional Element, Blood, 1997 (90) 9, pp. 3322-3331.

Newton et al, Protein Kinase C: Structure, Function, and Regulation, J. Biol. Chem., 1995 (270) 48, pp. 28495-28498.

Oktay et al, Integrin-mediated Activation of Focal Adhesion Kinase Is Required for Signaling to Jun NH2-terminal Kinase and Progression through the G1 Phase of the Cell Cycle, J. Cell. Biol., 1999 (145) 7, pp. 1461-1469.

Owens et al, Overexpression of the Focal Adhesion Kinase (p125 FAK) in Invasive Human Tumors 1, Cancer Research, 1995 (55), pp. 2752-2755.

Pines, Cyclins and cyclin-dependent kinases: take your partners, Trends in Biochemical Sciences, 1993 (18), pp. 195-197.

Richardson et al, A mechanism for regulation of the adhesion-associated protein tyrosine kinase pp125 FAK, Nature, 1996 (380), pp. 538-540.

Schaller et al, Autophosphorylation of the Focal Adhesion Kinase, pp125 FAK, Directs SH2-Dependent Binding of pp60src, Mol. Cell. Biol., 1994 (14), pp. 1680-1688.

Schlaepfer et al, Focal Adhesion Kinase Overexpression Enhances Ras-dependent Integrin Signaling to ERK2/Mitogen-activated Protein Kinase through Interactions with and Activation of c-Src, J. Biol. Chem., 1997 (272) 20, pp. 13189-13195.

Schlaepfer et al, Integrin-mediated signal transduction linked to Ras pathway by GRB2 binding to focal adhesion kinase, Nature, 1994 (372) 22, pp. 786-791.

Schlaepfer et al, Signaling through focal adhesion kinase, Prog. Biophy. Mol. Biol., 1999 (71), pp. 435-478.

Sieg et al, Required role of focal adhesion kinase (FAK) for integrin-stimulated cell migration, J. Cell Science, 1999 (112), pp. 2677-2691.

Vuori et al, Induction of p130cas Signaling Complex Formation upon Integrin-Mediated Cell Adhesion: a Role for Src Family Kinases, Mol. Cell. Biol., 1996 (16) 6, pp. 2606-2613.

Wang et al, p125 focal adhesion kinase promotes malignant astrocytoma cell proliferation in vivo, J. Cell Sci., 2000 (113), pp. 4221-4230.

Weiner et al, Expression of focal adhesion kinase gene and Invasive cancer, Lancet., 1993 (342), pp. 1024-1025.

Xing et al, Direct Interaction of v-Src with the Focal Adhesion Kinase Mediated by the Src SH2 Domain, Mol. Cell. Biol., 1994 (5), pp. 413-421.

Xu et al, Attenuation of the Expression of the Focal Adhesion Kinase Induces Apoptosis in Tumor Cells, Cell Growth Diff., 1996 (7), pp. 413-418.

Zhao et al, Regulation of the Cell Cycle by Focal Adhesion Kinase, J. Cell. Biol., 1998 (143) 7, pp. 1997-2008.

Zhong et al, Modulation of Hypoxia-inducible Factor 1 alpha Expression by the Epidermal Growth Factor/Phosphatidylinositol 3-Kinase/PTEN/AKT/FRAP Pathway in Human Prostate Cancer Cells: Implications for Tumor Angiogenesis and Therapeutics, Cancer Research, 2000 (60), pp. 1541-1545.

U.S. Appl. No. 12/173,191, filed Jul. 15, 2008, Halley et al.
U.S. Appl. No. 12/173,380, filed Jul. 15, 2008, Halley et al.

CYCLIC UREA DERIVATIVES, PREPARATION THEREOF AND PHARMACEUTICAL USE THEREOF AS KINASE INHIBITORS

The present invention relates to novel amino cyclic urea derivatives, to a process for preparing them, to their use as medicinal products, to pharmaceutical compositions containing them and to the pharmaceutical use of such derivatives for preventing and treating complaints that may be modulated by inhibiting the activity of protein kinases.

The present invention relates to novel amino cyclic urea derivatives that have inhibitory effects on protein kinases.

The products of the present invention may thus be used especially for preventing or treating complaints capable of being modulated by inhibiting the activity of protein kinases.

The inhibition and regulation of protein kinases especially constitute a powerful new mechanism of action for treating a large number of solid tumours.

Such complaints that the products of the present patent application can treat are thus most particularly solid tumours.

Such protein kinases belong especially to the following group:

IGF1, Raf, EGF, PDGF, VEGF, Tie2, KDR, Flt1-3, FAK, Src, Ab1, cKit, cdk1-9, Auroral-2, cdc7, Akt, Pdk, S6K, Jnk, IR, FLK-1, FGFR1, FGFR2, FGFR3, FGFR4, FGFR5, PLK, Pyk2, CDK7, CDK2 et EGFR.

Such protein kinases belong more especially to the following group: IGF1, cdc7, Auroral-2, Src, Jnk, FAK, KDR, IR, Tie2, CDK7, CDK2 et EGFR.

The protein kinase IGF1-R (Insulin Growth Factor-1 Receptor) is particularly indicated.

The protein kinase FAK is also indicated.

The protein kinase AKT is also indicated.

The present invention thus relates particularly to novel inhibitors of the IGF-1R receptor that may be used for oncology treatments.

The present invention also relates to novel FAK receptor inhibitors that may be used for oncology treatments.

The present invention also relates to novel AKT receptor inhibitors that may be used for oncology treatments.

Cancer remains a disease for which the existing treatments are clearly insufficient. Certain protein kinases, especially including IGF-1R (Insulin Growth Factor 1 Receptor), play an important role in many cancers. The inhibition of such protein kinases is potentially important in the chemotherapy of cancers, especially for suppressing the growth or survival of tumours. The present invention thus relates to the identification of novel products that inhibit such protein kinases.

Protein kinases participate in signalling events that control the activation, growth and differentiation of cells in response either to extracellular mediators or to changes in the environment. In general, these kinases belong to two groups: those that preferentially phosphorylate serine and/or threonine residues and those that preferentially phosphorylate tyrosine residues [S. K. Hanks and T. Hunter, FASEB. J., 1995, 9, pages 576-596]. The serine/threonine kinases are, for example, the isoforms of the protein kinases C [A. C. Newton, J. Biol. Chem., 1995, 270, pages 28495-28498] and a group of cycline-dependent kinases, for instance cdc2 [J. Pines, Trends in Biochemical Sciences, 1995, 18, pages 195-197]. Tyrosine kinases comprise growth factor receptors, for instance the epidermal growth factor (EGF) receptor [S. Iwashita and M. Kobayashi, Cellular Signalling, 1992, 4, pages 123-132], and cytosol kinases, for instance p56tck, p59fYn and ZAP-70 and the kinases csk [C. Chan et. al., Ann. Rev. Immunol., 1994, 12, pages 555-592].

Abnormally high levels of kinase protein activity have been implicated in many diseases, resulting from abnormal cellular functions. This may arise either directly or indirectly from a dysfunction in the mechanisms for controlling the kinase activity, linked, for example, to a mutation, an overexpression or an inappropriate activation of the enzyme, or an over or underproduction of cytokines or of growth factors, also involved in the transduction of the signals upstream or downstream of the kinases. In all these cases, a selective inhibition of the action of the kinases offers hope of a beneficial effect.

The type 1 receptor for the insulin-like growth factor (IGF-I-R) is a transmembrane receptor with tyrosine kinase activity which binds firstly to IGFI, but also to IGFII and to insulin with lower affinity. The binding of IGF1 to its receptor results in oligomerization of the receptor, the activation of tyrosine kinase, intermolecular autophosphorylation and the phosphorylation of cell substrates (main substrates: IRS1 and Shc). The receptor activated by its ligand induces mitogenic activity in normal cells. However, IGF-I-R plays an important role in "abnormal" growth.

Several clinical reports underline the important role of the IGF-I route in the development of human cancers:

IGF-I-R is often found overexpressed in many types of tumour (breast, colon, lung, sarcoma, etc.) and its presence is often associated with a more aggressive phenotype.

High concentrations of circulating IGF1 are strongly correlated with a risk of prostate cancer, lung cancer and breast cancer.

Furthermore, it has been widely documented that IGF-I-R is necessary for establishing and maintaining the transformed phenotype in vitro as in vivo [Baserga R, Exp. Cell. Res., 1999, 253, pages 1-6]. The kinase activity of IGF-I-R is essential for the transformation activity of several oncogenes: EGFR, PDGFR, the large T antigen of the SV40 virus, activated Ras, Raf, and v-Src. The expression of IGF-I-R in normal fibroblasts induces a neoplastic phenotype, which may then result in the formation of a tumour in vivo. The expression of IGF-I-R plays an important role in substrate-independent growth. IGF-I-R has also been shown to be a protector in chemotherapy-induced and radiation-induced apoptosis, and cytokine-induced apoptosis. Furthermore, the inhibition of endogenous IGF-I-R with a negative dominant, the formation of a triple helix or the expression of an antisense sequence brings about suppression of the transforming activity in vitro and reduction of tumour growth in animal models.

Among the kinases for which a modulation of the activity is desired, FAK (Focal Adhesion Kinase) is also a preferred kinase.

FAK is a cytoplasmic tyrosine kinase that plays an important role in transducing the signal transmitted by the integrins, a family of heterodimeric receptors of cellular adhesion. FAK and the integrins are colocalized in perimembrane structures known as adhesion plaques. It has been shown in many cell types that the activation of FAK and its phosphorylation on tyrosine residues and in particular its autophosphorylation on tyrosine 397 were dependent on the binding of the integrins to their extracellular ligands and thus induced during cellular adhesion [Kornberg L, et al. J. Biol. Chem. 267(33): 23439-442 (1992)]. The autophosphorylation on tyrosine 397 of FAK represents a binding site for another tyrosine kinase, Src, via its SH2 domain [Schaller et al. Mol. Cell. Biol. 14: 1680-1688 1994; Xing et al. Mol. Cell. Biol. 5: 413-421 1994]. Src can then phosphorylate FAK on tyrosine 925, thus recruiting the adapter protein Grb2 and inducing in certain cells activation of the ras and MAP kinase pathway involved in controlling cellular proliferation [Schlaepfer et al. Nature; 372: 786-

791 1994; Schlaepfer et al. Prog. Biophy. Mol. Biol. 71: 435-478 1999; Schlaepfer and Hunter, J. Biol. Chem. 272: 13189-13195 1997].

The activation of FAK can thus induce the jun NH2-terminal kinase (JNK) signalling pathway and result in the progression of the cells to the G1 phase of the cellular cycle [Oktay et al., J. Cell. Biol. 145: 1461-1469 1999]. Phosphatidylinositol-3-OH kinase (PI3-kinase) also binds to FAK on tyrosine 397 and this interaction might be necessary for the activation of PI3-kinase [Chen and Guan, Proc. Nat. Acad. Sci. USA. 91: 10148-10152 1994; Ling et al. J. Cell. Biochem. 73: 533-544 1999]. The FAK/Src complex phosphorylates various substrates, for instance paxillin and p130CAS in fibroblasts [Vuori et al. Mol. Cell. Biol. 16: 2606-2613 1996].

The results of numerous studies support the hypothesis that FAK inhibitors might be useful in treating cancer. Studies have suggested that FAK might play an important role in in vitro cell proliferation and/or survival. For example, in CHO cells, certain authors have demonstrated that the overexpression of p125FAK induces an acceleration of the G1 to S transition, suggesting that p125FAK promotes cellular proliferation [Zhao J.-H et al. J. Cell Biol. 143: 1997-2008 1998]. Other authors have shown that tumour cells treated with FAK antisense oligonucleotides lose their adhesion and go into apoptosis (Xu et al, Cell Growth Differ. 4: 413-418 1996). It has also been demonstrated that FAK promotes the migration of cells in vitro. Thus, fibroblasts that are deficient for the expression of FAK ("knockout" mice for FAK) show a rounded morphology and deficiencies in cell migration in response to chemotactic signals, and these defects are suppressed by reexpression of FAK [D J. Sieg et al., J. Cell Science. 112: 2677-91 1999]. The overexpression of the C-terminal domain of FAK (FRNK) blocks the stretching of adherent cells and reduces cellular migration in vitro [Richardson A. and Parsons J. T. Nature. 380 : 538-540 1996]. The overexpression of FAK in CHO or COS cells or in human astrocytoma cells promotes migration of the cells. The involvement of FAK in promoting the proliferation and migration of cells in numerous cell types in vitro suggests the potential role of FAK in neoplastic processes. A recent study has effectively demonstrated the increase in the proliferation of tumour cells in vivo after induction of the expression of FAK in human astrocytoma cells [Cary L. A. et al. J. Cell Sci. 109: 1787-94 1996; Wang D et al. J. Cell Sci. 113: 4221-4230 2000]. Furthermore, immunohistochemical studies on human biopsies have demonstrated that FAK is overexpressed in prostate cancer, breast cancer, thyroid cancer, cancer of the colon, melanoma, brain cancer and lung cancer, the level of expression of FAK being directly correlated to the tumours having the most aggressive phenotype [Weiner T M, et al. Lancet. 342 (8878): 1024-1025 1993; Owens et al. Cancer Research. 55: 2752-2755 1995; Maung K. et al. Oncogene 18: 6824-6828 1999; Wang D et al. J. Cell Sci. 113 : 4221-4230 2000].

Protein kinase AKT (also known as PKB) and phosphoinositide 3-kinase (PI3K) are involved in a cell signalling pathway that transmits signals from growth factors activating membrane receptors.

This transduction pathway is involved in numerous cellular functions: regulation of apoptosis, control of transcription and translation, glucose metabolism, angiogenesis and mitochondrial integrity. First identified as an important component of insulin-dependent signalling pathways regulating metabolic responses, serine/threonine kinase AKT was then identified as a mediator playing a key role in survival induced by growth factors. It has been shown that AKT can inhibit death by apoptosis induced by various stimuli, in a certain number of cell types and tumour cells. In accordance with these findings, it has been shown that AKT can, by phosphorylation of given serine residues, inactivate BAD, GSK3☐, caspase-9, and Forkhead transcription factor, and can activate IKKalpha and e-NOS. It is interesting to note that the protein BAD is found hyper-phosphorylated in 11 human tumour cell lines out of 41 studied. Furthermore, it has been shown that hypoxia modulates the induction of VEGF in cells transformed with Ha-ras by activating the PI3K/AKT pathway and by involving the binding sequence of the HIF-1 (hypoxia inducible factor-1) transcription factor known as HRE for "hypoxy-responsive element".

AKT plays a very important role in cancer pathologies. The amplification and/or overexpression of AKT has been reported in many human tumours, for instance gastric carcinoma (amplification of AKT1), ovary carcinomas, breast carcinoma or pancreatic carcinoma (amplification and overexpression of AKT2) and breast carcinomas deficient in oestrogen receptors, and also androgen-independent prostate carcinomas (overexpression of AKT3). Furthermore, AKT is constitutively activated in all the PTEN tumours, the PTEN phosphatase being deleted or inactivated by mutations in many types of tumours, for instance carcinomas of the ovary, of the prostate, of the endometrium, glioblastomas and melanomas. AKT is also involved in the oncogenic activation of bcr-abl (references: Khawaja A., Nature 1999, 401, 33-34; Cardone et al. Nature 1998, 282, 1318-1321; Kitada S. et al., Am J Pathol 1998 Jan; 152(1): 51-61; Mazure N M et al. Blood 1997, 90, 3322-3331; Zhong H. et al. Cancer Res. 2000, 60, 1541-1545).

One subject of the present invention is thus the products of general formula (I):

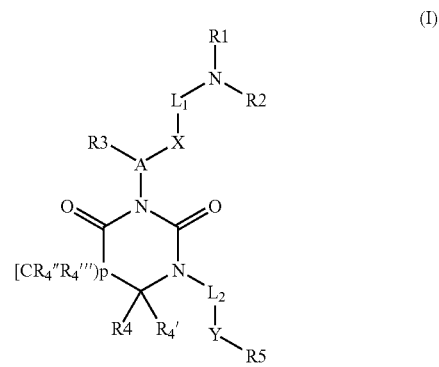

in which:
 p represents the integers 0, 1 and 2,
 A represents aryl, heteroaryl or a monocyclic or bicyclic fused carbocyclic or heterocyclic 5- to 11-membered radical, all these radicals optionally being substituted with one or more substituents, which may be identical or different, chosen from the values of R3;
 X represents a single bond or the following divalent radicals: —N(R6)-; —NH-alk-; alkylene; —O—; —C(O)—; —S(O)n-; —N(R6)-C(O)—; —NH—CO-alk-, —N(R6)-C(O)—N(R6')-; —N(R6)-C(S)—N(R6')-; —N(R6)-C(O)O—; —N(R6)-SO2-; —N(R6)-SO2-N(R6')-; —C(O)—N(R6)-; —SO2-NR6-; and —C(O)O—;
 L1 represents a single bond or the following divalent radicals: alkylene, alkenylene, alkynylene and cycloalkylene, all optionally substituted with one or more substituents, which may be identical or different, chosen from the values of R7; phenylene and heteroarylene, these last two radicals optionally substituted with one or more substituents chosen from the values of R8;

The radical NR1R2 is such that:

either R1 and R2, which may be identical or different, are such that:

R1 represents a hydrogen atom; alkyl, alkenyl, alkynyl and cycloalkyl, all optionally substituted with one or more substituents, which may be identical or different, chosen from the values of R7; aryl, heteroaryl, arylalkyl and heteroarylalkyl in which each of the aromatic rings may optionally be substituted with one or more substituents, which may be identical or different, chosen from the values of R8; —SO2R9; —C(O)R9; —C(O)OR9; —C(O)NR10R11, —C(S)NR10R11 and —SO2NR10R11;

and R2 represents a hydrogen atom; alkyl, alkenyl, alkynyl and cycloalkyl, all optionally substituted with one or more substituents, which may be identical or different, chosen from the values of R7;

or R1 and R2 form, together with the nitrogen atom to which they are attached, a 4- to 10-membered heterocycle optionally containing one or more other hetero atoms, which may be identical or different, chosen from O, N, NR12 and S, and optionally substituted with one or more substituents, which may be identical or different, chosen from the values of R7;

or NR1 with L1 or NR2 with $L_1$ together form a 4- to 10-membered heterocycle—optionally containing one or more other hetero atoms, which may be identical or different, chosen from O, N, NR12 and S, and optionally substituted with one or more substituents, which may be identical or different, chosen from the values of R7;

R3 represents a hydrogen atom; a halogen atom; hydroxyl; alkyl, alkenyl, alkynyl, cycloalkyl, alkoxy and alkylenedioxy, all optionally substituted with one or more substituents, which may be identical or different, chosen from the values of R7; —NR13R14; —C(O)R13; —S(O)$_n$R13; —C(O)OR13; —C(O)NR15R16; —S(O)$_n$NR15R16; SF5; nitro; cyano; 4- to 7-membered heterocycloalkyl optionally substituted with one or more radicals, which may be identical or different, chosen from halogen atoms and alkyl, alkoxy or oxo radicals; aryl and heteroaryl, these last two radicals optionally substituted with one or more substituents, which may be identical or different, chosen from the values of R8; being noted that when A represents a mono or bicyclic fused 1-membered radical, R3 represents in more oxo, R4, R4', R4" and R4'", which may be identical or different, are chosen from the values defined below for R4;

R4 represents a hydrogen atom; a halogen atom; an alkyl, alkenyl, alkynyl or cycloalkyl radical, all optionally substituted with one or more substituents, which may be identical or different, chosen from the values of R7; aryl and heteroaryl, these last two radicals optionally substituted with one or more substituents, which may be identical or different, chosen from the values of R8; oxo; it being understood that two substituents from among R4, R4' and R4" may form, with the carbon atom(s) to which they are attached, a 3- to 10-membered ring optionally containing one or more hetero atoms, which may be identical or different, chosen from O, S, N and NR12;

L2 is chosen from a single bond; an alkylene; alkenylene; alkynylene; cycloalkylene; —O—; —NR17-; —C(O)— and SO2 radical;

Y represents a saturated, partially saturated or unsaturated N-heterocycle optionally containing one or more hetero atoms, which may be identical or different, chosen from O, S, N and NR12 and optionally substituted with one or more substituents, which may be identical or different, chosen from the values of R5;

R5 represents a hydrogen atom; a halogen atom; an alkyl, alkenyl, alkynyl or cycloalkyl radical, all optionally substituted with one or more substituents, which may be identical or different, chosen from the values of R7; aryl, arylalkyl, heteroaryl and heteroarylalkyl, in which the aromatic rings are optionally substituted with one or more substituents, which may be identical or different, chosen from the values of R8; —OR18; —NR19R20; —NR19COR20; —NR19CONR19'R20; —NR19-S(O)2-R20; —NR19-S(O)2-NR19'R20; —COR18; COOR21; —CONR22R23; —S(O)nR18; —SO2NR22R23; cyano; nitro;

R6 is such that:

either R6 represents a hydrogen atom; an alkyl, alkenyl, alkynyl, acyl or cycloalkyl radical, all optionally substituted with one or more substituents, which may be identical or different, chosen from the values of R7; aryl and heteroaryl, these last two radicals optionally substituted with one or more substituents, which may be identical or different, chosen from the values of R8;

or R6 with NR1R2 together form a 4- to 8-membered heterocycle optionally containing one or more hetero atoms, which may be identical or different, chosen from O, S, N and NR12 and optionally substituted with one or more substituents, which may be identical or different, chosen from the values of R7;

or R6 with L1 together form a 4- to 8-membered heterocycle optionally containing one or more hetero atoms, which may be identical or different, chosen from O, S, N and NR12 and optionally substituted with one or more substituents, which may be identical or different, chosen from the values of R7;

R6', which may be identical to or different from R6, is chosen from the values of R6;

R7 represents a halogen atom; alkyl; cycloalkyl; cycloalkylalkyl; hydroxyl; alkoxy; cycloalkoxy; cyano; —CF3; —NR24R25; —NR26COR27; —NR26CONR26'R27; —NR26-S(O)2-R27; —NR26-S(O)2-NR26'R27; —COOR26; —COR26; —CO(NR24R25); S(O)nR26; —S(O)2NR24R25; 4- to 7-membered heterocycle optionally substituted with one or more substituents, which may be identical or different, chosen from OH and NH2 radicals, halogen atoms, and alkyl, alkoxy or oxo radicals; aryl optionally substituted with one or more substituents, which may be identical or different, chosen from halogen atoms and alkyl and alkoxy radicals; heteroaryl, optionally substituted with one or more substituents, which may be identical or different, chosen from halogen atoms and NH2, alkyl and alkoxy radicals; phenoxy, optionally substituted with one or more substituents, which may be identical or different, chosen from halogen atoms and alkyl and alkoxy radicals;

R8, which may be identical to or different from R7, represents the same values as R7 and in addition represents halogen atoms; nitro; —OCF3; alkylenedioxy; difluoromethylenedioxy; benzyl optionally substituted with one or more substituents, which may be identical or different, chosen from halogen atoms and alkyl and alkoxy radicals;

R9, which may be identical to or different from R6, represents the same values as R6;

R10 and R11, which may be identical to or different from each other and also which may be identical to or different from R6, are chosen from the same values as R6 and may optionally form, with the nitrogen atom to which they are attached, a 4- to 10-membered heterocycle optionally containing one or more hetero atoms, which may be identical or different, chosen from O, S, N and NR12 and optionally substituted with one or more substituents, which may be identical or different, chosen from the values of R7;

R12 represents a hydrogen atom; an alkyl, alkenyl, alkynyl, cycloalkyl, alkylCO or alkylSO$_2$ radical, all optionally substituted with one or more substituents, which may be identical or different, chosen from halogen atoms, OH, alkoxy and dialkylamino radicals; aryl and heteroaryl, these last two radicals optionally substituted with one or more substituents, which may be identical or different, chosen from halogen atoms and alkyl and alkoxy radicals;

R13, which may be identical to or different from R6, represents the same values as R6;

R14, which may be identical to or different from R13, represents the same values as R13 and also represents C(O)R28; C(O)N28R29; SO2R28 and SO2NR28R29;

R13 and R14 may optionally form, together with the nitrogen atom to which they are attached, a 4- to 10-membered heterocycle optionally containing one or more hetero atoms, which may be identical or different, chosen from O, S, N and NR12 and optionally substituted with one or more substituents, which may be identical or different, chosen from the values of R7;

R15 and R16, which may be identical to or different from each other and also which may be identical to or different from R13, are chosen from the same values as R13 and may optionally form, with the nitrogen atom to which they are attached, a 4- to 10-membered heterocycle optionally containing one or more hetero atoms, which may be identical or different, chosen from O, S, N and NR12 and optionally substituted with one or more substituents, which may be identical or different, chosen from the values of R7;

R17 represents a hydrogen atom, alkyl or cycloalkyl;

R18, which may be identical to or different from R6, represents the same values as R6;

R19 and R20, which may be identical to or different from each other and also which may be identical to or different from R6, are chosen from the same values as R6 and may optionally form, with the nitrogen atom to which they are attached, a 4- to 10-membered heterocycle optionally containing one or more hetero atoms, which may be identical or different, chosen from O, S, N and NR12 and optionally substituted with one or more substituents, which may be identical or different, chosen from the values of R7;

R21, which may be identical to or different from R13, represents the same values as R13 and also represents hydrogen;

R22 and R23, which may be identical to or different from each other and also which may be identical to or different from R6, are chosen from the same values as R6 and may optionally form, with the nitrogen atom to which they are attached, a 4- to 10-membered heterocycle optionally containing one or more hetero atoms, which may be identical or different, chosen from O, S, N and NR12 and optionally substituted with one or more substituents, which may be identical or different, chosen from the values of R7;

R24 and R25, which may be identical or different, represent a hydrogen atom or an alkyl, alkenyl or alkynyl radical optionally substituted with one or more substituents, which may be identical or different, chosen from halogen atoms and OH and alkoxy radicals, or alternatively R24 and R25 may optionally form, with the nitrogen atom to which they are attached, a 4- to 7-membered heterocycle optionally containing one or more hetero atoms, which may be identical or different, chosen from O, S, N, N-alkyl and N-C(O)alkyl, and optionally substituted with one or more substituents, which may be identical or different, chosen from halogen atoms and OH, alkyl, alkoxy and oxo radicals;

R26 represents a hydrogen atom or an alkyl, alkenyl or alkynyl radical optionally substituted with one or more substituents, which may be identical or different, chosen from halogen atoms and OH and alkoxy radicals;

R27, which may be identical to or different from R26, represents the same values as R26;

R26 and R27 may also optionally form, with the nitrogen atom to which they are attached, a 4- to 7-membered heterocycle optionally containing one or more hetero atoms, which may be identical or different, chosen from O, S, N, N-alkyl and N-C(O)alkyl, and optionally substituted with one or more substituents, which may be identical or different, chosen from halogen atoms and OH, alkyl, alkoxy and oxo radicals;

R28, which may be identical to or different from R26, represents the same values as R26;

R29, which may be identical to or different from R26, represents the same values as R26;

R30, which may be identical to or different from R26, represents the same values as R26;

n represents the integers 0, 1 and 2;

the said products of formula (I) being in any possible racemic, enantiomeric and diastereoisomeric isomer form, and also the addition salts with mineral acids and organic acids or with mineral bases and organic bases of the said products of formula (I).

One subject of the present invention is thus the products of general formula (I) as above defined in which p represents the integers 0, 1 and 2, A represents aryl, heteroaryl or a monocyclic or bicyclic fused carbocyclic or heterocyclic 5- to 11-membered radical, all these radicals optionally being substituted with one or more substituents, which may be identical or different, chosen from the values of R3;

X represents a single bond or the following divalent radicals: —N(R6)-; —O—; —C(O)—; —S(O)n-; —N(R6)-C(O)—; —N(R6)-C(O)—N(R6')-; —N(R6)-C(S)—N(R6')-; —N(R6)-C(O)O—; —N(R6)-SO2-; —N(R6)-SO2-N(R6')-; —C(O)—N(R6)-; —SO2-NR6-; and —C(O)O—;

L1 represents the following divalent radicals: alkylene, alkenylene, alkynylene and cycloalkylene, all optionally substituted with one or more substituents, which may be identical or different, chosen from the values of R7; phenylene and heteroarylene, these last two radicals optionally substituted with one or more substituents chosen from the values of R8;

The radical NR1R2 is such that either R1 and R2, which may be identical or different, are such that:

R1 represents a hydrogen atom; alkyl, alkenyl, alkynyl and cycloalkyl, all optionally substituted with one or more substituents, which may be identical or different, chosen from the values of R7; aryl, heteroaryl, arylalkyl and heteroarylalkyl in which each of the aromatic rings may optionally be substituted with one or more substituents, which may be identical or different, chosen from the values of R8; —SO2R9; —C(O)R9; —C(O)OR9; —C(O)NR10R11, —C(S)NR10R11 and —SO2NR10R11;

and R2 represents a hydrogen atom; alkyl, alkenyl, alkynyl and cycloalkyl, all optionally substituted with one or more substituents, which may be identical or different, chosen from the values of R7;

or R1 and R2 form, together with the nitrogen atom to which they are attached, a 4- to 10-membered heterocycle optionally containing one or more other hetero atoms, which may be identical or different, chosen from O, N, NR12 and S, and optionally substituted with one or more substituents, which may be identical or different, chosen from the values of R7;

or NR1 with L1 or NR2 with $L_1$ together form a 4- to 8-membered heterocycle optionally containing one or more other hetero atoms, which may be identical or different, chosen from O, N, NR12 and S, and optionally substituted with one or more substituents, which may be identical or different, chosen from the values of R7;

R3 represents a hydrogen atom; a halogen atom; hydroxyl; alkyl, alkenyl, alkynyl, cycloalkyl, alkoxy and alkylenedioxy, all optionally substituted with one or more substituents, which may be identical or different, chosen from the values of R7; —NR13R14; —C(O)R13; —S(O)$_n$R13; —C(O)OR13; —C(O)NR15R16; —S(O)$_n$NR15R16; SF5; nitro; cyano; 4- to 7-membered heterocycloalkyl optionally substituted with one or more radicals, which may be identical or different, chosen from halogen atoms and alkyl, alkoxy or oxo radicals; aryl and heteroaryl, these last two radicals optionally substituted with one or more substituents, which may be identical or different, chosen from the values of R8; being noted that when A represents a mono or bicyclic fused 11-membered radical, R3 represents in more oxo, R4, R4', R4" and R4''', which may be identical or different, are chosen from the values defined below for R4;

R4 represents a hydrogen atom; a halogen atom; an alkyl, alkenyl, alkynyl or cycloalkyl radical, all optionally substituted with one or more substituents, which may be identical or different, chosen from the values of R7; aryl and heteroaryl, these last two radicals optionally substituted with one or more substituents, which may be identical or different, chosen from the values of R8; oxo; it being understood that two substituents from among R4, R4' and R4" may form, with the carbon atom(s) to which they are attached, a 3- to 10-membered ring optionally containing one or more hetero atoms, which may be identical or different, chosen from O, S, N and NR12;

L2 is chosen from a single bond; an alkylene; alkenylene; alkynylene; cycloalkylene; —O—; —NR17-; —C(O)— and SO2 radical;

Y represents a saturated, partially saturated or unsaturated N-heterocycle optionally containing one or more hetero atoms, which may be identical or different, chosen from O, S, N and NR12 and optionally substituted with one or more substituents, which may be identical or different, chosen from the values of R5;

R5 represents a hydrogen atom; a halogen atom; an alkyl, alkenyl, alkynyl or cycloalkyl radical, all optionally substituted with one or more substituents, which may be identical or different, chosen from the values of R7; aryl, arylalkyl, heteroaryl and heteroarylalkyl, in which the aromatic rings are optionally substituted with one or more substituents, which may be identical or different, chosen from the values of R8; —OR18; —NR19R20; —NR19COR20; —NR19CONR19'R20; —NR19-S(O)2-R20; —NR19-S(O)2-NR19'R20; —COR18; COOR21; —CONR22R23; —S(O)nR18; —SO2NR22R23; cyano; nitro;

R6 is such that:

either R6 represents a hydrogen atom; an alkyl, alkenyl, alkynyl or cycloalkyl radical, all optionally substituted with one or more substituents, which may be identical or different, chosen from the values of R7; aryl and heteroaryl, these last two radicals optionally substituted with one or more substituents, which may be identical or different, chosen from the values of R8;

or R6 with NR1R2 together form a 4- to 8-membered heterocycle optionally containing one or more hetero atoms, which may be identical or different, chosen from O, S, N and NR12 and optionally substituted with one or more substituents, which may be identical or different, chosen from the values of R7;

or R6 with L1 together form a 4- to 8-membered heterocycle optionally containing one or more hetero atoms, which may be identical or different, chosen from O, S, N and NR12 and optionally substituted with one or more substituents, which may be identical or different, chosen from the values of R7;

R6', which may be identical to or different from R6, is chosen from the values of R6;

R7 represents a halogen atom; alkyl; cycloalkyle; cycloalkylalkyle; hydroxyl; alkoxy; cycloalkoxy; cyano; —CF3; —N24R25; —NR26COR27; —NR26CONR26'R27; —NR26-S(O)2-R27; —NR26-S(O)2-NR26'R27; —COOR26; —COR26; —CO(NR24R25); S(O)nR26; —S(O)2NR24R25; 4- to 7-membered heterocycle optionally substituted with one or more substituents, which may be identical or different, chosen from OH and NH2 radicals, halogen atoms, and alkyl, alkoxy or oxo radicals; aryl optionally substituted with one or more substituents, which may be identical or different, chosen from halogen atoms and alkyl and alkoxy radicals; heteroaryl, optionally substituted with one or more substituents, which may be identical or different, chosen from halogen atoms and NH2, alkyl and alkoxy radicals; phenoxy, optionally substituted with one or more substituents, which may be identical or different, chosen from halogen atoms and alkyl and alkoxy radicals;

R8, which may be identical to or different from R7, represents the same values as R7 and in addition represents halogen atoms; nitro; —OCF3; alkylenedioxy; difluoromethylenedioxy; benzyl optionally substituted with one or more substituents, which may be identical or different, chosen from halogen atoms and alkyl and alkoxy radicals;

R9, which may be identical to or different from R6, represents the same values as R6;

R10 and R11, which may be identical to or different from each other and also which may be identical to or different from R6, are chosen from the same values as R6 and may optionally form, with the nitrogen atom to which they are attached, a 4- to 10-membered heterocycle optionally containing one or more hetero atoms, which may be identical or different, chosen from O, S, N and NR12 and optionally substituted with one or more substituents, which may be identical or different, chosen from the values of R7;

R12 represents a hydrogen atom; an alkyl, alkenyl, alkynyl, cycloalkyl, alkylCO or alkylSO$_2$ radical, all optionally substituted with one or more substituents, which may be identical or different, chosen from halogen atoms, OH, alkoxy and dialkylamino radicals; aryl and heteroaryl, these last two radicals optionally substituted with one or more substituents, which may be identical or different, chosen from halogen atoms and alkyl and alkoxy radicals;

R13, which may be identical to or different from R6, represents the same values as R6;

R14, which may be identical to or different from R13, represents the same values as R13 and also represents C(O)R28; C(O)N28R29; SO2R28 and SO2NR28R29;

R13 and R14 may optionally form, together with the nitrogen atom to which they are attached, a 4- to 10-membered heterocycle optionally containing one or more hetero atoms, which may be identical or different, chosen from O, S, N and NR12 and optionally substituted with one or more substituents, which may be identical or different, chosen from the values of R7;

R15 and R16, which may be identical to or different from each other and also which may be identical to or different from R13, are chosen from the same values as R13 and may optionally form, with the nitrogen atom to which they are attached, a 4- to 10-membered heterocycle optionally containing one or more hetero atoms, which may be identical or different, chosen from O, S, N and NR12 and optionally substituted with one or more substituents, which may be identical or different, chosen from the values of R7;

R17 represents a hydrogen atom, alkyl or cycloalkyl;

R18, which may be identical to or different from R6, represents the same values as R6;

R19 and R20, which may be identical to or different from each other and also which may be identical to or different from R6, are chosen from the same values as R6 and may optionally form, with the nitrogen atom to which they are attached, a 4- to 10-membered heterocycle optionally containing one or more hetero atoms, which may be identical or different, chosen from O, S, N and NR12 and optionally substituted with one or more substituents, which may be identical or different, chosen from the values of R7;

R21, which may be identical to or different from R13, represents the same values as R13 and also represents hydrogen;

R22 and R23, which may be identical to or different from each other and also which may be identical to or different from R6, are chosen from the same values as R6 and may optionally form, with the nitrogen atom to which they are attached, a 4- to 10-membered heterocycle optionally containing one or more hetero atoms, which may be identical or different, chosen from O, S, N and NR12 and optionally substituted with one or more substituents, which may be identical or different, chosen from the values of R7;

R24 and R25, which may be identical or different, represent an alkyl, alkenyl or alkynyl radical optionally substituted with one or more substituents, which may be identical or different, chosen from halogen atoms and OH and alkoxy radicals, or alternatively R24 and R25 may optionally form, with the nitrogen atom to which they are attached, a 4- to 7-membered heterocycle optionally containing one or more hetero atoms, which may be identical or different, chosen from O, S, N, N-alkyl and N-C(O)alkyl, and optionally substituted with one or more substituents, which may be identical or different, chosen from halogen atoms and OH, alkyl, alkoxy and oxo radicals;

R26 represents a hydrogen atom or an alkyl, alkenyl or alkynyl radical optionally substituted with one or more substituents, which may be identical or different, chosen from halogen atoms and OH and alkoxy radicals;

R27, which may be identical to or different from R26, represents the same values as R26;

R26 and R27 may also optionally form, with the nitrogen atom to which they are attached, a 4- to 7-membered heterocycle optionally containing one or more hetero atoms, which may be identical or different, chosen from O, S, N, N-alkyl and N-C(O)alkyl, and optionally substituted with one or more substituents, which may be identical or different, chosen from halogen atoms and OH, alkyl, alkoxy and oxo radicals;

R28, which may be identical to or different from R26, represents the same values as R26;

R29, which may be identical to or different from R26, represents the same values as R26;

R30, which may be identical to or different from R26, represents the same values as R26;

n represents the integers 0, 1 and 2;

the said products of formula (I) being in any possible racemic, enantiomeric and diastereoisomeric isomer form, and also the addition salts with mineral acids and organic acids or with mineral bases and organic bases of the said products of formula (I).

In the products of formula (I), the value p which represents the integer 0, 1 or 2, and the value R4 which represents one or more substituents of the corresponding ring (R4, R4', R4", R4''') are thus obtained: it is thus understood that when p represents 0, 1 or 2, then the ring is optionally substituted, respectively, with 2, 4 or 6 substituents R4, which may be identical or different. It is noted that R4 also represents hydrogen. It is also noted that two substituents R4 may be borne by the same carbon of the ring or by two different carbons and, in these two cases, may form with the carbon(s) that bear(s) them, a cyclic radical which is itself optionally substituted as defined above.

In the products of formula (I) and subsequently, the terms indicated have the following meanings:

the term "Hal", "Halo" or halogen denotes fluorine, chlorine, bromine or iodine atoms, the term "alkyl radical", "alk", "Alk" or "ALK" denotes a linear or branched radical containing not more than 12 carbon atoms, chosen from methyl, ethyl, propyl, isopropyl, butyl, isobutyl, sec-butyl, tert-butyl, pentyl, isopentyl, sec-pentyl, tert-pentyl, neopentyl, hexyl, isohexyl, sec-hexyl, tert-hexyl, heptyl, octyl, nonyl, decyl, undecyl and dodecyl radicals, and also the linear or branched positional isomers thereof.

Mention is made more particularly of alkyl radicals containing not more than 6 carbon atoms, and especially methyl, ethyl, propyl, isopropyl, n-butyl, isobutyl, tert-butyl, linear or branched pentyl and linear or branched hexyl radicals.

the term "alkenyl radical" denotes a linear or branched radical containing not more than 12 carbon atoms and preferably 4 carbon atoms, chosen, for example, from the following values: ethenyl or vinyl, propenyl or allyl, 1-propenyl, n-butenyl, i-butenyl, 3-methyl-2-butenyl, n-pentenyl, hexenyl, heptenyl, octenyl, cyclohexylbutenyl and decenyl, and also the linear or branched positional isomers thereof.

Among the alkenyl values that may be mentioned more particularly are the values allyl or butenyl.

the term "alkynyl radical" denotes a linear or branched radical containing not more than 12 carbon atoms and preferably 4 carbon atoms, chosen, for example, from the following values: ethynyl, propynyl or propargyl, butynyl, n-butynyl, i-butynyl, 3-methyl-2-butynyl, pentynyl or hexynyl, and also the linear or branched positional isomers thereof.

Among the alkynyl values that are mentioned more particularly is the propargyl value.

the term "alkoxy radical" denotes a linear or branched radical containing not more than 12 carbon atoms and preferably 6 carbon atoms chosen, for example, from methoxy, ethoxy, propoxy, isopropoxy, linear, secondary or tertiary butoxy, pentoxy, hexoxy and heptoxy radicals, and also the linear or branched positional isomers thereof, the term "alkoxycarbonyl radical" or alkyl-O—CO— denotes a linear or branched radical containing not more than 12 carbon atoms, in which the alkyl radical has the meaning given above: examples that may be mentioned include methoxycarbonyl and ethoxycarbonyl radicals, the term "alkylenedioxy radical" or —O-alkylene-O— denotes a linear or branched radical containing not more than 12 carbon atoms, in which the alkylene radical has the meaning given above: examples that may be mentioned include methylenedioxy and ethylenedioxy radicals, the term "alkylsulphinyl" or alkyl-SO— denotes a linear or branched radical containing not more than 12 carbon atoms, in which the alkyl radical has the meaning given above and preferably contains 4 carbon atoms, the term "alkylsulphonyl" or alkyl-SO2-denotes a linear or branched radical containing not more than 12 carbon atoms, in which the alkyl radical has the meaning given above and preferably contains 4 carbon atoms, the term "alkylsulphonylcarbamoyl" or alkyl-SO2-NH—C(=O)— denotes a linear or branched radical containing not more than 12 carbon atoms, in which the alkyl radical has the meaning given above and preferably contains 4 carbon atoms, the term "alkylthio" or alkyl-S— denotes a linear or branched radical containing not more than 12 carbon atoms and especially represents methylthio, ethylthio, isopropylthio and heptylthio radicals, the term "cycloalkyl radical" denotes a 3- to 10-membered monocyclic or bicyclic carbocyclic radical and especially denotes cyclopropyl, cyclobutyl, cyclopentyl and cyclohexyl radicals, the term "—O-cycloalkyl radical" denotes a radical in which the cycloalkyl radical has the meaning given above, the term "cycloalkenyl radical" denotes a 3- to 10-membered monocyclic or bicyclic nonaromatic carbocyclic radical containing at least one double bond, and especially denotes cyclobutenyl, cyclopentenyl and cyclohexenyl radicals, the term "cycloalkylalkyl radical" denotes a radical in which cycloalkyl and alkyl are chosen from the values indicated above: this radical thus denotes, for example, cyclopropylmethyl, cyclopentylmethyl, cyclohexylmethyl and cycloheptylmethyl radicals, the term "acyl radical" or r-CO— denotes a linear or branched radical containing not more than 12 carbon atoms, in which the radical r represents a hydrogen atom or an alkyl, cycloalkyl, cycloalkenyl, cycloalkyl, heterocycloalkyl or aryl radical, these radicals having the values indicated above and being optionally substituted as indicated: examples that are mentioned include the formyl, acetyl, propionyl, butyryl or benzoyl radicals, or alternatively valeryl, hexanoyl, acryloyl, crotonoyl or carbamoyl, the term "acyloxy radical" means acyl-O— radicals in which acyl has the meaning given above: examples that are mentioned include acetoxy or propionyloxy radicals, the term "acylamino radical" means acyl-NH— radicals in which acyl has the meaning given above, the term "aryl radical" denotes unsaturated monocyclic radicals or unsaturated radicals consisting of fused carbocyclic rings. Examples of such aryl radicals that may be mentioned include phenyl or naphthyl radicals.

Mention is made more particularly of the phenyl radical.

the term "arylalkyl" means radicals resulting from the combination of the optionally substituted alkyl radicals mentioned above and the optionally substituted aryl radicals also mentioned above: examples that are mentioned include benzyl, phenylethyl, 2-phenethyl, triphenylmethyl or naphthalenemethyl radicals, the term "heterocyclic radical" denotes a saturated (heterocycloalkyl) or partially saturated or unsaturated (heteroaryl) 5- to 10-membered radical containing one or more hetero atoms, which may be identical or different, chosen from oxygen, nitrogen and sulphur atoms: the term "heterocyclic" preferably represents a saturated or partially unsaturated 4- to 7-membered heterocyclic radical optionally containing one or more hetero atoms, which may be identical or different, chosen from N, O and S.

Heterocycloalkyl radicals that may especially be mentioned include dioxolane, dioxane, dithiolane, thiooxolane, thiooxane, oxiranyl, oxolanyl, dioxolanyl, piperazinyl, piperidyl, pyrrolidyl, imidazolidinyl, pyrazolidinyl, morpholinyl, or tetrahydrofuryl, tetrahydrothienyl, chromanyl, dihydrobenzofuranyl, indolinyl, piperidyl, perhydropyranyl, pyrindolinyl, tetrahydroquinolyl, tetrahydroisoquinolyl and thioazolidinyl radicals, all these radicals being optionally substituted.

Among the heterocycloalkyl radicals that may especially be mentioned are optionally substituted piperazinyl, optionally substituted piperidyl, optionally substituted pyrrolidinyl, imidazolidinyl, pyrazolidinyl, morpholinyl and thioazolidinyl radicals: mention may also be made more particularly of optionally substituted morpholinyl, pyrrolidyl and piperazinyl radicals;

the term "heterocycloalkylalkyl radical" means radicals in which the heterocycloalkyl and alkyl residues have the above meanings;

among the 5-membered heteroaryl radicals that may be mentioned are furyl radicals such as 2-furyl, thienyl radicals such as 2-thienyl and 3-thienyl, and pyrrolyl, diazolyl, thiazolyl, thiadiazolyl, thiatriazolyl, isothiazolyl, oxazolyl, oxadiazolyl, 3- or 4-isoxazolyl, imidazolyl, pyrazolyl and isoxazolyl radicals.

Among the 6-membered heteroaryl radicals that may especially be mentioned are pyridyl radicals such as 2-pyridyl, 3-pyridyl and 4-pyridyl, and pyrimidyl, pyrimidinyl, pyridazinyl, pyrazinyl and tetrazolyl radicals;

as fused heteroaryl radicals containing at least one hetero atom chosen from sulphur, nitrogen and oxygen, examples that may be mentioned include benzothienyl such as 3-benzothienyl, benzofuryl, benzofuranyl, benzopyrrolyl, benzimidazolyl, benzoxazolyl, azaindolyl, thionaphthyl, indolyl, purinyl, quinolyl, isoquinolyl and naphthyridinyl.

Among the fused heteroaryl radicals that may be mentioned more particularly are benzothienyl, benzofuranyl, indolyl, quinolyl, benzimidazolyl, benzothiazolyl, furyl, imidazolyl, indolizinyl, isoxazolyl, isoquinolyl, isothiazolyl, oxadiazolyl, pyrazinyl, pyridazinyl, pyrazolyl, pyridyl, pyrimidinyl, pyrrolyl, quinazolinyl, 1,3,4-thiadiazolyl, thiazolyl and thienyl radicals and triazolyl groups, these radicals optionally being substituted as indicated for the heteroaryl radicals;

The term "patient" denotes human beings, but also other mammals.

The term "prodrug" denotes a product that may be converted in vivo via metabolic mechanisms (such as hydrolysis) into a product of formula (I). For example, an ester of a product of formula (I) containing a hydroxyl group may be converted by hydrolysis in vivo into its parent molecule. Alternatively, an ester of a product of formula (I) containing a carboxyl group may be converted by in vivo hydrolysis into its parent molecule.

Examples of esters of the products of formula (I) containing a hydroxyl group that may be mentioned include the acetates, citrates, lactates, tartrates, malonates, oxalates, salicylates, propionates, succinates, fumarates, maleates, methylenebis-β-hydroxynaphthoates, gentisates, isethionates, dip-tolyltartrates, methanesulphonates, ethanesulphonates, benzenesulphonates, p-toluenesulphonates, cyclohexylsulphamates and quinates.

Esters of products of formula (I) that are particularly useful, containing a hydroxyl group, may be prepared from acid residues such as those described by Bundgaard et. al., J. Med. Chem., 1989, 32, page 2503-2507: these esters especially include substituted (aminomethyl)benzoates, dialkylaminomethylbenzoates in which the two alkyl groups may be linked together or may be interrupted with an oxygen atom or with an optionally substituted nitrogen atom, i.e. an alkylated nitrogen atom, or alternatively (morpholinomethyl)benzoates, e.g. 3- or 4-(morpholinomethyl)benzoates, and (4-alkylpiperazin-1-yl)benzoates, e.g. 3- or 4-(4-alkylpiperazin-1-yl)benzoates.

The carboxyl radical(s) of the products of formula (I) may be salified or esterified with various groups known to those skilled in the art, among which nonlimiting examples that may be mentioned include the following compounds:

among the salification compounds, mineral bases such as, for example, one equivalent of sodium, potassium, lithium, calcium, magnesium or ammonium, or organic bases such as, for example, methylamine, propylamine, trimethylamine, diethylamine, triethylamine, N,N-dimethylethanolamine, tris(hydroxymethyl)aminomethane, ethanolamine, pyridine, picoline, dicyclohexylamine, morpholine, benzylamine, procaine, lysine, arginine, histidine or N-methylglucamine, among the esterification compounds, alkyl radicals to form alkoxycarbonyl groups such as, for example, methoxycarbonyl, ethoxycarbonyl, tert-butoxycarbonyl or benzyloxycarbonyl, these alkyl radicals possibly being substituted with radicals chosen, for example, from halogen atoms and hydroxyl, alkoxy, acyl, acyloxy, alkylthio, amino or aryl radicals, such as, for example, in chloromethyl, hydroxypropyl, methoxymethyl, propionyloxymethyl, methylthiomethyl, dimethylaminoethyl, benzyl or phenethyl groups.

The term "esterified carboxyl" means, for example, radicals such as alkyloxycarbonyl radicals, for example methoxycarbonyl, ethoxycarbonyl, propoxycarbonyl, butyl or tert-butyloxycarbonyl, cyclobutyloxycarbonyl, cyclopentyloxycarbonyl or cyclohexyloxycarbonyl.

Mention may also be made of radicals formed with readily cleavable ester residues, such as methoxymethyl or ethoxymethyl radicals; acyloxyalkyl radicals such as pivaloyloxymethyl, pivaloyloxyethyl, acetoxymethyl or acetoxyethyl; alkyloxycarbonyloxyalkyl radicals such as methoxycarbonyloxy methyl or ethyl radicals, and isopropyloxycarbonyloxy methyl or ethyl radicals.

A list of such ester radicals may be found, for example, in European patent EP 0 034 536.

The term "amidated carboxyl" means radicals of the type —CONRxRy in which the amino radicals —NRxRy have the meanings given above: especially, Rx and Ry, which may be identical or different, represent a hydrogen atom, a cyclic radical as defined above or below or an alkyl radical containing from 1 to 4 carbon atoms such as methyl, ethyl, propyl, isopropyl, butyl, isobutyl, sec-butyl or tert-butyl radicals and especially amino, alkylamino and dialkylamino radicals, all these cyclic and alkyl radicals being optionally substituted.

The term "alkylamino radical" means, for example, linear or branched methylamino, ethylamino, propylamino or butylamino radicals. Alkyl radicals containing not more than 4 carbon atoms are preferred, the alkyl radicals possibly being chosen from the alkyl radicals mentioned above.

The term "dialkylamino radical" means, for example, dimethylamino, diethylamino and methylethylamino radicals. As previously, alkyl radicals containing not more than 4 carbon atoms, chosen from the list indicated above, are preferred.

The term "salified carboxyl" means the salts formed, for example, with one equivalent of sodium, potassium, lithium, calcium, magnesium or ammonium. Mention may also be made of the salts formed with organic bases such as methylamine, propylamine, trimethylamine, diethylamine and triethylamine. The sodium salt is preferred.

When the products of formula (I) comprise an amino radical that may be salified with an acid, it is clearly understood that these acid salts also form part of the invention. Mention may be made of the salts obtained, for example, with hydrochloric acid or methanesulphonic acid.

The addition salts with mineral or organic acids of the products of formula (I) may be, for example, the salts formed with hydrochloric acid, hydrobromic acid, hydriodic acid, nitric acid, sulphuric acid, phosphoric acid, propionic acid, acetic acid, trifluoroacetic acid, formic acid, benzoic acid, maleic acid, fumaric acid, succinic acid, tartaric acid, citric acid, oxalic acid, glyoxylic acid, aspartic acid, ascorbic acid, alkylmonosulphonic acids such as, for example, methanesulphonic acid, ethanesulphonic acid or propanesulphonic acid, alkyldisulphonic acids such as, for example, methanedisulphonic acid or α,β-ethanedisulphonic acid, arylmonosulphonic acids such as benzenesulphonic acid, and aryldisulphonic acids.

It may be recalled that stereoisomerism may be defined in its broad sense as the isomerism of compounds having the same structural formulae but whose various groups are arranged differently in space, especially such as in monosubstituted cyclohexanes whose substituent may be in an axial or equatorial position, and the various possible rotational conformations of ethane derivatives. However, there is another type of stereoisomerism, due to the different spatial arrangements of fixed substituents, either on double bonds or on rings, which is often referred to as geometrical isomerism or cis-trans isomerism. The term "stereoisomer" is used in the present patent application in its broadest sense and thus relates to all the compounds indicated above.

A subject of the present invention is thus the products of general formula (I) as defined above in which A represents a phenyl or heteroaryl radical or a monocyclic or bicyclic fused carbocyclic or heterocyclic 5- to 11-membered radical, optionally substituted with one or more substituents, which may be identical or different, chosen from the values of R3, with R3 and the other substituents of the said products of formula (I) being chosen from the values defined for R3 and for the said substituents, the said products of formula (I) being in any possible racemic, enantiomeric or diastereoisomeric isomer form, and also the addition salts with mineral and organic acids or with mineral and organic bases of the said products of formula (I).

In the said products of formula (I):

A more particularly represents a phenyl, a 5 to 6-membered heteroaryl or a condensed heterocyclic ring system selected from the list:

1,2,3,4-tetrahydro-quinolin, 1,2,3,4-tetrahydro-isoquinolin, indolyl, 2,3-dihydro-1H-indolyl, 2,3-dihydro-1H-isoindolyl, 2,3-dihydro-benzothiazole, tetrahydroquinoline or tetrahydroisoquinoline, all these radicals being optionally substituted with one or more radicals chosen from the values of R3;

A even more particularly represents a phenyl or 1,2,3,4-tetrahydro-quinolin, 1,2,3,4-tetrahydro-isoquinolin, indolyl, 2,3-dihydro-1H-indolyl or 2,3-dihydro-1H-isoindolyl, all optionally substituted with one or more substituents, which may be identical or different, chosen from alkyl, alkoxy, cycloalkyl, alkylamino and dialkylamino radicals, each alkyl radical being optionally substituted with one or more fluorine atom; and —OCF3, SCF3 and SO2CF3 radicals.

A most particularly represents a phenyl or indolinyl radical optionally substituted with one or more substituents, which may be identical or different, chosen from alkyl, alkoxy, SCF3, SO2CF3 and —OCF3 radicals; the other substituents of the said products of formula (I) being chosen from all the values defined for the said substituents, the said products of formula (I) being in any possible racemic, enantiomeric and diastereoisomeric isomer form, and also the addition salts with mineral and organic acids or with mineral and organic bases of the said products of formula (I).

One subject of the present invention is thus the products of general formula (I) as defined above in which: X represents a single bond or the following divalent radicals: —N(R6)-, —O—, —C(O)—, —S(O)n-, —N(R6)-C(O)—, —N(R6)-C(O)—N(R6')-, —N(R6)-SO2-, —C(O)—N(R6)- and —SO2 NR6;

with R6 and R6', which may be identical or different, and the other substituents of the said products of formula (I) being chosen from all the values defined for R6 and R6' and for the said substituents, the said products of formula (I) being in all the possible racemic, enantiomeric and diastereoisomeric isomer forms, and also the addition salts with mineral and organic acids or with mineral and organic bases of the said products of formula (I).

In the said products of formula (I):

X more particularly represents a single bond or the following divalent radicals: —N(R6)-, —O—, —C(O)—, —S(O)n-, —N(R6)-C(O)— and —N(R6)-SO2-;

X most particularly represents a single bond or the following divalent radicals: —N(R6)-, —O—, —C(O)—, and —NH—C(O)—;

with R6 and the other substituents of the said products of formula (I) being chosen from all the values defined for R6 and the said substituents, the said products of formula (I) being in all the possible racemic, enantiomeric and diastereoisomeric isomer forms, and also the addition salts with mineral and organic acids or with mineral and organic bases of the said products of formula (I).

One subject of the present invention is thus the products of general formula (I) as defined above in which L1 represents an alkylene radical containing 1 to 4 carbon atoms and optionally substituted with one or several substituents chosen from the values of R7, with R7 and the other substituents of the said products of formula (I) being chosen from all the values defined for R7 and for the substituents, the said products of formula (I) being in all the possible racemic, enantiomeric and diastereoisomeric isomer forms, and also the addition salts with mineral and organic acids or with mineral and organic bases of the said products of formula (I).

In the said products of formula (I):

L1 more particularly represents an alkylene radical containing 1 to 4 carbon atoms and optionally substituted with one or more substituents, which may be identical or different, chosen from halogen atoms (F), and OH and alkoxy radicals;

L1 represents even more particularly particularly an alkylene radical containing 1 to 4 carbon atoms optionally substituted with a hydroxyl radical;

L1 most particularly represents an alkylene radical containing 1 to 4 carbon atoms;

the other substituents of the said products of formula (I) among all the values defined for the said substituents, the said products of formula (I) being in all the possible racemic, enantiomeric and diastereoisomeric isomer forms, and also the addition salts with mineral and organic acids or with mineral and organic bases of the said products of formula (I).

One subject of the present invention is thus the products of general formula (I) as defined above in which the radical NR1R2 is such that:

either R1 and R2, which may be identical or different, are such that:

R1 represents a hydrogen atom, an alkyl or cycloalkyl radical, these last two radicals being optionally substituted with one or more substituents, which may be identical or different, chosen from the values of R7; aryl, heteroaryl, arylalkyl, heteroarylalkyl in which each of the aromatic rings may be optionally substituted with one or more substituents, which may be identical or different, chosen from the values of R8;

and R2 represents a hydrogen atom, an alkyl or cycloalkyl radical, these last two radicals being optionally substituted with one or more substituents, which may be identical or different, chosen from the values of R7;

or R1 and R2 form, together with the nitrogen atom to which they are attached, a 4- to 10-membered heterocycle optionally containing one or more other heteroatoms, which may be identical or different, chosen from O, N, NR12 and S and optionally substituted with one or more substituents, which may be identical or different, chosen from the values of R7;

or NR1 with L1 or NR2 with $L_1$ together form a 4- to 8-membered heterocycle optionally substituted with one or more substituents, which may be identical or different, chosen from the values of R7;

with R7, R8, R12 and L1 and the other substituents of the said products of formula (I) being chosen from all the values defined for R7, R8, R12 and L1 and for the said substituents, the said products of formula (I) being in all the possible racemic, enantiomeric and diastereoisomeric isomer forms, and also the addition salts with mineral and organic acids or with mineral and organic bases of the said products of formula (I).

In the said products of formula (I):

the radical NR1R2 is particularly defined as follows:

either R1 and R2, which may be identical or different, are such that:

R1 represents a hydrogen atom, an alkyl or cycloalkyl radical, these last two radicals being optionally substituted with one or more substituents, which may be identical or different, chosen from the values of R7; aryl and heteroaryl, both optionally substituted with one or more substituents, which may be identical or different, chosen from the values of R8;

and R2 represents a hydrogen atom, an alkyl or cycloalkyl radical, these last two radicals being optionally substituted with one or more substituents, which may be identical or different, chosen from the values of R7;

or R1 and R2 form, together with the nitrogen atom to which they are attached, a 4- to 10-membered heterocycle optionally containing one or more other hetero atoms, which may be identical or different, chosen from O, N, N-alkyl and S and optionally substituted with one or more substituents, which may be identical or different, chosen from the values of R7;

or NR1 with L1 or NR2 with $L_1$ together form a 4- to 8-membered heterocycle optionally substituted with one or more substituents, which may be identical or different, chosen from the values of R7;

the radical NR1R2 is more particularly defined as follows:

either R1 and R2, which may be identical or different, are such that:

R1 represents an alkyl or cycloalkyl radical optionally substituted with one or more substituents, which may be identical or different, chosen from halogen atoms (F) and hydroxyl; alkoxy; cyano, free or esterified carboxyl, phenyl, 3- to 7-membered cycloalkyl, alkylamino, dialkylamino, —NHCO-alkyl, —CO(NH-alkyl), CO(Ndialkyl) radicals and 5-, 6- or 7-membered saturated, partially saturated or unsaturated heterocyclyl radicals containing one or more hetero atoms, which may be identical or different, chosen from O, S, N, NH or N-alkyl and optionally substituted with one or more substituents, which may be identical or different, chosen from halogen atoms and alkyl, NH2 and alkoxy radicals;

or alternatively R1 represents a phenyl radical or a saturated, partially saturated or unsaturated 4- to 7-membered heterocyclic radical, itself containing one or more hetero atoms chosen from O, S, N, NH and N-alkyl, and optionally substituted with one or more radicals chosen from halogen atoms, alkyl, NH2 and alkoxy radicals;

and R2 represents a hydrogen atom, an alkyl or cycloalkyl radical optionally substituted with one or more halogen atoms;

or R1 and R2 form, together with the nitrogen atom to which they are attached, a 4- to 7-membered heterocycle optionally containing one or more other hetero atoms, which may be identical or different, chosen from O, N, NH, N-alkyl and S and optionally substituted with one or more substituents, which may be identical or different, chosen from halogen atoms, alkyl, alkoxy, CF3 and free or esterified carboxyl radicals;

or NR1R2 and $L_1$ together form a 4- to 7-membered heterocycle optionally substituted with one or more substituents, which may be identical or different, chosen from halogen atoms, alkyl and alkoxy and free or esterified carboxyl radicals;

the radical NR1R2 is even more particularly defined as follows:

either R1 and R2, which may be identical or different, are such that:

R1 represents an alkyl radical optionally substituted with one or more radicals chosen from halogen atoms and hydroxyl, alkoxy, cyano, free or esterified carboxyl, phenyl and 3- to 7-membered cycloalkyl radicals, and saturated, partially saturated or unsaturated 4- to 7-membered heterocyclic radical, itself containing one or more hetero atoms, which may be identical or different, chosen from O, S, N, NH and N-alkyl and optionally substituted with one or more alkyl radicals, and or alternatively R1 represents a 3- to 7-membered cycloalkyl radical, a phenyl radical or a saturated, partially saturated or unsaturated 4- to 7-membered heterocyclic radical, itself containing one or more hetero atoms chosen from O, S, N, NH and N-alkyl, and optionally substituted with one or more alkyl radicals and R2 represents a hydrogen atom or an alkyl radical optionally substituted with one or more halogen atoms;

or R1 and R2 form, with the nitrogen atom to which they are attached, a saturated or unsaturated 4- to 7-membered heterocyclic radical optionally containing one or more other hetero atoms chosen from O, S, N, NH and N-alkyl, this radical formed by R1 and R2 with N being itself optionally substituted with one or more radicals, which may be identical or different, chosen from alkyl, CF3 and free or esterified carboxyl radicals, or NR1 with L1 or NR2 and L1 together form a saturated or unsaturated 4- to 7-membered heterocycle containing at least one nitrogen atom and optionally containing one or more other hetero atoms chosen from O, S, N, NH and N-alkyl, this radical formed by NR1R2 with L1d itself being optionally substituted with one or more radicals chosen from alkyl and free or esterified carboxyl radicals, with R7, R8 and L1 and the other substituents of the said products of the formula (I) being chosen from all the values defined for R7, R8 and L1 and for the said substituents, the said products of formula (I) being in all the possible racemic, enantiomeric and diastereoisomeric isomer forms, and also the addition salts with mineral and organic acids or with mineral and organic bases of the said products of formula (I).

One subject of the present invention is thus the products of general formula (I) as defined below, in which R3 represents a hydrogen atom, a halogen atom; an alkyl, cycloalkyl, alkoxy or alkylenedioxy radical, all optionally substituted with one or more substituents, which may be identical or different, chosen from the values of R7; —NR13R14; —C(O)R13; —S(O)$_n$R13; —C(O)NR15R16; —S(O)$_n$NR15R16; aryl and heteroaryl, these last two radicals optionally substituted with one or more substituents, which may be identical or different, chosen from the values of R8;

with R7, R8, R13, R14, R15 and R16 and the other substituents of the said products of formula (I) being chosen from all the values defined for R7, R8, R13, R14, R15 and R16 and for the said substituents, the said products of formula (I) being in all the possible racemic, enantiomeric and diastereoisomeric isomer forms, and also the addition salts with mineral and organic acids or with mineral and organic bases of the said products of formula (I).

In the said products of formula (I):

R3 more particularly represents a hydrogen atom; alkyl, alkoxy and cycloalkyl radicals optionally substituted with one or more halogen atoms; OCF3 and S(O)$_n$-alkyl radicals, the alkyl residue containing 1 to 4 carbon atoms and being optionally substituted with one or more halogen atoms; alkylamino, optionally substituted with one or more halogen atoms; dialkylamino, in which the two alkyl residues may optionally form with the nitrogen atom to which they are attached a 4- to 10-membered heterocyclic radical optionally containing one or more other hetero atoms, which may be identical or different, chosen from O, N, N-alkyl and S and optionally substituted with one or more substituents, which may be identical or different, chosen from halogen atoms (F) and alkyl and alkoxy radicals;

R3 particularly represents one or more substituents of the ring A, which may be identical or different, chosen from alkyl, alkoxy, cycloalkyl, alkylamino and dialkylamino, each optionally substituted with one or more halogen atoms and in which alkyl and alcoxy contain up to 4 carbon atoms; OCF3; SCF3; and SO2CF3;

R3 especially represents one or more substituents of the ring A, which may be identical or different, chosen from a hydrogen atom and alkyl, OCH3, SCF3 and —OCF3 radicals; the ring A and the other substituents of the said products of formula (I) being chosen from all the values defined for the ring A and for the said substituents, the said products of formula (I) being in all the possible racemic, enantiomeric and diastereoisomeric isomer forms, and also the addition salts with mineral and organic acids or with mineral and organic bases of the said products of formula (I).

A subject of the present invention is thus the products of general formula (I) as defined above, in which R4 represents a hydrogen atom, a halogen atom (F), an alkyl or cycloalkyl radical, all optionally substituted with one or more substituents, which may be identical or different, chosen from the values of R7; it being understood that two substituents R4 may form, with the carbon atom(s) to which they are attached, a 3- to 7-membered ring optionally containing one or more hetero atoms, which may be identical or different, chosen from O, S, N and N-alkyl;

with R7 and the other substituents of the said products of formula (I) being chosen from all the values defined for R7 and for the said substituents, the said products of formula (I) being in all the possible racemic, enantiomeric and diastereoisomeric isomer forms, and also the addition salts with mineral and organic acids or with mineral and organic bases of the said products of formula (I).

In the said products of formula (I):

R4 more particularly represents a hydrogen atom, a halogen atom and an alkyl or cycloalkyl radical optionally substituted with one or more halogen atoms; it being understood that two substituents R4 may form, with the carbon atom to which they are attached, a 3- to 5-membered carbo or heterocyclic spirocyclic ring;

R4 even more particularly represents hydrogen, alkyl or spiro cycloalkyl; the other substituents of the said products of formula (I) being chosen from all the values defined for the said substituents, the said products of formula (I) being in all the possible racemic, enantiomeric and diastereoisomeric isomer forms, and also the addition salts with mineral and organic acids or with mineral and organic bases of the said products of formula (I).

In the said products of formula (I), R4 may especially represent hydrogen and alkyl, it being understood that two substituents R4 borne by the same carbon, can form, together with the carbon atom to which they are attached, a 3- to 6-membered cycloalkyl or heterocycloalkyl radical containing a nitrogen atom;

more particularly, R4 represents hydrogen and CH3, it being understood that two substituents R4, borne by the same carbon, can form, together with the carbon atom to which they are attached, a cycloalkyl radical containing from 3 to 6 carbon atoms or an azetidinyl, pyrrolidinyl or piperidyl radical.

When two substituents R4 borne by the same carbon form, together with the carbon atom to which they are attached, a cyclic radical, the ring formed is especially a cycloalkyl radical containing from 3 to 6 carbon atoms, and more particularly a cyclopropyl radical;

the other substituents of the said products of formula (I) being chosen from all the values defined for the said substituents, the said products of formula (I) being in all the possible racemic, enantiomeric and diastereoisomeric isomer forms, and also the addition salts with mineral and organic acids or with mineral and organic bases of the said products of formula (I).

One subject of the present invention is thus the products of general formula (I) as defined above in which L2 is chosen from a single bond and an alkylene, cycloalkylene, —O— or —NR17— radical, the other substituents of the said products of formula (I) being chosen from all the values defined for the said substituents, the said products of formula (I) being in all the possible racemic, enantiomeric and diastereoisomeric isomer forms, and also the addition salts with mineral and organic acids or with mineral and organic bases of the said products of formula (I).

In the said products of formula (I):

L2 especially represents cycloalkylene, —O— and —NR17—; L2 more particularly represents a single bond and methylene;

L2 even more particularly represents —CH2, the other substituents of the said products of formula (I) being chosen from all the values defined for the said substituents, the said products of formula (I) being in all the possible racemic, enantiomeric and diastereoisomeric isomer forms, and also the addition salts with mineral and organic acids or with mineral and organic bases of the said products of formula (I).

A subject of the present invention is thus the products of general formula (I) as defined above in which Y represents an N-heterocycle optionally containing one or more hetero atoms, which may be identical or different, chosen from O, S and N and optionally substituted with one or more substituents, which may be identical or different, chosen from the values of R5;

with R5 and the other substituents of the said products of formula (I) being chosen from all the values defined for R5 and for the said substituents, the said products of formula (I) being in all the possible racemic, enantiomeric and diastereoisomeric isomer forms, and also the addition salts with mineral and organic acids or with mineral and organic bases of the said products of formula (I).

In the said products of formula (I):

Y especially represents a monocyclic or bicyclic heteroaryl radical chosen from pyridyl, pyrimidinyl, pyridazine, pyrazine, azaindolyl, quinolyl, isoquinolyl, cinnolinyl, quinazolinyl, thiazolyl, imidazolyl, oxazolyl, pyrazolyl, isoxazolyl, 1H-pyrrolo[2,3-b]pyridyl, furazanyl, morpholinyl, pyrrolidinyl, indazolyl, 3H-imidazo-(4,5b)-pyridine, 1H-pyrazolo-(3,4b)-pyridine, 1H-pyrazolo-(3,4d)-pyrimidine, piperidyl, thienyl, indolyl, pyrrolyl, purinyl, benzoxazinyl, benzimidazolyl, these radicals being optionally substituted with one or more radicals chosen from the values of R5;

Y particularly represents a heteroaryl radical chosen from pyridyl, pyrimidinyl, azaindolyl, quinolyl, isoquinolyl, cinnolinyl, quinazolinyl, thiazolyl, imidazolyl, oxazolyl, pyrazolyl and isoxazolyl, these radicals being optionally substituted with one or more substituents, which may be identical or different, chosen from the values of R5;

Y more particularly represents a heteroaryl radical chosen from pyridyl, pyrimidinyl, quinolyl, isoquinolyl; azaindolyl, quinazolinyl, thiazolyl, imidazolyl, pyrazolyl, furazanyl and isoxazolyl radicals, these radicals being optionally substituted with one or more radicals chosen from the values of R5;

Y even more particularly represents a heteroaryl radical chosen from pyrid-4-yl, pyrid-3-yl, pyrimidin-4-yl, quinolin-4-yl, quinolin-3-yl, isoquinolin-5-yl, azaindol-4-yl and quinazolin-4-yl, these radicals being optionally substituted with one or more substituents, which may be identical or different, chosen from the values of R5;

Y most particularly represents a heteroaryl radical chosen from pyrid-4-yl, pyrimidin-4-yl, quinolin-4-yl, isoquinolin- 5-yl, azaindol-4-yl and quinazolin-4-yl, these radicals being optionally substituted with one or more substituents, which may be identical or different, chosen from the values of R5;

Y more specifically represents 4-pyridyl and 4-quinolyl radicals, optionally substituted with one or more radicals chosen from the values of R5 defined in any one of the claims;

with R5 and the other substituents of the said products of formula (I) being chosen from all the values defined for R5 and for the said substituents, the said products of formula (I) being in all the possible racemic, enantiomeric and diastereoisomeric isomer forms, and also the addition salts with mineral and organic acids or with mineral and organic bases of the said products of formula (I).

A subject of the present invention is thus the products of general formula (I) as defined above, in which R5 more particularly represents a hydrogen atom, a halogen atom or an alkyl, cycloalkyl, —NHR20, —NHCOR20, —NHCONR19R20 or —NH—S(O)2-R20 radical;

R5 even more particularly represents a hydrogen atom, a halogen atom; an alkyl, cycloalkyl, NH2, —NH-cycloalkyl, —NHCO-alkyl, —NHCO-cycloalkyl, —NHCONH-alkyl or —NHCON(dialkyl) radical, the alkyl and cycloalkyl residues being optionally substituted with one or more radicals, which may be identical or different, chosen from halogen atoms (F) and alkoxy, morpholinyl, piperidyl, piperazinyl, N-methylpiperazinyl and COOH radicals; NH-aryl, NH-heteroaryl, —NHCO-aryl and —NHCO-heteroaryl in which the aromatic residues are optionally substituted with one or more radicals chosen from halogen atoms and alkyl, alkoxy and COOH radicals;

with the two alkyl groups of —NHCON(dialkyl) can be linked together to form a ring that optionally can contain oner or more O, N, S and optionally can be substituted by F or alkyl;

with R19, R20 and the other substituents of the said products of formula (I) being as above defined, the said products of formula (I) being in all the possible racemic, enantiomeric and diastereoisomeric isomer forms, and also the addition salts with mineral and organic acids or with mineral and organic bases of the said products of formula (I).

A subject of the present invention is thus, particularly, the products of formula (I) as defined above corresponding to formula (Ia):

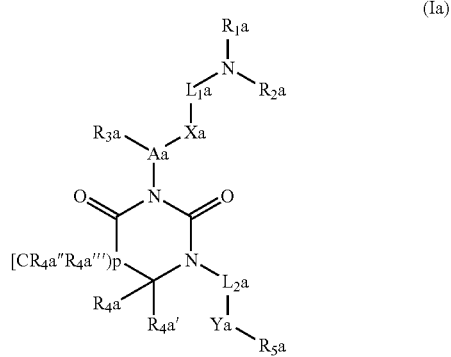

in which:

p represents the integers 0, 1 and 2,

Aa represents phenyl, heteroaryl and a monocyclic or bicyclic fused carbocyclic or heterocyclic 5- to 11-membered radical, optionally substituted with one or more substituents, which may be identical or different, chosen from the values of R3a;

Xa represents a single bond or the following divalent radicals: —N(R6a)-; —O—; —C(O)—; —S(O)n-; —N(R6a)-C(O)—; —N(R6a)-C(O)—N(R6'a)-; —N(R6a)-SO2-; —C(O)—N(R6a)-; —SO2—NR6a-;

L1a represents an alkylene radical containing 1 to 4 carbon atoms and optionally substituted with one or more substituents chosen from the values of R7a;

the radical NR1aR2a is such that:

either R1a and R2a, which may be identical or different, are such that:

R1a represents a hydrogen atom; alkyl and cycloalkyl, these last two radicals being optionally substituted with one or more substituents, which may be identical or different, chosen from the values of R7a; aryl, heteroaryl, arylalkyl and heteroarylalkyl in which each of the aromatic rings may be optionally substituted with one or more substituents, which may be identical or different, chosen from the values of R8a;

and R2a represents a hydrogen atom, alkyl and cycloalkyl, these last two radicals being optionally substituted with one or more substituents, which may be identical or different, chosen from the values of R7a;

or R1a and R2a form, together with the nitrogen atom to which they are attached, a 4- to 10-membered heterocycle optionally containing one or more other hetero atoms, which may be identical or different, chosen from O, N, NR12a and S and optionally substituted with one or more substituents, which may be identical or different, chosen from the values of R7a;

or NR1a with L1a or NR2a with L1a together form a 4- to 8-membered heterocycle optionally substituted with one or more substituents, which may be identical or different, chosen from the values of R7a;

R3a represents a hydrogen atom, a halogen atom; an alkyl, cycloalkyl, alkoxy or alkylenedioxy radical, all optionally substituted with one or more substituents, which may be identical or different, chosen from the values of R7a; —NR13aR14a; —C(O)R13a; —S(O)$_n$R13a; —C(O)NR15aR16a; —S(O)$_n$NR15aR16a; aryl and heteroaryl, these last two radicals being optionally substituted with one or more substituents, which may be identical or different, chosen from the values of R8a;

R4a, R4a', R4a" and R4a'", which may be identical or different, are chosen from the values defined below for R4a;

R4a represents a hydrogen atom, a halogen atom, an alkyl or cycloalkyl radical, all optionally substituted with one or more substituents, which may be identical or different, chosen from the values of R7a; it being understood that two substituents from among R4a, R4a' and R4a" may form, with the carbon atom(s) to which they are attached, a 3- to 7-membered ring optionally containing one or more hetero atoms, which may be identical or different, chosen from O, S, N and N-alkyl;

L2a is chosen from a single bond; alkylene; cycloalkylene; —O— and —NR17a-;

Ya represents an N-heterocycle optionally containing one or more hetero atoms, which may be identical or different, chosen from O, S and N and optionally substituted with one or more substituents, which may be identical or different, chosen from the values of R5a;

R5a represents a hydrogen atom, a halogen atom, an alkyl or cycloalkyl radical, optionally substituted with one or more substituents, which may be identical or different, chosen from the values of R7a; aryl, arylalkyl, heteroaryl and heteroarylalkyl, in which the aromatic rings are optionally substituted with one or more substituents, which may be identical or different, chosen from the values of R8a; —OR18a; —NR19aR20a; —NR19aCOR20a; —NR19aCONR19'aR20a; —NR19a-S(O)2-R20a; —NR19a-S(O)2-NR19a'R20a; —COR18a; COOR21a; —CONR22aR23a; —S(O)nR18a; —SO2NR22aR23a; cyano;

R6a is such that:

either R6a represents a hydrogen atom or an alkyl or cycloalkyl radical, all optionally substituted with one or more substituents, which may be identical or different, chosen from the values of R7a;

or R6a with NR1aR2a together form a 5- to 7-membered heterocycle optionally substituted with one or more substituents, which may be identical or different, chosen from the values of R7a;

or R6a with L1a together form a 5- to 7-membered heterocycle optionally substituted with one or more substituents, which may be identical or different, chosen from the values of R7a;

R6a', which may be identical to or different from R6a, is chosen from the values of R6a, R7a represents a halogen atom; an alkyl; hydroxyl (OH); alkoxy; cycloalkoxy; cyano radical; —CF3; —N24aR25a; —NR26aCOR27a; —NR26aCONR26a'R27a; —NR26a-S(O)2-R27a; —NR26a-S(O)2-NR26a'R27a; —COOR26a; —COR26a; —CO(NR24aR25a); S(O)nR26a; —S(O)2NR24aR25a; a 4- to 7-membered heterocycle optionally substituted with one or more substituents, which may be identical or different, chosen from OH and NH2 radicals, halogen atoms, and alkyl, alkoxy or oxo radicals; aryl optionally substituted with one or more substituents, which may be identical or different, chosen from halogen atoms and alkyl and alkoxy radicals; heteroaryl, optionally substituted with one or more substituents, which may be identical or different, chosen from halogen atoms and NH2, alkyl and alkoxy radicals; phenoxy, optionally substituted with one or more substituents, which may be identical or different, chosen from halogen atoms and alkyl and alkoxy radicals;

R8a, which may be identical to or different from R7a, represents the same values as R7a and also represents halogen atoms, —OCF3, alkylenedioxy and difluoromethylenedioxy radicals;

R12a represents a hydrogen atom or an alkyl, cycloalkyl, alkylCO or alkylSO$_2$ radical, all optionally substituted with one or more substituents, which may be identical or different, chosen from halogen atoms and alkoxy radicals;

R13a represents an alkyl or cycloalkyl radical optionally substituted with one or more substituents, which may be identical or different, chosen from the values of R7a; a phenyl radical optionally substituted with one or more substituents, which may be identical or different, chosen from halogen atoms, alkyl and alkoxy radicals; a 5- or6-membered heteroaryl radical optionally substituted with one or more substituents, which may be identical or different, chosen from halogen atoms, alkyl and alkoxy radicals;

R14a represents an alkyl or cycloalkyl radical optionally substituted with one or more substituents, which may be identical or different, chosen from the values of R7a; C(O)R28a;

R13a and R14a may optionally form, together with the nitrogen atom to which they are attached, a 4- to 7-membered heterocycle optionally containing one or more hetero atoms, which may be identical or different, chosen from O, S, N and Nalkyl and optionally substituted with one or more substituents, which may be identical or different, chosen from the values of R7a;

R15a and R16a, which may be identical to or different from each other and also identical to or different from R13a, are chosen from the same values as R13a and may optionally form, with the nitrogen atom to which they are attached, a 4- to 7-membered heterocycle optionally containing one or more hetero atoms which may be identical or different, chosen from O, S, N and NR12A and optionally substituted with one or more substituents, which may be identical or different, chosen from the values of R7a;

R17a represents a hydrogen atom or an alkyl or cycloalkyl radical;

R18a, which may be identical to or different from R6a, represents the same values as R6a;

R19a represents a hydrogen atom or an alkyl or cycloalkyl radical;

R20a represents a hydrogen atom or an alkyl or cycloalkyl radical optionally substituted with one or more substituents, which may be identical or different, chosen from the values of R7a; aryl and heteroaryl, optionally substituted with one or more substituents, which may be identical or different, chosen from the values of R8a;

R19a and R20a, which may be identical to or different from each other, may also form, with the nitrogen atom to which they are attached, a 4- to 7-membered heterocycle optionally containing one or more hetero atoms, which may be identical or different, chosen from O, S, N and NR12a and optionally substituted with one or more substituents, which may be identical or different, chosen from the values of R7a;

R21a, which may be identical to or different from R13a, is chosen from the values of R13a and also represents a hydrogen atom;

R22a and R23a, which may be identical to or different from each other and identical to or different from R6a, are chosen from the values of R6a and may also form, with the nitrogen atom to which they are attached, a 4- to 7-membered heterocycle optionally containing one or more hetero atoms, which may be identical or different, chosen from O, S, N and NR12a and optionally substituted with one or more substituents, which may be identical or different, chosen from the values of R7a;

R24a and R25a, which may be identical or different, represent an alkyl radical optionally substituted with one or more substituents, which may be identical or different, chosen from halogen atoms, and OH and alkoxy radicals, or alternatively R24a and R25a may optionally form, with the nitrogen atom to which they are attached, a 4- to 7-membered heterocycle optionally containing one or more hetero atoms, which may be identical or different, chosen from O, S, N, N-alkyl and N-C(O)alkyl, and optionally substituted with one or more substituents, which may be identical or different, chosen from halogen atoms (F) and OH, alkyl, alkoxy or oxo radicals;

R26a represents a hydrogen atom or an alkyl radical optionally substituted with one or more substituents, which may be identical or different, chosen from halogen atoms (F) and OH and alkoxy radicals;

R27a, which may be identical to or different from R26a, is chosen from the values of R26a;

R26a and R27a, may also optionally form, with the nitrogen atom to which they are attached, a 4- to 7-membered heterocycle optionally containing one or more hetero atoms, which may be identical or different, chosen from O, S, N, N-alkyl and N—C(O)alkyl, and optionally substituted with one or more substituents, which may be identical or different, chosen from halogen atoms and OH, alkyl, alkoxy or oxo radicals;

R28a, which may be identical to or different from R26a, is chosen from the values of R26a;

R29a, which may be identical to or different from R26a, is chosen from the values of R26a;

R30a, which may be identical to or different from R26a, is chosen from the values of R26a;

n represents the integers 0, 1 and 2;

p represents the integers 0, 1 and 2;

the said products of formula (Ia) being in all the possible racemic, enantiomeric and diastereoisomeric isomer forms, and also the addition salts with mineral and organic acids or with mineral and organic bases of the said products of formula (Ia).

A subject of the invention is especially the products of formula (I) as defined above such that p represents the integer 0, the other substituents of the said products of formula (I) each having any one of the values defined in the present invention.

A subject of the invention is especially the products of formula (I) as defined above such that p represents the integer 1, the other substituents of the said products of formula (I) having any one of the values defined in the present invention.

A subject of the invention is especially the products of formula (I) as defined above such that p represents the integer 2, the other substituents of the said products of formula (I) having the values defined in the present invention.

A subject of the present invention is, more particularly, 5 the products of formula (I) or (Ia) as defined above corresponding to formula (Ib):

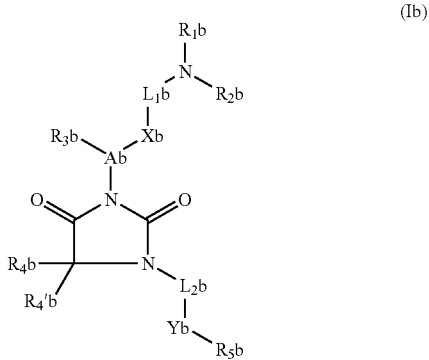

(Ib)

Ab represents phenyl, heteroaryl or a carbocyclic or heterocyclic 7- to 11-membered cyclic radical, optionally substituted with one or more substituents, which may be identical or different, chosen from the values of R3b;

Xb represents a single bond or the following divalent radicals: —N(R6b)-; —O—; —C(O)—; —S(O)n-; —N(R6b)-C(O)— and —N(R6b)-SO2-;

L1b represents an alkylene radical containing 1 to 4 carbon atoms and optionally substituted with one or more substituents, which may be identical or different, chosen from halogen atoms and OH and alkoxy radicals;

the radical NR1bR2b is such that:

either R1b and R2b, which may be identical or different, are such that:

R1b represents a hydrogen atom or an alkyl or cycloalkyl radical, these last two radicals being optionally substituted with one or more substituents, which may be identical or different, chosen from the values of R7b; aryl and heteroaryl, both optionally substituted with one or more substituents, which may be identical or different, chosen from the values of R8b;

and R2b represents a hydrogen atom or an alkyl or cycloalkyl radical, these last two radicals being optionally substituted with one or more substituents, which may be identical or different, chosen from the values of R7b;

or R1b and R2b form, together with the nitrogen atom to which they are attached, a 4- to 10-membered heterocycle optionally containing one or more other hetero atoms, which may be identical or different, chosen from O, N, N-alkyl and S and optionally substituted with one or more substituents, which may be identical or different, chosen from the values of R7b;

or NR1b with L1b or NR2b with L1b together form a 4- to 8-membered heterocycle optionally substituted with one or more substituents, which may be identical or different, chosen from the values of R7b;

R3b represents a hydrogen atom, an alkyl, alkoxy (—OCH3) or cycloalkyl radical, optionally substituted with one or more fluorine atoms; OCF3 and S(O)$_n$-alkyl radicals, the alkyl residue containing 1 to 4 carbon atoms and being optionally substituted with one or more F; alkylamino, optionally substituted with one or more F; dialkylamino, in which the two alkyl residues may optionally form, with the nitrogen atom to which they are attached, a 4- to 10-membered heterocyclic radical optionally containing one or more other hetero atoms, which may be identical or different, chosen from O, N, N-alkyl and S and optionally substituted with one or more substituents, which may be identical or different, chosen from F and alkyl and alkoxy radicals;

R4b and R4'b, which may be identical or different, represent a hydrogen atom, a halogen atom F and an alkyl or cycloalkyl radical, optionally substituted with one or more F; it being understood that two substituents R4b may form, with the carbon atom to which they are attached, a 3- to 5-membered spirocyclic ring;

L2b is chosen from a single bond and methylene;

Yb represents a monocyclic or bicyclic heteroaryl radical chosen from pyridyl, pyrimidinyl, pyridazine, pyrazine, azaindolyl, quinolyl, isoquinolyl, cinnolinyl, quinazolinyl, thiazolyl, imidazolyl, oxazolyl, pyrazolyl, isoxazolyl, 1H-pyrrolo[2,3-b]pyridyl, furazanyl, morpholinyl, pyrrolidinyl, indazolyl, 3H-imidazo-(4,5b)-pyridine, 1H-pyrazolo-(3,4b)-pyridine, 1H-pyrazolo-(3,4d)-pyrimidine, piperidyl, thienyl, indolyl, pyrrolyl, purinyl, benzoxazinyl, benzimidazolyl, these radicals being optionally substituted with one or more radicals chosen from the values of R5b;

R5b represents a hydrogen atom; a halogen atom; alkyl; cycloalkyl; —NHR20b; —NHCOR20b; —NHCONR19bR20b; —NH—S(O)2-R20b;

R6b represents a hydrogen atom or an alkyl radical containing from 1 to 4 carbon atoms;

R6b and NR1bR2b may optionally together form a 5- to 7-membered heterocycle optionally substituted with one or more radicals, which may be identical or different, chosen from the values of R7b;

R7b represents a halogen atom ; hydroxyl; cyano; COOH; —CF3; alkyl, alkoxy, alkylamino, dialkylamino, —NHCO-alkyl, —CO(NH-alkyl) and CO(Ndialkyl) in which the alkyl residues are optionally substituted with one or more substituents, which may be identical or different, chosen from halogen atoms, OH and methoxy; an aryl radical optionally substituted with one or more substituents, which may be identical or different, chosen from halogen atoms and alkyl and alkoxy radicals; a 4- to 7-membered heterocycle; heteroaryl, optionally substituted with one or more substituents, which may be identical or different, chosen from halogen atoms and NH2, alkyl and alkoxy radicals;

R8b, which may be identical to or different from R7b, is chosen from the values of R7b and in addition represents halogen atoms and —OCF3, alkylenedioxy and difluoromethylenedioxy radicals;

R19b represents a hydrogen atom or an alkyl or cycloalkyl radical;

R20b represents a hydrogen atom or an alkyl or cycloalkyl radical optionally substituted with one or more substituents, which may be identical or different, chosen from the values of R7b; aryl and heteroaryl, optionally substituted with one or more substituents, which may be identical or different, chosen from the values of R8b;

R19b and R20b, which may be identical to or different from each other, may also form, with the nitrogen atom to which they are attached, a 4- to 7-membered heterocycle optionally containing one or more hetero atoms, which may be identical or different, chosen from O, S, N and Nalkyl and optionally substituted with one or more substituents, which may be identical or different, chosen from the values of R7b;

n represents the integers 0, 1 and 2;

the said products of formula (Ib) being in all the possible racemic, enantiomeric and diastereoisomeric isomer forms, and also the addition salts with mineral and organic acids or with mineral and organic bases of the said products of formula (Ib).

A subject of the present invention is, even more particularly, the products of formula (I), (Ia) or (Ib) as defined above, corresponding to formula (Ic):

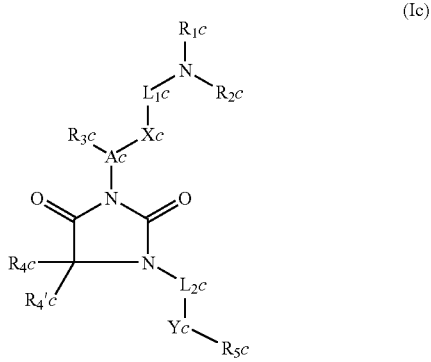

(Ic)

in which

A represents a phenyl, a 5 to 6-membered heteroaryl or a condensed heterocyclic ring system selected from the list: 1,2,3,4-tetrahydro-quinolin, 1,2,3,4-tetrahydro-isoquinolin, indolyl, 2,3-dihydro-1H-indolyl, 2,3-dihydro-1H-isoindolyl, 2,3-dihydro-benzothiazole, tetrahydroquinoline or tetrahydroisoquinoline;

all these radicals being optionally substituted with one or more substituents, which may be identical or different, chosen from alkyl, alkoxy, cycloalkyl, alkylamino and dialkylamino radicals, each alkyl radical being optionally substituted with one or more F; —OCF3, SCF3 and SO2CF3 radicals;

Xc represents a single bond or the following divalent radicals: —N(R6c)-; —O—; —C(O)—; and —N(R6c)-C(O)—;

L1c represents an alkylene radical containing 1 to 4 carbon atoms, optionally substituted with a hydroxyl radical;

either R1c and R2c, which may be identical or different, are such that:

R1c represents an alkyl or cycloalkyl radical optionally substituted with one or more substituents, which may be identical or different, chosen from halogen atoms; hydroxyl; alkoxy; cyano, free or esterified carboxyl, phenyl, 3- to 7-membered cycloalkyl, alkylamino, dialkylamino, —NHCO-alkyl, —CO(NH-alkyl), CO(Ndialkyl) and saturated, partially saturated or unsaturated 5-, 6- or7-membered heteroaryl radicals containing one or more hetero atoms, which may be identical or different, chosen from O, S, N, NH and N-alkyl and optionally substituted with one or more substituents, which may be identical or different, chosen from halogen atoms and alkyl, NH2 and alkoxy radicals; or alternatively R1c represents a phenyl radical or a saturated, partially saturated or unsaturated 4- to 7-membered heterocyclic radical, itself containing one or more hetero atoms chosen from O, S, N, NH and N-alkyl, and optionally substituted with one or more radicals chosen from halogen atoms and alkyl, NH2 and alkoxy radicals;

and R2c represents a hydrogen atom or an alkyl or cycloalkyl radical optionally substituted with one or more halogen atoms;

or R1c and R2c form, together with the nitrogen atom to which they are attached, a 4- to 7-membered heterocycle optionally containing one or more other hetero atoms, which may be identical or different, chosen from O, N, NH, N-alkyl and S and optionally substituted with one or more substituents, which may be identical or different, chosen from halogen atoms and alkyl, alkoxy, CF3 and free or esterified carboxyl radicals;

or NR1c with L1c or NR2c with L1C together form a 4- to 7-membered heterocycle optionally substituted with one or more substituents, which may be identical or different, chosen from halogen atoms, and alkyl, alkoxy and free or esterified carboxyl radicals;

L2c is chosen from a single bond and methylene;

R4c and R4'c, which may be identical or different, represent a hydrogen atom, an alkyl or cycloalkyl radical optionally substituted with one or more halogen atoms; it being understood that two substituents R4c may form, with the carbon atom to which they are attached, a 3-membered to 5-membered spirocyclic ring;

Yc represents a heteroaryl radical chosen from pyrid-4-yl, pyrimidin-4-yl, quinolin-4-yl, isoquinolin-5-yl; azaindol-4-yl and quinazolin-4-yl, these radicals being optionally substituted with one or more substituents, which may be identical or different, chosen from the values of R5c;

R5c represents a hydrogen atom, a halogen atom; an alkyl, cycloalkyl, NH2, —NH-cycloalkyl, —NHCO-alkyl, —NHCO-cycloalkyl, —NHCONH-alkyl or —NHCON(dialkyl) radical, the alkyl and cycloalkyl residues being optionally substituted with one or more radicals, which may be identical or different, chosen from halogen atoms (F) and alkoxy, morpholinyl, piperidyl, piperazinyl, N-methyl-piperazinyl and COOH radicals; NH-aryl, NH-heteroaryl, —NHCO-aryl and —NHCO-heteroaryl in which the aromatic residues are optionally substituted with one or more radicals chosen from halogen atoms and alkyl, alkoxy and COOH radicals;

R6c represents a hydrogen atom or an alkyl radical containing from 1 to 4 carbon atoms;

R6c and NR1cR2c may optionally together form a 5- to 7-membered heterocycle optionally substituted with one or more radicals, which may be identical or different, chosen from halogen atoms (F) and alkyl and alkoxy radicals, the said products of formula (Ic) being in all the possible racemic, enantiomeric and diastereoisomeric isomer forms, and also the addition salts with mineral and organic acids or with mineral and organic bases of the said products of formula (Ic).

As illustrations of radicals according to the present invention, without, however, limiting the present invention, examples may be given of NR1 forming a ring with L1 or NR2 forming a ring with L1, as follows:

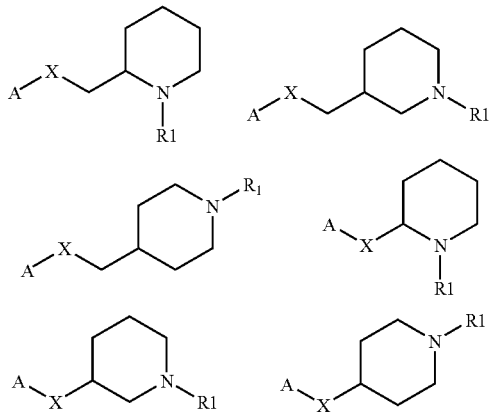

The examples that follow give, without limiting the scope of the present invention, an illustration of radicals that R2 may form with R6.

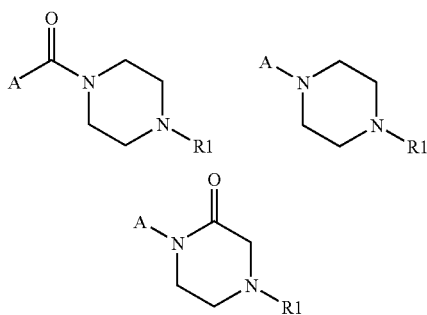

The examples that follow give, without limiting the scope of the present invention, an illustration of radicals that R6 can form with L1.

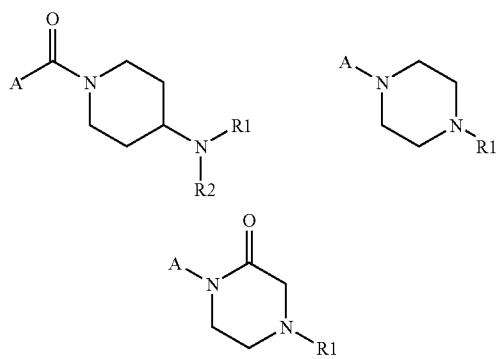

The examples that follow give, without limiting the scope of the present invention, an illustration of radicals that A can represent as a fused heterocyclic radical.

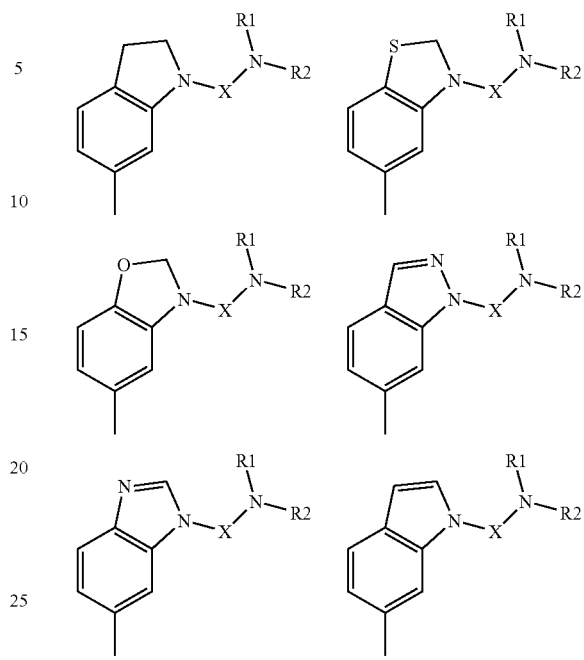

The examples that follow give, without limiting the scope of the present invention, an illustration of 3- to 10-membered cyclic radicals that two substituents R4 can form, together with the carbon atom(s) to which they are attached:

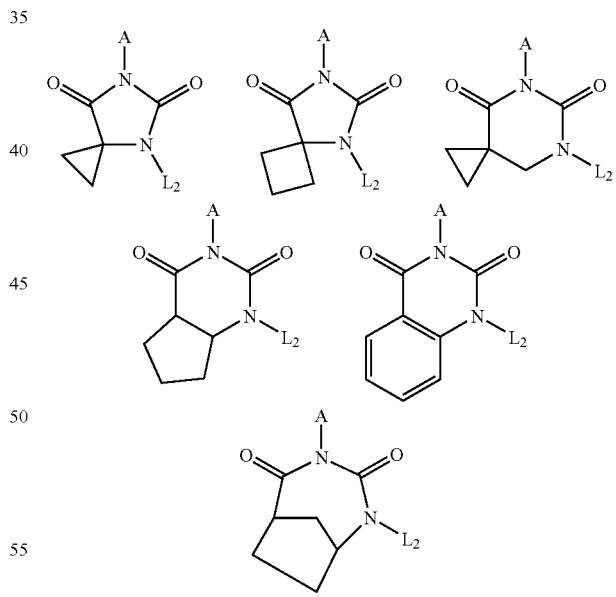

A subject of the present invention is, particularly, the products of formula (I) as defined above in which A represents a phenyl, 2,3-dihydro-1H-indolyl, or indolyl radical optionally substituted with one or more radicals chosen from the values of R3, X represents a single bond, —NH-alk-, alkylene, —O—, —Nalk-CO—, —NH—CO, —NH—CO-alk-, —NH—CO—NH—, —CO—NH—, —SO2, —NR6d or —CO—, L1 represents a single bond, an alkylene radical containing 1 to 5 carbon atoms optionally substituted with a hydroxyl radical, an cycloalkylalkyl radical, a phenyl radical, R1 and R2, which may be identical or different, are such that:

either R1 represents a hydrogen atom, an alkyl radical optionally substituted with one or more radicals chosen from halogen atoms and hydroxyl, alkoxy, NH2, NH(alk), N(alk)2, cyano, free or esterified carboxyl, phenyl and 3- to 7-membered cycloalkyl radicals and a saturated, partially saturated or unsaturated 4- to 7-membered heterocyclic radical, itself optionally substituted with one or more alkyl radicals and containing one or more hetero atoms, which may be identical or different, chosen from O, S, N, NH and N-alkyl, or R1 represents a 3- to 7-membered cycloalkyl radical, a phenyl radical or a saturated, partially saturated or unsaturated 4- to 7-membered heterocyclic radical, itself optionally substituted with one or more alkyl radicals and containing one or more hetero atoms chosen from O, S, N, NH and N-alkyl, and R2 represents a hydrogen atom or an alkyl radical, or R1 and R2 form, with the nitrogen atom to which they are attached, a saturated or unsaturated 4- to 7-membered heterocyclic radical optionally containing one or more other hetero atoms chosen from O, S, N, NH and N-alkyl, this radical formed by R1 and R2 with N being itself optionally substituted with one or more radicals chosen from alkyl, halogen, NH2, NH(alk), N(alk)2, CF3 and free or esterified carboxyl radicals, all the above alkyl and alkoxy radicals being linear or branched and containing up to 6 carbon atoms, or NR1R2 forms with L1 a saturated or unsaturated 4- to -10-membered heterocycle containing at least one nitrogen atom and optionally containing one or more other hetero atoms chosen from O, S, N, NH and N-alkyl, this radical formed by NR1R2 with L1 being itself optionally substituted with one or more radicals chosen from alkyl, cycloalkyl and free or esterified carboxyl radicals, R3 represents one or more substituents of the ring A, which may be identical or different, chosen from a hydrogen atom and an alkyl or alkoxy radical containing up to 4 carbon atoms, optionally substituted with one or more F; alkyl-S(O)n optionally substituted by F; OCF3;SO2CF2; or SCF3; with n representing 0 or 2;

R4 and R4', which may be identical or different, are chosen from a hydrogen atom and an alkyl radical containing up to 4 carbon atoms, R6 represents a hydrogen atom, an acyl radical optionally substituted with one or more F or an alkyl radical containing from 1 to 4 carbon atoms, L2 represents an alkylene radical, Y2 represents a quinolyl, pyridyl or pyrimidinyl radical, optionally substituted by NH2;

the said products of formula (I) being in all the possible racemic, enantiomeric and diastereoisomeric isomer forms, and also the addition salts with mineral and organic acids or with mineral and organic bases of the said products of formula (I).

A subject of the present invention is, most particularly, the products of formula (I) as defined above corresponding to formula (Id):

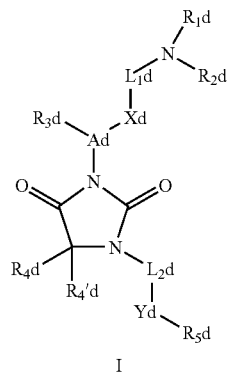

in which:

Ad represents a phenyl or indolyl radical optionally substituted with one or more radicals chosen from the values of R3d, Xd represents —O—, —NH—CO—, —NR6 or —CO—, L1d represents an alkylene radical containing 1 to 3 carbon atoms optionally substituted with a hydroxyl radical, R1d and R2d, which may be identical or different, are such that:

either R1d represents an alkyl radical optionally substituted with one or more radicals chosen from halogen atoms and hydroxyl, alkoxy, cyano, free or esterified carboxyl, phenyl and 3- to 7-membered cycloalkyl radicals and a saturated, partially saturated or unsaturated 4- to 7-membered heterocyclic radical, itself optionally substituted with one or more alkyl radicals and containing one or more hetero atoms, which may be identical or different, chosen from O, S, N, NH and N-alkyl, or R1d represents a 3- to 7-membered cycloalkyl radical, a phenyl radical or a saturated, partially saturated or unsaturated 4- to 7-membered heterocyclic radical, itself optionally substituted with one or more alkyl radicals and containing one or more hetero atoms chosen from O, S, N, NH and N-alkyl, and R2d represents a hydrogen atom or an alkyl radical, or R1d and R2d form, with the nitrogen atom to which they are attached, a saturated or unsaturated 4- to 7-membered heterocyclic radical optionally containing one or more other hetero atoms chosen from O, S, N, NH and N-alkyl, this radical formed by R1d and R2d with N being itself optionally substituted with one or more radicals chosen from alkyl, CF3 and free or esterified carboxyl radicals, all the above alkyl and alkoxy radicals being linear or branched and containing up to 6 carbon atoms, or NR1dR2d forms with L1d a saturated or unsaturated 4- to 8-membered heterocycle containing at least one nitrogen atom and optionally containing one or more other hetero atoms chosen from O, S, N, NH and N-alkyl, this radical formed by NR1dR2d with L1d being itself optionally substituted with one or more radicals chose from alkyl and free or esterified carboxyl radicals, R3d represents one or more substituents of the ring Ad, which may be identical or different, chosen from a hydrogen atom and an alkyl or alkoxy radical containing up to 4 carbon atoms, optionally substituted with one or more F; OCF3; SO2CF3; or SCF3;

R4d and R4'd, which may be identical or different, are chosen from a hydrogen atom and an alkyl radical containing up to 4 carbon atoms, L2d represents an alkylene radical, Y2d represents a quinolyl, pyridyl or pyrimidinyl radical, the said products of formula (Id) being in all the possible racemic, enantiomeric and diastereoisomeric isomer forms, and also the addition salts with mineral and organic acids or with mineral and organic bases of the said products of formula (Id).

In the products of formula (Id), R1d and R2d are especially such that:

either R1d and R2d, which may be identical or different, are such that:

R1d represents an alkyl radical (1 to 6C) optionally substituted with one or more radicals chosen from halogen atoms and hydroxyl; alkoxy; cyano; free and esterified carboxyl; phenyl; cyclopropyl, cyclopentyl, cyclohexyl, isoxazolyl, furyl, pyrazinyl, morpholinyl, pyridyl and isothiazolyl radicals, optionally substituted with one or more alkyl radicals, or R2a represents a cyclopropyl, cyclopentyl, cyclohexyl, phenyl, hexahydropyran, pyrrolidinyl, piperidyl or pyridyl radical optionally substituted with one or more alkyl radicals, and R2d represents a hydrogen atom or an alkyl radical or R1d and R2d form, with the nitrogen atom to which they are attached, a morpholinyl, piperidyl, piperazinyl or pyrrolidinyl radical, optionally substituted with one or more radicals chosen from alkyl, CF3 and free or esterified carboxyl radicals, all the above alkyl and alkoxy radicals being linear or branched and containing up to 6 carbon atoms, or NR1dR2d forms with L1d a piperidyl radical optionally substituted with one or more radicals chosen from alkyl and free or esterified carboxyl radicals.

A subject of the present invention is especially the products of formula (I), (Ia), (Ib), (Ic) or (Id) as defined above in which, when A represents a phenyl radical, then X represents —O—, —NR6 or —NH—CO, the other substituents of the said products of formula (I), (Ia), (Ib), (Ic) or (Id) being chosen from all the values defined for the said substituents, the said products of formula (I), (Ia), (Ib), (Ic) or (Id) being in all the possible racemic, enantiomeric and diastereoisomeric isomer forms, and also the addition salts with mineral and organic acids or with mineral and organic bases of the said products of formula (I), (Ia), (Ib), (Ic) or (Id).

A subject of the present invention is also especially the products of formula (I), (Ia), (Ib), (Ic) or (Id) as defined above in which, A represents an indolinyl radical, X represents —O—, —NR6, —CO— or —NR6-CO and the other substituents of the said products of formula (I), (Ia), (Ib), (Ic) or (Id) being chosen from all the values defined for the said substituents, the said products of formula (I), (Ia), (Ib), (Ic) or (Id) being in all the possible racemic, enantiomeric and diastereoisomeric isomer forms, and also the addition salts with mineral and organic acids or with mineral and organic bases of the said products of formula (I), (Ia), (Ib), (Ic) or (Id).

A subject of the present invention is, more specifically, the products of formula (I) as defined above, the names of which are given hereinbelow:

N-[5-(4,4-Dimethyl-2,5-dioxo-3-pyridin-4-ylmethyl-imidazolidin-1-yl)-2-trifluoromethoxy-phenyl]-2-morpholin-4-yl-acetamide N-[5-(4,4-Dimethyl-2,5-dioxo-3-pyridin-4-ylmethyl-imidazolidin-1-yl)-2-trifluoromethoxy-phenyl]-2-(dimethyl-morpholin-4-yl)-acetamide trifluoroacetate 2-Cyclopentylamino-N-[5-(4,4-dimethyl-2,5-dioxo-3-pyridin-4-ylmethyl-imidazolidin-1-yl)-2-trifluoromethoxy-phenyl]-acetamide trifluoroacetate N-[5-(4,4-Dimethyl-2,5-dioxo-3-pyridin-4-ylmethyl-imidazolidin-1-yl)-2-trifluoromethoxy-phenyl]-2-(2,2,2-trifluoro-ethylamino)-acetamide trifluoroacetate 2-Diethylamino-N-[5-(4,4-dimethyl-2,5-dioxo-3-pyridin-4-ylmethyl-imidazolidin-1-yl)-2-trifluoromethoxy-phenyl]-acetamide trifluoroacetate N-[5-(4,4-Dimethyl-2,5-dioxo-3-pyridin-4-ylmethyl-imidazolidin-1-yl)-2-trifluoromethoxy-phenyl]-2-thiomorpholin-4-yl-acetamide trifluoroacetate N-[5-(4,4-Dimethyl-2,5-dioxo-3-pyridin-4-ylmethyl-imidazolidin-1-yl)-2-trifluoromethoxy-phenyl]-2-pyrrolidin-1-yl-acetamide trifluoroacetate N-[5-(4,4-Dimethyl-2,5-dioxo-3-pyridin-4-ylmethyl-imidazolidin-1-yl)-2-trifluoromethoxy-phenyl]-2-(4-methyl-piperazin-1-yl)-acetamide trifluoroacetate N-[5-(4,4-Dimethyl-2,5-dioxo-3-pyridin-4-ylmethyl-imidazolidin-1-yl)-2-trifluoromethoxy-phenyl]-2-piperidin-1-yl-acetamide trifluoroacetate N-[5-(4,4-Dimethyl-2,5-dioxo-3-pyridin-4-ylmethyl-imidazolidin-1-yl)-2-trifluoromethoxy-phenyl]-2-[(pyridin-2-ylmethyl)-amino]-acetamide trifluoroacetate N-[5-(4,4-Dimethyl-2,5-dioxo-3-pyridin-4-ylmethyl-imidazolidin-1-yl)-2-trifluoromethoxy-phenyl]-2-[(pyridin-3-ylmethyl)-amino]-acetamide trifluoroacetate N-[5-(4,4-Dimethyl-2,5-dioxo-3-pyridin-4-ylmethyl-imidazolidin-1-yl)-2-trifluoromethoxy-phenyl]-2-[(pyridin-4-ylmethyl)-amino]-acetamide trifluoroacetate N-[5-(4,4-Dimethyl-2,5-dioxo-3-pyridin-4-ylmethyl-imidazolidin-1-yl)-2-trifluoromethoxy-phenyl]-2-(2-hydroxyethylamino)-acetamide trifluoroacetate N-[5-(4,4-Dimethyl-2,5-dioxo-3-pyridin-4-ylmethyl-imidazolidin-1-yl)-2-trifluoromethoxy-phenyl]-2-(2-methoxyethylamino)-acetamide trifluoroacetate 2-Dimethylamino-N-[5-(4,4-dimethyl-2,5-dioxo-3-pyridin-4-ylmethyl-imidazolidin-1-yl)-2-trifluoromethoxy-phenyl]-acetamide trifluoroacetate 2-(Cyanomethyl-amino)-N-[5-(4,4-dimethyl-2,5-dioxo-3-pyridin-4-ylmethyl-imidazolidin-1-yl)-2-trifluoromethoxy-phenyl]-acetamide trifluoroacetate N-[5-(4,4-Dimethyl-2,5-dioxo-3-pyridin-4-ylmethyl-imidazolidin-1-yl)-2-trifluoromethoxy-phenyl]-2-(4-methyl-piperidin-1-yl)-acetamide N-[5-(4,4-Dimethyl-2,5-dioxo-3-pyridin-4-ylmethyl-imidazolidin-1-yl)-2-trifluoromethoxy-phenyl]-2-(4-methyl-[1,4]diazepan-1-yl)-acetamide trifluoroacetate 2-tert-Butylamino-N-[5-(4,4-dimethyl-2,5-dioxo-3-pyridin-4-ylmethyl-imidazolidin-1-yl)-2-trifluoromethoxy-phenyl]-acetamide trifluoroacetate N-[5-(4,4-Dimethyl-2,5-dioxo-3-pyridin-4-ylmethyl-imidazolidin-1-yl)-2-trifluoromethoxy-phenyl]-2-(1,2,2-trimethyl-propylamino)-acetamide trifluoroacetate ({[5-(4,4-Dimethyl-2,5-dioxo-3-pyridin-4-ylmethyl-imidazolidin-1-yl)-2-trifluoromethoxy-phenylcarbamoyl]-methyl}-amino)-acetic acid methyl ester; compound with trifluoro-acetic acid 2-(2,2-Difluoro-ethylamino)-N-[5-(4,4-dimethyl-2,5-dioxo-3-pyridin-4-ylmethyl-imidazolidin-1-yl)-2-trifluoromethoxy-phenyl]-acetamide; compound with trifluoro-acetic acid N-[5-(4,4-Dimethyl-2,5-dioxo-3-pyridin-4-ylmethyl-imidazolidin-1-yl)-2-trifluoromethoxy-phenyl]-2-(4,4-dimethyl-piperidin-1-yl)-acetamide N-[5-(4,4-Dimethyl-2,5-dioxo-3-pyridin-4-ylmethyl-imidazolidin-1-yl)-2-trifluoromethoxy-phenyl]-2-(4-trifluoromethyl-piperidin-1-yl)-acetamide N-[5-(4,4-Dimethyl-2,5-dioxo-3-pyridin-4-ylmethyl-imidazolidin-1-yl)-2-trifluoromethoxy-phenyl]-2-[1,4]oxazepan-4-yl-acetamide 1-{[5-(4,4-Dimethyl-2,5-dioxo-3-pyridin-4-ylmethyl-imidazolidin-1-yl)-2-trifluoromethoxy-phenylcarbamoyl]-methyl}-pyrrolidine-3-carboxylic acid methyl ester 2-Azetidin-1-yl-N-[5-(4,4-dimethyl-2,5-dioxo-3-pyridin-4-ylmethyl-imidazolidin-1-yl)-2-trifluoromethoxy-phenyl]-acetamide N-[5-(4,4-Dimethyl-2,5-dioxo-3-pyridin-4-ylmethyl-imidazolidin-1-yl)-2-trifluoromethoxy-phenyl]-2-(2-fluoro-ethylamino)-acetamide N-[5-(4,4-Dimethyl-2,5-dioxo-3-pyridin-4-ylmethyl-imidazolidin-1-yl)-2-trifluoromethoxy-phenyl]-2-[(2-methoxy-ethyl)-methyl-amino]-acetamide ({[5-(4,4-Dimethyl-2,5-dioxo-3-pyridin-4-ylmethyl-imidazolidin-1-yl)-2-trifluoromethoxy-phenylcarbamoyl]-methyl}-amino)-acetic acid trifluoroacetate 2-Cyclohexylamino-N-[5-(4,4-dimethyl-2,5-dioxo-3-pyridin-4-ylmethyl-imidazolidin-1-yl)-2-trifluoromethoxy-phenyl]-acetamide trifluoroacetate 2-Cyclopropylamino-N-[5-(4,4-dimethyl-2,5-dioxo-3-pyridin-4-ylmethyl-imidazolidin-1-yl)-2-trifluoromethoxy-phenyl]-acetamide trifluoroacetate N-[5-(4,4-Dimethyl-2,5-dioxo-3-pyridin-4-ylmethyl-imidazolidin-1-yl)-2-trifluoromethoxy-phenyl]-3-morpholin-4-yl-propionamide trifluoroacetate N-[5-(4,4-Dimethyl-2,5-dioxo-3-pyridin-4-ylmethyl-imidazolidin-1-yl)-2-trifluoromethoxy-phenyl]-3-(dimethyl-morpholin-4-yl)-propionamide trifluoroacetate N-[5-(4,4-Dimethyl-2,5-dioxo-3-pyridin-4-ylmethyl-imidazolidin-1-yl)-2-trifluoromethoxy-phenyl]-3-(4-methyl-piperazin-1-yl)-propionamide trifluoroacetate N-[5-(4,4-Dimethyl-2,5-dioxo-3-pyridin-4-ylmethyl-imidazolidin-1-yl)-2-trifluoromethoxy-phenyl]-3-piperidin-1-yl-propionamide trifluoroacetate N-[5-(4,4-Dimethyl-2,5-dioxo-3-pyridin-4-ylmethyl-imidazolidin-1-yl)-2-trifluoromethoxy-phenyl]-3-thiomorpholin-4-yl-propionamide trifluoroacetate N-[5-(4,4-Dimethyl-2,5-dioxo-3-pyridin-4-ylmethyl-imidazolidin-1-yl)-2-trifluoromethoxy-phenyl]-3-pyrrolidin-1-yl-propionamide trifluoroacetate 3-Cyclopentylamino-N-[5-(4,4-dimethyl-2,5-dioxo-3-pyridin-4-ylmethyl-imidazolidin-1-yl)-2-trifluoromethoxy-phenyl]-propionamide trifluoroacetate N-[5-(4,4-Dimethyl-2,5-dioxo-3-pyridin-4-ylmethyl-imidazolidin-1-yl)-2-trifluoromethoxy-phenyl]-3-(2,2,2-trifluoro-ethylamino)-propionamide; compound with trifluoro-acetic acid 3-Diethylamino-N-[5-(4,4-dimethyl-2,5-dioxo-3-pyridin-4-ylmethyl-imidazolidin-1-yl)-2-trifluoromethoxy-phenyl]-propionamide trifluoroacetate N-[5-(4,4-Dimethyl-2,5-dioxo-3-pyridin-4-ylmethyl-imidazolidin-1-yl)-2-isopropyl-phenyl]-2-morpholin-4-yl-acetamide trifluoroacetate N-[5-(4,4-Dimethyl-2,5-dioxo-3-pyridin-4-ylmethyl-imidazolidin-1-yl)-2-isopropyl-phenyl]-2-piperidin-1-yl-acetamide trifluoroacetate N-[5-(4,4-Dimethyl-2,5-dioxo-3-pyridin-4-ylmethyl-imidazolidin-1-yl)-2-isopropyl-phenyl]-2-(4-methyl-piperazin-1-yl)-acetamide trifluoroacetate 2-Dimethylamino-N-[5-(4,4-dimethyl-2,5-dioxo-3-pyridin-4-ylmethyl-imidazolidin-1-yl)-2-isopropyl-phenyl]-acetamide trifluoroacetate 2-Diethylamino-N-[5-(4,4-dimethyl-2,5-dioxo-3-pyridin-4-ylmethyl-imidazolidin-1-yl)-2-isopropyl-phenyl]-acetamide trifluoroacetate 2-tert-Butylamino-N-[5-(4,4-dimethyl-2,5-dioxo-3-pyridin-4-ylmethyl-imidazolidin-1-yl)-2-isopropyl-phenyl]-acetamide trifluoroacetate 2-Cyclopentylamino-N-[5-(4,4-dimethyl-2,5-dioxo-3-pyridin-4-ylmethyl-imidazolidin-1-yl)-2-isopropyl-phenyl]-acetamide trifluoroacetate 1-Methyl-piperidine-4-carboxylic acid [5-(4,4-dimethyl-2,5-dioxo-3-pyridin-4-ylmethyl-imidazolidin-1-yl)-2-trifluoromethoxy-phenyl]-amide, trifluoro-acetate 3-[3-(2-Cyclopentylamino-ethoxy)-4-methoxy-phenyl]-5,5-dimethyl-1-quinolin-4-ylmethyl-imidazolidine-2,4-dione 3-(3-{2-[(Furan-2-ylmethyl)-amino]-ethoxy}-4-methoxy-phenyl)-5,5-dimethyl-1-quinolin-4-ylmethyl-imidazolidine-2,4-dione 3-{3-[2-(2-Hydroxy-1-phenyl-ethylamino)-ethoxy]-4-methoxy-phenyl}-5,5-dimethyl-1-quinolin-4-ylmethyl-imidazolidine-2,4-dione 3-[3,3-Dimethyl-1-(2-morpholin-4-yl-acetyl)-2,3-dihydro-1H-indol-6-yl]-5,5-dimethyl-1-quinolin-4-ylmethyl-imidazolidine-2,4-dione 3-[3,3-Dimethyl-1-(2-thiomorpholin-4-yl-acetyl)-2,3-dihydro-1H-indol-6-yl]-5,5-dimethyl-1-quinolin-4-ylmethyl-imidazolidine-2,4-dione 3-{4-Methoxy-3-[2-(2-morpholin-4-yl-ethylamino)-ethoxy]-phenyl}-5,5-dimethyl-1-quinolin-4-ylmethyl-imidazolidine-2,4-dione 3-[4-Methoxy-3-(2-pyrrolidin-1-yl-ethoxy)-phenyl]-5,5-dimethyl-1-quinolin-4-ylmethyl-imidazolidine-2,4-dione 3-(4-Methoxy-3-{2-[(pyridin-2-ylmethyl)-amino]-ethoxy}-phenyl)-5,5-dimethyl-1-quinolin-4-ylmethyl-imidazolidine-2,4-dione 3-{4-Methoxy-3-[2-(tetrahydro-pyran-4-ylamino)-ethoxy]-phenyl}-5,5-dimethyl-1-quinolin-4-ylmethyl-imidazolidine-2,4-dione 3-{4-Methoxy-3-[2-(1-methyl-piperidin-4-ylamino)-ethoxy]-phenyl}-5,5-dimethyl-1-quinolin-4-ylmethyl-imidazolidine-2,4-dione 3-{3-[2-Hydroxy-3-(tetrahydro-pyran-4-ylamino)-propoxy]-4-methoxy-phenyl}-5,5-dimethyl-1-quinolin-4-ylmethyl-imidazolidine-2,4-dione 3-{3-[2-Hydroxy-3-(pyridin-4-ylamino)-propoxy]-4-methoxy-phenyl}-5,5-dimethyl-1-quinolin-4-ylmethyl-imidazolidine-2,4-dione 3-{3-[2-Hydroxy-3-(1-methyl-piperidin-4-ylamino)-propoxy]-4-methoxy-phenyl}-5,5-dimethyl-1-quinolin-4-ylmethyl-imidazolidine-2,4-dione the said products of formula (I) being in all the possible racemic, enantiomeric and diastereoisomeric isomer forms, and also the addition salts with mineral and organic acids or with mineral and organic bases of the said products of formula (I).

A subject of the present invention is thus, particularly, the products of formula (I) as defined in any one of the claims, the names of which are given hereinbelow:

N-[5-(4,4-Dimethyl-2,5-dioxo-3-pyridin-4-ylmethyl-imidazolidin-1-yl)-2-trifluoromethoxy-phenyl]-2-morpholin-4-yl-acetamide N-[5-(4,4-Dimethyl-2,5-dioxo-3-pyridin-4-ylmethyl-imidazolidin-1-yl)-2-trifluoromethoxy-phenyl]-2-(dimethyl-morpholin-4-yl)-acetamide trifluoroacetate 2-Cyclopentylamino-N-[5-(4,4-dimethyl-2,5-dioxo-3-pyridin-4-ylmethyl-imidazolidin-1-yl)-2-trifluoromethoxy-phenyl]-acetamide trifluoroacetate N-[5-(4,4-Dimethyl-2,5-dioxo-3-pyridin-4-ylmethyl-imidazolidin-1-yl)-2-trifluoromethoxy-phenyl]-2-(2,2,2-trifluoro-ethylamino)-acetamide trifluoroacetate 2-Diethylamino-N-[5-(4,4-dimethyl-2,5-dioxo-3-pyridin-4-ylmethyl-imidazolidin-1-yl)-2-trifluoromethoxy-phenyl]-acetamide trifluoroacetate N-[5-(4,4-Dimethyl-2,5-dioxo-3-pyridin-4-ylmethyl-imidazolidin-1-yl)-2-trifluoromethoxy-phenyl]-2-thiomorpholin-4-yl-acetamide trifluoroacetate N-[5-(4,4-Dimethyl-2,5-dioxo-3-pyridin-4-ylmethyl-imidazolidin-1-yl)-2-trifluoromethoxy-phenyl]-2-pyrrolidin-1-yl-acetamide trifluoroacetate N-[5-(4,4-Dimethyl-2,5-dioxo-3-pyridin-4-ylmethyl-imidazolidin-1-yl)-2-trifluoromethoxy-phenyl]-2-(4-methyl-piperazin-1-yl)-acetamide trifluoroacetate N-[5-(4,4-Dimethyl-2,5-dioxo-3-pyridin-4-ylmethyl-imidazolidin-1-yl)-2-trifluoromethoxy-phenyl]-2-piperidin-1-yl-acetamide trifluoroacetate N-[5-(4,4-Dimethyl-2,5-dioxo-3-pyridin-4-ylmethyl-imidazolidin-1-yl)-2-trifluoromethoxy-phenyl]-2-[(pyridin-2-ylmethyl)-amino]-acetamide trifluoroacetate N-[5-(4,4-Dimethyl-2,5-dioxo-3-pyridin-4-ylmethyl-imidazolidin-1-yl)-2-trifluoromethoxy-phenyl]-2-[(pyridin-3-ylmethyl)-amino]-acetamide trifluoroacetate N-[5-(4,4-Dimethyl-2,5-dioxo-3-pyridin-4-ylmethyl-imidazolidin-1-yl)-2-trifluoromethoxy-phenyl]-2-[(pyridin-4-ylmethyl)-amino]-acetamide trifluoroacetate N-[5-(4,4-Dimethyl-2,5-dioxo-3-pyridin-4-ylmethyl-imidazolidin-1-yl)-2-trifluoromethoxy-phenyl]-2-(2-hydroxy-ethylamino)-acetamide trifluoroacetate N-[5-(4,4-Dimethyl-2,5-dioxo-3-pyridin-4-ylmethyl-imidazolidin-1-yl)-2-trifluoromethoxy-phenyl]-2-(2-methoxy-ethylamino)-acetamide trifluoroacetate 2-Dimethylamino-N-[5-(4,4-dimethyl-2,5-dioxo-3-pyridin-4-ylmethyl-imidazolidin-1-yl)-2-trifluoromethoxy-phenyl]-acetamide trifluoroacetate 2-(Cyanomethyl-amino)-N-[5-(4,4-dimethyl-2,5-dioxo-3-pyridin-4-ylmethyl-imidazolidin-1-yl)-2-trifluoromethoxy-phenyl]-acetamide trifluoroacetate N-[5-(4,4-Dimethyl-2,5-dioxo-3-pyridin-4-ylmethyl-imidazolidin-1-yl)-2-trifluoromethoxy-phenyl]-2-(4-methyl-piperidin-1-yl)-acetamide N-[5-(4,4-Dimethyl-2,5-dioxo-3-pyridin-4-ylmethyl-imidazolidin-1-yl)-2-trifluoromethoxy-phenyl]-2-(4-methyl-[1,4]diazepan-1-yl)-acetamide trifluoroacetate 2-tert-Butylamino-N-[5-(4,4-dimethyl-2,5-dioxo-3-pyridin-4-ylmethyl-imidazolidin-1-yl)-2-trifluoromethoxy-phenyl]-acetamide trifluoroacetate N-[5-(4,4-Dimethyl-2,5-dioxo-3-pyridin-4-ylmethyl-imidazolidin-1-yl)-2-trifluoromethoxy-phenyl]-2-(1,2,2-trimethyl-propylamino)-acetamide trifluoroacetate ({[5-(4,4-Dimethyl-2,5-dioxo-3-pyridin-4-ylmethyl-imidazolidin-1-yl)-2-trifluoromethoxy-phenylcarbamoyl]-methyl}-amino)-acetic acid methyl ester; compound with trifluoro-acetic acid 2-(2,2-Difluoro-ethylamino)-N-[5-(4,4-dimethyl-2,5-dioxo-3-pyridin-4-ylmethyl-imidazolidin-1-yl)-2-trifluoromethoxy-phenyl]-acetamide; compound with trifluoro-acetic acid N-[5-(4,4-Dimethyl-2,5-dioxo-3-pyridin-4-ylmethyl-imidazolidin-1-yl)-2-trifluoromethoxy-phenyl]-2-(4,4-dimethyl-piperidin-1-yl)-acetamide N-[5-(4,4-Dimethyl-2,5-dioxo-3-pyridin-4-ylmethyl-imidazolidin-1-yl)-2-trifluoromethoxy-phenyl]-2-(4-trifluoromethyl-piperidin-1-yl)-acetamide N-[5-(4,4-Dimethyl-2,5-dioxo-3-pyridin-4-ylmethyl-imidazolidin-1-yl)-2-trifluoromethoxy-phenyl]-2-[1,4]oxazepan-4-yl-acetamide 1-{[5-(4,4-Dimethyl-2,5-dioxo-3-pyridin-4-ylmethyl-imidazolidin-1-yl)-2-trifluoromethoxy-phenylcarbamoyl]-methyl}-pyrrolidine-3-carboxylic acid methyl ester 2-Azetidin-1-yl-N-[5-(4,4-dimethyl-2,5-dioxo-3-pyridin-4-ylmethyl-imidazolidin-1-yl)-2-trifluoromethoxy-phenyl]-acetamide N-[5-(4,4-Dimethyl-2,5-dioxo-3-pyridin-4-ylmethyl-imidazolidin-1-yl)-2-trifluoromethoxy-phenyl]-2-(2-fluoro-ethylamino)-acetamide N-[5-(4,4-Dimethyl-2,5-dioxo-3-pyridin-4-ylmethyl-imidazolidin-1-yl)-2-trifluoromethoxy-phenyl]-2-[(2-methoxy-ethyl)-methyl-amino]-acetamide ({[5-(4,4-Dimethyl-2,5-dioxo-3-pyridin-4-ylmethyl-imidazolidin-1-yl)-2-trifluoromethoxy-phenylcarbamoyl]-methyl}-amino)-acetic acid trifluoroacetate 2-Cyclohexylamino-N-[5-(4,4-dimethyl-2,5-dioxo-3-pyridin-4-ylmethyl-imidazolidin-1-yl)-2-trifluoromethoxy-phenyl]-acetamide trifluoroacetate 2-Cyclopropylamino-N-[5-(4,4-dimethyl-2,5-dioxo-3-pyridin-4-ylmethyl-imidazolidin-1-yl)-2-trifluoromethoxy-phenyl]-acetamide trifluoroacetate N-[5-(4,4-Dimethyl-2,5-dioxo-3-pyridin-4-ylmethyl-imidazolidin-1-yl)-2-trifluoromethoxy-phenyl]-3-morpholin-4-yl-propionamide trifluoroacetate N-[5-(4,4-Dimethyl-2,5-dioxo-3-pyridin-4-ylmethyl-imidazolidin-1-yl)-2-trifluoromethoxy-phenyl]-3-(dimethyl-morpholin-4-yl)-propionamide trifluoroacetate N-[5-(4,4-Dimethyl-2,5-dioxo-3-pyridin-4-ylmethyl-imidazolidin-1-yl)-2-trifluoromethoxy-phenyl]-3-(4-methyl-piperazin-1-yl)-propionamide trifluoroacetate N-[5-(4,4-Dimethyl-2,5-dioxo-3-pyridin-4-ylmethyl-imidazolidin-1-yl)-2-trifluoromethoxy-phenyl]-3-piperidin-1-yl-propionamide trifluoroacetate N-[5-(4,4-Dimethyl-2,5-dioxo-3-pyridin-4-ylmethyl-imidazolidin-1-yl)-2-trifluoromethoxy-phenyl]-3-thiomorpholin-4-yl-propionamide trifluoroacetate N-[5-(4,4-Dimethyl-2,5-dioxo-3-pyridin-4-ylmethyl-imidazolidin-1-yl)-2-trifluoromethoxy-phenyl]-3-pyrrolidin-1-yl-propionamide trifluoroacetate 3-Cyclopentylamino-N-[5-(4,4-dimethyl-2,5-dioxo-3-pyridin-4-ylmethyl-imidazolidin-1-yl)-2-trifluoromethoxy-phenyl]-propionamide trifluoroacetate N-[5-(4,4-Dimethyl-2,5-dioxo-3-pyridin-4-ylmethyl-imidazolidin-1-yl)-2-trifluoromethoxy-phenyl]-3-(2,2,2-trifluoro-ethylamino)-propionamide; compound with trifluoro-acetic acid 3-Diethylamino-N-[5-(4,4-dimethyl-2,5-dioxo-3-pyridin-4-ylmethyl-imidazolidin-1-yl)-2-trifluoromethoxy-phenyl]-propionamide trifluoroacetate N-[5-(4,4-Dimethyl-2,5-dioxo-3-pyridin-4-ylmethyl-imidazolidin-1-yl)-2-isopropyl-phenyl]-2-morpholin-4-yl-acetamide trifluoroacetate N-[5-(4,4-Dimethyl-2,5-dioxo-3-pyridin-4-ylmethyl-imidazolidin-1-yl)-2-isopropyl-phenyl]-2-piperidin-1-yl-acetamide trifluoroacetate N-[5-(4,4-Dimethyl-2,5-dioxo-3-pyridin-4-ylmethyl-imidazolidin-1-yl)-2-isopropyl-phenyl]-2-(4-methyl-piperazin-1-yl)-acetamide trifluoroacetate 2-Dimethylamino-N-[5-(4,4-dimethyl-2,5-dioxo-3-pyridin-4-ylmethyl-imidazolidin-1-yl)-2-isopropyl-phenyl]-acetamide trifluoroacetate 2-Diethylamino-N-[5-(4,4-dimethyl-2,5-dioxo-3-pyridin-4-ylmethyl-imidazolidin-1-yl)-2-isopropyl-phenyl]-acetamide trifluoroacetate 2-tert-Butylamino-N-[5-(4,4-dimethyl-2,5-dioxo-3-pyridin-4-ylmethyl-imidazolidin-1-yl)-2-isopropyl-phenyl]-acetamide trifluoroacetate 2-Cyclopentylamino-N-[5-(4,4-dimethyl-2,5-dioxo-3-pyridin-4-ylmethyl-imidazolidin-1-yl)-2-isopropyl-phenyl]-acetamide trifluoroacetate 1-Methyl-piperidine-4-carboxylic acid [5-(4,4-dimethyl-2,5-dioxo-3-pyridin-4-ylmethyl-imidazolidin-1-yl)-2-trifluoromethoxy-phenyl]-amide, trifluoro-acetate 3-[3-(2-Cyclopentylamino-ethoxy)-4-methoxy-phenyl]-5,5-dimethyl-1-quinolin-4-ylmethyl-imidazolidine-2,4-dione 3-(3-{2-[(Furan-2-ylmethyl)-amino]-ethoxy}-4-methoxy-phenyl)-5,5-dimethyl-1-quinolin-4-ylmethyl-imidazolidine-2,4-dione 3-{3-[2-(2-Hydroxy-1-phenyl-ethylamino)-ethoxy]-4-methoxy-phenyl}-5,5-dimethyl-1-quinolin-4-ylmethyl-imidazolidine-2,4-dione 3-[3,3-Dimethyl-1-(2-morpholin-4-yl-acetyl)-2,3-dihydro-1H-indol-6-yl]-5,5-dimethyl-1-quinolin-4-ylmethyl-imidazolidine-2,4-dione 3-[3,3-Dimethyl-1-(2-thiomorpholin-4-yl-acetyl)-2,3-dihydro-1H-indol-6-yl]-5,5-dimethyl-1-quinolin-4-ylmethyl-imidazolidine-2,4-dione the said products of formula (I) being in all the possible racemic, enantiomeric and diastereoisomeric isomer forms, and also the addition salts with mineral and organic acids or with mineral and organic bases of the said products of formula (I).

The compounds of general formulae Ia, Ib and Ic in which X' denotes NR6, O or S are in accordance with the reaction sequences described in Scheme 1.

To this end, an intermediate of general formula 1a, in which the variables have the abovementioned meanings and in which X' denotes NH2, OH or SH, is reacted with a difunctional alkylating agent of general formula 1b, for instance a haloalkanal acetal. The reaction is performed in bulk or in an inert organic solvent, optionally in the presence of a base. A preferred alkylating agent is bromoacetaldehyde diethyl acetal.

From the aldehyde obtained by hydrolysis of the acetal, compounds according to the invention of general formula Ib are then obtained by reductive amination. The compounds in which the bonding group L1 is substituted with a hydroxyl (Ia) are prepared by converting the aldehyde to the corresponding epoxide and subsequent decyclization with amines.

One variant for access to I describes the direct alkylation of compounds of general formula 1a with an aminoalkyl halide of general formula Hal-L$_1$-N(R1R2). In the case where X' represents OH and SH, this reaction is preferably performed in an organic solvent such as ethyl acetate, DMF, NMP or acetone, in the presence of a base such as potassium tert-butoxide, potassium carbonate or caesium carbonate. In the case where X' denotes NH2, the process preferably proceeds first with acylation and the intermediate amide is used for the alkylation. Preferred acyl radicals are acetyl and trifluoroacetyl. Removal of the acyl group once the alkylation has been performed then gives rise to compounds according to the invention, which may be optionally converted into compounds of general formula Ic via additional steps.

Scheme 1

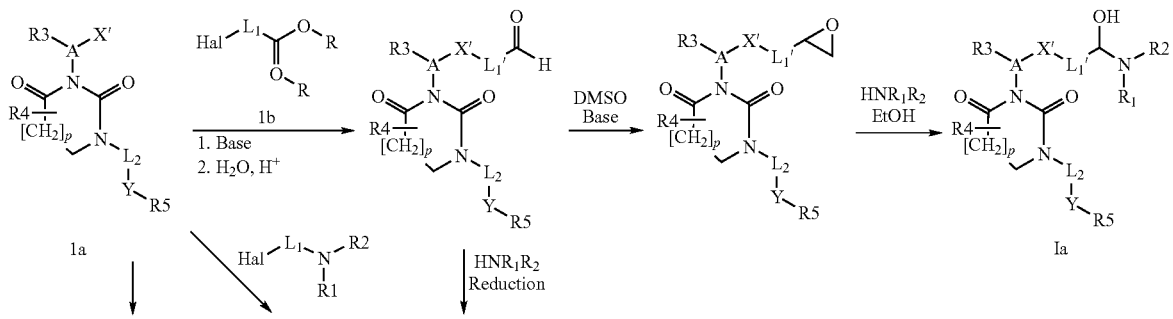

-continued

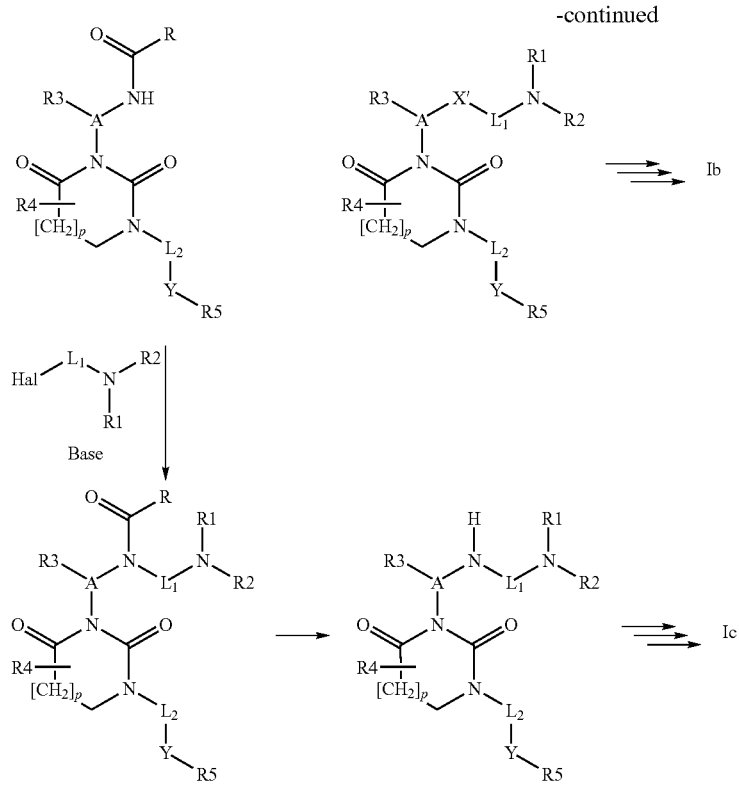

The starting substances of general formula 1a (X'=NH2) required for this sequence may be prepared in accordance with the process summarized in Scheme 2. A suitably substituted nitroaniline, which may be obtained, for example, by nitration of the corresponding aniline, is, in the present case, converted into the corresponding isocyanate or into a derivative of similar reactivity, in an inert solvent under the action of phosgene, diphosgene, triphosgene or carbonyldiimidazole, in the presence or absence of an auxiliary base, and reacted with a compound of general formula 2a to give rise to the heterocyclic compounds of general formula 2b. 2a are preferably obtained by reductive amination of the corresponding amino acid derivative with an aldehyde of general formula R5-Y-L$_2$'-CHO.

As a variant, the intermediates of general formula 1a (X'=NH2) may also be prepared by direct nitration of compounds of general formula 2c.

The subsequent reduction of the nitro compound 2b is performed by catalytic hydrogenation in the presence of a heterogeneous or homogeneous transition metal catalyst, preferably a heterogeneous transition metal catalyst. As a variant, to this end, the reduction may also be performed with a non-precious metal in the presence of an acid. Preferred reagents for this reaction are zinc and dilute hydrochloric acid, particularly preferably zinc and glacial acetic acid.

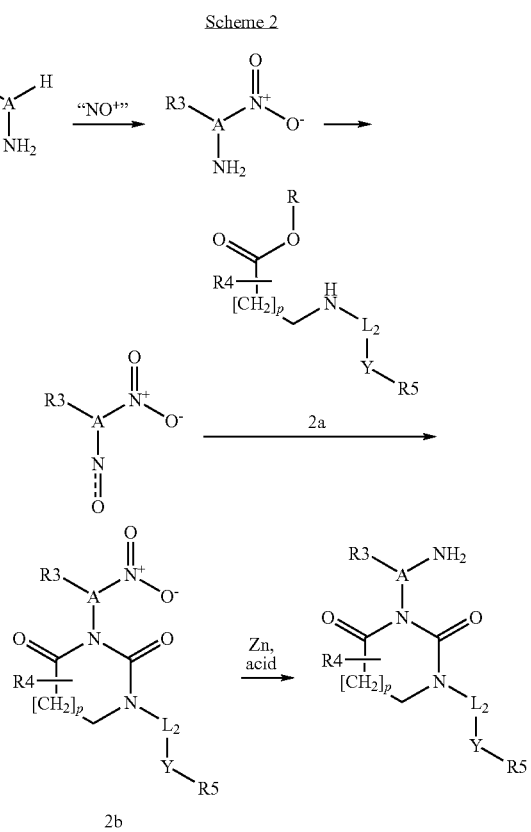

Scheme 2

2c

Similarly, constituent components of general formula 1a (X'=NH2, OH, SH), are obtained when a correspondingly substituted synthon 3a, optionally protected on reactive groups, is converted into the corresponding isocyanate or into a derivative of similar reactivity, under the action of phosgene, diphosgene, triphosgene or carbonyldiimidazole, in the presence or absence of an auxiliary base, and condensed with an amino acid derivative of general formula 2b, in an inert solvent, for instance THF, toluene, dioxane or ethyl acetate, optionally in the presence of an auxiliary base, for instance triethylamine or potassium tert-butoxide. The reaction temperature is preferably between room temperature and the reflux point of the solvent, particularly preferably at the reflux point. As a variant, the cyclization may also be performed in aqueous-acidic solution at elevated temperature.

3a

One variant of the process for preparing the compounds of general formulae Ia, Ib and Ic, in which X' denotes NR6, O or S, consists in converting the constituent components of general formulae 3a-d into the corresponding isocyanate or into a derivative of similar reactivity, with phosgene, diphosgene, triphosgene or carbonyldiimidazole, in the presence or absence of an auxiliary base, and in then reacting them with an amino acid derivative of general formula 2a under the conditions mentioned for the preparation of 1a. The intermediates thus obtained are then converted into compounds of general formulae Ia-c in a manner similar to that for the reactions described in Scheme 1.

3b

3c

3d

3e

The arylamines 3a are in part described in the literature or may be obtained in accordance with conversions known to those skilled in the art from derivatives known in the literature. The starting substances 3b-e are obtained from 3a via synthetic routes that are in principle similar to the reaction sequences described in Scheme 1. For the conversion, the free amino group is, in the present case, protected with the usual protecting groups or masked in the form of a nitro function, and reduced at a subsequent stage.

The compounds according to the invention of general formula Id in which X' denotes —N(R6)-C(O)—, —N(R6)-C(O)—N(R6')-, —N(R6)-C(S)—N(R6')-, —N(R6)-C(O)O—, —N(R6)-SO2— or —N(R6)-SO2-N(R6') are obtained by reacting an intermediate of general formula 4a with a difunctional reagent, for instance, activated halocarboxylic acids, haloisocyanates, isothiocyanates or halosulphonyl chlorides (Scheme 3). Preferred reagents are chloroacetyl chloride, acryloyl chloride, 2-chloropropionyl chloride and chloromethanesulphonyl chloride, and also homologues thereof. The coupling is preferably performed in an inert solvent at low temperature. The use of a base is optional. Among the intermediates formed, the compounds of general formula Id are obtained by reaction with a suitably substituted amine. This reaction may be performed in an inert organic solvent or in bulk, optionally in the presence of an auxiliary base.

By using acryloyl chloride in the first step, aminopropionylamides according to the invention are obtained after reaction with amines.

As a variant, 4a may also be reacted directly with amino-substituted difunctional reagents of general formula 4b to give rise to compounds of general formula Id.

Scheme 3

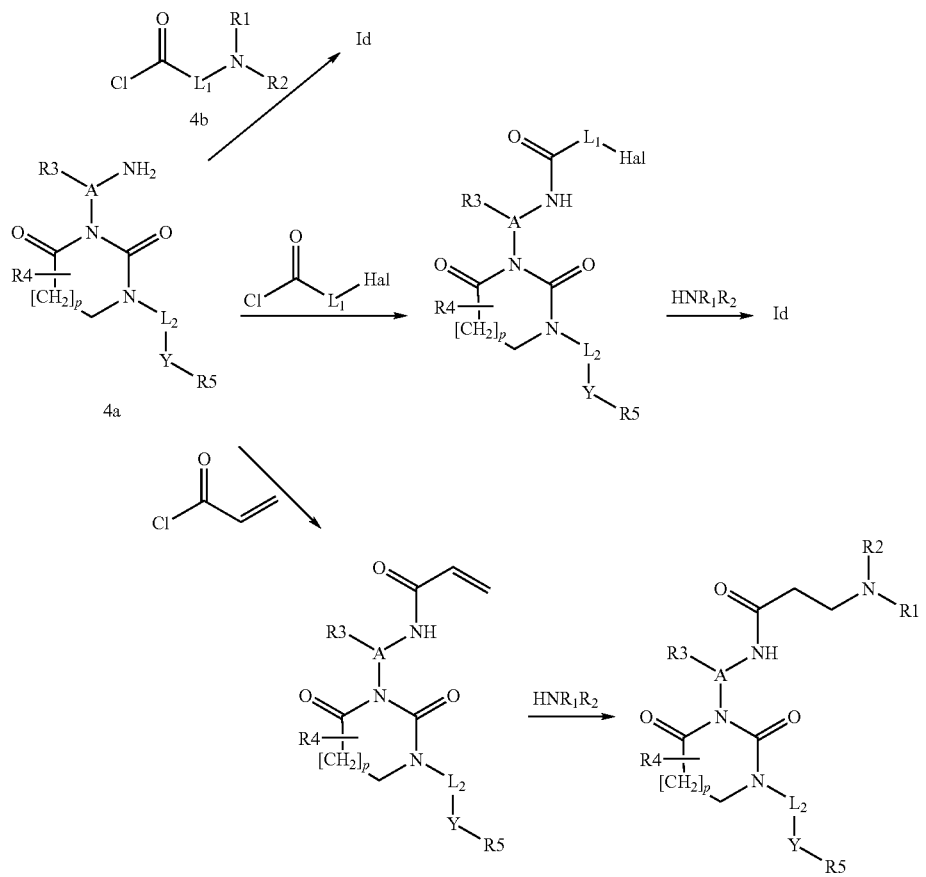

The compounds of general formula I in which X denotes —N(R6)-C(O)— and R2 and L1 form a nucleus are obtained by reacting compounds of general formula 4a with an activated amino acid derivative of general formula 5. The amino acid may be activated by conversion into the acid chloride or via amide coupling reactions that are sufficiently known to those skilled in the art. The products initially obtained, Ie, may be converted into other compounds Ie according to the invention via other conversions.

Scheme 4

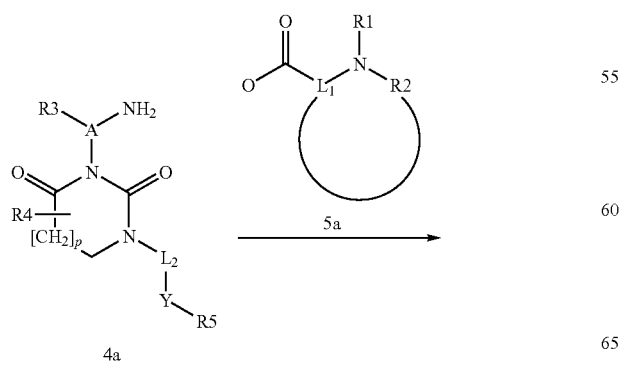

-continued

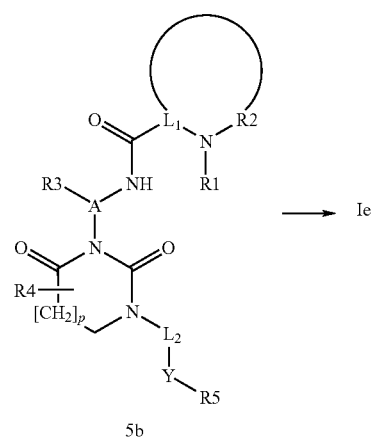

Other cyclic derivatives in which X represents the above-mentioned meanings may be obtained in accordance with similar processes.

The compounds of general formula I, in which X' denotes —C(O)—N(R6)-, —SO2-NR6- or —C(O)O—, are obtained in accordance with Scheme 5. The intermediates 6b, in which -T denotes —COOH, —COO-Alkyl, —SO2OH, —SO2Cl or —SO2F, are, in the present case, prepared by a reaction sequence as has just been described in Scheme 2. The compounds 6a are commercially available or may be prepared from commercially available derivatives via conversions known to those skilled in the art. The condensation of 6b with a reagent of formula V-$L_1$-N(R1R2) when V represents NH2, NR6, hydrogen or hydroxyl then gives the desired compounds. In the case where T denotes —COOH or —SO2OH, 6b is first activated by the action of agents such as, for example, thionyl chloride, oxalyl chloride or phosphorus pentachloride. As a variant, the activation may also be performed with coupling agents known to those skilled in the art, for instance TOTU or DCC.

Scheme 5

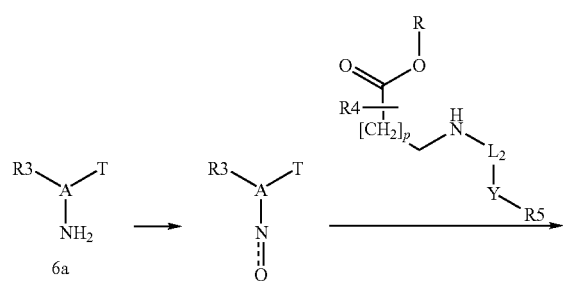

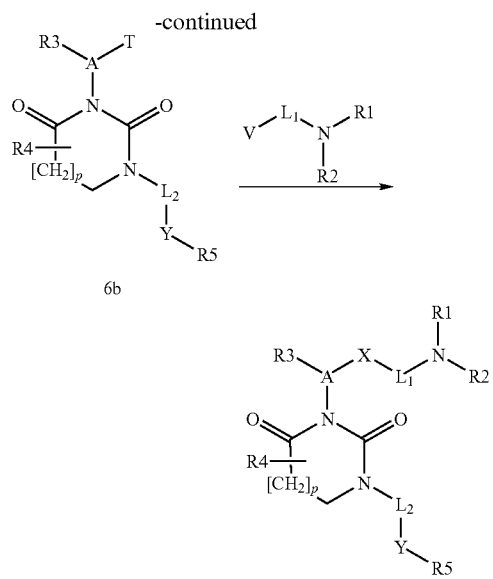

Scheme 6 illustrates, by way of example, the way in which compounds in which A denotes a system containing a fused homocyclic or heterocyclic nucleus may be prepared.

To this end, the system containing nucleus A is first linked to the central heterocycle in accordance with the reaction sequence described for compound 2b. Next, the compounds of general formula I are then obtained by alkylation, acylation, sulphonylation, carbamoylation or thiocarbamoylation and additional reactions of the derivatives thus obtained.

Scheme 6

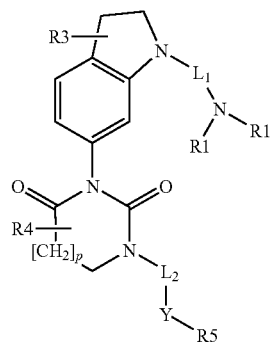

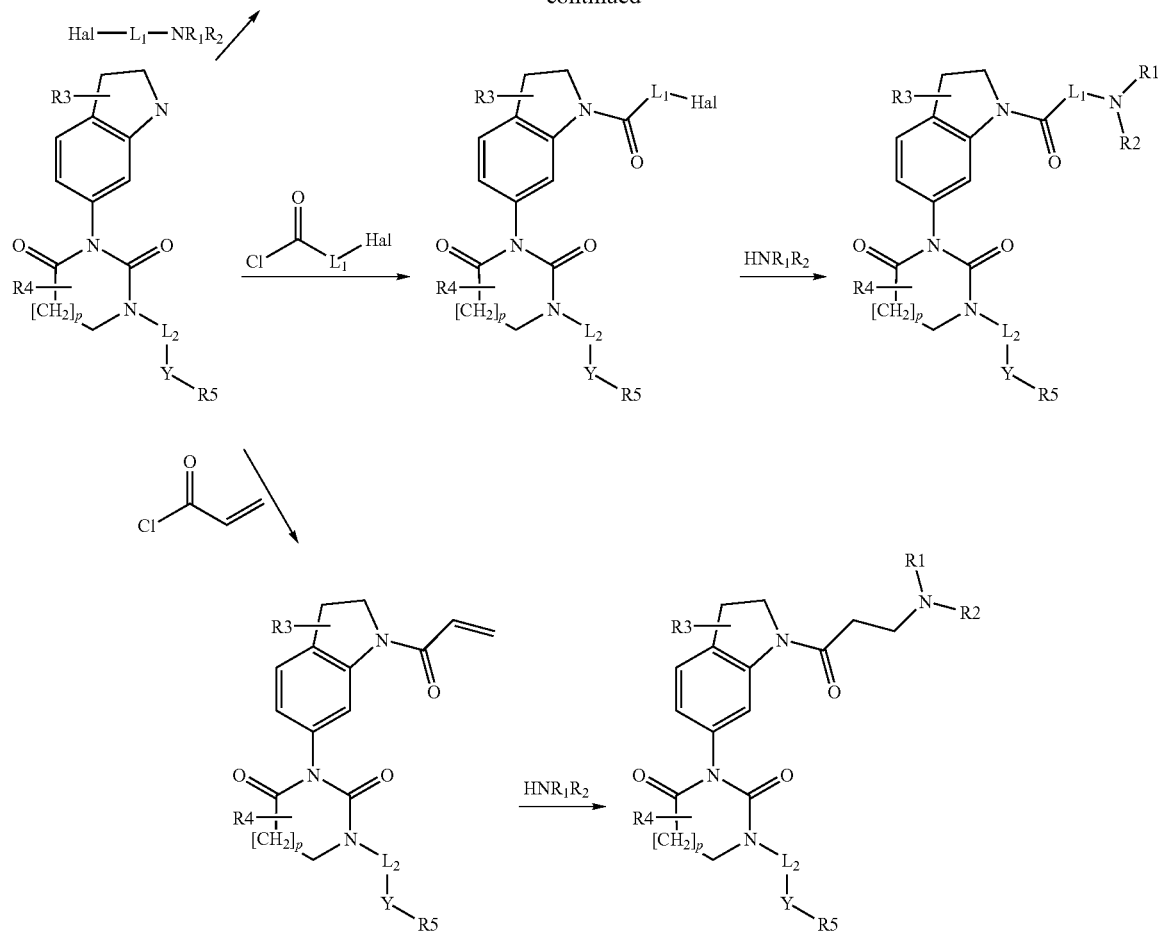

The derivatives of general formula R3-A-NH2 required for the reaction, may be obtained in accordance or by analogy with processes known in the literature. Thus, the indolines required for the illustrated example may be prepared as described in document U.S. Pat. No. 6,114,365.

The compounds of general formula I may moreover be obtained by reacting an amino acid derivative of general formula 7a with an isocyanate 7b or an analogue of similar reactivity, in which Z denotes a group A-, R3A- or R3A(X')- or denotes

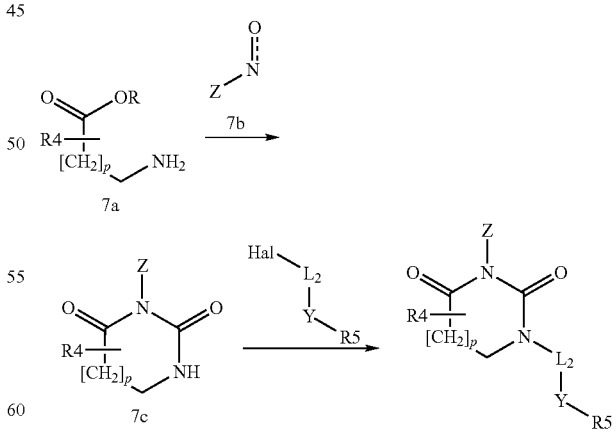

(Scheme 7) The intermediates 7c formed are then converted into compounds of general formula I by alkylation with a halide Hal-$L_2$-Y-R5 or another reagent of similar reactivity. The alkylation reactions are preferably performed in an organic solvent, for instance dimethylformamide, N-methylpyrrolidone, ethyl acetate or acetone, in the presence of a base, for instance potassium carbonate, caesium carbonate, sodium hydride or potassium tert-butoxide. The bases dimethylformamide and caesium carbonate are preferably used.

All the processes for preparing compounds of general formula 1 are distinguished by the fact that the relative sequence of the individual steps is modifiable and may be adapted to the respective needs, determined by the reactivity of the intermediates.

The invention also describes all the reactions on compounds of general formula I, which again lead to compounds of general formula I. Thus, compounds of general formula I in which X denotes —N(R6)-C(O)— and R6 denotes H may be converted by alkylation into compounds of general formula I, in which R6 denotes an alkyl or a cycloalkyl. The conversion of a radical YR5, which denotes a chloropyridine, into a radical YR5, which denotes aminopyridine, may serve as an additional example.

It may be noted that all the reactions for the synthesis of the compounds of formula (I) are well known per se to those skilled in the art and may be performed under standard conditions in accordance with or similar to procedures described in the literature, for example in Houben-Weyl, Methoden der Organischen Chemie (Methods of Organic Chemistry), Thieme-Verlag, Stuttgart, or Organic Reactions, John Wiley & Sons, New York or in R. C. Larock in: Comprehensive Organic Transformations, VCH publishers, 1989. Depending on the individual circumstances, in order to avoid side reactions during the synthesis of a compound of formula (I), it may be necessary or advantageous to temporarily block functional groups by introducing protecting groups, and to deprotect them at a subsequent stage in the synthesis, or to introduce functional groups in the form of precursor groups which are converted into the desired functional groups in a subsequent reaction step. Such synthetic strategies and such protecting groups and precursor groups that are suitable in an individual case are known to those skilled in the art. Standard practices are described, for example, in T. W. Greene and P. G. M. Wuts: "Protective Groups in Organic Chemistry" John Wiley and Sons, 1991. If so desired, the compounds of formula (I) may be purified via common purification procedures, for example by recrystallization or chromatography. The starting materials for the preparation of the compounds of formula (I) are commercially available or may be prepared in accordance with or analogously to literature procedures. The compounds obtained via the abovementioned synthetic methods constitute an additional subject of the present invention.

The products that are the subject of the present invention are endowed with advantageous pharmacological properties: it has been found that they especially have inhibitory properties on protein kinases.

Among these protein kinases, mention is especially made of IGF1R.

Mention is also made of FAK. Mention is also made of AKT.

These properties thus make the products of general formula (I) of the present invention usable as medicinal products for treating malignant tumours.

The products of formula (I) may also be used in the veterinary field.

One subject of the invention is thus, as medicinal products, the products of formula (I) as defined above, and also prodrugs thereof, the said products of formula (I) being in all the possible racemic, enantiomeric and diastereoisomeric isomer forms, and also the pharmaceutically acceptable addition salts with mineral and organic acids or with mineral and organic bases of the said products of formula (I).

A subject of the invention is thus the use, as medicinal products, of the products of formula (Ia), (Ib), (Ic) or (Id) as defined above, and also prodrugs thereof, the said products of formula (Ia), (Ib), (Ic) or (Id) being in all the possible racemic, enantiomeric and diastereoisomeric isomer forms, and also the pharmaceutically acceptable addition salts with mineral and organic acids or with mineral and organic bases of the said products of formula (Ia), (Ib), (Ic) or (Id).

A subject of the invention is thus, most particularly, the use, as medicinal products, of the products of formula (I), the names of which are given hereinbelow:

N-[5-(4,4-Dimethyl-2,5-dioxo-3-pyridin-4-ylmethyl-imidazolidin-1-yl)-2-trifluoromethoxy-phenyl]-2-morpholin-4-yl-acetamide N-[5-(4,4-Dimethyl-2,5-dioxo-3-pyridin-4-ylmethyl-imidazolidin-1-yl)-2-trifluoromethoxy-phenyl]-2-(dimethyl-morpholin-4-yl)-acetamide trifluoroacetate 2-Cyclopentylamino-N-[5-(4,4-dimethyl-2,5-dioxo-3-pyridin-4-ylmethyl-imidazolidin-1-yl)-2-trifluoromethoxy-phenyl]-acetamide trifluoroacetate N-[5-(4,4-Dimethyl-2,5-dioxo-3-pyridin-4-ylmethyl-imidazolidin-1-yl)-2-trifluoromethoxy-phenyl]-2-(2,2,2-trifluoro-ethylamino)-acetamide trifluoroacetate 2-Diethylamino-N-[5-(4,4-dimethyl-2,5-dioxo-3-pyridin-4-ylmethyl-imidazolidin-1-yl)-2-trifluoromethoxy-phenyl]-acetamide trifluoroacetate N-[5-(4,4-Dimethyl-2,5-dioxo-3-pyridin-4-ylmethyl-imidazolidin-1-yl)-2-trifluoromethoxy-phenyl]-2-thiomorpholin-4-yl-acetamide trifluoroacetate N-[5-(4,4-Dimethyl-2,5-dioxo-3-pyridin-4-ylmethyl-imidazolidin-1-yl)-2-trifluoromethoxy-phenyl]-2-pyrrolidin-1-yl-acetamide trifluoroacetate N-[5-(4,4-Dimethyl-2,5-dioxo-3-pyridin-4-ylmethyl-imidazolidin-1-yl)-2-trifluoromethoxy-phenyl]-2-(4-methyl-piperazin-1-yl)-acetamide trifluoroacetate N-[5-(4,4-Dimethyl-2,5-dioxo-3-pyridin-4-ylmethyl-imidazolidin-1-yl)-2-trifluoromethoxy-phenyl]-2-piperidin-1-yl-acetamide trifluoroacetate N-[5-(4,4-Dimethyl-2,5-dioxo-3-pyridin-4-ylmethyl-imidazolidin-1-yl)-2-trifluoromethoxy-phenyl]-2-[(pyridin-2-ylmethyl)-amino]-acetamide trifluoroacetate N-[5-(4,4-Dimethyl-2,5-dioxo-3-pyridin-4-ylmethyl-imidazolidin-1-yl)-2-trifluoromethoxy-phenyl]-2-[(pyridin-3-ylmethyl)-amino]-acetamide trifluoroacetate N-[5-(4,4-Dimethyl-2,5-dioxo-3-pyridin-4-ylmethyl-imidazolidin-1-yl)-2-trifluoromethoxy-phenyl]-2-[(pyridin-4-ylmethyl)-amino]-acetamide trifluoroacetate N-[5-(4,4-Dimethyl-2,5-dioxo-3-pyridin-4-ylmethyl-imidazolidin-1-yl)-2-trifluoromethoxy-phenyl]-2-(2-hydroxy-ethylamino)-acetamide trifluoroacetate N-[5-(4,4-Dimethyl-2,5-dioxo-3-pyridin-4-ylmethyl-imidazolidin-1-yl)-2-trifluoromethoxy-phenyl]-2-(2-methoxy-ethylamino)-acetamide trifluoroacetate 2-Dimethylamino-N-[5-(4,4-dimethyl-2,5-dioxo-3-pyridin-4-ylmethyl-imidazolidin-1-yl)-2-trifluoromethoxy-phenyl]-acetamide trifluoroacetate 2-(Cyanomethyl-amino)-N-[5-(4,4-dimethyl-2,5-dioxo-3-pyridin-4-ylmethyl-imidazolidin-1-yl)-2-trifluoromethoxy-phenyl]-acetamide trifluoroacetate N-[5-(4,4-Dimethyl-2,5-dioxo-3-pyridin-4-ylmethyl-imidazolidin-1-yl)-2-trifluoromethoxy-phenyl]-2-(4-methyl-piperidin-1-yl)-acetamide N-[5-(4,4-Dimethyl-2,5-dioxo-3-pyridin-4-ylmethyl-imidazolidin-1-yl)-2-trifluoromethoxy-phenyl]-2-(4-methyl-[1,4]diazepan-1-yl)-acetamide trifluoroacetate 2-tert-Butylamino-N-[5-(4,4-dimethyl-2,5-dioxo-3-pyridin-4-ylmethyl-imidazolidin-1-yl)-2-trifluoromethoxy-phenyl]-acetamide trifluoroacetate N-[5-(4,4-Dimethyl-2,5-dioxo-3-pyridin-4-ylmethyl-imidazolidin-1-yl)-2-trifluoromethoxy-phenyl]-2-(1,2,2-trimethyl-propylamino)-acetamide trifluoroacetate ({[5-(4,4-Dimethyl-2,5-dioxo-3-pyridin-4-ylmethyl-imidazolidin-1-yl)-2-trifluoromethoxy-phenylcarbamoyl]-methyl}-amino)-acetic acid methyl ester; compound with trifluoro-acetic acid 2-(2,2-Difluoro-ethylamino)-N-[5-(4,4-dimethyl-2,5-dioxo-3-pyridin-4-ylmethyl-imidazolidin-1-yl)-2-trifluoromethoxy-phenyl]-acetamide; compound with trifluoroacetic acid N-[5-(4,4-Dimethyl-2,5-dioxo-3-pyridin-4-ylmethyl-imidazolidin-1-yl)-2-trifluoromethoxy-phenyl]-2-(4,4-dimethyl-piperidin-1-yl)-acetamide N-[5-(4,4-Dimethyl-2,5-dioxo-3-pyridin-4-ylmethyl-imidazolidin-1-yl)-2-trifluoromethoxy-phenyl]-2-(4-trifluoromethyl-piperidin-1-yl)-acetamide N-[5-(4,4-Dimethyl-2,5-dioxo-3-pyridin-4-ylmethyl-imidazolidin-1-yl)-2-trifluoromethoxy-phenyl]-2-[1,4]oxazepan-4-yl-acetamide 1-{[5-(4,4-Dimethyl-2,5-dioxo-3-pyridin-4-ylmethyl-imidazolidin-1-yl)-2-trifluoromethoxy-phenylcarbamoyl]-methyl}-pyrrolidine-3-carboxylic acid methyl ester 2-Azetidin-1-yl-N-[5-(4,4-dimethyl-2,5-dioxo-3-pyridin-4-ylmethyl-imidazolidin-1-yl)-2-trifluoromethoxy-phenyl]-acetamide N-[5-(4,4-Dimethyl-2,5-dioxo-3-pyridin-4-ylmethyl-imidazolidin-1-yl)-2-trifluoromethoxy-phenyl]-2-(2-fluoro-ethylamino)-acetamide N-[5-(4,4-Dimethyl-2,5-dioxo-3-pyridin-4-ylmethyl-imidazolidin-1-yl)-2-trifluoromethoxy-phenyl]-2-[(2-methoxy-ethyl)-methyl-amino]-acetamide ({[5-(4,4-Dimethyl-2,5-dioxo-3-pyridin-4-ylmethyl-imidazolidin-1-yl)-2-trifluoromethoxy-phenylcarbamoyl]-methyl}-amino)-acetic acid trifluoroacetate 2-Cyclohexylamino-N-[5-(4,4-dimethyl-2,5-dioxo-3-pyridin-4-ylmethyl-imidazolidin-1-yl)-2-trifluoromethoxy-phenyl]-acetamide trifluoroacetate 2-Cyclopropylamino-N-[5-(4,4-dimethyl-2,5-dioxo-3-pyridin-4-ylmethyl-imidazolidin-1-yl)-2-trifluoromethoxy-phenyl]-acetamide trifluoroacetate N-[5-(4,4-Dimethyl-2,5-dioxo-3-pyridin-4-ylmethyl-imidazolidin-1-yl)-2-trifluoromethoxy-phenyl]-3-morpholin-4-yl-propionamide trifluoroacetate N-[5-(4,4-Dimethyl-2,5-dioxo-3-pyridin-4-ylmethyl-imidazolidin-1-yl)-2-trifluoromethoxy-phenyl]-3-(dimethyl-morpholin-4-yl)-propionamide trifluoroacetate N-[5-(4,4-Dimethyl-2,5-dioxo-3-pyridin-4-ylmethyl-imidazolidin-1-yl)-2-trifluoromethoxy-phenyl]-3-(4-methyl-piperazin-1-yl)-propionamide trifluoroacetate N-[5-(4,4-Dimethyl-2,5-dioxo-3-pyridin-4-ylmethyl-imidazolidin-1-yl)-2-trifluoromethoxy-phenyl]-3-piperidin-1-yl-propionamide trifluoroacetate N-[5-(4,4-Dimethyl-2,5-dioxo-3-pyridin-4-ylmethyl-imidazolidin-1-yl)-2-trifluoromethoxy-phenyl]-3-thiomorpholin-4-yl-propionamide trifluoroacetate N-[5-(4,4-Dimethyl-2,5-dioxo-3-pyridin-4-ylmethyl-imidazolidin-1-yl)-2-trifluoromethoxy-phenyl]-3-pyrrolidin-1-yl-propionamide trifluoroacetate 3-Cyclopentylamino-N-[5-(4,4-dimethyl-2,5-dioxo-3-pyridin-4-ylmethyl-imidazolidin-1-yl)-2-trifluoromethoxy-phenyl]-propionamide trifluoroacetate N-[5-(4,4-Dimethyl-2,5-dioxo-3-pyridin-4-ylmethyl-imidazolidin-1-yl)-2-trifluoromethoxy-phenyl]-3-(2,2,2-trifluoro-ethylamino)-propionamide; compound with trifluoro-acetic acid 3-Diethylamino-N-[5-(4,4-dimethyl-2,5-dioxo-3-pyridin-4-ylmethyl-imidazolidin-1-yl)-2-trifluoromethoxy-phenyl]-propionamide trifluoroacetate N-[5-(4,4-Dimethyl-2,5-dioxo-3-pyridin-4-ylmethyl-imidazolidin-1-yl)-2-isopropyl-phenyl]-2-morpholin-4-yl-acetamide trifluoroacetate N-[5-(4,4-Dimethyl-2,5-dioxo-3-pyridin-4-ylmethyl-imidazolidin-1-yl)-2-isopropyl-phenyl]-2-piperidin-1-yl-acetamide trifluoroacetate N-[5-(4,4-Dimethyl-2,5-dioxo-3-pyridin-4-ylmethyl-imidazolidin-1-yl)-2-isopropyl-phenyl]-2-(4-methyl-piperazin-1-yl)-acetamide trifluoroacetate 2-Dimethylamino-N-[5-(4,4-dimethyl-2,5-dioxo-3-pyridin-4-ylmethyl-imidazolidin-1-yl)-2-isopropyl-phenyl]-acetamide trifluoroacetate 2-Diethylamino-N-[5-(4,4-dimethyl-2,5-dioxo-3-pyridin-4-ylmethyl-imidazolidin-1-yl)-2-isopropyl-phenyl]-acetamide trifluoroacetate 2-tert-Butylamino-N-[5-(4,4-dimethyl-2,5-dioxo-3-pyridin-4-ylmethyl-imidazolidin-1-yl)-2-isopropyl-phenyl]-acetamide trifluoroacetate 2-Cyclopentylamino-N-[5-(4,4-dimethyl-2,5-dioxo-3-pyridin-4-ylmethyl-imidazolidin-1-yl)-2-isopropyl-phenyl]-acetamide trifluoroacetate 1-Methyl-piperidine-4-carboxylic acid [5-(4,4-dimethyl-2,5-dioxo-3-pyridin-4-ylmethyl-imidazolidin-1-yl)-2-trifluoromethoxy-phenyl]-amide, trifluoro-acetate 3-[3-(2-Cyclopentylamino-ethoxy)-4-methoxy-phenyl]-5,5-dimethyl-1-quinolin-4-ylmethyl-imidazolidine-2,4-dione 3-(3-{2-[(Furan-2-ylmethyl)-amino]-ethoxy}-4-methoxy-phenyl)-5,5-dimethyl-1-quinolin-4-ylmethyl-imidazolidine-2,4-dione 3-{3-[2-(2-Hydroxy-1-phenyl-ethylamino)-ethoxy]-4-methoxy-phenyl}-5,5-dimethyl-1-quinolin-4-ylmethyl-imidazolidine-2,4-dione 3-[3,3-Dimethyl-1-(2-morpholin-4-yl-acetyl)-2,3-dihydro-1H-indol-6-yl]-5,5-dimethyl-1-quinolin-4-ylmethyl-imidazolidine-2,4-dione 3-[3,3-Dimethyl-1-(2-thiomorpholin-4-yl-acetyl)-2,3-dihydro-1H-indol-6-yl]-5,5-dimethyl-1-quinolin-4-ylmethyl-imidazolidine-2,4-dione 3-{4-Methoxy-3-[2-(2-morpholin-4-yl-ethylamino)-ethoxy]-phenyl}-5,5-dimethyl-1-quinolin-4-ylmethyl-imidazolidine-2,4-dione 3-[4-Methoxy-3-(2-pyrrolidin-1-yl-ethoxy)-phenyl]-5,5-dimethyl-1-quinolin-4-ylmethyl-imidazolidine-2,4-dione 3-(4-Methoxy-3-{2-[(pyridin-2-ylmethyl)-amino]-ethoxy}-phenyl)-5,5-dimethyl-1-quinolin-4-ylmethyl-imidazolidine-2,4-dione 3-{4-Methoxy-3-[2-(tetrahydro-pyran-4-ylamino)-ethoxy]-phenyl}-5,5-dimethyl-1-quinolin-4-ylmethyl-imidazolidine-2,4-dione 3-{4-Methoxy-3-[2-(1-methyl-piperidin-4-ylamino)-ethoxy]-phenyl}-5,5-dimethyl-1-quinolin-4-ylmethyl-imidazolidine-2,4-dione 3-{3-[2-Hydroxy-3-(tetrahydro-pyran-4-ylamino)-propoxy]-4-methoxy-phenyl}-5,5-dimethyl-1-quinolin-4-ylmethyl-imidazolidine-2,4-dione 3-{3-[2-Hydroxy-3-(pyridin-4-ylamino)-propoxy]-4-methoxy-phenyl}-5,5-dimethyl-1-quinolin-4-ylmethyl-imidazolidine-2,4-dione 3-{3-[2-Hydroxy-3-(1-methyl-piperidin-4-ylamino)-propoxy]-4-methoxy-phenyl}-5,5-dimethyl-1-quinolin-4-ylmethyl-imidazolidine-2,4-dione and also the prodrugs thereof, the said products of formula (I) being in all the possible racemic, enantiomeric and diastereoisomeric isomer forms, and also the pharmaceutically acceptable addition salts with mineral and organic acids or with mineral and organic bases of the said products of formula (I).

A subject of the invention is thus, most particularly, the use, as medicinal products, of the products of formula (I), the names of which are given hereinbelow:

N-[5-(4,4-Dimethyl-2,5-dioxo-3-pyridin-4-ylmethyl-imidazolidin-1-yl)-2-trifluoromethoxy-phenyl]-2-morpholin-4-yl-acetamide N-[5-(4,4-Dimethyl-2,5-dioxo-3-pyridin-4-ylmethyl-imidazolidin-1-yl)-2-trifluoromethoxy-phenyl]-2-(dimethyl-morpholin-4-yl)-acetamide trifluoroacetate 2-Cyclopentylamino-N-[5-(4,4-dimethyl-2,5-dioxo-3-pyridin-4-ylmethyl-imidazolidin-1-yl)-2-trifluoromethoxy-phenyl]-acetamide trifluoroacetate N-[5-(4,4-Dimethyl-2,5-dioxo-3-pyridin-4-ylmethyl-imidazolidin-1-yl)-2-trifluoromethoxy-phenyl]-2-(2,2,2-trifluoro-ethylamino)-acetamide trifluoroacetate 2-Diethylamino-N-[5-(4,4-dimethyl-2,5-dioxo-3-pyridin-4-ylmethyl-imidazolidin-1-yl)-2-trifluoromethoxy-phenyl]-acetamide trifluoroacetate N-[5-(4,4-Dimethyl-2,5-dioxo-3-pyridin-4-ylmethyl-imidazolidin-1-yl)-2-trifluoromethoxy-phenyl]-2-thiomorpholin-4-yl-acetamide trifluoroacetate N-[5-(4,4-Dimethyl-2,5-dioxo-3-pyridin-4-ylmethyl-imidazolidin-1-yl)-2-trifluoromethoxy-phenyl]-2-pyrrolidin-1-yl-acetamide trifluoroacetate N-[5-(4,4-Dimethyl-2,5-dioxo-3-pyridin-4-ylmethyl-imidazolidin-1-yl)-2-trifluoromethoxy-phenyl]-2-(4-methyl-piperazin-1-yl)-acetamide trifluoroacetate N-[5-(4,4-Dimethyl-2,5-dioxo-3-pyridin-4-ylmethyl-imidazolidin-1-yl)-2-trifluoromethoxy-phenyl]-2-piperidin-1-yl-acetamide trifluoroacetate N-[5-(4,4-Dimethyl-2,5-dioxo-3-pyridin-4-ylmethyl-imidazolidin-1-yl)-2-trifluoromethoxy-phenyl]-2-[(pyridin-2-ylmethyl)-amino]-acetamide trifluoroacetate N-[5-(4,4-Dimethyl-2,5-dioxo-3-pyridin-4-ylmethyl-imidazolidin-1-yl)-2-trifluoromethoxy-phenyl]-2-[(pyridin-3-ylmethyl)-amino]-acetamide trifluoroacetate N-[5-(4,4-Dimethyl-2,5-dioxo-3-pyridin-4-ylmethyl-imidazolidin-1-yl)-2-trifluoromethoxy-phenyl]-2-[(pyridin-4-ylmethyl)-amino]-acetamide trifluoroacetate N-[5-(4,4-Dimethyl-2,5-dioxo-3-pyridin-4-ylmethyl-imidazolidin-1-yl)-2-trifluoromethoxy-phenyl]-2-(2-hydroxy-ethylamino)-acetamide trifluoroacetate N-[5-(4,4-Dimethyl-2,5-dioxo-3-pyridin-4-ylmethyl-imidazolidin-1-yl)-2-trifluoromethoxy-phenyl]-2-(2-methoxy-ethylamino)-acetamide trifluoroacetate 2-Dimethylamino-N-[5-(4,4-dimethyl-2,5-dioxo-3-pyridin-4-ylmethyl-imidazolidin-1-yl)-2-trifluoromethoxy-phenyl]-acetamide trifluoroacetate 2-(Cyanomethyl-amino)-N-[5-(4,4-dimethyl-2,5-dioxo-3-pyridin-4-ylmethyl-imidazolidin-1-yl)-2-trifluoromethoxy-phenyl]-acetamide trifluoroacetate N-[5-(4,4-Dimethyl-2,5-dioxo-3-pyridin-4-ylmethyl-imidazolidin-1-yl)-2-trifluoromethoxy-phenyl]-2-(4-methyl-piperidin-1-yl)-acetamide N-[5-(4,4-Dimethyl-2,5-dioxo-3-pyridin-4-ylmethyl-imidazolidin-1-yl)-2-trifluoromethoxy-phenyl]-2-(4-methyl-[1,4]diazepan-1-yl)-acetamide trifluoroacetate 2-tert-Butylamino-N-[5-(4,4-dimethyl-2,5-dioxo-3-pyridin-4-ylmethyl-imidazolidin-1-yl)-2-trifluoromethoxy-phenyl]-acetamide trifluoroacetate N-[5-(4,4-Dimethyl-2,5-dioxo-3-pyridin-4-ylmethyl-imidazolidin-1-yl)-2-trifluoromethoxy-phenyl]-2-(1,2,2-trimethyl-propylamino)-acetamide trifluoroacetate ({[5-(4,4-Dimethyl-2,5-dioxo-3-pyridin-4-ylmethyl-imidazolidin-1-yl)-2-trifluoromethoxy-phenylcarbamoyl]-methyl}-amino)-acetic acid methyl ester; compound with trifluoro-acetic acid 2-(2,2-Difluoro-ethylamino)-N-[5-(4,4-dimethyl-2,5-dioxo-3-pyridin-4-ylmethyl-imidazolidin-1-yl)-2-trifluoromethoxy-phenyl]-acetamide; compound with trifluoro-acetic acid N-[5-(4,4-Dimethyl-2,5-dioxo-3-pyridin-4-ylmethyl-imidazolidin-1-yl)-2-trifluoromethoxy-phenyl]-2-(4,4-dimethyl-piperidin-1-yl)-acetamide N-[5-(4,4-Dimethyl-2,5-dioxo-3-pyridin-4-ylmethyl-imidazolidin-1-yl)-2-trifluoromethoxy-phenyl]-2-(4-trifluoromethyl-piperidin-1-yl)-acetamide N-[5-(4,4-Dimethyl-2,5-dioxo-3-pyridin-4-ylmethyl-imidazolidin-1-yl)-2-trifluoromethoxy-phenyl]-2-[1,4]oxazepan-4-yl-acetamide 1-{[5-(4,4-Dimethyl-2,5-dioxo-3-pyridin-4-ylmethyl-imidazolidin-1-yl)-2-trifluoromethoxy-phenylcarbamoyl]-methyl}-pyrrolidine-3-carboxylic acid methyl ester 2-Azetidin-1-yl-N-[5-(4,4-dimethyl-2,5-dioxo-3-pyridin-4-ylmethyl-imidazolidin-1-yl)-2-trifluoromethoxy-phenyl]-acetamide N-[5-(4,4-Dimethyl-2,5-dioxo-3-pyridin-4-ylmethyl-imidazolidin-1-yl)-2-trifluoromethoxy-phenyl]-2-(2-fluoro-ethylamino)-acetamide N-[5-(4,4-Dimethyl-2,5-dioxo-3-pyridin-4-ylmethyl-imidazolidin-1-yl)-2-trifluoromethoxy-phenyl]-2-[(2-methoxy-ethyl)-methyl-amino]-acetamide ({[5-(4,4-Dimethyl-2,5-dioxo-3-pyridin-4-ylmethyl-imidazolidin-1-yl)-2-trifluoromethoxy-phenylcarbamoyl]-methyl}-amino)-acetic acid trifluoroacetate 2-Cyclohexylamino-N-[5-(4,4-dimethyl-2,5-dioxo-3-pyridin-4-ylmethyl-imidazolidin-1-yl)-2-trifluoromethoxy-phenyl]-acetamide trifluoroacetate 2-Cyclopropylamino-N-[5-(4,4-dimethyl-2,5-dioxo-3-pyridin-4-ylmethyl-imidazolidin-1-yl)-2-trifluoromethoxy-phenyl]-acetamide trifluoroacetate N-[5-(4,4-Dimethyl-2,5-dioxo-3-pyridin-4-ylmethyl-imidazolidin-1-yl)-2-trifluoromethoxy-phenyl]-3-morpholin-4-yl-propionamide trifluoroacetate N-[5-(4,4-Dimethyl-2,5-dioxo-3-pyridin-4-ylmethyl-imidazolidin-1-yl)-2-trifluoromethoxy-phenyl]-3-(dimethyl-morpholin-4-yl)-propionamide trifluoroacetate N-[5-(4,4-Dimethyl-2,5-dioxo-3-pyridin-4-ylmethyl-imidazolidin-1-yl)-2-trifluoromethoxy-phenyl]-3-(4-methyl-piperazin-1-yl)-propionamide trifluoroacetate N-[5-(4,4-Dimethyl-2,5-dioxo-3-pyridin-4-ylmethyl-imidazolidin-1-yl)-2-trifluoromethoxy-phenyl]-3-piperidin-1-yl-propionamide trifluoroacetate N-[5-(4,4-Dimethyl-2,5-dioxo-3-pyridin-4-ylmethyl-imidazolidin-1-yl)-2-trifluoromethoxy-phenyl]-3-thiomorpholin-4-yl-propionamide trifluoroacetate N-[5-(4,4-Dimethyl-2,5-dioxo-3-pyridin-4-ylmethyl-imidazolidin-1-yl)-2-trifluoromethoxy-phenyl]-3-pyrrolidin-1-yl-propionamide trifluoroacetate 3-Cyclopentylamino-N-[5-(4,4-dimethyl-2,5-dioxo-3-pyridin-4-ylmethyl-imidazolidin-1-yl)-2-trifluoromethoxy-phenyl]-propionamide trifluoroacetate N-[5-(4,4-Dimethyl-2,5-dioxo-3-pyridin-4-ylmethyl-imidazolidin-1-yl)-2-trifluoromethoxy-phenyl]-3-(2,2,2-trifluoro-ethylamino)-propionamide; compound with trifluoro-acetic acid 3-Diethylamino-N-[5-(4,4-dimethyl-2,5-dioxo-3-pyridin-4-ylmethyl-imidazolidin-1-yl)-2-trifluoromethoxy-phenyl]-propionamide trifluoroacetate N-[5-(4,4-Dimethyl-2,5-dioxo-3-pyridin-4-ylmethyl-imidazolidin-1-yl)-2-isopropyl-phenyl]-2-morpholin-4-yl-acetamide trifluoroacetate N-[5-(4,4-Dimethyl-2,5-dioxo-3-pyridin-4-ylmethyl-imidazolidin-1-yl)-2-isopropyl-phenyl]-2-piperidin-1-yl-acetamide trifluoroacetate N-[5-(4,4-Dimethyl-2,5-dioxo-3-pyridin-4-ylmethyl-imidazolidin-1-yl)-2-isopropyl-phenyl]-2-(4-methyl-piperazin-1-yl)-acetamide trifluoroacetate 2-Dimethylamino-N-[5-(4,4-dimethyl-2,5-dioxo-3-pyridin-4-ylmethyl-imidazolidin-1-yl)-2-isopropyl-phenyl]-acetamide trifluoroacetate 2-Diethylamino-N-[5-(4,4-dimethyl-2,5-dioxo-3-pyridin-4-ylmethyl-imidazolidin-1-yl)-2-isopropyl-phenyl]-acetamide trifluoroacetate 2-tert-Butylamino-N-[5-(4,4-dimethyl-2,5-dioxo-3-pyridin-4-ylmethyl-imidazolidin-1-yl)-2-isopropyl-phenyl]-acetamide trifluoroacetate 2-Cyclopentylamino-N-[5-(4,4-dimethyl-2,5-dioxo-3-pyridin-4-ylmethyl-imidazolidin-1-yl)-2-isopropyl-phenyl]-acetamide trifluoroacetate 1-Methyl-piperidine-4-carboxylic acid [5-(4,4-dimethyl-2,5-dioxo-3-pyridin-4-ylmethyl-imidazolidin-1-yl)-2-trifluoromethoxy-phenyl]-amide, trifluoro-acetate 3-[3-(2-Cyclopentylamino-ethoxy)-4-methoxy-phenyl]-5,5-dimethyl-1-quinolin-4-ylmethyl-imidazolidine-2,4-dione 3-(3-{2-[(Furan-2-ylmethyl)-amino]-ethoxy}-4-methoxy-phenyl)-5,5-dimethyl-1-quinolin-4-ylmethyl-imidazolidine-2,4-dione 3-{3-[2-(2-Hydroxy-1-phenyl-ethylamino)-ethoxy]-4-methoxy-phenyl}-5,5-dimethyl-1-quinolin-4-ylmethyl-imidazolidine-2,4-dione 3-[3,3-Dimethyl-1-(2-morpholin-4-yl-acetyl)-2,3-dihydro-1H-indol-6-yl]-5,5-dimethyl-1-quinolin-4-ylmethyl-imidazolidine-2,4-dione 3-[3,3-Dimethyl-1-(2-thiomorpholin-4-yl-acetyl)-2,3-dihydro-1H-indol-6-yl]-5,5-dimethyl-1-quinolin-4-ylmethyl-imidazolidine-2,4-dione and also the prodrugs thereof, the said products of formula (I) being in all the possible racemic, enantiomeric and diastereoisomeric isomer forms, and also the pharmaceutically acceptable addition salts with mineral and organic acids or with mineral and organic bases of the said products of formula (I).

The products may be administered via the parenteral, buccal, perlingual, rectal or topical route.

A subject of the invention is thus pharmaceutical compositions, characterized in that they contain, as active principle, at least one of the medicinal products of formula (I) as defined above.

These compositions may be in the form of injectable solutions or suspensions, tablets, coated tablets, capsules, syrups, suppositories, creams, ointments and lotions. These pharmaceutical forms are prepared according to the usual methods. The active principle may be incorporated into excipients usually used in these compositions, such as aqueous or nonaqueous vehicles, talc, gum arabic, lactose, starch, magnesium stearate, cocoa butter, fatty substances of animal or plant origin, paraffin derivatives, glycols, various wetting, dispersing or emulsifying agents, and preserving agents.

The usual dose, which varies according to the individual treated and the complaint under consideration, may be, for example, from 10 mg to 500 mg per day orally in man.

The present invention thus relates to the use of products of formula (I) as defined above or of pharmaceutically acceptable salts of the said products of formula (I) for the preparation of medicinal products for inhibiting the activity of protein kinases and especially of a protein kinase.

The present invention thus relates to the use of products of formula (I) as defined above or of pharmaceutically acceptable salts of the said products of formula (I) in which the protein kinase is a protein tyrosine kinase.

The present invention thus relates to the use of products of formula (I) as defined above or of pharmaceutically acceptable salts of the said products of formula (I) in which the protein kinase is chosen from the following group: IGF1, Raf, EGF, PDGF, VEGF, Tie2, KDR, Flt1-3, FAK, Src, Ab1, cKit, cdk1-9, Aurora1-2, cdc7, Akt, Pdk, S6K, Jnk, IR, FLK-1, FGFR1, FGFR2, FGFR3, FGFR4, FGFR5, PLK, Pyk2, CDK7, CDK2 et EGFR.

More particularly such protein kinase is chosen from the following group:

IGF1, cdc7, Aurora1-2, Src, Jnk, FAK, KDR, IR, Tie2, CDK7, CDK2 et EGFR.

The present invention thus relates particularly to the use of products of formula (I) as defined above or of pharmaceutically acceptable salts of the said products of formula (I) in which the protein kinase is IGF1R.

The present invention also relates to the use of products of formula (I) as defined above or of pharmaceutically acceptable salts of the said products of formula (I) in which the protein kinase is FAK.

The present invention also relates to the use of products of formula (I) as defined above or of pharmaceutically acceptable salts of the said products of formula (I) in which the protein kinase is AKT.

The present invention also relates to the use of products of formula (I) as defined above or of pharmaceutically acceptable salts of the said products of formula (I) in which the protein kinase is in a cell culture, and also to this use in a mammal.

The present invention thus relates to the use of products of formula (I) as defined above or of pharmaceutically acceptable salts of the said products of formula (I) for the preparation of a medicinal product for preventing or treating a disease characterized by deregulation of the activity of a protein kinase and especially such a disease in a mammal.

The present invention relates to the use of products of formula (I) as defined above or of pharmaceutically acceptable salts of the said products of formula (I) for the preparation of a medicinal product for preventing or treating a disease belonging to the following group: disorders of blood vessel proliferation, fibrotic disorders, disorders of mesangial cell proliferation, acromegaly, metabolic disorders, allergies, asthma, Crohn's disease, thrombosis, diseases of the nervous system, retinopathy, psoriasis, rheumatoid arthritis, diabetes, muscle degeneration, aging, age related macula degeneration, oncology diseases and cancer.

The present invention thus relates to the use of products of formula (I) as defined above or of pharmaceutically acceptable salts of the said products of formula (I) for the preparation of a medicinal product for treating oncology diseases.

The present invention relates particularly to the use of products of formula (I) as defined above or of pharmaceutically acceptable salts of the said products of formula (I) for the preparation of a medicinal product for treating cancers.

Among these cancers, the present invention is most particularly of interest in the treatment of solid tumours and the treatment of cancers that are resistant to cytotoxic agents.

Among these cancers, the present invention relates most particularly to the treatment of breast cancer, stomach cancer, cancer of the colon, lung cancer, cancer of the ovaries, cancer of the uterus, brain cancer, cancer of the kidney, cancer of the larynx, cancer of the lymphatic system, cancer of the thyroid, cancer of the urogenital tract, cancer of the tract including the seminal vesicle and prostate, bone cancer, cancer of the pancreas and melanomas. The present invention is even more particularly of interest in treating breast cancer, cancer of the colon and lung cancer.

The present invention also relates to the use of products of formula (I) as defined above or of pharmaceutically acceptable salts of the said products of formula (I) for the preparation of a medicinal product for cancer chemotherapy. As medicinal products according to the present invention for cancer chemotherapy, the products of formula (I) according to the present invention may be used alone or in combination with chemotherapy or radiotherapy or alternatively in combination with other therapeutic agents.

The present invention thus relates especially to the pharmaceutical compositions as defined above, characterized in that they are used as medicinal products, in particular for cancer chemotherapy.

The present invention thus relates especially to the pharmaceutical compositions as defined above containing, in addition to the active principles, other chemotherapy medicinal products for combating cancer.

Such therapeutic agents may be commonly used antitumour agents.

As examples of known inhibitors of protein kinases, mention may be made especially of butyrolactone, flavopiridol, 2-(2-hydroxyethylamino)-6-benzylamino-9-methylpurine, olomucine, Glivec and Iressa.

The products of formula (I) according to the present invention may thus also be advantageously used in combination with antiproliferative agents: as examples of such antiproliferative agents, but without, however, being limited to this list, mention may be made of aromatase inhibitors, antioestrogens, the topoisomerase I inhibitors, the topoisomerase II inhibitors, microtubule-active agents, alkylating agents, histone deacetylase inhibitors, farnesyl transferase inhibitors, COX-2 inhibitors, MMP inhibitors, mTOR inhibitors, antineoplastic antimetabolites, platinum compounds, compounds that reduce the activity of protein kinases and also anti-angiogenic compounds, gonadorelin agonists, antiandrogens, bengamides, biphosphonates and trastuzumab.

Examples that may thus be mentioned include anti-microtubule agents, for instance taxoids, vinca alkaloids, alkylating agents such as cyclophosphamide, DNA-intercalating agents, for instance cis-platinum, agents that are interactive on topoisomerase, for instance camptothecin and derivatives, anthracyclines, for instance adriamycin, antimetabolites, for instance 5-fluorouracil and derivatives, and the like.

The present invention thus relates to products of formula (I) as protein kinase inhibitors, the said products of formula (I) being in any possible racemic, enantiomeric or diastereoisomeric isomer form, and also the addition salts of the said products of formula (I) with pharmaceutically acceptable mineral and organic acids or with pharmaceutically acceptable mineral and organic bases, and also the prodrugs thereof.

The present invention relates particularly to products of formula (I) as defined above as IGF1R inhibitors.

The present invention also relates to products of formula (I) as defined above as FAK inhibitors.

The present invention also relates to products of formula (I) as defined above as AKT inhibitors.

The present invention relates more particularly to the products of formula (Ia), (Ib), (Ic) and in particular (Id) as defined above as IGF1R inhibitors.

The experimental section hereinbelow more particularly gives an illustration of the above synthetic schemes.

The examples whose preparation follows illustrate the present invention without, however, limiting it.

EXAMPLE 1a 3-nitro-4-(trifluormethoxy)-aniline 20 g (112.9 mmol) 4-(trifluormethoxy)-aniline were dissolved in to 50ml conc. sulfuric acid and treated at −5° C. with a mixture of 24 ml conc. sulfuric acid and 6 ml nitric acid. After stirring the mixture at 0° C. for 3 h, the reaction mixture was poured on 1 L ice water and made alkaline with 200 ml conc. aqueous ammonium hydroxide. The resulting solution was extracted with ethyl acetate, the combined organic phases were dried and evaporated to dryness. The residue was purified by flash chromatography (Silica gel, methylene chloride:methanol=98: 2) and subsequent recrystallization from methylenchoride/heptane. Yield: 14.8 g MS(ES+): m/e=223
LC/MS Retention time [min]=1.84

EXAMPLE 1b 5,5-Dimethyl-3-(3-nitro-4-trifluormethoxy-phenyl)-1-pyridin-4-ylmethyl-imidazolidine-2,4-dione 29 g (146.5 mmol) diphosgene in 300 ml 1,2-dichlorethane were treated at −20° C. with a solution of 13 g (58.6 mmol) 3-nitro-4-(trifluormethoxy)-aniline in 20 ml 1,2-dichlorethane. The mixture was allowed to come to room temperature and then was heated to 50° C. for 3 h. After standing over night, the solvent was evaporated and the residual oil was taken up in 250 ml THF. 13 g (58.6 mmol) 2-methyl-2-[(pyridin-4-ylmethyl)-amino]-propionic acid methyl ester in 250 ml THF were added and the mixture was heated to 40° C. for 1 h. The solvent was evaporated and the residue purified by flash chromatography (Silica gel, methylene chloride: methanol=95:5). Yield: 19.7 g.

MS(ES+): m/e=425
LC/MS Retention time [min]=1.61

EXAMPLE 1c 3-(3-amino-4-trifluormethoxy-phenyl)-5,5-dimethyl-1-pyridin-4-ylmethyl-imidazolidine-2,4-dione 8.8 g (20.7 mmol) 5,5-dimethyl-3-(3-nitro-4-trifluormethoxy-phenyl)-1-pyridin-4-ylmethyl-imidazolidine-2,4-dione were dissolved in 200 ml semi-conc. hydrochloric acid. 30 g zinc dust were added in portions and the resulting mixture was refluxed for 1 h, cooled to RT, diluted with 100 ml water and extracted with ethyl acetate. The aqueous phase was made alkaline with saturated sodium hydroxide solution and extracted with methylene chloride. Separating zinc salts were removed by filtration over cellite. Evaporation of the combined organic phases and flash chromatography of the residue (Silica gel, methylene chloride:methanol=95:5) gave 4.7 g of the desired product.

MS(ES+): m/e=395
LC/MS Retention time [min]=1.27

EXAMPLE 1d

N-[5-(4,4-Dimethyl-2,5-dioxo-3-pyridin-4-ylmethyl-imidazolidin-1-yl)-2-trifluoromethoxy-phenyl]-2-chloro-acetamide 500 mg (1.27 mmol) 3-(3-amino-4-trifluormethoxy-phenyl)-5,5-dimethyl-1-pyridin-4-ylmethyl-imidazolidine-2,4-dione and 172 mg (1.33 mmol) Hünig's base were dissolved in 20 ml 1,2-dichloroethane. The mixture was cooled to −20° C. and treated with a solution of 143 mg (1.27 mmol) chloroacetylchlorid in 15 ml 1,2-dichloroethane. After stirring 1 h at 0° C., 5 ml ethanolic hydrochlric acid were added and the mixture evaporated to dryness. The raw material, containing huening's base hydrochloride was used without further purification.

MS(ES+): m/e=472
LC/MS Retention time [min]=

EXAMPLE 1e

N-[5-(4,4-Dimethyl-2,5-dioxo-3-pyridin-4-ylmethyl-imidazolidin-1-yl)-2-trifluoromethoxy-phenyl]-2-morpholin-4-yl-acetamide 50 mg N-[5-(4,4-Dimethyl-2,5-dioxo-3-pyridin-4-ylmethyl-imidazolidin-1-yl)-2-trifluoromethoxy-phenyl]-2-chloro-acetamide (raw material, as described above) owere dissolved in 2 ml morpholine and heated for 1 h to 50° C. Subsequently, the mixture was poured on ice and extracted with ethylacetate. The combined organic phases were evaporated to dryness and the residue was purified by flash chromoatography (Silica gel, methylene chloride:methanol=1.98: 22.95:5) Yield: 20 mg MS(ES+): m/e=522
LC/MS Retention time [min]=0.97

EXAMPLE 2

N-[5-(4,4-Dimethyl-2,5-dioxo-3-pyridin-4-ylmethyl-imidazolidin-1-yl)-2-trifluoromethoxy-phenyl]-2-(dimethyl-morpholin-4-yl)-acetamide trifluoroacetate The title compound was prepared as described for example 1e using 2 ml cis-2,6-dimethylmorpholine. The raw material was purified by preparative HPLC. (C18 reversed phase column, elution with a water (0.1% trifluoracetic acid)/acetonitrile gradient) Yield: 25 mg MS(ES+): m/e=550
LC/MS Retention time [min]=1.04

EXAMPLE 3

2-Cyclopentylamino-N-[5-(4,4-dimethyl-2,5-dioxo-3-pyridin-4-ylmethyl-imidazolidin-1-yl)-2-trifluoromethoxy-phenyl]-acetamide trifluoroacetate The title compound was prepared as described for example 2 using 2 ml cyclopentylamine Yield: 18 mg MS(ES+): m/e=520
LC/MS Retention time [min]=1.11

EXAMPLE 4

N-[5-(4,4-Dimethyl-2,5-dioxo-3-pyridin-4-ylmethyl-imidazolidin-1-yl)-2-trifluoromethoxy-phenyl]-2-(2,2,2-trifluoro-ethylamino)-acetamide trifluoroacetate The title compound was prepared as described for example 2 using 2 ml 2,2,2-trifluoroethylamine in 1 ml N-methylpyrrolidone
Yield: 10 mg
MS(ES+): m/e=534
LC/MS Retention time [min]=1.57

EXAMPLE 5

2-Diethylamino-N-[5-(4,4-dimethyl-2,5-dioxo-3-pyridin-4-ylmethyl-imidazolidin-1-yl)-2-trifluoromethoxy-phenyl]-acetamide trifluoroacetate The title compound was prepared as described for example 2 using 2 ml diethylamine Yield: 12 mg MS(ES+): m/e=508
LC/MS Retention time [min]=1.05

EXAMPLE 6

N-[5-(4,4-Dimethyl-2,5-dioxo-3-pyridin-4-ylmethyl-imidazolidin-1-yl)-2-trifluoromethoxy-phenyl]-2-thiomorpholin-4-yl-acetamide trifluoroacetate The title compound was prepared as described for example 2 using 100 mg (0.21 mmol) N-[5-(4,4-Dimethyl-2,5-dioxo-3-pyridin-4-ylmethyl-imidazolidin-1-yl)-2-trifluoromethoxy-phenyl]-2-chloro-acetamide (raw material, as described above) and 2 ml thiomorpholine Yield: 26 mg MS(ES+): m/e=538
LC/MS Retention time [min]=0.94

EXAMPLE 7

N-[5-(4,4-Dimethyl-2,5-dioxo-3-pyridin-4-ylmethyl-imidazolidin-1-yl)-2-trifluoromethoxy-phenyl]-2-pyrrolidin-1-yl-acetamide trifluoroacetate The title compound was prepared as described for example 6 using 2 ml pyrrolidine. Yield: 24 mg MS(ES+): m/e=506
LC/MS Retention time [min]=1.05

EXAMPLE 8

N-[5-(4,4-Dimethyl-2,5-dioxo-3-pyridin-4-ylmethyl-imidazolidin-1-yl)-2-trifluoromethoxy-phenyl]-2-(4-methyl-piperazin-1-yl)-acetamide trifluoroacetate The title compound was prepared as described for example 2 using 2 ml N-methylpiperazine. Yield: 16 mg MS(ES+): m/e=535
LC/MS Retention time [min]=1.01

EXAMPLE 9

N-[5-(4,4-Dimethyl-2,5-dioxo-3-pyridin-4-ylmethyl-imidazolidin-1-yl)-2-trifluoromethoxy-phenyl]-2-piperidin-1-yl-acetamide trifluoroacetate The title compound was prepared as described for example 2 using 2 ml piperidine. Yield: 20 mg MS(ES+): m/e=520
LC/MS Retention time [min]=0.92

EXAMPLE 10

N-[5-(4,4-Dimethyl-2,5-dioxo-3-pyridin-4-ylmethyl-imidazolidin-1-yl)-2-trifluoromethoxy-phenyl]-2-[(pyridin-2-ylmethyl)-amino]-acetamide trifluoroacetate The title compound was prepared as described for example 6 using 2 ml 2-(aminomethyl)-pyridine. Yield: 35 mg
MS(ES+): m/e=543
LC/MS Retention time [min]=1.18

EXAMPLE 11

N-[5-(4,4-Dimethyl-2,5-dioxo-3-pyridin-4-ylmethyl-imidazolidin-1-yl)-2-trifluoromethoxy-phenyl]-2-[(pyridin-3-ylmethyl)-amino]-acetamide trifluoroacetate The title compound was prepared as described for example 6 using 2 ml 3-(aminomethyl)-pyridine. Yield: 32 mg
MS(ES+): m/e=543
LC/MS Retention time [min]=0.87

EXAMPLE 12

N-[5-(4,4-Dimethyl-2,5-dioxo-3-pyridin-4-ylmethyl-imidazolidin-1-yl)-2-trifluoromethoxy-phenyl]-2-[(pyridin-4-ylmethyl)-amino]-acetamide trifluoroacetate The title compound was prepared as described for example 6 using 2 ml 4-(aminomethyl)-pyridine. Yield: 35 mg
MS(ES+): m/e=543
LC/MS Retention time [min]=0.97

EXAMPLE 13

N-[5-(4,4-Dimethyl-2,5-dioxo-3-pyridin-4-ylmethyl-imidazolidin-1-yl)-2-trifluoromethoxy-phenyl]-2-(2-hydroxy-ethylamino)-acetamide trifluoroacetate The title compound was prepared as described for example 6 using 2 ml ethanolamine. Yield: 36 mg
MS(ES+): m/e=496
LC/MS Retention time [min]=0.82

EXAMPLE 14

N-[5-(4,4-Dimethyl-2,5-dioxo-3-pyridin-4-ylmethyl-imidazolidin-1-yl)-2-trifluoromethoxy-phenyl]-2-(2-methoxy-ethylamino)-acetamide trifluoroacetate The title compound was prepared as described for example 6 using 2 ml 2-methoxyethylamine. Yield: 33 mg
MS(ES+): m/e=510
LC/MS Retention time [min]=1.14

EXAMPLE 15

2-Dimethylamino-N-[5-(4,4-dimethyl-2,5-dioxo-3-pyridin-4-ylmethyl-imidazolidin-1-yl)-2-trifluoromethoxy-phenyl]-acetamide trifluoroacetate The title compound was prepared as described for example 6 using 2 ml of 2M solution of dimethylamine DMF. Yield: 12 mg
MS(ES+): m/e=480
LC/MS Retention time [min]=0.85

EXAMPLE 16

2-(Cyanomethyl-amino)-N-[5-(4,4-dimethyl-2,5-dioxo-3-pyridin-4-ylmethyl-imidazolidin-1-yl)-2-trifluoromethoxy-phenyl]-acetamide trifluoroacetate The title compound was prepared as described for example 6 using 2 ml aminoacetonitril. Yield: 18 mg
MS(ES+): m/e=491
LC/MS Retention time [min]=1.20

EXAMPLE 17

N-[5-(4,4-Dimethyl-2,5-dioxo-3-pyridin-4-ylmethyl-imidazolidin-1-yl)-2-trifluoromethoxy-phenyl]-2-(4-methyl-piperidin-1-yl)-acetamide The title compound was prepared as described for example 2 using 150 mg (0.21 mmol) N-[5-(4,4-Dimethyl-2,5-dioxo-3-pyridin-4-ylmethyl-imidazolidin-1-yl)-2-trifluoromethoxy-phenyl]-2-chloro-acetamide (raw material, as described above) and 1 ml 4-methylpiperidine. Yield: 30 mg
MS(ES+): m/e=534
LC/MS Retention time [min]=1.07

EXAMPLE 18

N-[5-(4,4-Dimethyl-2,5-dioxo-3-pyridin-4-ylmethyl-imidazolidin-1-yl)-2-trifluoromethoxy-phenyl]-2-(4-methyl-[1,4]diazepan-1-yl)-acetamide trifluoroacetate The title compound was prepared as described for example 17 using 1 ml N-methylhomopiperazine. Yield: 60 mg
MS(ES+): m/e=549
LC/MS Retention time [min]=0.87

EXAMPLE 19

2-tert-Butylamino-N-[5-(4,4-dimethyl-2,5-dioxo-3-pyridin-4-ylmethyl-imidazolidin-1-yl)-2-trifluoromethoxy-phenyl]-acetamide trifluoroacetate The title compound was prepared as described for example 17 using 1 ml tert.-butylamine. Yield: 52 mg
MS(ES+): m/e=508
LC/MS Retention time [min]=0.92

EXAMPLE 20

N-[5-(4,4-Dimethyl-2,5-dioxo-3-pyridin-4-ylmethyl-imidazolidin-1-yl)-2-trifluoromethoxy-phenyl]-2-(1,2,2-trimethyl-propylamino)-acetamide trifluoroacetate The title compound was prepared as described for example 17 using 1 ml 2-amino-3,3-dimethylbutane. Yield: 60 mg
MS(ES+): m/e=536
LC/MS Retention time [min]=1.13

EXAMPLE 21

({[5-(4,4-Dimethyl-2,5-dioxo-3-pyridin-4-ylmethyl-imidazolidin-1-yl)-2-trifluoromethoxy-phenylcarbamoyl]-methyl}-amino)-acetic acid methyl ester; Compound with Trifluoro-Acetic Acid The title compound was prepared as described for example 17 using glycimethylester hydrochloride and Hünig's base in DMF.
MS(ES+): m/e=524
LC/MS Retention time [min]=0.92

EXAMPLE 22

2-(2,2-Difluoro-ethylamino)-N-[5-(4,4-dimethyl-2,5-dioxo-3-pyridin-4-ylmethyl-imidazolidin-1-yl)-2-trifluoromethoxy-phenyl]-acetamide; Compound with Trifluoro-Acetic Acid The title compound was prepared as described for example 17 using 1 ml 2,2-difluorethylamine. Yield: 50 mg
MS(ES+): m/e=516
LC/MS Retention time [min]=1.03

EXAMPLE 23

N-[5-(4,4-Dimethyl-2,5-dioxo-3-pyridin-4-ylmethyl-imidazolidin-1-yl)-2-trifluoromethoxy-phenyl]-2-(4,4-dimethyl-piperidin-1-yl)-acetamide The title compound was prepared as described for example 1e using 100 mg N-[5-(4,4-Dimethyl-2,5-dioxo-3-pyridin-4-ylmethyl-imidazolidin-1-yl)-2-trifluoromethoxy-phenyl]-2-chloro-acetamide (raw material, as described above) and 15 mg 4,4-dimethylpiperidine. Yield: 2.5 mg
MS(ES+): m/e=548
LC/MS Retention time [min]=1.09

EXAMPLE 24

N-[5-(4,4-Dimethyl-2,5-dioxo-3-pyridin-4-ylmethyl-imidazolidin-1-yl)-2-trifluoromethoxy-phenyl]-2-(4-trifluoromethyl-piperidin-1-yl)-acetamide The title compound was prepared as described for example 1e using 1 ml 4-(trifluormethyl)piperidine
MS(ES+): m/e=588
LC/MS Retention time [min]=1.30

EXAMPLE 25

N-[5-(4,4-Dimethyl-2,5-dioxo-3-pyridin-4-ylmethyl-imidazolidin-1-yl)-2-trifluoromethoxy-phenyl]-2-[1,4]oxazepan-4-yl-acetamide The title compound was prepared as described for example 1e using 1 ml homomorpholine hydrochlorid and Hünig's base.
Yield: 10 mg
MS(ES+): m/e=536
LC/MS Retention time [min]=0.91

EXAMPLE 26

1-{[5-(4,4-Dimethyl-2,5-dioxo-3-pyridin-4-ylmethyl-imidazolidin-1-yl)-2-trifluoromethoxy-phenylcarbamoyl]-methyl}-pyrrolidine-3-carboxylic acid methyl ester The title compound was prepared as described for example 1e using 1 ml methyl-3-pyrrolidinecarboxylate in 1 ml. Yield: 22 mg.
MS(ES+): m/e=564
LC/MS Retention time [min]=1.11

EXAMPLE 27

2-Azetidin-1-yl-N-[5-(4,4-dimethyl-2,5-dioxo-3-pyridin-4-ylmethyl-imidazolidin-1-yl)-2-trifluoromethoxy-phenyl]-acetamide The title compound was prepared as described for example 6 using 1 ml azetidine in 1 ml DMF. Yield: 85 mg.
MS(ES+): m/e=492
LC/MS Retention time [min]=0.88

EXAMPLE 28

N-[5-(4,4-Dimethyl-2,5-dioxo-3-pyridin-4-ylmethyl-imidazolidin-1-yl)-2-trifluoromethoxy-phenyl]-2-(2-fluoro-ethylamino)-acetamide The title compound was prepared as described for example 1e using 2-fluoroethylamine hydrochlorid and Hünig's base.
Yield: 10 mg
MS(ES+): m/e=498
LC/MS Retention time [min]=0.93

EXAMPLE 29

N-[5-(4,4-Dimethyl-2,5-dioxo-3-pyridin-4-ylmethyl-imidazolidin-1-yl)-2-trifluoromethoxy-phenyl]-2-[(2-methoxy-ethyl)-methyl-amino]-acetamide The title compound was prepared as described for example 1e using 1 ml N-(2-methoxyethyl)-methylamine. Yield: 10 mg
MS(ES+): m/e=524
LC/MS Retention time [min]=0.91

EXAMPLE 30

({[5-(4,4-Dimethyl-2,5-dioxo-3-pyridin-4-ylmethyl-imidazolidin-1-yl)-2-trifluoromethoxy-phenylcarbamoyl]-methyl}-amino)-acetic acid trifluoroacetate 100 mg (0.16 mmol) ({[5-(4,4-Dimethyl-2,5-dioxo-3-pyridin-4-ylmethyl-imidazolidin-1-yl)-2-trifluoromethoxy-phenylcarbamoyl]-methyl}-amino)-acetic acid methyl ester trifluoro acetate were dissolved in 5 ml dioxane/water (9/1) and treated with 9.3 mg (0.39 mmol) lithium hydroxide. After stirring for 1H at 50° C., the solvent was evaporated and the residue was purified by preparative HPLC. (C18 reversed phase column, elution with a water (0.1% trifluoracetic acid)/acetonitrile gradient) Yield: 10 mg.
MS(ES+): m/e=510
LC/MS Retention time [min]=0.93

EXAMPLE 31

2-Cyclohexylamino-N-[5-(4,4-dimethyl-2,5-dioxo-3-pyridin-4-ylmethyl-imidazolidin-1-yl)-2-trifluoromethoxy-phenyl]-acetamide trifluoroacetate The title compound was prepared as described for example 2 using 200 mg (0.43 mmol) N-[5-(4,4-Dimethyl-2,5-dioxo-3-pyridin-4-ylmethyl-imidazolidin-1-yl)-2-trifluoromethoxy-phenyl]-2-chloro-acetamide and 1 ml cyclohexylamine. Yield: 90 mg.
MS(ES+): m/e=534
LC/MS Retention time [min]=1.09

EXAMPLE 32

2-Cyclopropylamino-N-[5-(4,4-dimethyl-2,5-dioxo-3-pyridin-4-ylmethyl-imidazolidin-1-yl)-2-trifluoromethoxy-phenyl]-acetamide trifluoroacetate The title compound was prepared as described for example 2 using 250 mg (0.53 mmol) N-[5-(4,4-Dimethyl-2,5-dioxo-3-pyridin-4-ylmethyl-imidazolidin-1-yl)-2-trifluoromethoxy-phenyl]-2-chloro-acetamide, 1 ml cyclopropylamin and 1 ml DMF. Yield: 85 mg
MS(ES+): m/e=492
LC/MS Retention time [min]=0.89

EXAMPLE 33a

N-[5-(4,4-Dimethyl-2,5-dioxo-3-pyridin-4-ylmethyl-imidazolidin-1-yl)-2-trifluoromethoxy-phenyl]-acrylamide 1000 mg (2.54 mmol) 3-(3-amino-4-trifluormethoxy-phenyl)-5,5-dimethyl-1-pyridin-4-ylmethyl-imidazolidine-2,4-dione were dissolved in 25 ml 1,2-dichloroethane. The mixture was cooled to −20° C. and treated with a solution of 272 mg (3.00 mmol) acrylic acid chloride in 5 ml 1,2-dichloroethane. The mixture was allowed to reach RT, and then evapoarted to dryness. The raw material was used without further purification.
MS(ES+): m/e=

EXAMPLE 33b

33b N-[5-(4,4-Dimethyl-2,5-dioxo-3-pyridin-4-ylmethyl-imidazolidin-1-yl)-2-trifluoromethoxy-phenyl]-3-morpholin-4-yl-propionamide trifluoroacetate 50 mg N-[5-(4,4-Dimethyl-2,5-dioxo-3-pyridin-4-ylmethyl-imidazolidin-1-yl)-2-trifluoromethoxy-phenyl]-acrylamide (raw material, as described above) were dissolved in 1 ml morpholine stirred at RT for 1 h. Subsequently, the mixture was poured on ice and extracted with ethylacetate. The combined organic phases were evaporated to dryness and the residue was purified by by preparative HPLC. (C18 reversedd phase column, elution with a water (0.1% trifluoracetic acid)/acetonitrile gradient) Yield: 13.5 mg
MS(ES+): m/e=536
LC/MS Retention time [min]=0.93

EXAMPLE 34

N-[5-(4,4-Dimethyl-2,5-dioxo-3-pyridin-4-ylmethyl-imidazolidin-1-yl)-2-trifluoromethoxy-phenyl]-3-(dimethyl-morpholin-4-yl)-propionamide trifluoroacetate The title compound was prepared as described for example 33b using 1 ml 2,6-dimethylmorpholine. Yield: 57 mg
MS(ES+): m/e=564
LC/MS Retention time [min]=1.05

EXAMPLE 35

N-[5-(4,4-Dimethyl-2,5-dioxo-3-pyridin-4-ylmethyl-imidazolidin-1-yl)-2-trifluoromethoxy-phenyl]-3-(4-methyl-piperazin-1-yl)-propionamide trifluoroacetate The title compound was prepared as described for example 33b using 200 mg N-[5-(4,4-Dimethyl-2,5-dioxo-3-pyridin-4-ylmethyl-imidazolidin-1-yl)-2-trifluoromethoxy-phenyl]-acrylamide (raw material, as described above) and 1 ml N-methylpiperazine. Yield: 85 mg
MS(ES+): m/e=549
LC/MS Retention time [min]=0.82

EXAMPLE 36

N-[5-(4,4-Dimethyl-2,5-dioxo-3-pyridin-4-ylmethyl-imidazolidin-1-yl)-2-trifluoromethoxy-phenyl]-3-piperidin-1-yl-propionamide trifluoroacetate The title compound was prepared as described for example 35 using 1 ml piperidine. Yield: 118 mg
MS(ES+): m/e=534
LC/MS Retention time [min]=0.99

EXAMPLE 37

N-[5-(4,4-Dimethyl-2,5-dioxo-3-pyridin-4-ylmethyl-imidazolidin-1-yl)-2-trifluoromethoxy-phenyl]-3-thiomorpholin-4-yl-propionamide trifluoroacetate The title compound was prepared as described for example 35 using 1 ml thiomorpholine. Yield: 105 mg
MS(ES+): m/e=552
LC/MS Retention time [min]=1.02

EXAMPLE 38

N-[5-(4,4-Dimethyl-2,5-dioxo-3-pyridin-4-ylmethyl-imidazolidin-1-yl)-2-trifluoromethoxy-phenyl]-3-pyrrolidin-1-yl-propionamide trifluoroacetate The title compound was prepared as described for example 35 using 1 ml pyrrolidine. Yield: 100 mg
MS(ES+): m/e=520
LC/MS Retention time [min]=0.98

EXAMPLE 39

3-Cyclopentylamino-N-[5-(4,4-dimethyl-2,5-dioxo-3-pyridin-4-ylmethyl-imidazolidin-1-yl)-2-trifluoromethoxy-phenyl]-propionamide trifluoroacetate The title compound was prepared as described for example 35 using 1 ml cyclopentylamine. Yield: 65 mg MS(ES+): m/e=534
LC/MS Retention time [min]=1.08

EXAMPLE 40

N-[5-(4,4-Dimethyl-2,5-dioxo-3-pyridin-4-ylmethyl-imidazolidin-1-yl)-2-trifluoromethoxy-phenyl]-3-(2,2-trifluoro-ethylamino)-propionamide; Compound with Trifluoro-Acetic Acid The title compound was prepared as described for example 35 using 1 ml trifluorethylamine. Yield: 49 mg MS(ES+): m/e=548
LC/MS Retention time [min]=1.02

EXAMPLE 41

3-Diethylamino-N-[5-(4,4-dimethyl-2,5-dioxo-3-pyridin-4-ylmethyl-imidazolidin-1-yl)-2-trifluoromethoxy-phenyl]-propionamide trifluoroacetate The title compound was prepared as described for example 35 using 1 ml diethylamine. Yield: 75 mg MS(ES+): m/e=522
LC/MS Retention time [min]=1.00

EXAMPLE 42a 4-isopropyl-3-nitroaniline 25 g (185 mmol) 4-isopropyl-aniline were dissolved in to 260 ml conc. sulfuric acid and treated at −5° C. with 17.9 g nitric acid (65%). After stirring the mixture at 0° C. for 0.5 h, the reaction mixture was poured on ice water and the precipitating product collected via filtration and dried. The resulting 23.8 g product were essentially pure and were used for the subsequent step without further purification.

MS(ES+): m/e=181
LC/MS Retention time [min]=1.96

EXAMPLE 42b 5,5-Dimethyl-3-(3-nitro-4-isopropylphenyl)-1-pyridin-4-ylmethyl-imidazolidine-2,4-dione 6.04 g (30 mmol) diphosgene in 50 ml 1,2-dichlorethane were treated at −20° C. with a solution of 2 g (11.1 mmol) 3-nitro-4-isopropyl-aniline in 20 ml 1,2-dichlorethane. The mixture was allowed to come to room temperature and then was heated to 50° C. for 5 h. After standing over night, the solvent was evaporated and the residual oil was taken up in 40 ml THF. 3.93 g (18.7 mmol) 2-methyl-2-[(pyridin-4-ylmethyl)-amino]-propionic acid methyl ester in 30 ml THF were added and the mixture was refluxed for 6 h. The solvent was evaporated and the residue taken up in ethylacetate and washed with water. THe organic phase was dried, the solvent evaporated and the residue was purified by preparative HPLC. (C18 reversed phase column, elution with a water (0.1% trifluoracetic acid)/acetonitrile gradient) Yield: 2.7 g.

MS(ES+): m/e=441
LC/MS Retention time [min]=1.67

EXAMPLE 42c 3-(3-amino-4-isopropyl-phenyl)-5,5-dimethyl-1-pyridin-4-ylmethyl-imidazolidine-2,4-dione 2.64 g (6.90 mmol) 5,5-dimethyl-3-(3-nitro-4-isopropyl-phenyl)-1-pyridin-4-ylmethyl-imidazolidine-2,4-dione were dissolved in 50 ml acetic acid. 7.22 g zinc dust were added in portions while temperature was kept below 45° C. The mixture was stirred for 1 h at RT, then diluted with 100 ml water, made alkaline with 6N sodium hydroxide solution and extracted with methylene chloride. Separating zinc salts were removed by filtration over cellite. Evaporation of the combined organic phases yielded 1.53 g product that were used without further purification.

MS(ES+): m/e=353
LC/MS Retention time [min]=0.91

EXAMPLE 42d

N-[5-(4,4-Dimethyl-2,5-dioxo-3-pyridin-4-ylmethyl-imidazolidin-1-yl)-2-isopropyl-phenyl]-2-chloro-acetamide 1.37 mg (3.89 mmol) 3-(3-amino-4-isopropyl-phenyl)-5,5-dimethyl-1-pyridin-4-ylmethyl-imidazolidine-2,4-dione and 528 mg (4.08 mmol) Hünig's base were dissolved in 50 ml 1,2-dichloroethane. The mixture was cooled to −20° C. and treated with a solution of 439 mg (3.89 mmol) chloroacetylchlorid in 20 ml 1,2-dichloroethane. After stirring 1 h at 0° C., 25 ml ethanolic hydrochloric acid were added and the mixture evaporated to dryness. The raw material, containing huening's base hydrochloride was used without further purification.

EXAMPLE 42e

N-[5-(4,4-Dimethyl-2,5-dioxo-3-pyridin-4-ylmethyl-imidazolidin-1-yl)-2-isopropyl-phenyl]-2-morpholin-4-yl-acetamide trifluoroacetate The title compound was prepared as described for example 2 using 150 mg N-[5-(4,4-Dimethyl-2,5-dioxo-3-pyridin-4-ylmethyl-imidazolidin-1-yl)-2-isopropyl-phenyl]-2-chloro-acetamide (raw material as described above) and 1 ml of the appropriate amine. The raw material was purified by preparative HPLC. (C18 reversed phase column, elution with a water (0.1% trifluoracetic acid)/acetonitrile gradient)

Yield: 70 mg
MS(ES+): m/e=480
LC/MS Retention time [min]=0.95

EXAMPLE 43

N-[5-(4,4-Dimethyl-2,5-dioxo-3-pyridin-4-ylmethyl-imidazolidin-1-yl)-2-isopropyl-phenyl]-2-piperidin-1-yl-acetamide trifluoroacetate The title compound was prepared as described for example 2 using 150 mg N-[5-(4,4-Dimethyl-2,5-dioxo-3-pyridin-4-ylmethyl-imidazolidin-1-yl)-2-isopropyl-phenyl]-2-chloro-acetamide (raw material as described above) (raw amterial as described above) and 1 ml of the appropriate amine. The raw material was purified by preparative HPLC. (C18 reversed phase column, elution with a water (0.1% trifluoracetic acid)/acetonitrile gradient) Yield: 80 mg
MS(ES+): m/e=478
LC/MS Retention time [min]=0.96

EXAMPLE 44

N-[5-(4,4-Dimethyl-2,5-dioxo-3-pyridin-4-ylmethyl-imidazolidin-1-yl)-2-isopropyl-phenyl]-2-(4-methyl-piperazin-1-yl)-acetamide trifluoroacetate The title compound was prepared as described for example 2 using 150 mg N-[5-(4,4-Dimethyl-2,5-dioxo-3-pyridin-4-ylmethyl-imidazolidin-1-yl)-2-isopropyl-phenyl]-2-chloro-acetamide (raw material as described above) and 1 ml of the appropriate amine. The raw material was purified by preparative HPLC. (C18 reversed phase column, elution with a water (0.1% trifluoracetic acid) /acetonitrile gradient)
Yield: 30 mg
MS(ES+): m/e=491
LC/MS Retention time [min]=0.94

EXAMPLE 45

2-Dimethylamino-N-[5-(4,4-dimethyl-2,5-dioxo-3-pyridin-4-ylmethyl-imidazolidin-1-yl)-2-isopropyl-phenyl]-acetamide trifluoroacetate The title compound was prepared as described for example 2 using 150 mg N-[5-(4,4-Dimethyl-2,5-dioxo-3-pyridin-4-ylmethyl-imidazolidin-1-yl)-2-isopropyl-phenyl]-2-chloro-acetamide (raw material as described above) and 1 ml of a 2 m solution of dimethylamine in DMF. The raw material was purified by preparative HPLC. (C18 reversed phase column, elution with a water (0.1% trifluoracetic acid)/acetonitrile gradient) Yield: 25 mg
MS(ES+): m/e=438
LC/MS Retention time [min]=0.98

EXAMPLE 46

2-Diethylamino-N-[5-(4,4-dimethyl-2,5-dioxo-3-pyridin-4-ylmethyl-imidazolidin-1-yl)-2-isopropyl-phenyl]-acetamide trifluoroacetate The title compound was prepared as described for example 2 using 150 mg N-[5-(4,4-Dimethyl-2,5-dioxo-3-pyridin-4-ylmethyl-imidazolidin-1-yl)-2-isopropyl-phenyl]-2-chloro-acetamide (raw material as described above) and 1 ml of the appropriate amine. The raw material was purified by preparative HPLC. (C18 reversed phase column, elution with a water (0.1% trifluoracetic acid)/acetonitrile gradient)
Yield: 65 mg
MS(ES+): m/e=466
LC/MS Retention time [min]=1.00

EXAMPLE 47

2-tert-Butylamino-N-[5-(4,4-dimethyl-2,5-dioxo-3-pyridin-4-ylmethyl-imidazolidin-1-yl)-2-isopropyl-phenyl]-acetamide trifluoroacetate The title compound was prepared as described for example 2 using 150 mg N-[5-(4,4-Dimethyl-2,5-dioxo-3-pyridin-4-ylmethyl-imidazolidin-1-yl)-2-isopropyl-phenyl]-2-chloro-acetamide (raw material as described above) and 1 ml of the appropriate amine. The raw material was purified by preparative HPLC. (C18 reversed phase column, elution with a water (0.1% trifluoracetic acid)/acetonitrile gradient)
Yield: 50 mg
MS(ES+): m/e=466
LC/MS Retention time [min]=0.91

EXAMPLE 48

2-Cyclopentylamino-N-[5-(4,4-dimethyl-2,5-dioxo-3-pyridin-4-ylmethyl-imidazolidin-1-yl)-2-isopropyl-phenyl]-acetamide trifluoroacetate The title compound was prepared as described for example 2 using 150 mg N-[5-(4,4-Dimethyl-2,5-dioxo-3-pyridin-4-ylmethyl-imidazolidin-1-yl)-2-isopropyl-phenyl]-2-chloro-acetamide (raw material as described above) and 1 ml of the appropriate amine. The raw material was purified by preparative HPLC. (C18 reversed phase column, elution with a water (0.1% trifluoracetic acid)/acetonitrile gradient)
Yield: 50 mg
MS(ES+): m/e=478
LC/MS Retention time [min]=1.08

EXAMPLE 49

1-Methyl-piperidine-4-carboxylic acid [5-(4,4-dimethyl-2,5-dioxo-3-pyridin-4-ylmethyl-imidazolidin-1-yl)-2-trifluoromethoxy-phenyl]-amide, trifluoroacetate 48 mg (0.26 mmol) 1-methyl-piperidine-4-carboxylic acid hydrochloride were dissolved in 5 ml thionyl chloride and heated to reflux for 30 min. The excess thionyl choride was removed by evaporation and the resulting acid chloride dissolved in 5 ml methylene chloride. This solution was added to a solution of 100 mg (0.25 mmol) 3-(3-amino-4-trifluormethoxy-phenyl)-5,5-dimethyl-1-pyridin-4-ylmethyl-imidazolidine-2,4-dione and 111 mg (0.68 mmol) huenig's base and the mixture was stirred overnight at RT and heated to reflux for 1 h. The mixture was poured on saturated sodium bicarbonate solution, extracted with ethylacetate, then dried and evaporated. The residue was was purified by preparative HPLC. (C18 reversed phase column, elution with a water (0.1% trifluoracetic acid)/acetonitrile gradient)
Yield: 10 mg
MS(ES+): m/e=520
LC/MS Retention time [min]=0.86

EXAMPLE 50

1-Methyl-piperidine-3-carboxylic acid [5-(4,4-dimethyl-2,5-dioxo-3-pyridin-4-ylmethyl-imidazolidin-1-yl)-2-trifluoromethoxy-phenyl]-amide; compound with trifluoro-acetic acid 270 mg (1.50 mmol) 1-methyl-piperidine-3-carboxylic acid hydrochloride were suspended in 20 ml methylene chloride, 216 mg (1.70 mmol) oxalyl chloride follwoed by 11 mg DMF were added and the mixture stirred at RT for 15 h. The solvent was removed by evaporation. To 30 mg (0.15 mmol) of the resulting acid chloride hydrochloride were given a solution of 39 mg (0.10 mmol) 3-(3-amino-4-trifluormethoxy-phenyl)-5,5-dimethyl-1-pyridin-4-ylmethyl-imidazolidine-2,4-dione and 12 mg (0.10 mmol) DMAP in 3 ml methylene chloride. After stirring for 2 h at RT, the mixture was poured on diluted sodium bicarbonate solution, extracted with methylene chloride, then dried and evaporated. The residue was was purified by preparative HPLC. (C18 reversed phase column, elution with a water (0.1% trifluoracetic acid)/ acetonitrile gradient) Yield: 8 mg MS(ES+): m/e=520

LC/MS Retention time [min]=0.92

EXAMPLE 51a 2-(2,2-Diethoxy-ethoxy)-1-methoxy-4-nitro-benzene

A suspension of 7.50 g 2-methoxy-5-nitro-phenol, 9.61 g 2-bromo-1,1-diethoxy-ethane and 15.89 g cesium carbonate in 75 ml N,N-dimethylformamide was stirred at 100° C. for 4 hours. After cooling to room temperature the reaction mixture was treated with an aqueous 1% solution of sodium hydroxide and extracted twice with ethyl acetate. The organic layer was dried over anhydrous sodium sulfate. After filtration and concentration of the solvent under reduced pressure the residue was dissolved in a mixture of ethyl acetate and n-heptane. After removal of the ethyl acetate under reduced pressure the resulting residue was filtered off and the clear solution concentrated under reduced pressure. The residue was directly subjected to the subsequent reaction without further purification. Yield: 9.45 g MS(ES+): m/e=–

1H-NMR (250 MHz, DMSO/TMS): d=7.92 (d, 1H); 7.82 (s, 1H); 7.19 (d, 1H); 4.83 (t, 1H); 4.08 (d, 2H); 3.90 (s, 3H); 3.62 (m, 4H); 1.13 (t, 6H)

EXAMPLE 51a 3-(2,2-Diethoxy-ethoxy)-4-methoxy-phenylamine

A mixture of 10.70 g 2-(2,2-diethoxy-ethoxy)-1-methoxy-4-nitro-benzene and 1.20 g of 10% palladium on carbon in 150 ml methanol was stirred for 2 hours under hydrogen atmosphere. The reaction mixture was filtered through a chem elut cartridge and the compound eluted with additional methanol. After contration under reduced pressure the residue was directly subjected to the subsequent reaction without further purification.

Yield: 7.90 g

1H-NMR (400 MHz,DMSO/TMS): d=6.65 (d, 1H); 6.28 (d, 1H); 6.09 (dd, 1H); 4.77 (t, 1H); 4.66 (s, 2H); 3.83 (d, 2H); 3.62 (m, 7H); 1.14 (t, 6H)

EXAMPLE 51c

3-[3-(2,2-Diethoxy-ethoxy)-4-methoxy-phenyl]-5,5-dimethyl-1-quinolin-4-ylmethyl-imidazolidine-2,4-dione To a solution of 317 mg di-imidazol-1-yl-methanone and 20 mg imidazole in 4 ml tetrahydrofuran a solution of 500 mg 3-(2,2-diethoxy-ethoxy)-4-methoxy-phenylamine in 2 ml tetrahydrofuran was slowly added at 0° C. After stirring at 0° C. for 1 hour 505 mg 2-methyl-2-[(quinolin-4-ylmethyl)-amino]-propionic acid methyl ester were added and the reaction mixture was allowed to warm up to room temperature. After 2 hours stirring at room temperature the solution was heated for 2 hours at 70° C. After cooling to room temperature the solvent of the mixture was removed under reduced pressure and the residue was purified by preparative HPLC (C18 reverse phase column, elution with a water/acetonitrile gradient with 0.1% trifluoracetic acid). Lyophilization of the solution yielded a white solid. Yield: 300 mg MS(ES+): m/e=508

1H-NMR (400 MHz, DMSO/TMS): d=8.88 (d, 1H); 8.27 (d, 1H); 8.08 (d, 1H); 7.83 (t, 1H); 7.70 (t, 1H); 7.59 (d, 1H); 7.16 (s, 1H); 7.09 (d, 1H); 7.03 (d, 1H); 5.13 (s, 2H); 4.84 (t, 1H); 3.95 (d, 2H); 3.82 (s, 3H); 3.69 (m, 2H); 3.56 (m, 2H); 1.43 (s, 6H); 1.15 (t, 6H)

EXAMPLE 51d

[5-(4,4-Dimethyl-2,5-dioxo-3-quinolin-4-ylmethyl-imidazolidin-1-yl)-2-methoxy-phenoxy]-acetaldehyde 410 mg 3-[3-(2,2-Diethoxy-ethoxy)-4-methoxy-phenyl]-5,5-dimethyl-1-quinolin-4-ylmethyl-imidazolidine-2,4-dione were dissolved in 8 ml 1,4-dioxane and 2.05 ml of an aqueous 1 N solution of hydrochloric acid were added. The mixture was stirred for 2 hours at 80° C. Removal of the solvent under reduced pressure yielded a white solid, which was coevaporated twice with toluene. Yield: 340 mg MS(ES+): m/e=434

1H-NMR (400 MHz, DMSO/TMS): d=9.70 (s, 1H); 9.15 (d, 1H); 8.50 (d, 1H); 8.35 (d, 1H); 8.10 (t, 1H); 8.02 (d, 1H); 7.95 (t, 1H); 7.10 (m, 3H); 5.33 (s, 2H); 4.82 (s, 2H); 3.84 (s, 3H); 1.48 (s, 6H)

EXAMPLE 51e

3-[4-Methoxy-3-(2-morpholin-4-yl-ethoxy)-phenyl]-5,5-dimethyl-1-quinolin-4-ylmethyl-imidazolidine-2,4-dione A solution of 20 mg [5-(4,4-dimethyl-2,5-dioxo-3-quinolin-4-ylmethyl-imidazolidin-1-yl)-2-methoxy-phenoxy]-acetaldehyde in 1 ml 1,2-dichloroethane was treated with 8.02 mg morpholine and 14.62 mg sodium triacetoxyborohydride. After stirring of the reaction mixture for 16 hours the solvent was removed under reduced pressure. The residue was purified by preparative HPLC (C18 reverse phase column, elution with a water/acetonitrile gradient with 0.1% trifluoroacetic acid). Lyophilization of the solution yielded a white solid. The product was obtained as its trifluoroacetate salt.

Yield: 8.6 mg

MS(ES+): m/e=505

1H-NMR (500 MHz, DMSO/TMS): d=9.98 (s, 1H); 8.89 (d, 1H); 8.37 (d, 1H); 8.09 (d, 1H); 7.84 (t, 1H); 7.72 (t, 1H); 7.63 (d, 1H); 7.15 (m, 3H); 5.15 (s, 2H); 4.35 (t, 2H); 4.03 (m, 2H); 3.85 (s, 3H); 3.73 (m, 2H); 1.44 (s, 6H)

EXAMPLE 52

3-[4-Methoxy-3-(2-morpholin-4-yl-ethoxy)-phenyl]-5,5-dimethyl-1-quinolin-4-ylmethyl-imidazolidine-2,4-dione The following compounds were prepared in analogy to example 51e by using 70 mg [5-(4,4-dimethyl-2,5-dioxo-3-quinolin-4-ylmethyl-imidazolidin-1-yl)-2-methoxy-phenoxy]-acetaldehyde as starting material and the corresponding amines instead of morpholine.

The product was obtained as its trifluoroacetate salt.

Yield: 44 mg

MS(ES+): m/e=503

1H-NMR (500 MHz, DMSO/TMS): d=9.31 (s, 1H); 8.94 (d, 1H); 8.32 (d, 1H); 8.12 (d, 1H); 7.88 (t, 1H); 7.75 (t, 1H); 7.68 (d, 1H); 7.15 (m, 3H); 5.18 (s, 2H); 4.32 (t, 2H); 3.85 (s, 3H); 3.06 (m, 2H); 1.85 (m, 2H); 1.69 (m, 4H); 1.45 (s, 6H)

EXAMPLE 53

3-{4-Methoxy-3-[2-(4-methyl-piperazin-1-yl)-ethoxy]-phenyl}-5,5-dimethyl-1-quinolin-4-ylmethyl-imidazolidine-2,4-dione Yield: 50 mg
MS(ES+): m/e=518
1H-NMR (500 MHz, DMSO/TMS): d=8.93 (d, 1H); 8.32 (d, 1H); 8.12 (d, 1H); 7.88 (t, 1H); 7.75 (t, 1H); 7.68 (d, 1H); 7.10 (m, 3H); 5.16 (s, 2H); 4.15 (m, 2H); 3.82 (s, 3H); 3.05 (m, 2H); 2.78 (s, 3H); 1.44 (s, 6H)

EXAMPLE 54

3-{4-Methoxy-3-[2-(2-methoxy-ethylamino)-ethoxy]-phenyl}-5,5-dimethyl-1-quinolin-4-ylmethyl-imidazolidine-2,4-dione The product was obtained as its trifluoroacetate salt.
Yield: 23.4 mg
MS(ES+): m/e=493
1H-NMR (500 MHz, DMSO/TMS): d=8.92 (d, 1H); 8.73 (m, 2H); 8.29 (d, 1H); 8.10 (d, 1H); 7.85 (t, 1H); 7.73 (t, 1H); 7.64 (d, 1H); 7.15 (m, 3H); 5.15 (s, 2H); 4.25 (t, 2H); 3.84 (s, 3H); 3.40 (m, 2H); 3.33 (s, 3H); 3.28 (m, 2H); 1.44 (s, 6H)

EXAMPLE 55

3-[3-(2-Cyclopentylamino-ethoxy)-4-methoxy-phenyl]-5,5-dimethyl-1-quinolin-4-ylmethyl-imidazolidine-2,4-dione The product was obtained as its trifluoroacetate salt.
Yield: 53.2 mg
MS(ES+): m/e=503
1H-NMR (500 MHz, DMSO/TMS): d=8.92 (d, 1H); 8.70 (m, 2H); 8.29 (d, 1H); 8.10 (d, 1H); 7.85 (t, 1H); 7.73 (t, 1H); 7.64 (d, 1H); 7.15 (m, 3H); 5.16 (s, 2H); 4.23 (t, 2H); 3.85 (s, 3H); 3.37 (m, 2H); 2.02 (m, 2H); 1.72 (m, 2H); 1.58 (m, 4H); 1.44 (s, 6H)

EXAMPLE 56

3-(4-Methoxy-3-{2-[(5-methyl-isoxazol-3-ylmethyl)-amino]-ethoxy}-phenyl)-5,5-dimethyl-1-quinolin-4-ylmethyl-imidazolidine-2,4-dione The product was obtained as its trifluoroacetate salt.
Yield: 60.1 mg
MS(ES+): m/e=530
1H-NMR (500 MHz, DMSO/TMS): d=9.43 (m, 2H); 8.90 (d, 1H); 8.30 (d, 1H); 8.10 (d, 1H); 8.85 (t, 1H); 7.73 (t, 1H); 7.64 (d, 1H); 7.15 (m, 3H); 6.42 (s, 1H); 5.16 (s, 2H); 4.44 (s, 2H); 4.28 (t, 2H); 3.85 (s, 3H); 2.45 (s, 3H); 1.44 (s, 6H)

EXAMPLE 57

3-(3-{2-[(Furan-2-ylmethyl)-amino]-ethoxy}-4-methoxy-phenyl)-5,5-dimethyl-1-quinolin-4-ylmethyl-imidazolidine-2,4-dione The product was obtained as its trifluoroacetate salt.
Yield: 17.6 mg
MS(ES+): m/e=515
1H-NMR (500 MHz, DMSO/TMS): d=9.23 (m, 2H); 8.91 (d, 1H); 8.29 (d, 1H); 8.10 (d, 1H); 7.85 (t, 1H); 7.83 (dd, 1H); 7.73 (t, 1H); 7.64 (d, 1H); 7.15 (m, 3H); 6.68 (d, 1H); 6.55 (dd, 1H); 5.16 (s, 2H); 4.39 (m, 2H); 4.24 (t, 2H); 3.85 (s, 3H); 1.44 (s, 6H)

EXAMPLE 58

3-(4-Methoxy-3-{2-[(5-methyl-pyrazin-2-ylmethyl)-amino]-ethoxy}-phenyl)-5,5-dimethyl-1-quinolin-4-ylmethyl-imidazolidine-2,4-dione The product was obtained as its trifluoroacetate salt.
Yield: 27.5 mg
MS(ES+): m/e=541
1H-NMR (500 MHz, DMSO/TMS): d=9.33 (m, 2H); 8.93 (d, 1H); 8.67 (s, 1H); 8.63 (s, 1H); 8.29 (d, 1H); 8.11 (d, 1H); 7.87 (t, 1H); 7.75 (t, 1H); 7.66 (d, 1H); 7.15 (m, 3H); 5.16 (s, 2H); 4.52 (m, 2H); 4.30 (t, 2H); 3.85 (s, 3H); 2.55 (s, 3H); 1.44 (s, 6H)

EXAMPLE 59

3-{4-Methoxy-3-[2-(2-morpholin-4-yl-ethylamino)-ethoxy]-phenyl}-5,5-dimethyl-1-quinolin-4-ylmethyl-imidazolidine-2,4-dione The following compounds were prepared in analogy to example 51e by using 80 mg [5-(4,4-dimethyl-2,5-dioxo-3-quinolin-4-ylmethyl-imidazolidin-1-yl)-2-methoxy-phenoxy]-acetaldehyde as starting material and the corresponding amines instead of morpholine.
Yield: 14.4 mg
MS(ES+): m/e=548
1H-NMR (500 MHz, DMSO/TMS): d=8.91 (d, 1H); 8.29 (d, 1H); 8.11 (d, 1H); 7.85 (t, 1H); 7.73 (t, 1H); 7.63 (d, 1H); 7.15 (m, 3H); 5.16 (s, 2H); 4.26 (t, 2H); 3.85 (s, 3H); 1.44 (s, 6H)

EXAMPLE 60

3-{4-Methoxy-3-[2-(2-pyridin-4-yl-ethylamino)-ethoxy]-phenyl}-5,5-dimethyl-1-quinolin-4-ylmethyl-imidazolidine-2,4-dione The product was obtained as its trifluoroacetate salt.
Yield: 26.2 mg
MS(ES+): m/e=540
1H-NMR (500 MHz, DMSO/TMS): d=8.93 (d, 1H); 8.86 (m, 2H); 8.68 (d, 2H); 8.30 (d, 1H); 8.11 (d, 1H); 7.85 (t, 1H); 7.74 (t, 1H); 7.65 (d, 1H); 7.55 (d, 2H); 7.15 (m, 3H); 5.16 (s, 2H); 4.26 (t, 2H); 3.80 (s, 3H); 3.10 (t, 2H); 1.44 (s, 6H)

EXAMPLE 61

3-[4-Methoxy-3-(2-pyrrolidin-1-yl-ethoxy)-phenyl]-5,5-dimethyl-1-quinolin-4-ylmethyl-imidazolidine-2,4-dione The product was obtained as its trifluoroacetate salt.
Yield: 42.5 mg
MS(ES+): m/e=489
1H-NMR (500 MHz, DMSO/TMS): d=10.05 (s, 1H); 8.91 (d, 1H); 8.70 (s, 1H); 8.28 (d, 1H); 8.10 (d, 1H); 7.85 (t, 1H); 7.72 (t, 1H); 7.64 (d, 1H); 7.15 (m, 3H); 5.15 (s, 2H); 4.29 (t, 2H); 3.85 (s, 3H); 3.20-3.05 (m, 6H); 2.10-1.80 (m, 4H); 1.44 (s, 6H)

EXAMPLE 62

3-{3-[2-(2-Hydroxy-ethylamino)-ethoxy]-4-methoxy-phenyl}-5,5-dimethyl-1-quinolin-4-ylmethyl-imidazolidine-2,4-dione Yield: 10.3 mg
MS(ES+): m/e=479
1H-NMR (500 MHz, DMSO/TMS): d=8.90 (d, 1H); 8.65 (m, 2H); 8.29 (d, 1H); 8.10 (d, 1H); 7.85 (t, 1H); 7.73 (t, 1H); 7.63 (d, 1H); 7.15 (m, 3H); 5.15 (s, 2H); 4.25 (t, 2H); 3.83 (s, 3H); 3.70 (t, 2H); 3.41 (m, 2H); 3.15 (m, 2H); 1.44 (s, 6H)

EXAMPLE 63

3-[3-(2-Ethylamino-ethoxy)-4-methoxy-phenyl]-5,5-dimethyl-1-quinolin-4-ylmethyl-imidazolidine-2,4-dione Yield: 18.1 mg
MS(ES+): m/e=463
1H-NMR (500 MHz, DMSO/TMS): d=8.90 (d, 1H); 8.58 (m, 2H); 8.29 (d, 1H); 8.10 (d, 1H); 7.85 (t, 1H); 7.73 (t, 1H); 7.63 (d, 1H); 7.15 (m, 3H); 5.15 (s, 2H); 4.21 (t, 2H); 3.85 (s, 3H); 3.38 (t, 2H); 3.08 (q, 2H); 1.45 (s, 6H); 1.23 (t, 3H)

EXAMPLE 64

3-(4-Methoxy-3-{2-[(pyridin-2-ylmethyl)-amino]-ethoxy}-phenyl)-5,5-dimethyl-1-quinolin-4-ylmethyl-imidazolidine-2,4-dione Yield: 46.7 mg
MS(ES+): m/e=526
1H-NMR (500 MHz, DMSO/TMS): d=9.30 (s, 1H); 8.92 (d, 1H); 8.66 (m, 1H); 8.29 (d, 1H); 8.11 (d, 1H); 7.93 (t, 1H); 7.85 (t, 1H); 7.73 (t, 1H); 7.65 (d, 1H); 7.52 (d, 1H); 7.45 (m, 1H); 7.15 (m, 3H); 5.15 (s, 2H); 4.51 (m, 2H); 4.30 (t, 2H); 3.85 (s, 3H); 3.46 (m, 2H); 1.44 (s, 6H)

EXAMPLE 65

3-(4-Methoxy-3-{2-[(thiazol-2-ylmethyl)-amino]-ethoxy}-phenyl)-5,5-dimethyl-1-quinolin-4-ylmethyl-imidazolidine-2,4-dione Yield: 37.8 mg
MS(ES+): m/e=532
1H-NMR (500 MHz, DMSO/TMS): d=9.55 (s, 1H); 8.90 (d, 1H); 8.27 (d, 1H); 8.11 (d, 1H); 7.97 (d, 1H); 7.90 (d, 1H); 7.85 (t, 1H); 7.73 (t, 1H); 7.65 (d, 1H); 7.15 (m, 3H); 5.15 (s, 2H); 4.77 (m, 2H); 4.29 (t, 2H); 3.85 (s, 3H); 1.44 (s, 6H)

EXAMPLE 66

3-{4-Methoxy-3-[2-(2-pyridin-3-yl-ethylamino)-ethoxy]-phenyl}-5,5-dimethyl-1-quinolin-4-ylmethyl-imidazolidine-2,4-dione Yield: 41.2 mg
MS(ES+): m/e=540
1H-NMR (500 MHz, DMSO/TMS): d=8.92 (d, 1H); 8.82 (s, 2H); 8.59 (m, 2H); 8.29 (d, 1H); 8.11 (d, 1H); 7.88 (m, 2H); 7.75 (t, 1H); 7.65 (d, 1H); 7.55 (m, 1H); 7.15 (m, 3H); 5.17 (s, 2H); 4.26 (t, 2H); 3.81 (s, 3H); 3.42 (m, 4H); 3.05 (m, 2H); 1.44 (s, 6H)

EXAMPLE 67

3-(4-Methoxy-3-{2-[(pyridin-4-ylmethyl)-amino]-ethoxy}-phenyl)-5,5-dimethyl-1-quinolin-4-ylmethyl-imidazolidine-2,4-dione Yield: 39.8 mg
MS(ES+): m/e=526
1H-NMR (500 MHz, DMSO/TMS): d=9.28 (s, 2H); 8.93 (d, 1H); 8.71 (d, 2H); 8.31 (d, 1H); 8.12 (d, 1H); 7.87 (t, 1H); 7.75 (t, 1H); 7.68 (d, 1H); 7.59 (d, 2H); 7.15 (m, 3H); 5.18 (s, 2H); 4.40 (m, 2H); 4.27 (t, 2H); 3.85 (s, 3H); 3.43 (m, 2H); 1.44 (s, 6H)

EXAMPLE 68

3-{4-Methoxy-3-[2-(tetrahydro-pyran-4-ylamino)-ethoxy]-phenyl}-5,5-dimethyl-1-quinolin-4-ylmethyl-imidazolidine-2,4-dione Yield: 42.6 mg
MS(ES+): m/e=519
1H-NMR (500 MHz, DMSO/TMS): d=8.90 (d, 1H); 8.75 (s, 2H); 8.29 (d, 1H); 8.11 (d, 1H); 7.85 (t, 1H); 7.73 (t, 1H); 7.64 (d, 1H); 7.15 (m, 3H); 5.15 (s, 2H); 4.25 (t, 2H); 3.93 (m, 2H); 3.85 (s, 3H); 3.43 (m, 2H); 3.32 (t, 2H); 2.00 (m, 2H); 1.56 (m, 2H); 1.44 (s, 6H)

EXAMPLE 69

3-{3-[2-(2-Hydroxy-1-phenyl-ethylamino)-ethoxy]-4-methoxy-phenyl}-5,5-dimethyl-1-quinolin-4-ylmethyl-imidazolidine-2,4-dione Yield: 15.2 mg
MS(ES+): m/e=555
1H-NMR (500 MHz, DMSO/TMS): d=9.19 (s, 2H); 8.90 (d, 1H); 8.28 (d, 1H); 8.11 (d, 1H); 7.85 (t, 1H); 7.73 (t, 1H); 7.65 (d, 1H); 7.58 (d, 2H); 7.46 (m, 3H); 7.15 (m, 3H); 5.70 (s, 1H); 5.15 (s, 2H); 4.54 (m, 1H); 4.25 (t, 2H); 3.85 (s, 3H); 3.28 (m, 2H); 3.17 (m, 2H); 1.43 (s, 6H)

EXAMPLE 70

3-{4-Methoxy-3-[2-(1-methyl-piperidin-4-ylamino)-ethoxy]-phenyl}-5,5-dimethyl-1-quinolin-4-ylmethyl-imidazolidine-2,4-dione The title compound was prepared in analogy to example 51e by using 100 mg [5-(4,4-dimethyl-2,5-dioxo-3-quinolin-4-ylmethyl-imidazolidin-1-yl)-2-methoxy-phenoxy]-acetaldehyde as starting material and 4-amino-1-methylpiperidine instead of morpholine.

Yield: 25.0 mg
MS(ES+): m/e=532
1H-NMR (500 MHz, DMSO/TMS): d=8.87 (d, 1H); 8.25 (d, 1H); 8.08 (d, 1H); 7.82 (t, 1H); 7.69 (t, 1H); 7.59 (d, 1H); 7.12 (s, 1H); 7.07 (d, 1H); 7.02 (dd, 1H); 5.13 (s, 2H); 4.00 (t, 2H); 3.81 (s, 3H); 2.91 (t, 2H); 2.70 (m, 2H); 2.45 (m, 1H); 2.14 (s, 3H); 1.92 (m, 2H); 1.78 (m, 2H); 1.43 (s, 6H); 1.25 (m, 3H)

EXAMPLE 71b

3-{2-[5-(4,4-Dimethyl-2,5-dioxo-3-quinolin-4-ylmethyl-imidazolidin-1-yl)-2-methoxy-phenoxy]-ethylamino}-pyrrolidine-1-carboxylic acid tert-butyl ester The title compound was prepared in analogy to example 51e by using 70 mg [5-(4,4-dimethyl-2,5-dioxo-3-quinolin-4-ylmethyl-imidazolidin-1-yl)-2-methoxy-phenoxy]-acetaldehyde as starting material and 3-amino-pyrrolidine-1-carboxylic acid tert-butyl ester instead of morpholine. The product was obtained as its trifluoroacetate salt. Yield: 44 mg MS(ES+): m/e=604

1H-NMR (500 MHz, DMSO/TMS): d=8.97 (m, 2H); 8.90 (d, 1H); 8.29 (d, 1H); 8.10 (d, 1H); 7.85 (t, 1H); 7.73 (t, 1H); 7.64 (d, 1H); 7.15 (m, 3H); 5.15 (s, 2H); 4.24 (t, 2H); 3.95 (m, 2H); 3.85 (s, 3H); 3.70-3.40 (m, 3H); 3.29 (m, 2H); 2.25 (m, 1H); 2.09 (m, 1H); 1.44 (s, 6H); 1.41 (s, 9H)

EXAMPLE 71a

3-{4-Methoxy-3-[2-(pyrrolidin-3-ylamino)-ethoxy]-phenyl}-5,5-dimethyl-1-quinolin-4-ylmethyl-imidazolidine-2,4-dione A solution of 40 mg 3-{2-[5-(4,4-dimethyl-2,5-dioxo-3-quinolin-4-ylmethyl-imidazolidin-1-yl)-2-methoxy-phenoxy]-ethylamino}-pyrrolidine-1-carboxylic acid tert-butyl ester in 2 ml of a 8 N solution of hydrochloric acid in methanol was stirred for 1 hour at room temperature. After removal of the solvent under reduced pressure the residue was dissolved in a mixture of 2 ml water and 1 ml acetonitrile. Lyophilization of the resulting mixture yielded a white foam. The product was obtained as its hydrochloric salt.

Yield: 25.1 mg

MS(ES+): m/e=504

1H-NMR (500 MHz, DMSO/TMS): d=9.35 (m, 1H); 9.26 (m, 1H); 8.97 (d, 1H); 8.34 (d, 1H); 8.16 (d, 1H); 7.93 (t, 1H); 7.78 (m, 2H); 7.15 (m, 3H); 5.20 (s, 2H); 4.29 (t, 2H); 4.06 (m, 1H); 3.85 (s, 3H); 3.25 (m, 1H); 2.36 (m, 1H); 2.20 (m, 1H); 1.45 (s, 6H)

EXAMPLE 72

3-{3-[2-Hydroxy-3-(tetrahydro-pyran-4-ylamino)-propoxy]-4-methoxy-phenyl}-5,5-dimethyl-1-quinolin-4-ylmethyl-imidazolidine-2,4-dione To a solution of 60.92 mg trimethylsulfoxonium iodide in 1 ml dimethyl sulfoxide 6.64 mg sodium hydride were added at room temperature. After stirring for 10 minutes 100 mg [5-(4,4-dimethyl-2,5-dioxo-3-quinolin-4-ylmethyl-imidazolidin-1-yl)-2-methoxy-phenoxy]-acetaldehyde were added and the mixture stirred for additional 1 hour at room temperature. After concentration under reduced pressure the residue was partitioned between 2 ml ethyl acetate and 2 ml of a saturated aqueous solution of ammonium chloride. The organic layer was dried over sodium sulfate. After filtration the solvent was removed under reduced pressure. The residue was dissolved in 1 ml ethanol and 23.37 mg tetrahydro-pyran-4-ylamine were added. The resulting solution was stirred for 1 hour at 70° C. After cooling to room temperature the solvent of the mixture was removed under reduced pressure and the residue was purified by preparative HPLC (C18 reverse phase column, elution with a water/acetonitrile gradient with 0.1% trifluoroacetic acid). Lyophilization of the solution yielded a white solid. Yield: 12.8 mg MS(ES+): m/e=549

1H-NMR (500 MHz, DMSO/TMS): d=8.90 (d, 1H); 8.55 (m, 2H); 8.29 (d, 1H); 8.10 (d, 1H); 7.85 (t, 1H); 7.73 (t, 1H); 7.64 (d, 1H); 7.08 (m, 3H); 5.93 (m, 1H); 5.15 (s, 2H); 4.18 (m, 1H); 3.95 (m, 4H); 3.83 (s, 3H); 3.20 (m, 1H); 3.06 (m, 1H); 1.95 (m, 2H); 1.59 (m, 2H); 1.43 (s, 6H)

EXAMPLE 73

3-{3-[2-Hydroxy-3-(4-methyl-piperazin-1-yl)-propoxy]-4-methoxy-phenyl}-5,5-dimethyl-1-quinolin-4-ylmethyl-imidazolidine-2,4-dione The following compound was prepared in analogy to example 72 by using 100 mg [5-(4,4-dimethyl-2,5-dioxo-3-quinolin-4-ylmethyl-imidazolidin-1-yl)-2-methoxy-phenoxy]-acetaldehyde as starting material and 1-methyl-piperazine instead of tetrahydro-pyran-4-ylamine. Yield: 7.9 mg MS(ES+): m/e=548

1H-NMR (500 MHz, DMSO/TMS): d=8.92 (d, 1H); 8.29 (d, 1H); 8.11 (d, 1H); 7.85 (t, 1H); 7.73 (t, 1H); 7.65 (d, 1H); 7.10 (m, 3H); 5.15 (s, 2H); 4.15 (s, 1H); 3.95 (d, 2H); 3.82 (s, 3H); 2.75 (m, 2H); 1.43 (s, 6H)

EXAMPLE 74

3-(3-{2-Hydroxy-3-[(pyridin-4-ylmethyl)-amino]-propoxy}-4-methoxy-phenyl)-5,5-dimethyl-1-quinolin-4-ylmethyl-imidazolidine-2,4-dione The following compound was prepared in analogy to example 72 by using 100 mg [5-(4,4-dimethyl-2,5-dioxo-3-quinolin-4-ylmethyl-imidazolidin-1-yl)-2-methoxy-phenoxy]-acetaldehyde as starting material and pyridin-4-yl-methylamine instead of tetrahydro-pyran-4-ylamine. The product was obtained as its trifluoroacetate salt. Yield: 10.2 mg MS(ES+): m/e=556

1H-NMR (500 MHz, DMSO/TMS): d=9.13 (s, 2H); 8.92 (d, 1H); 8.69 (d, 2H); 8.30 (d, 1H); 8.10 (d, 1H); 7.86 (t, 1H); 7.73 (t, 1H); 7.66 (d, 1H); 7.57 (d, 2H); 7.08 (m, 3H); 5.15 (s, 2H); 4.30 (m, 2H); 4.22 (m, 1H); 4.00 (m, 1H); 3.95 (m, 1H); 3.78 (s, 3H); 3.23 (m, 1H); 3.07 (m, 1H); 1.44 (s, 6H)

EXAMPLE 75

3-[3-(2-Hydroxy-3-morpholin-4-yl-propoxy)-4-methoxy-phenyl]-5,5-dimethyl-1-quinolin-4-ylmethyl-imidazolidine-2,4-dione The following compounds were prepared in analogy to example 72 by using the corresponding amines instead of tetrahydro-pyran-4-ylamine.

Yield: 23.4 mg

MS(ES+): m/e=535

1H-NMR (500 MHz, DMSO/TMS): d=8.92 (d, 1H); 8.30 (d, 1H); 8.10 (d, 1H); 7.86 (t, 1H); 7.73 (t, 1H); 7.65 (d, 1H); 7.10 (m, 3H); 6.03 (m, 1H); 5.15 (s, 2H); 4.34 (m, 1H); 3.98 (m, 4H); 3.83 (s, 3H); 3.55-3.12 (m, 8H); 1.44 (s, 6H)

EXAMPLE 76

3-{3-[2-Hydroxy-3-(pyridin-4-ylamino)-propoxy]-4-methoxy-phenyl}-5,5-dimethyl-1-quinolin-4-ylmethyl-imidazolidine-2,4-dione Yield: 20.3 mg MS(ES+): m/e=542

1H-NMR (500 MHz, DMSO/TMS): d=8.90 (d, 1H); 8.30 (d, 1H); 8.10 (m, 4H); 7.85 (t, 1H); 7.73 (t, 1H); 7.64 (d, 1H); 7.16 (s, 1H); 7.13 (d, 1H); 7.08 (dd, 1H); 6.82 (d, 2H); 5.70 (m, 1H); 5.15 (s, 2H); 4.39 (m, 1H); 4.15 (m, 2H); 4.00 (m, 1H); 3.92 (m, 1H); 3.74 (s, 3H); 1.44 (s, 6H)

EXAMPLE 77

3-{3-[2-Hydroxy-3-(1-methyl-piperidin-4-ylamino)-propoxy]-4-methoxy-phenyl}-5,5-dimethyl-1-quinolin-4-ylmethyl-imidazolidine-2,4-dione The following compound was prepared in analogy to example 72 by using 4-amino-1-methyl-piperidine instead of tetrahydro-pyran-4-ylamine. In this case the crude product was purified in addition by preparative HPLC (C18 reverse phase column, elution with a water/acetonitrile gradient with 0.1% trifluoroacetic acid). Lyophilization of the solution yielded a white solid. Yield: 3.0 mg MS(ES+): m/e=562

1H-NMR (500 MHz, DMSO/TMS): d=8.90 (d, 1H); 8.77 (m, 1H); 8.28 (d, 1H); 8.10 (d, 1H); 7.97 (m, 1H); 7.84 (t, 1H); 7.73 (t, 1H); 7.62 (d, 1H); 7.12 (m, 3H); 5.95 (m, 1H); 5.15 (s, 2H); 4.50 (m, 1H); 4.18 (m, 1H); 4.00-2.70 (m, 8H); 3.83 (s, 3H); 3.18 (s, 3H); 2.25 (m, 1H); 2.06 (m, 2H); 1.75 (m, 1H); 1.44 (s, 6H)

EXAMPLE 78

3-{3-[2-Hydroxy-3-(pyrrolidin-3-ylamino)-propoxy]-4-methoxy-phenyl}-5,5-dimethyl-1-quinolin-4-ylmethyl-imidazolidine-2,4-dione The following compound was prepared in analogy to example 72 by using 3-amino-pyrrolidine-1-carboxylic acid tert-butyl ester instead of tetrahydro-pyran-4-ylamine. In this case the crude product was dissolved in 2 ml of a 8 N solution of hydrochloric acid in methanol and the resulting solution was stirred for 1 hour at room temperature. After removal of the solvent under reduced pressure the residue was dissolved in a mixture of 2 ml water and 1 ml acetonitrile. After lyophilisation of the solution the residue was purified in addition by preparative HPLC (C18 reverse phase column, elution with a water/acetonitrile gradient with 0.1% trifluoroacetic acid). Lyophilization of the solution yielded a white solid.

Yield: 8.5 mg

MS(ES+): m/e=534

1H-NMR (500 MHz, DMSO/TMS): d=9.00 (m, 2H); 8.90 (d, 1H); 8.28 (d, 1H); 8.10 (d, 1H); 7.84 (t, 1H); 7.73 (t, 1H); 7.63 (d, 1H); 7.12 (m, 3H); 5.95 (m, 1H); 5.15 (s, 2H); 4.17 (m, 1H); 3.99 (m, 3H); 3.84 (s, 3H); 3.25 (m, 2H); 3.12 (m, 1H); 2.34 (m, 1H); 2.06 (m, 1H); 1.44 (s, 6H)

EXAMPLE 79a 3-(1-Acetyl-3,3-dimethyl-2,3-dihydro-1H-indol-6-yl)-5,5-dimethyl-1-quinolin-4-ylmethyl-imidazolidine-2,4-dione 1-(6-Amino-3,3-dimethyl-2,3-dihydro-indol-1-yl)-ethanone was prepared according to a procedure published by Daniel Elbaum et al. Patent Application U.S. Pat. No. 6,114,365. The title compound was prepared in analogy to example 51c by using 100 mg 1-(6-amino-3,3-dimethyl-2,3-dihydro-indol-1-yl)-ethanone instead of 2-amino-thiazole-5-carboxylic acid methyl ester. Yield: 28 mg MS(ES+): m/e=457

1H-NMR (500 MHz, DMSO/TMS): d=8.97 (d, 1H); 8.34 (d, 1H), 8.14 (d, 1H); 8.08 (s, 1H); 7.93 (t, 1H); 7.77 (m, 2H); 7.49 (d, 1H); 7.12 (d, 1H); 5.23 (s, 2H); 3.93 (s, 2H); 2.19 (s, 3H); 1.45 (s, 6H); 1.35 (s, 6H)

EXAMPLE 79b 3-(3,3-Dimethyl-2,3-dihydro-1H-indol-6-yl)-5,5-dimethyl-1-quinolin-4-ylmethyl-imidazolidine-2,4-dione 230 mg 3-(1-acetyl-3,3-dimethyl-2,3-dihydro-1H-indol-6-yl)-5,5-dimethyl-1-quinolin-4-ylmethyl-imidazolidine-2,4-dione were dissolved in 5 ml water and 5 ml of an aqueous 2 N solution of hydrochloric acid in a process vial. After sealing with a teflon septum the vial was placed in the microwave cavity and the reaction mixture was stirred for 15 minutes at 120° C. by microwave-assisted heating (Emrys Optimizer, Personal Chemistry). The solvent was removed under reduced pressure and the residue purified by preparative HPLC (C18 reverse phase column, elution with a water/acetonitrile gradient with 0.1% trifluoroacetic acid). Lyophilization of the solution yielded a white solid.

MS(ES+): m/e=414

1H-NMR (500 MHz, DMSO/TMS):d=8.97 (d, 1H); 8.34 (d, 1H); 8.15 (d, 1H);7.93 (t, 1H); 7.69 (t, 1H); 7.73 (d, 1H); 7.18 (d, 1H); 6.78 (m, 2H); 5.20 (s, 2H); 3.32 (s, 2H); 1.44 (s, 6H); 1.28 (s, 6H)

EXAMPLE 79c

3-[3,3-Dimethyl-1-(2-morpholin-4-yl-acetyl)-2,3-dihydro-1H-indol-6-yl]-5,5-dimethyl-1-quinolin-4-ylmethyl-imidazolidine-2,4-dione To a solution of 50 mg 3-(3,3-dimethyl-2,3-dihydro-1H-indol-6-yl)-5,5-dimethyl-1-quinolin-4-ylmethyl-imidazolidine-2,4-dione in 1 ml 1,2-dichloroethane 0.04 ml ethyl-diisopropylamine and 13.67 mg chloroacetylchloride were added at 0° C. After stirring for 1 hour at 0° C. 10.5 mg morpholine were added and the reaction mixture was stirred for 1 hour at room temperature. Then 10.5 mg morpholine were added and the mixture was stirred for further 16 hours at room temperature. After removing of the solvent under reduced pressure the residue was purified by preparative HPLC (C18 reverse phase column, elution with a water/acetonitrile gradient with 0.1% trifluoroacetic acid). Lyophilization of the solution yielded a white solid.

Yield: 26.0 mg

MS(ES+): m/e=542

1H-NMR (500 MHz, DMSO/TMS): d=10.28 (m, 1H); 8.92 (d, 1H); 8.28 (d, 1H); 8.15 (s, 1H); 8.11 (d, 1H); 7.86 (t, 1H); 7.73 (t, 1H); 7.65 (d, 1H); 7.48 (d, 1H); 7.25 (d, 1H); 5.17

(s, 2H); 4.45 (m, 2H); 3.90 (m, 6H); 3.48 (m, 2H); 3.23 (m, 2H); 1.45 (s, 6H); 1.38 (s, 6H)

EXAMPLE 80

3-[3,3-Dimethyl-1-(2-thiomorpholin-4-yl-acetyl)-2,3-dihydro-1H-indol-6-yl]-5,5-dimethyl-1-quinolin-4-ylmethyl-imidazolidine-2,4-dione The following compound was prepared in analogy to example 79c by using thiomorpholine instead of morpholine.
Yield: 12.5 mg
MS(ES+): m/e=558
1H-NMR (500 MHz, DMSO/TMS): d=9.95 (m, 1H); 8.90 (d, 1H); 8.28 (d, 1H); 8.15 (s, 1H); 8.10 (d, 1H); 7.86 (t, 1H); 7.73 (t, 1H); 7.65 (d, 1H); 7.48 (d, 1H); 7.25 (d, 1H); 5.17 (s, 2H); 4.45 (m, 2H); 3.90 (s, 2H); 3.33 (m, 2H); 3.10 (m, 2H); 2.95 (m, 2H); 1.45 (s, 6H); 1.38 (s, 6H)

LC/UV/MS experiments have been conducted with a Waters 1525 pump, a Waters 2488 UV detector, and a multiplexed ESI-TOF mass spectrometer (Micromass MUX-LCT) using YMC J'sphere H80 (30*2.1 mm, 4 u, 80 A) columns. UV data have been recorded at 220 nm and at 254 nm. For gradient separation, H2O+0.05% TFA and ACN+0.05% TFA are mixed in 95:5 (0 min) to 5:95 (3.4 min) to 5:95 (4.4 min) ratios at a flow rate of 1 ml min-1.

EXAMPLE 81

N-[5-(4,4-Dimethyl-2,5-dioxo-3-pyridin-4-ylmethylimidazolidin-1-yl)-2-isopropylphenyl]-2-(4-methylpiperidin-1-yl)acetamide; Compound with Trifluoroacetic Acid The title compound was prepared as described for example 42e.
M+H+measured=492
LC/MS retention time [min]=1.36

EXAMPLE 82

N-[5-(4,4-Dimethyl-2,5-dioxo-3-pyridin-4-ylmethylimidazolidin-1-yl)-2-isopropylphenyl]-2-(2,2,2-trifluoroethylamino)acetamide; Compound with Trifluoroacetic Acid The title compound was prepared as described for example 42e.
M+H+measured=492
LC/MS retention time [min]=1.17

EXAMPLE 83

N-[5-(4,4-Dimethyl-2,5-dioxo-3-pyridin-4-ylmethylimidazolidin-1-yl)-2-trifluoromethoxyphenyl]nicotinamide; Compound with Trifluoroacetic Acid 51 mg (0.51 mmol) of triethylamine and 45 mg (0.25 mmol) of 3-nicotinyl chloride are added to 100 mg (0.25 mmol) of 3-(3-amino-4-trifluoromethoxyphenyl)-5,5-dimethyl-1-pyridin-4-ylmethylimidazolidine-2,4-dione in 5 ml of THF and stirred at RT for 6 h. For workup, the mixture was added to water, extracted with ethyl acetate, dried and concentrated. The remaining residue was purified by means of preparative HPLC (RP18, acetonitrile/water, 0.1% TFA). Yield: 50 mg.
M+H+measured=500
LC/MS retention time [min]=1.04

EXAMPLE 84

2-(2,2-Difluoroethylamino)-N-[5-(4,4-dimethyl-2,5-dioxo-3-pyridin-4-ylmethylimadazolidin-1-yl)-2-isopropylphenyl]acetamide; Compound with Trifluoroacetic Acid The title compound was prepared as described for example 42e using 1 ml of difluoroethylamine.
Yield: 80 mg
M+H+measured 474
LC/MS retention time [min]=0.95

EXAMPLE 85

2-({[5-(4,4-Dimethyl-2,5-dioxo-3-pyridin-4-ylmethylimidazolidine-1-yl)-2-trifluoromethoxyphenylcarbamoyl]methyl}amino)acetamide; Compound with Trifluoroacetic Acid The title compound was prepared as described for example 2 using 69 mg (0.63 mmol) of glycinamide hydrochloride in 5 ml of DMF and 162 mg (1.26 mmol) of Hünig's base.
M+H+measured=509
LC/MS retention time [min]=0.53

EXAMPLE 86

N-[5-(4,4-Dimethyl-2,5-dioxo-3-pyridin-4-ylmethylimidazolidin-1-yl)-2-trifluoromethoxyphenyl]-3-pyridin-3-ylpropionamide 1.0 g (6.6 mmol) of 2-pyridylpropionic acid are dissolved in 20 ml of methylene chloride, 1.92 g (15.1 mmol) of oxalyl chloride and 3 drops of DMF are added, and the mixture is stirred at RT for 3.5 h and finally concentrated. 78 mg (0.38 mmol) of the remaining acid chloride hydrochloride are dissolved in 5 ml of methylene chloride and added to a solution of 100 mg (0.25 mmol) of 3-(3-amino-4-trifluoromethoxyphenyl)-5,5-dimethyl-1-pyridin-4-ylmethylimidazolidine-2,4-dione and 38.5 mg (0.38 mmol) of triethylamine in 7.5 ml of methylene chloride. After stirring for 2.5 hours at RT, the mixture is concentrated and the remaining residue is purified by means of preparative HPLC (RP18, acetonitrile/water, 0.1% TFA). The free bases are obtained from the fractions of value by treatment with sodium hydrogencarbonate solution.
Yield: 40 mg
M+H+measured=528
LC/MS retention time [min] 0.97

EXAMPLE 87

N-[5-(4,4-Dimethyl-2,5-dioxo-3-pyridin-4-ylmethylimidazolidin-1-yl)-2-trifluoromethoxyphenyl]-3-thiazol-2-ylpropionamide was prepared as described for example 86.
M+H+measured=534
LC/MS retention time [min]=1.15

EXAMPLE 88

N-[5-(4,4-Dimethyl-2,5-dioxo-3-pyridin-4-ylmethylimidazolidin-1-yl)-2-trifluoromethoxyphenyl]-2-pyridin-2-ylacetamide 1.0 g (5.8 mmol) of 2-pyridyl acetic acid hydrochloride were dissolved in 7.5 ml of acetyl chloride, 2.40 g (11.5 mmol) of phosphorous pentachloride were added and the mixture was stirred overnight. Subsequently, the mixture was admixed with 670 mg of acetone, and the precipitate as a solid was filtered off with suction, washed with acetyl chloride and diethyl ether and dried under reduced pressure.

73.1 mg (0.38 mmol) of the crude acid chloride dissolved in 5 ml of dichloromethane were added to a solution of 100 mg (0.25 mmol) of 3-(3-amino-4-trifluoromethoxyphenyl)-5,5-dimethyl-1-pyridin-4-ylmethylimadazolidine-2,4-dione and 39 mg (0.38 mmol) of triethylamine in 7.5 ml of dichloromethane. After 2 h at RT, the mixture is concentrated and the remaining residue is purified by means of preparative HPLC (RP18, acetonitrile/water, 0.1% TFA). The free bases are obtained from the fractions of value by treating with sodium hydrogencarbonate solution.

Yield: 40 mg
M+H+measured=514
LC/MS retention time [min]=1.02

EXAMPLE 89

N-[5-(4,4-Dimethyl-2,5-dioxo-3-pyridin-4-ylmethylimidazolidin-1-yl)-2-trifluoromethoxyphenyl]-2-(2-methylbenzimidazol-1-yl)acetamide was prepared as described for example 88.
M+H+measured=567
LC/MS retention time [min]=1.06

EXAMPLE 90

N-[5-(4,4-Dimethyl-2,5-dioxo-3-pyridin-4-ylmethylimidazolidin-1-yl)-2-trifluoromethoxyphenyl]-2-pyridin-3-ylacetamide was prepared as described for example 88.
M+H+measured=514
LC/MS retention time [min]=0.92

EXAMPLE 91

3-[4-Isopropylamino-3-(4-methylpiperazine-1-carbonyl)phenyl]-5,5-dimethyl-1-pyridin-4-ylmethylimidazolidine-2,4-dione a) N-(4-methylpiperazin-1-yl)-2-isopropylamino-5-nitrobenzamide 20 g (77 mmol) of methyl 3-bromo-5-nitrobenzoate were dissolved in 200 ml of THF, 11.4 g (192 mmol) of isopropylamine were added dropwise and the mixture was stirred at 60° C. for 16 h. Subsequently, the precipitate was filtered off with suction and the filtrate was concentrated. 20 g of crude material remained.

64 ml (160 mmol) of n-butyllithium (2.5 m in hexane) were added dropwise at 0° C. to 76 ml of N-methylpiperazine and, after stirring at RT for 1 hour, a solution of 19 g of the crude intermediate (approx. 79 mmol) in 100 ml of THF was added dropwise. After stirring at RT for 1 hour, 200 ml of water are added and the mixture is extracted with ethyl acetate. The residue remaining after concentration and drying of the organic phases is purified by flash chromatography (silica gel, 9:1 methylene chloride/methanol). Yield: 20 g b) N-(4-methylpiperazin-1-yl)-5-amino-2-isopropylamino-benzamide 2.0 g (6.5 mmol) of N-(4-methylpiperazin-1-yl)-2-isopropylamino-5-nitrobenzamide were dissolved in 40 ml of glacier acetic acid and 6.8 g of zinc powder were added gradually at 45-50° C. For workup, 40 ml of water were added, the mixture was extracted once with ethyl acetate, the water phase was alkalized with NaOH, and the mixture was extracted repeatedly with methylene chloride. The residue remaining after drying and concentration (1.9 g) could be used for the next reaction without further purification.

c) the Title Compound was Prepared Analogously to the Process Described for Ex. 136a) by Use of N-(4-methylpiperazin-1-yl)-5-amino-2-isopropylaminobenzamide M+H+measured=479
LC/MS retention time [min]=0.85

EXAMPLE 92

5-(4,4-Dimethyl-2,5-dioxo-3-pyridin-4-ylmethylimidazolidin-1-yl)-2-isopropoxy-N-piperidin-4-ylmethylbenzamide hydrochloride 941 mg (4.67 mmol) of 2-chloro-5-nitrobenzoate acid was heated with 10 ml of thionyl chloride to reflux until gas evolution had ended. Subsequently, the mixture was concentrated and coevaporated twice with toluene. The residue is taken up in 10 ml of methylene chloride and added dropwise to a solution of 1000 mg (4.67 mmol) of 4-(aminomethyl)-1-Boc-piperidine and 567 mg (5.6 mmol) of triethylamine. After 1 hour at RT, the mixture is poured onto sat. sodium bicarbonate solution, extracted with ethyl acetate, dried and concentrated.

1350 mg of the crude product were added slowly at 0° C. to a sodium isopropoxide solution (obtained by addition of 500 mg of NaH (96%) to 50 ml of isopropanol), and the mixture was stirred at RT for 2 h. After 1 h at RT, the mixture was poured onto ice, extracted with ethyl acetate, dried and concentrated.

1200 mg of the crude product were hydrogenated in 50 ml of ethanol with 20 mg of Pd on carbon. For workup, the mixture was filtered off with suction, concentrated and purified by flash chromatography (silica gel, methylene chloride:methanol=98:2). Yield: 920 mg of N-(piperidin-4-ylmethyl)-5-amino-2-isopropoxybenzamide The title compound was obtained analogously to example 1b by reaction of 50 mg of N-(piperidin-4-ylmethyl)-5-amino-2-isopropoxybenzamide with diphosgene and subsequent reaction with methyl 2-methyl-2-[(pyridin-4-ylmethyl)amino]propionate. The BOC group was detached by heating the crude product with aqueous TFA and the crude product was purified by means of preparative HPLC. (RP18, acetonitrile/water, 0.1% TFA).

Yield: 64 mg
M+H+measured=494
LC/MS retention time [min]=0.93

EXAMPLE 93

N-[5-(4,4-dimethyl-2,5-dioxo-3-pyridin-4-ylmethylimidazolidin-1-yl)-2-trifluoromethoxyphenyl]-3H-imidazole-4-carboxamide; compound with trifluoroacetic acid 168 mg (1.5 mmol) of imidazole-4-carboxylic acid were dissolved in 5 ml of dichloromethane, 216 mg (1.7 mmol) of oxalyl chloride and 11 mg (0.15 mmol) of DMF were added, and the mixture was stirred at RT overnight and finally concentrated.

A solution of 39 mg (0.1 mmol) of 3-(3-amino-4-trifluoromethoxyphenyl)-5,5-dimethyl-1-pyridin-4-ylmethylimidazolidine-2,4-dione in 3 ml of dichloromethane and 12 mg (0.1 mmol) of DMAP were added to 28 mg of the remaining solid and the mixture was heated under reflux for 2 h. For workup, the mixture was added to water, alkalized, extracted with CH2Cl2, dried and concentrated. The remaining residue was purified by means of preparative HPLC (RP18, acetonitrile/water, 0.1% TFA).

Yield: 30 mg
M+H+measured=489
LC/MS retention time [min]=1.02

EXAMPLE 94

N-[5-(4,4-dimethyl-2,5-dioxo-3-pyridin-4-ylmethylimidazolidin-1-yl)-2-trifluoromethoxyphenyl]-1-methyl-3-piperidinecarboxamide; compound with trifluoroacetic acid was prepared as described for example 93.
M+H+measured=520
LC/MS retention time [min]=0.92

EXAMPLE 95

3-[3-(Azetidin-3-ylamino)-4-trifluoromethoxyphenyl]-5,5-dimethyl-1-pyridin-4-ylmethylimidazolidine-2,4-dione; Compound with Trifluoroacetic Acid 394 mg (1 mmol) of 3-(3-amino-4-trifluoromethoxyphenyl)-5,5-dimethyl-1-pyridin-4-ylmethylimidazolidine-2,4-dione were dissolved in 1 ml of DMF, 166 mg (1.2 mmol) of potassium carbonate and 413 mg (1.3 mmol) of 1-(diphenylmethyl)-3-azetidine methanesulphonate were added, and the mixture was stirred at 80° C. for 5 h. For workup, the mixture was added to ice-water, extracted with CH2Cl2, dried and concentrated. The remaining residue was purified by means of preparative HPLC (RP18, acetonitrile/water, 0.1% TFA). The intermediate obtained in this way was dissolved in 3 ml of methanol, admixed with 10 mg of 5% Pd/C and 50 mg (0.8 mmol) of ammonium formate, and heated under reflux for 2 h. The residue remaining after filtration and evaporation was purified by means of preparative HPLC (RP18, acetonitrile/water, 0.1% TFA).

M+H+measured=450
LC/MS retention time [min]=0.86

EXAMPLE 96

3-[3-(2-Dimethylaminoethylamino)-4-trifluoromethoxyphenyl]-5,5-dimethyl-1-pyridin-4-ylmethylimidazolidine-2,4-dione; Compound with Trifluoroacetic Acid a) N-[5-(4,4-dimethyl-2,5-dioxo-3-pyridin-4-ylmethylimidazolidin-1-yl)-2-trifluoromethoxyphenyl]-2,2,2-trifluoroacetamide; compound with trifluoroacetic acid 394 mg (1.0 mmol) of 3-(3-amino-4-trifluoromethoxyphenyl)-5,5-dimethyl-1-pyridin-4-ylmethylimidazolidine-2,4-dione were dissolved in 5 ml of 4:1 dichloromethane/pyridine and cooled to 0° C., and 252 mg (1.2 mmol) of trifluoroacetic anhydride dissolved in 5 ml of 4:1 dichloromethane/pyridine were added dropwise at 0° C. After stirring at RT, the mixture was added to ice-water, extracted with CH2Cl2, concentrated and dried. The remaining residue was purified by means of preparative HPLC (RP18, acetonitrile/water, 0.1% TFA).

Yield: 550 mg b) 60 mg (0.1 mmol) of N-[5-(4,4-dimethyl-2,5-dioxo-3-pyridin-4-ylmethylimidazolidin-1-yl)-2-trifluoromethoxyphenyl]-2,2,2-trifluoroacetamide, TFA salt were dissolved in 3 ml of ethyl acetate, 18 mg (0.13 mmol) of 2-dimethyl (amino)ethylamine.HCl, 69 mg (0.5 mmol) of potassium carbonate and 1 drop of water were added, and the mixture was heated under reflux for 12 h. For workup, the mixture was added to water, alkalized, extracted with ethyl acetate, dried and concentrated. The remaining residue is purified by means of preparative HPLC (RP18, acetonitrile/water, 0.1% TFA).

Yield: 30 mg.
M+H+measured=466
LC/MS retention time [min] 0.98

EXAMPLE 97

5,5-Dimethyl-1-pyridin-4-ylmethyl-3-[3-(2-pyrrolidin-1-ylethylamino)-4-trifluoromethoxyphenyl]imidazolidine-2,4-dione; Compound with Trifluoroacetic Acid prepared as described for example 96
M+H+measured=492
LC/MS retention time [min]=1.03

EXAMPLE 98

N-[5-(4,4-Dimethyl-2,5-dioxo-3-pyridin-4-ylmethylimidazolidin-1-yl)-2-trifluoromethoxyphenyl]-2,2,2-trifluoro-N-(2-piperidin-1-ylethyl)acetamide; Compound with Trifluoroacetic Acid prepared as described for example 96. Preparative HPLC of the product mixture (RP18, acetonitrile/water, 0.1% TFA) gives, in addition to the main product of example 97, the title compound as a further reaction product.
M+H+measured=602
LC/MS retention time [min]=1.26

EXAMPLE 99

5,5-Dimethyl-3-[3-(2-piperidin-1-ylethylamino)-4-trifluoromethoxyphenyl]-1-pyridin-4-ylmethylimidazolidine-2,4-dione prepared as described for example 96
M+H+measured=506
LC/MS retention time [min]=1.05

EXAMPLE 100

3-[3-(2-Diisopropylaminoethylamino)-4-trifluoromethoxyphenyl]-5,5-dimethyl-1-pyridin-4-ylmethylimidazolidine-2,4-dione prepared as described for example 96
M+H+measured=522
LC/MS retention time [min]=1.14

EXAMPLE 101

3-[3-(2-Diethylaminoethylamino)-4-trifluoromethoxyphenyl]-5,5-dimethyl-1-pyridin-4-ylmethylimidazolidine-2,4-dione prepared as described for example 96
M+H+measured=494
LC/MS retention time [min]=0.99

EXAMPLE 102

5,5-Dimethyl-3-{3-[(2-methylthiazol-4-ylmethyl)amino]-4-trifluoromethoxyphenyl}-1-pyridin-4-ylmethylimidazolidine-2,4-dione prepared as described for example 96
M+H+measured=506
LC/MS retention time [min]=1.25

EXAMPLE 103

3-[3-(1-Cyclohexylazetidin-3-ylamino)-4-trifluoromethoxyphenyl]-5,5-dimethyl-1-pyridin-4-ylmethyl-imidazolidine-2,4-dione 300 mg (0.76 mmol) of 3-(3-amino-4-trifluoromethoxyphenyl)5,5-dimethyl-1-pyridin-4-ylmethylimidazolidine-2,4-dione were dissolved in 15 ml of ethyl acetate, admixed with 492 mg (1.52 mmol) of 1-cyclohexylazetidin-3-yl methanesulphonate oxalate and 631 mg (4.56 mmol) of K2CO3, and heated under reflux for 4 h. To complete the reaction, a further 49 mg (0.15 mmol) of 1-cyclohexylazetidin-3-yl methanesulphonate oxalate and 63 mg (0.46 mmol) of K2CO3 were added, and the mixture was stirred under reflux once again for 2 h. Subsequently, the mixture was concentrated and the residue purified by flash chromatography (150 g of silica gel/95:5 CH2C12:CH3OH).
Yield: 13 mg
M+H+measured=532
LC/MS retention time [min]=1.12

EXAMPLE 104

3-{5-tert-Butyl-1-[2-(4-methylpiperazin-1-yl)-2-oxoethyl]-1H-pyrazol-3-yl}-5,5-dimethyl-1-pyridin-4-ylmethylimidazolidine-2,4-dione; Compound with Trifluoroacetic Acid a) 2-(3-amino-5-tert-butylpyrazol-1-yl)-1-(4-methylpiperazin-1-yl)ethanone 1.90 g (13.7 mmol) of 3-amino-tert-butylpyrazole were dissolved under argon in 60 ml of abs. DMF, 1.89 g (13.7 mmol) of potassium carbonate and 1.96 g (11.1 mmol) of 2-chloro-1-(4-methylpiperazin-1-yl)ethanone were added, and the mixture was stirred at 80° C. for 2 h. To complete the reaction, a further 0.49 g (2.6 mmol) of 2-chloro-1-(4-methylpiperazin-1-yl)ethanone was added and the mixture was stirred at 80° C. for a further 3.5 h. For workup, the mixture was admixed with 10% sodium chloride solution, extracted with ethyl acetate, dried and concentrated by rotary evaporation. The remaining residue is purified by means of flash chromatography (silica gel, methylene chloride:methanol=85:15)
Yield: 1.85 g 229 mg (1.1 mmol) of methyl 2-methyl-2-[(pyridin-4-ylmethyl)amino]propionate were initially charged at 0° C. in 5 ml of THF under argon, 196 mg (1.2 mmol) of 1,1-carbonyldiimidazole were added, and the mixture was stirred at 0° C. for 15 min and at RT for 1 h. Subsequently, 285 mg (1.0 mmol) of 2-(3-amino-5-tert-butylpyrazol-1-yl)-1-(4-methylpiperazin-1-yl)ethanone dissolved in 2.5 ml of DMF were added and the mixture was stirred at 50° C. for 3 h and at 75° C. for 1 h. For workup, the mixture was concentrated, taken up in water, extracted with ethyl acetate, dried and concentrated. The remaining residue was purified by means of preparative HPLC (RP18, acetonitrile/water, 0.1% TFA).
Yield: 35 mg (TFA salt)
M+H+measured 482
LC/MS retention time [min]=0.96

EXAMPLE 105

N-[5-(4,4-Dimethyl-2,5-dioxo-3-pyridin-4-ylmethylimidazolidin-1-yl)-2-trifluoromethyl-sulphanylphenyl]-2-morpholin-4-ylacetamide; Compound with Trifluoroacetic Acid a) 5,5-Dimethyl-3-(3-nitro-4-trifluoromethyl-sulphanylphenyl)-1-pyridin-4-ylmethylimidazolidine-2,4-dione; trifluoroacetic acid salt 4.0 g (7.9 mmol) of 5,5-dimethyl-1-pyridin-4-ylmethyl-3-(4-trifluoromethylsulphanylphenyl)imidazolidine-2,4-dione were dissolved in 150 ml of acetonitrile, and a total 2.4 g (18.1 mmol) of nitronium tetrafluoroborate were added at 0° C. over several hours. After the mixture had been heated slowly to RT, the solvent was removed, and the residue was taken up in 100 ml of water, basified with 10 ml of conc. ammonia and extracted with methylene chloride. The residue remaining after drying, filtration and evaporation was purified by means of preparative HPLC (RP18, acetonitrile/water, 0.1% TFA).
Yield: 420 mg of title compound (and also 620 mg of isomeric 5,5-dimethyl-3-(2-nitro-4-trifluoromethylsulphanylphenyl)-1-pyridin-4-ylmethylimidazolidine-2,4-dione)

b) 370 mg (0.67 mmol) of 3-(3-nitro-4-trifluoromethyl-sulphanylphenyl)-5,5-dimethyl-1-pyridin-4-ylmethyl-imidazolidine-2,4-dione are dissolved in 5 ml of glacial acetic acid, 655 mg (10.0 mmol) of zinc powder are added with gentle cooling up to a temperature of 40° C., and the mixture is stirred at RT for 1.5 h.

Subsequently, the mixture is diluted with water and the acidic solution is extracted with a little ethyl acetate. The remaining water phase is alkalized with 6 M NaOH, and extracted with ethyl acetate, dried and concentrated.
Yield: 270 mg c) N-[5-(4,4-Dimethyl-2,5-dioxo-3-pyridin-4-ylmethylimidazolidin-1-yl)-2-trifluoromethyl-sulphanylphenyl]-2-morpholin-4-ylacetamide; compound with trifluoroacetic acid The compound was prepared according to the process described under example id and e starting from 100 mg (0.24 mmol) of 3-(3-amino-4-trifluoromethylsulphanylphenyl)-5,5-dimethyl-1-pyridin-4-ylmethylimidazolidin-2,4-dione.
Yield: 40 mg
M+H+measured=538
LC/MS retention time [min]=1.1

EXAMPLE 106

N-[5-(4,4-Dimethyl-2,5-dioxo-3-pyridin-4-ylmethylimidazolidin-1-yl)-2-trifluoromethyl-sulphanylphenyl]-2-piperidin-1-ylacetamide; compound with trifluoroacetic acid The compound was prepared according to the process described under example 1d and e starting from 47 mg (0.11 mmol) of 3-(3-amino-4-trifluoromethylsulphanylphenyl)-5,5-dimethyl-1-pyridin-4-ylmethylimidazolidin-2,4-dione using 1 ml of piperidine.
Yield: 7 mg
M+H+measured=536
LC/MS retention time [min]=1.05

EXAMPLE 107

2-tert-Butylamino-N-[5-(4,4-dimethyl-2,5-dioxo-3-pyridin-4-ylmethylimidazolidin-1-yl)-2-trifluoromethyl-sulphanylphenyl]acetamide; Compound with Trifluoroacetic Acid The compound was prepared according to the process described under example 1d and e starting from 47 mg (0.11 mmol) of 3-(3-amino-4-trifluoromethylsulphanylphenyl)-5,5-dimethyl-1-pyridin-4-ylmethylimidazolidine-2,4-dione using 1 ml of tert-butylamine.
Yield: 5 mg
M+H+measured=524
LC/MS retention time [min]=1.04

EXAMPLE 108

N-[5-(4,4-Dimethyl-2,5-dioxo-3-pyridin-4-ylmethylimidazolidin-1-yl)-2-trifluoromethoxyphenyl]-2-morpholin-4-ylpropionamide 125 mg (0.32 mmol) of 3-(3-amino-4-trifluoromethoxyphenyl)-5,5-dimethyl-1-pyridin-4-ylmethylimidazolidine-2,4-dione were initially charged in 5 ml of CH2Cl2, cooled to −20° C., and admixed with 43 mg (0.34 mmol) of Hünig's base, and 48 mg of 2-chloropropionyl chloride were added dropwise. After stirring at 40° C. for 2 h and standing overnight, 1 ml of ethaolic HCl was added and the mixture was concentrated to dryness.
The residue was dissolved in 1 ml of morpholine and stirred at 100° C. for 2 h. For workup, the mixture was added to water, extracted with ethyl acetate, dried and concentrated.
The remaining residue is purified by means of flash chromatography (silica gel, methylene chloride:methanol=95:5).
The 140 mg of racemate obtained in this way was separated by chiral prep. Chromatography.
M+H+measured=536
LC/MS retention time [min]=0.9

EXAMPLE 109

N-[5-(4,4-Dimethyl-2,5-dioxo-3-pyridin-4-ylmethylimidazolidin-1-yl)-2-trifluoromethoxyphenyl]-2-morpholin-4-ylpropionamide preparation as described for example 108
M+H+measured=536
LC/MS retention time [min]=0.92

EXAMPLE 110

N-[5-(4,4-Dimethyl-2,5-dioxo-3-pyridin-4-ylmethylimidazolidin-1-yl)-2-trifluoromethoxyphenyl]-2-piperidine-1-ylpropionamide; Compound with Trifluoroacetic Acid preparation as described for example 108
M+H+measured=534
LC/MS retention time [min]=1

EXAMPLE 111

2-Cyclohexylamino-N-[5-(4,4-dimethyl-2,5-dioxo-3-pyridin-4-ylmethylimidazolidin-1-yl)-2-trifluoromethoxyphenyl]propionamide; Compound with Trifluoroacetic Acid preparation as described for example 108
M+H+measured=548
LC/MS retention time [min]=1.11

EXAMPLE 112

2-Cyclopropylamino-N-[5-(4,4-dimethyl-2,5-dioxo-3-pyridin-4-ylmethylimidazolidin-1-yl)-2-trifluoromethoxyphenyl]propionamide; Compound with Trifluoroacetic Acid preparation as described for example 108
M+H+measured=506
LC/MS retention time [min]=0.97

EXAMPLE 113

2-Cyclopentylamino-N-[5-(4,4-dimethyl-2,5-dioxo-3-pyridin-4-ylmethylimidazolidin-1-yl)-2-trifluoromethoxyphenyl]propionamide; Compound with Trifluoroacetic Acid preparation as described for example 108
M+H+measured=534
LC/MS retention time [min]=1.13

EXAMPLE 114

N-[5-(4,4-Dimethyl-2,5-dioxo-3-pyridin-4-ylmethylimidazolidin-1-yl)-2-trifluoromethoxyphenyl]-2-(pyrrolidine-3-ylamino)propionamide hydrochloride preparation as described for example 108
M+H+measured=535
LC/MS retention time [min]=0.89

EXAMPLE 115

2-Diethylamino-N-[5-(4,4-dimethyl-2,5-dioxo-3-pyridin-4-ylmethylimidazolidin-1-yl)-2-trifluoromethoxyphenyl]propionamide; Compound with Trifluoroacetic Acid preparation as described for example 108
M+H+measured=522
LC/MS retention time [min]=1.01

EXAMPLE 116

N-[5-(4,4-Dimethyl-2,5-dioxo-3-pyridin-4-ylmethylimidazolidin-1-yl)-2-trifluoromethoxyphenyl]-2-(2,2,2-trifluoroethylamino)propionamide; Compound with Trifluoroacetic Acid preparation as described for example 108
M+H+measured=548
LC/MS retention time [min]=1.36

EXAMPLE 117

N-[5-(4,4-Dimethyl-2,5-dioxo-3-pyridin-4-ylmethylimidazolidin-1-yl)-2-trifluoromethoxyphenyl]-2-[1,4]oxazepan-4-ylpropionamide; Compound with Trifluoroacetic Acid preparation as described for example 108
M+H+measured=550
LC/MS retention time [min]=1.02

EXAMPLE 118

N-[5-(4,4-Dimethyl-2,5-dioxo-3-pyridin-4-ylmethylimidazolidin-1-yl)-2-trifluoromethoxyphenyl]-2-[methyl-(1-methylpyrrolidin-3-yl)amino]propionamide preparation as described for example 108
M+H+measured=563
LC/MS retention time [min]=0.97

EXAMPLE 119

N-[5-(4,4-dimethyl-2,5-dioxo-3-pyridin-4-ylmethylimidazolidin-1-yl)-2-trifluoromethoxyphenyl]-3-dimethylamino-4-methylpentamide a) N-[5-(4,4-dimethyl-2,5-dioxo-3-pyridin-4-ylmethylimidazolidin-1-yl)-2-trifluoromethoxyphenyl]-4-methylpent-2-enamide; compound with trifluoroacetic acid 240 mg (2.1 mmol) of 4-methyl-2-pentenecarboxylic acid were initially charged in 3 ml of methylene chloride and 794 mg (6.3 mmol) of oxalyl chloride were added at 0° C. After stirring at RT for 3 h, the mixture was concentrated and coevaporated twice with toluene. 278 mg of the acid chloride obtained in this way, dissolved in 5 ml of 1,2-dichloroethane, were added at −20° C. to a solution of 500 mg (1.27 mmol) of 3-(3-amino-4-trifluoromethoxyphenyl)-5,5-dimethyl-1-pyridin-4-ylmethylimidazolidine-2,4-dione in 10 ml of 1,2-dichloroethane, and stirred at RT for 1 h. For workup, the mixture was concentrated by rotary evaporation and the remaining residue was purified by means of preparative HPLC (RP18, acetonitrile/water, 0.1% TFA).
Yield: 250 mg b) 100 mg (0.16 mmol) of N-[5-(4,4-dimethyl-2,5-dioxo-3-pyridin-4-ylmethylimidazolidin-1-yl)-2-trifluoromethoxyphenyl]-4-methylpent-2-enamide (TFA salt) were dissolved in 0.5 ml of DMF, 1 ml of dimethylamine solution (40% in H2O) were added and the mixture was stirred at 50° C. for 8 h. For workup, the mixture was concentrated by rotary evaporation and the remaining residue was purified by means of preparative HPLC (RP18, acetonitrile/water, 0.1% TFA).
Yield: 17 mg
M+H+measured=536
LC/MS retention time [min]=1.03

EXAMPLE 120

N-[5-(4,4-Dimethyl-2,5-dioxo-3-pyridin-4-ylmethylimidazolidin-1-yl)-2-trifluoromethoxyphenyl]-1,2,3,4-tetrahydroisoquinoline-1-carboxamide; Compound with Trifluoroacetic Acid 152 mg (0.38 mmol) of FMOC-L-1,2,3,4-tetrahydroisoquinoline-1-carboxylic acid are initially charged in 10 ml of CH2Cl2, 55 mg (0.43 mmol) of oxalyl chloride and 3 mg of DMF are added under argon, and the mixture is stirred at RT overnight. Subsequently, the mixture was concentrated by rotary evaporation and 100 mg (0.25 mmol) of 3-(3-amino-4-trifluoromethoxyphenyl)-5,5-dimethyl-1-pyridin-4-ylmethylimidazolidine-2,4-dione dissolved in 7.5 ml of methylene chloride were added. After addition of 31 mg (0.25 mmol) of DMAP, the mixture was stirred at RT for 7 h. For workup, the mixture was concentrated and the remaining residue was purified by means of preparative HPLC (RP18, acetonitrile/water, 0.01% TFA). The 90 mg of FMOC derivative (TFA salt) remaining after freeze-drying of the fraction of value were deprotected by stirring in a 20% solution of piperidine in DMF for 1 hour. The end product was obtained by concentration by rotary evaporation and again by preparative HPLC (RP18, acetonitrile/water, 0.01% TFA). Yield: 38 mg of white solid (TFA salt)
M+H+measured=554
LC/MS retention time [min]=1.13

EXAMPLE 121

N-[5-(4,4-Dimethyl-2,5-dioxo-3-pyridin-4-ylmethylimidazolidin-1-yl)-2-trifluoromethoxyphenyl]-(S)-piperidine-2-carboxamide prepared as described for example 120
M+H+measured=506
LC/MS retention time [min]=0.97

EXAMPLE 122

3-[3,3-Dimethyl-1-((R)-1,2,3,4-tetrahydroisoquinoline-1-carbonyl)-2,3-dihydro-1H-indol-6-yl]-5,5-dimethyl-1-pyridin-4-ylmethylimidazolidine-2,4-dione prepared as described for example 120
M+H+measured=524
LC/MS retention time [min]=1.1

EXAMPLE 123

3-[3,3-Dimethyl-1-((S)-piperidine-2-carbonyl)-2,3-dihydro-1H-indol-6-yl]-5,5-dimethyl-1-pyridin-4-ylmethylimidazolidine-2,4-dione prepared as described for example 120
M+H+measured=476
LC/MS retention time [min]=0.96

EXAMPLE 124

3-[3,3-Dimethyl-1-((R)-piperidine-2-carbonyl)-2,3-dihydro-1H-indol-6-yl]-5,5-dimethyl-1-pyridin-4-ylmethylimidazolidine-2,4-dione prepared as described for example 120
M+H+measured=476
LC/MS retention time [min]=0.96

EXAMPLE 125

3-[1-(1-tert-Butylazetidine-2-carbonyl)-3,3-dimethyl-2,3-dihydro-1H-indol-6-yl]-5,5-dimethyl-1-pyridin-4-ylmethylimidazolidine-2,4-dione prepared as described for example 120
M+H+measured=504
LC/MS retention time [min]=1.08

EXAMPLE 126

N-[5-(4,4-Dimethyl-2,5-dioxo-3-pyridin-4-ylmethylimidazolidine-1-yl)-2-trifluoromethoxyphenyl]-(R)-piperidine-2-carboxamide prepared as described for example 120
M+H+measured=506
LC/MS retention time [min]=0.97

EXAMPLE 127

(R)-2-Amino-N-[5-(4,4-dimethyl-2,5-dioxo-3-pyridin-4-ylmethylimidazolidin-1-yl)-2-trifluoromethoxyphenyl]-2-phenylacetamide prepared as described for example 120
M+H+measured=528
LC/MS retention time [min]=1.09

EXAMPLE 128

(S)-2-Amino-3-cyclohexyl-N-[5-(4,4-dimethyl-2,5-dioxo-3-pyridin-4-ylmethylimidazolidin-1-yl)-2-trifluoromethoxyphenyl]propionamide prepared as described for example 120
M+H+measured=548
LC/MS retention time [min]=1.25

EXAMPLE 129

(R)-2-Amino-3-cyclohexyl-N-[5-(4,4-dimethyl-2,5-dioxo-3-pyridin-4-ylmethylimidazolidin-1-yl)-2-trifluoromethoxyphenyl]propionamide prepared as described for example 120
M+H+measured=548
LC/MS retention time [min]=1.23

EXAMPLE 130

N-[5-(4,4-Dimethyl-2,5-dioxo-3-pyridin-4-ylmethylimidazolidin-1-yl)-2-trifluoromethoxyphenyl]-3-methylamino-3-phenylpropionamide prepared as described for example 120
M+H+measured=556
LC/MS retention time [min]=1.09

EXAMPLE 131

(R)-2-Amino-N-[5-(4,4-dimethyl-2,5-dioxo-3-pyridin-4-ylmethylimidazolidin-1-yl)-2-trifluoromethoxyphenyl]-3-phenylpropionamide prepared as described for example 120
M+H+measured=542
LC/MS retention time [min]=1.09

EXAMPLE 132

N-[5-(4,4-Dimethyl-2,5-dioxo-3-pyridin-4-ylmethylimidazolidin-1-yl)-2-trifluoromethoxyphenyl]-1-tert-butylazetidine-2-carboxamide prepared as described for example 120
M+H+measured=534
LC/MS retention time [min]=1.04

EXAMPLE 133

3-[3,3-Dimethyl-1-((S)-1,2,3,4-tetrahydroisoquinoline-1-carbonyl)-2,3-dihydro-1H-indol-6-yl]-5,5-dimethyl-1-pyridin-4-ylmethylimidazolidine-2,4-dione prepared as described for example 120
M+H+measured=524
LC/MS retention time [min]=1.1

EXAMPLE 134

N-[5-(4,4-Dimethyl-2,5-dioxo-3-pyridin-4-ylmethylimidazolidin-1-yl)-2-trifluoromethoxyphenyl]-1,2,3,4-tetrahydroisoquinoline-1-carboxamide; Compound with Trifluoroacetic Acid prepared as described for example 120
M+H+measured=554
LC/MS retention time [min]=1.1

EXAMPLE 135

N-[5-(4,4-Dimethyl-2,5-dioxo-3-pyridin-4-ylmethylimidazolidin-1-yl)-2-trifluoromethoxyphenyl]-2-amino-4-methylpentamide; Compound with Trifluoroacetic Acid prepared as described for example 120
M+H+measured=508
LC/MS retention time [min]=1.09

EXAMPLE 136

3-[3,3-Dimethyl-1-(2-morpholin-4-ylacetyl)-2,3-dihydro-1H-indol-6-yl]-5,5-dimethyl-1-pyridin-4-ylmethylimidazolidine-2,4-dione a) 3-(1-acetyl-3,3-dimethyl-2,3-dihydro-1H-indol-6-yl)-5,5-dimethyl-1-pyridin-4-ylmethylimidazolidine-2,4-dione 7.26 g (36.7 mmol) of diphosgene were initially charged at −20° C. in 80 ml of 1,2-dichloroethane, and 3.0 g (14.5 mmol) of 1-(6-amino-3,3-dimethyl-2,3-dihydroindol-1-yl)ethanone, dissolved in 80 ml of 1,2-dichloroethane, were added dropwise. After stirring at RT for 2 h and reflux for 1 h, the mixture was concentrated fully. The remaining residue was dissolved in 80 ml of THF, added to a solution of 3.06 g (14.7 mmol) of methyl 2-methyl-2-[(pyridin-4-ylmethyl)amino]propionate in 80 ml of THF, and heated under reflux for 8 h. The residue remaining after evaporation was purified by means of preparative HPLC (RP18, acetonitrile/water, 0.1% TFA). Yield: 4.69 g.

b) 3-(3,3-dimethyl-2,3-dihydro-1H-indol-6-yl)-5,5-dimethyl-1-pyridin-4-ylmethylimidazolidine-2,4-dione 1.9 g (3.65 mmol) of the above compound were dissolved in 8 ml of dioxane and 8 ml of 2N HCl, and the mixture was heated in a microwave at 120° C. for 15 min. Subsequently, the mixture was concentrated, taken up with sodium carbonate solution, extracted with ethyl acetate, dried and concentrated by rotary evaporation. Yield: 1.3 g.

c) 440 mg (1.2 mmol) of 3-(3,3-dimethyl-2,3-dihydro-1H-indol-6-yl)-5,5-dimethyl-1-pyridin-4-ylmethylimidazolidine-2,4-dione were dissolved in 5 ml of 1,2-dichloroethane and cooled to −20° C., and a solution of 163 mg (1.44 mmol) of chloroacetyl chloride dissolved in 5 ml of 1,2-dichloroethane was added dropwise.

The crude product remaining after concentration was used for the subsequent reactions without further purification.

d) 3-[3,3-dimethyl-1-(2-morpholin-4-ylacetyl)-2,3-dihydro-1H-indol-6-yl]-5,5-dimethyl-1-pyridin-4-ylmethylimidazolidine-2,4-dione 120 mg (approx. 0.3 mmol) of the above crude product were dissolved in 2.5 ml of 1,2-dichloroethane, added to a solution of 0.9 mmol of morpholine in 1,2-dichloroethane and stirred at 60° C. for 2 h. Subsequently, the mixture was poured onto ice-water, extracted with methylene chloride, dried and concentrated. The remaining residue was purified by means of preparative HPLC (RP18, acetonitrile/water, 0.1% TFA).

Yield: 15 mg
M+H+measured=492
LC/MS retention time [min]=0.95

EXAMPLE 137

3-[3,3-Dimethyl-1-(2-thiomorpholin-4-ylacetyl)-2,3-dihydro-1H-indol-6-yl]-5,5-dimethyl-1-pyridin-4-ylmethylimidazolidine-2,4-dione prepared as described for example 136 by use of thiomorpholine instead of morpholine.
M+H+measured=508
LC/MS retention time [min]=0.99

EXAMPLE 138

3-[3,3-Dimethyl-1-(2-piperidin-1-ylacetyl)-2,3-dihydro-1H-indol-6-yl]-5,5-dimethyl-1-pyridin-4-ylmethylimidazolidine-2,4-dione prepared as described for example 136 by use of piperidine instead of morpholine.
M+H+measured=490
LC/MS retention time [min]=1

EXAMPLE 139

3-{3,3-Dimethyl-1-[2-(4-methylpiperazin-1-yl)acetyl]-2,3-dihydro-1H-indol-6-yl}-5,5-dimethyl-1-pyridin-4-ylmethylimidazolidine-2,4-dione prepared as described for example 136 by use of 1-methylpiperazine instead of morpholine.
M+H+measured=505
LC/MS retention time [min]=0.92

EXAMPLE 140

3-{1-[2-(3,5-Dimethylpiperazin-1-yl)acetyl]-3,3-dimethyl-2,3-dihydro-1H-indol-6-yl}-5,5-dimethyl-1-pyridin-4-ylmethylimidazolidine-2,4-dione prepared as described for example 136 by use of 2,6-dimethylpiperazine instead of morpholine.
M+H+measured=519
LC/MS retention time [min]=0.89

EXAMPLE 141

3-{3,3-Dimethyl-1-[2-(4-methylperhydro-1,4-diazepin-1-yl)acetyl]-2,3-dihydro-1H-indol-6-yl}-5,5-dimethyl-1-pyridin-4-ylmethylimidazolidine-2,4-dione prepared as described for example 136 by use of N-methylhomopiperazine instead of morpholine.
M+H+measured=519
LC/MS retention time [min]=0.81

EXAMPLE 142

3-[3,3-Dimethyl-1-[2-pyrrolidin-1-ylacetyl)-2,3-dihydro-1H-indol-6-yl]-5,5-dimethyl-1-pyridin-4-ylmethylimidazolidine-2,4-dione prepared as described for example 136 by use of pyrrolidine instead of morpholine.
M+H+measured=476
LC/MS retention time [min]=0.81

EXAMPLE 143

3-[1-(2-Diethylaminoacetyl)-3,3-dimethyl-2,3-dihydro-1H-indol-6-yl]-5,5-dimethyl-1-pyridin-4-ylmethylimidazolidine-2,4-dione prepared as described for example 136 by use of diethylamine instead of morpholine.
M+H+measured=478
LC/MS retention time [min]=0.97

EXAMPLE 144

3-(1-{2-[((S)-1-Ethylpyrrolidin-2-ylmethyl)amino]acetyl}-3,3-dimethyl-2,3-dihydro-1H-indol-6-yl)-5,5-dimethyl-1-pyridin-4-ylmethylimidazolidine-2,4-dione prepared as described for example 136 by use of (S)-(−)-2-aminomethyl-1-ethylpyrrolidine instead of morpholine.
M+H+measured=533
LC/MS retention time [min]=0.88

EXAMPLE 145

3-(1-{2-[((R)-1-Ethylpyrrolidin-2-ylmethyl)amino]acetyl}-3,3-dimethyl-2,3-dihydro-1H-indol-6-yl)-5,5-dimethyl-1-pyridin-4-ylmethylimidazolidine-2,4-dione prepared as described for example 136 by use of (R)-(+)-1-ethyl-2-aminomethylpyrrolidine instead of morpholine.
M+H+measured=533
LC/MS retention time [min]=0.89

EXAMPLE 146

3-[1-(2-Cyclopropylaminoacetyl)-3,3-dimethyl-2,3,-dihydro-1H-indol-6-yl]-5,5-dimethyl-1-pyridin-4-ylmethylimidazolidine-2,4-dione prepared as described for example 136 by use of cyclopropylamine instead of morpholine.
M+H+measured=462
LC/MS retention time [min]=0.95

EXAMPLE 147

3-[1-(2-Cyclopentylaminoacetyl)-3,3-dimethyl-2,3-dihydro-1H-indol-6-yl]-5,5-dimethyl-1-pyridin-4-ylmethylimidazolidine-2,4-dione prepared as described for example 136 by use of cyclopentylamine instead of morpholine.
M+H+measured=490
LC/MS retention time [min]=1.06

EXAMPLE 148

3-[1-(2-Cyclohexylaminoacetyl)-3,3-dimethyl-2,3-dihydro-1H-indol-6-yl]-5,5-dimethyl-1-pyridin-4-ylmethylimidazolidine-2,4-dione prepared as described for example 136 by use of cyclohexylamine instead of morpholine.
M+H+measured=504
LC/MS retention time [min]=1.19

EXAMPLE 149

3-[1-(2-Hexahydropyrrolo[1,2-a]pyrazin-2-ylacetyl)-3,3-dimethyl-2,3-dihydo-1H-indol-6-yl]-5,5-dimethyl-1-pyridin-4-ylmethylimidazolidine-2,4-dione prepared as described for example 136 by use of octahydropyrrolo[1,2-A]pyrazine instead of morpholine.
M+H+measured=531
LC/MS retention time [min]=0.99

EXAMPLE 150

3-{1-[2-(3-Dimethylamino-2,2-dimethylpropylamino)acetyl]-3,3-dimethyl-2,3-dihydro-1H-indol-6-yl}-5,5-dimethyl-1-pyridin-4-ylmethylimidazolidine-2,4-dione prepared as described for example 136 by use of N,N-dimethylneopentanamide instead of morpholine.
M+H+measured=535
LC/MS retention time [min]=0.85

EXAMPLE 151

3-{1-[2-(4-Isopropylpiperazin-1-yl)acetyl]-3,3-dimethyl-2,3-dihydro-1H-indol-6-yl}-5,5-dimethyl-1-pyridin-4-ylmethylimidazolidine-2,4-dione prepared as described for example 136 by use of isopropylpiperazine instead of morpholine.
M+H+measured=533
LC/MS retention time [min]=1

EXAMPLE 152

3-[3,3-Dimethyl-1-(2-perhydro-1,4-oxazepin-1-ylacetyl)-2,3-dihydro-1H-indol-6-yl]-5,5-dimethyl-1-pyridin-4-ylmethylimidazolidine-2,4-dione prepared as described for example 136 by use of homomorpholine hydrochloride and Hünig's base instead of morpholine.
M+H+measured=506
LC/MS retention time [min]=0.94

EXAMPLE 153

3-{1-[2-((S)-3-Dimethylaminopyrrolidin-1-yl)acetyl]-3,3-dimethyl-2,3-dihydro-1H-indol-6-yl}-5,5-dimethyl-1-pyridin-4-ylmethylimidazolidine-2,4-dione prepared as described for example 136 by use of (3S)-(−)-3-(dimethylamino)pyrrolidine instead of morpholine.
M+H+measured=519
LC/MS retention time [min]=0.85

EXAMPLE 154

3-[1-(2-tert-Butylaminoacetyl)-3,3-dimethyl-2,3-dihydro-1H-indol-6-yl]-5,5-dimethyl-1-pyridin-4-ylmethylimidazolidine-2,4-dione prepared as described for example 136 by use of tert-butylamine instead of morpholine.
M+H+measured=478
LC/MS retention time [min]=1.02

EXAMPLE 155

3-{3,3-Dimethyl-1-[2-(2,2,2-trifluoroethylamino)
acetyl]-2,3-dihydro-1H-indol-6-yl}-5,5-dimethyl-1-
pyridin-4-ylmethylimidazolidine-2,4-dione prepared as described for example 136 by use of trifluoroethylamine instead of morpholine.
M+H+measured=504
LC/MS retention time [min]=1.11

EXAMPLE 156

3-[1-(2-Dimethylaminoacetyl)-3,3-dimethyl-2,3-
dihydro-1H-indol-6-yl]-5,5-dimethyl-1-pyridin-4-
ylmethylimidazolidine-2,4-dione prepared as described for example 136 by use of dimethylamine (2M in THF) instead of morpholine.
M+H+measured=450
LC/MS retention time [min]=0.98

EXAMPLE 157

3-[1-(2-Iopropylaminoacetyl)-3,3-dimethyl-2,3-dihydro-1H-indol-6-yl]-5,5-dimethyl-1-pyridin-4-ylmethylimidazolidine-2,4-dione prepared as described for example 136 by use of isopropylamine instead of morpholine.
M+H+measured=464
LC/MS retention time [min]=0.97

EXAMPLE 158

3-[1-(2-Cyclobutylaminoacetyl)-3,3-dimethyl-2,3-
dihydro-1H-indol-6-yl]-5,5-dimethyl-1-pyridin-4-
ylmethylimidazolidine-2,4-dione prepared as described for example 136 by use of cyclobutylamine instead of morpholine.
M+H+measured=476
LC/MS retention time [min]=0.99

EXAMPLE 159

3-{1-[2-(2-Amino-2-methylpropylamino)acetyl]-3,3-
dimethyl-2,3-dihydro-1H-indol-6-yl}-5,5-dimethyl-
1-pyridin-4-ylmethylimidazolidine-2,4-dione prepared as described for example 136 by use of 1,2-diamino-2-methylpropane instead of morpholine.
M+H+measured=493
LC/MS retention time [min]=0.87

EXAMPLE 160

3-{1-[2-((R)-3-Dimethylaminopyrrolidine-1-yl)
acetyl]-3,3-dimethyl-2,3-dihydro-1H-indol-6-yl}-5,
5-dimethyl-1-pyridin-4-ylmethylimidazolidine-2,4-
dione prepared as described for example 136 by use of (3R)-(+)-3-(dimethylamino)pyrrolidine instead of morpholine.
M+H+measured=519
LC/MS retention time [min]=0.89

EXAMPLE 161

3-(3,3-Dimethyl-1-{2-[methyl(1-methylpyrrolidin-3-
yl)amino]acetyl}-2,3-dihydro-1H-indol-6-yl)-5,5-
dimethyl-1-pyridin-4-ylmethylimidazolidine-2,4-
dione prepared as described for example 136 by use of N,N-dimethyl-3-aminopyrrolidine instead of morpholine.
M+H+measured=519
LC/MS retention time [min]=0.85

EXAMPLE 162

3-(1-{2-[1-Hydroxycyclopropylmethyl)amino]
acetyl}-3,3-dimethyl-2,3-dihydro-1H-indol-6-yl)-5,
5-dimethyl-1-pyridin-4-ylmethylimidazolidine-2,4-
dione prepared as described for example 136 by use of 1-(aminomethyl)cyclopropanol instead of morpholine.
M+H+measured=492
LC/MS retention time [min]=0.97

EXAMPLE 163

2-{2-[6-(4,4-Dimethyl-2,5-dioxo-3-pyridin-4-ylm-
ethylimidazolidin-1-yl)-3,3-dimethyl-2,3-dihydro-
1H-indol-1-yl]-2-oxoethylamino}acetamide prepared as described for example 136 by use of glycinamide hydrochloride and Hünig's base instead of morpholine.
M+H+measured=479
LC/MS retention time [min]=0.95

EXAMPLE 164

3-[1-(2-Azetidin-1-ylacetyl)-3,3-dimethyl-2,3-dihydro-1H-indol-6-yl]-5,5-dimethyl-1-pyridin-4-ylmethylimidazolidine-2,4-dione prepared as described for example 136 by use of azetidine instead of morpholine.
M+H+measured=462
LC/MS retention time [min]=0.94

EXAMPLE 165

3-{3,3-Dimethyl-1-[2-(pyrrolidin-3-ylamino)acetyl]-
2,3-dihydro-1H-indol-6-yl)-5,5-dimethyl-1-pyridin-
4-ylmethylimidazolidine-2,4-dione; compound prepared as described for example 136 by use of 3-amino-1-N-BOC-pyrrolidine instead of morpholine and subsequent detachment of the BOC group with 2N HCl.
M+H+measured=491
LC/MS retention time [min]=0.87

EXAMPLE 166

N-(Piperidin-4-yl)-6-(4,4-dimethyl-2,5-dioxo-3-pyridin-4-ylmethylimidazolidin-1-yl)-3,3-dimethyl-2,3-dihydroindole-1-carboxamide 1.00 g (2.74 mmol) of 3-(3,3-dimethyl-2,3-dihydro-1H-indol-6-yl)-5,5-dimethyl-1-pyridin-4-ylmethylimidazolidine-2,4-dione were dissolved in 10 ml of THF, and a solution of 609 mg (2.74 mmol) of 4-isocyanatotrifluoroacetylpiperidine in 10 ml of THF was added dropwise, partly reacted. After heating under reflux for 5 h, the mixture was concentrated, the remaining residue was taken up in 2 ml of dioxane/2N HCl (1:1), and heated in a microwave at 120° C. for 15 min. For workup, the mixture was concentrated and the remaining residue was purified by means of preparative HPLC (RP18, acetonitrile/water, 0.1% TFA). After release of the base by treating with sodium hydrogencarbonate solution, 240 mg of the title compound remain.

From unhydrolysed intermediate compound obtained analogously to the above preparation method, pure N-(piperidin-4-yl)-6-(4,4-dimethyl-2,5-dioxo-3-pyridin-4-ylmethylimidazolidin-1-yl)-3,3-dimethyl-2,3-dihydroindole-1-carboxamide were obtained by preparative HPLC (RP18, acetonitrile/water, 0.1% TFA).
M+H+measured=491
LC/MS retention time [min]=0.96

EXAMPLE 167

3-[3,3-Dimethyl-1-(pyridine-2-carbonyl)-2,3-dihydro-1H-indol-6-yl]-5,5-dimethyl-1-pyridin-4-ylmethylimidazolidine-2,4-dione 100 mg (0.27 mmol) of 3-[3,3-dimethyl-2,3-dihydro-1H-indol-6-yl]-5,5-dimethyl-1-pyridin-4-ylmethylimidazolidine-2,4-dione were dissolved in 5 ml of dichloromethane, 107 mg (0.82 mmol) of Hünig's base and 73 mg (0.41 mmol) of picolinyl chloride hydrochloride were added, and the mixture was stirred at RT for 15 h. For workup, the mixture was concentrated and the remaining residue was purified by means of preparative HPLC (RP18, acetonitrile/water, 0.1% TFA). After release of the base by treating with sodium hydrogencarbonate solution, 22 mg of the title compound remain.
M+H+measured=470
LC/MS retention time [min]=1.2

EXAMPLE 168

3-[3,3-Dimethyl-1-(pyridine-3-carbonyl)-2,3-dihydro-1H-indol-6-yl]-5,5-dimethyl-1-pyridin-4-ylmethylimidazolidine-2,4-dione prepared as described for example 167
M+H+measured=470
LC/MS retention time [min]=1.02

EXAMPLE 169

5,5-Dimethyl-1-pyridin-4-ylmethyl-3-{3-[(pyridin-2-ylmethyl)amino]-4-trifluoromethoxyphenyl}imidazolidine-2,4-dione prepared as described for example 96
M+H+measured=486
LC/MS retention time [min]=0.95

EXAMPLE 170

1-[5-(4,4-Dimethyl-2,5-dioxo-3-pyridin-4-ylmethylimidazolidin-1-yl)-2-trifluoromethoxyphenyl]-3-[1-(2,2,2-trifluoroacetyl)piperdin-4-yl]urea; Compound with Trifluoroacetic Acid prepared as described for example 166
M+H+measured=617
LC/MS retention time [min]=1.33

EXAMPLE 171

1-[5-(4,4-Dimethyl-2,5-dioxo-3-pyridin-4-ylmethylimidazolidin-1-yl)-2-trifluoromethoxyphenyl]-3-piperidin-4-ylurea prepared as described for example 166
M+H+measured=521
LC/MS retention time [min]=0.94

EXAMPLE 172

3-[1-(2-Dimethylamino-2-phenylacetyl)-3,3-dimethyl-2,3-dihydro-1H-indol-6-yl]-5,5-dimethyl-1-pyridin-4-ylmethylimidazolidine-2,4-dione prepared as described for example 136c) by use of chlorophenylacetyl chloride, dimethylamine in 1,2-dichloroethane as a solvent
M+H+measured=526
LC/MS retention time [min]=1.06

EXAMPLE 173

3-[1-(2-Azetidin-1-yl-2-phenylacetyl)-3,3-dimethyl-2,3-dihydro-1H-indol-6-yl]-5,5-dimethyl-1-pyridin-4-ylmethylimidazolidine-2,4-dione prepared as described for example 136c) by use of chlorophenylacetyl chloride in 1,2-dichloroethane as a solvent
M+H+measured=538
LC/MS retention time [min]=1.11

EXAMPLE 174

3-[1-(2-Isopropylamino-2-phenylacetyl)-3,3-dimethyl-2,3-dihydro-1H-indol-6-yl]-5,5-dimethyl-1-pyridin-4-ylmethylimidazolidine-2,4-dione prepared as described for example 136c) by use of chlorophenylacetyl chloride in 1,2-dichloroethane as a solvent
M+H+measured=540
LC/MS retention time [min]=1.13

EXAMPLE 175

3-[1-(2-Cyclopropylamino-2-phenylacetyl)-3,3-dimethyl-2,3-dihydro-1H-indol-6-yl]-5,5-dimethyl-1-pyridin-4-ylmethylimidazolidine-2,4-dione prepared as described for example 136c) by use of chlorophenylacetyl chloride in 1,2-dichloroethane as a solvent
M+H+measured=538
LC/MS retention time [min]=1.12

EXAMPLE 176

3-[1-(2-Cyclobutylamino-2-phenylacetyl)-3,3-dimethyl-2,3-dihydro-1H-indol-6-yl]-5,5-dimethyl-1-pyridin-4-ylmethylimidazolidine-2,4-dione prepared as described for example 136c) by use of chlorophenylacetyl chloride in 1,2-dichloroethane as a solvent
M+H+measured=552
LC/MS retention time [min]=1.16

EXAMPLE 177

3-[1-(2-Cyclopentylamino-2-phenylacetyl)-3,3-dimethyl-2,3-dihydro-1H-indol-6-yl]-5,5-dimethyl-1-pyridin-4-ylmethylimidazolidine-2,4-dione prepared as described for example 136c) by use of chlorophenylacetyl chloride in 1,2-dichloroethane as a solvent
M+H+measured=566
LC/MS retention time [min]=1.19

EXAMPLE 178

3-[3,3-Dimethyl-1-(pyridine-2-sulphonyl)-2,3-dihydro-1H-indol-6-yl]-5,5-dimethyl-1-pyridin-4-ylmethylimidazolidine-2,4-dione 100 mg (0.27 mmol) of 3-(3,3-dimethyl-2,3-dihydro-1H-indol-6-yl)-5,5-dimethyl-1-pyridin-4-ylmethylimidazolidine-2,4-dione were initially charged in 1 ml of pyridine, and 88 mg (0.41 mmol) of 2-pyridylsulphonyl chloride hydrochloride were added. For workup, the mixture was concentrated fully and the residue purified by flash chromatography (100 g of silica gel/95:5 CH2Cl1:CH3OH).
Yield: 80 mg
M+H+measured=506
LC/MS retention time [min]=1.28

EXAMPLE 179

3-[3,3-Dimethyl-1-(pyridine-3-sulphonyl)-2,3-dihydro-1H-indol-6-yl]-5,5-dimethyl-1-pyridin-4-ylmethylimidazolidine-2,4-dione prepared as described for example 178
M+H+measured=506
LC/MS retention time [min]=1.27

EXAMPLE 180

3-[3,3-Dimethyl-1-pyridin-2-ylmethyl-2,3-dihydro-1H-indol-6-yl]-5,5-dimethyl-1-pyridin-4-ylmethylimidazolidine-2,4-dione prepared as described for example 96 by reaction of 3-(3,3-dimethyl-2,3-dihydro-1H-indol-6-yl)-5,5-dimethyl-1-pyridin-4-ylmethylimidazolidine-2,4-dione with 2-bromomethylpyridine
M+H+measured=456
LC/MS retention time [min]=1.05

EXAMPLE 181

3-[1-(1-Cyclohexylazetidin-3-yl)-3,3-dimethyl-2,3-dihydro-1H-indol-6-yl]-5,5-dimethyl-1-pyridin-4-ylmethylimidazolidine-2,4-dione prepared as described for example 96 by reaction of 3-(3,3-dimethyl-2,3-dihydro-1H-indol-6-yl)-5,5-dimethyl-1-pyridin-4-ylmethylimidazolidine-2,4-dione with 1-cyclohexylazetidin-3-yl methanesulphonate oxalate
M+H+measured=502
LC/MS retention time [min]=1.16

EXAMPLE 182

N-(1-Cyclopropylpiperidin-4-yl)-6-(4,4-dimethyl-2,5-dioxo-3-pyridin-4-ylmethylimidazolidin-1-yl)-3,3-dimethyl-2,3-dihydroindole-1-carboxamide 50 mg (0.1 mmol) of 1-[5-(4,4-dimethyl-2,5-dioxo-3-pyridin-4-ylmethylimidazolidin-1-yl)-2-trifluoromethoxyphenyl)-3-piperidin-4-ylurea were dissolved in 2 ml of methanol, 1 g of molecular sieve (4 Å), 53 mg of glacial acetic acid, 77 mg (0.44 mmol) of [(1-ethoxycyclopropyl)oxy]trimethylsilane and 17 mg (0.26 mmol) of sodium cyanatoborohydride were added, and the mixture was heated under reflux for 1 h. Subsequently, the mixture was filtered and concentrated, and the remaining residue was purified by flash chromatography (silica gel, 95:5 methylene chloride/methanol).
Yield: 22 mg
M+H+measured=531
LC/MS retention time [min]=1.08

EXAMPLE 183

N-(1-Methylpiperidin-4-yl)-6-(4,4-dimethyl-2,5-dioxo-3-pyridin-4-ylmethylimidazolidin-1-yl)-3,3-dimethyl-2,3-dihydroindole-1-carboxamide prepared as described for example 182 by use of formaldehyde (37% in water) instead of [(1-ethoxycyclopropyl)oxy]trimethylsilane
M+H+measured=505
LC/MS retention time [min]=1.07

EXAMPLE 184

N-(1-Ethylpiperidin-4-yl)-6-(4,4-dimethyl-2,5-dioxo-3-pyridin-4-ylmethylimidazolidin-1-yl)-3,3-dimethyl-2,3-dihydroindole-1-carboxamide prepared as described for example 182 by use of acetaldehyde instead of [(1-ethoxycyclopropyl)oxy]trimethylsilane
M+H+measured=519
LC/MS retention time [min]=0.99

EXAMPLE 185

N-(1-Isobutylpiperidin-4-yl)-6-(4,4-dimethyl-2,5-dioxo-3-pyridin-4-ylmethylimidazolidin-1-yl)-3,3-dimethyl-2,3-dihydroindole-1-carboxamide prepared as described for example 182 by use of isobutyraldehyde instead of [(1-ethoxycyclopropyl)oxy]trimethylsilane
M+H+measured=547

EXAMPLE 186

N-(1-Isopropylpiperidin-4-yl)-6-(4,4-dimethyl-2,5-dioxo-3-pyridin-4-ylmethylimidazolidin-1-yl)-3,3-dimethyl-2,3-dihydroindole-1-carboxamide prepared as described for example 182 by use of acetone instead of [(1-ethoxycyclopropyl)oxy]trimethylsilane
M+H+measured=533
LC/MS retention time [min]=1.01

EXAMPLE 187

N-(Piperidin-4-ylamide)-6-[3-(2-aminopyrimidin-4-ylmethyl)-4,4-dimethyl-2,5-dioxoimidazolidin-1-yl]-3,3-dimethyl-2,3-dihydroindole-1-carboxamide a) 3-(1-acetyl-3,3-dimethyl-2,3-dihydro-1H-indol-6-yl)-5,5-dimethyl-1-(2-methylsulphanylpyrimidin-4-ylmethyl)imidazolidine-2,4-dione 2.40 g (7.6 mmol) of 1-(6-amino-3,3-dimethyl-2,3-dihydroindol-1-yl)ethanone were initially charged in 10 ml of DMF, 2.72 g (8.36 mmol) of caesium carbonate were added, and the mixture was stirred at RT for 30 min. Subsequently, 6.66 g (9.12 mmol) of 4-bromomethyl-2-methylthiopyrimidine (30% in THF) were added and the mixture was stirred at RT for 15 h. For workup, the mixture was filtered with suction from the precipitate and concentrated, and the remaining residue was purified by flash chromatography (silica gel, 95:5 methylene chloride/methanol).

Yield 3.5 g b) 3-(1-acetyl-3,3-dimethyl-2,3-dihydro-1H-indol-6-yl)-1-(2-methanesulphonylpyrimidin-4-ylmethyl)-5,5-dimethylimidazolidine-2,4-dione 3.5 g (7.72 mmol) of 3-(1-acetyl-3,3-dimethyl-2,3-dihydro-1H-indol-6-yl)-5,5-dimethyl-1-(2-methylsulphanylpyrimidin-4-ylmethyl)imidazolidine-2,4-dione were dissolved in 50 ml of methylene chloride, and a solution of 4.65 g (23.1 mmol) of m-chloroperbenzoic acid (85%) in 10 ml of methylene chloride was added gradually. After a total of 15 h at RT, the mixture was concentrated and the remaining residue was purified by flash chromatography (silica gel, 95:5 methylene chloride/methanol).

Yield 3.7 g c) 1-(2-aminopyrimidin-4-ylmethyl)-3-(3,3-dimethyl-2,3-dihydro-1H-indol-6-yl)-5,5-dimethylimidazolidine-2,4-dione 3.7 g (7.62 mmol) of 3-(1-acetyl-3,3-dimethyl-2,3-dihydro-1H-indol-6-yl)-1-(2-methanesulphonylpyrimidin-4-ylmethyl)-5,5-dimethylimidazolidine-2,4-dione were dissolved in 10 ml of dioxane, 10 ml of aqueous ammonia solution (33%) were added, and the mixture was heated in a microwave at 120° C. for 20 minutes. Subsequently, the mixture was concentrated and the remaining crude 3-(1-acetyl-3,3-dimethyl-2,3-dihydro-1H-indol-6-yl)-1-(2-methanesulphonylpyrimidin-4-ylmethyl)-5,5-dimethylimidazolidine-2,4-dione (3.7 g) was heated in a microwave with 5 ml of dioxane and 5 ml of 2 N HCl at 120° C. for 20 min. For workup, the mixture was concentrated, taken up in sodium carbonate solution, extracted with ethyl acetate, dried and concentrated. The remaining residue was purified by flash chromatography (silica gel, 95:5 methylene chloride/methanol).

Yield 1.7 g d) N-piperidin-4-yl-6-[3-(2-aminopyrimidin-4-ylmethyl)-4,4-dimethyl-2,5-dioxoimidazolidin-1-yl]-3,3-dimethyl-2,3-dihydroindole-1-carboxamide 200 mg (0.53 mmol) of 1-(2-aminopyrimidin-4-ylmethyl)-3-(3,3-dimethyl-2,3-dihydro-1H-indol-6-yl)-5,5-dimethylimidazolidine-2,4-dione were dissolved in 3 ml of THF, and a solution of 118 mg (0.53 mmol) of 4-isocyanatotrifluoroacetylpiperidine in 3 ml of THF was added. After stirring at RT for 1 h, the mixture is concentrated and taken up in 3 ml of dioxane and 3 ml of 2 N HCl, and the mixture is heated in a microwave at 120° C. for 15 min. For workup, the mixture was concentrated and the remaining residue was purified by means of preparative HPLC (RP18, acetonitrile/water, 0.1% TFA). After release of the base by treating with sodium hydrogencarbonate solution, 60 mg of the title compound were obtained.

M+H+measured=507
LC/MS retention time [min]=0.98

EXAMPLE 188

1-(2-Aminopyrimidin-4-ylmethyl)-3-[1-(2-tert-butylaminoacetyl)-3,3-dimethyl-2,3-dihydro-1H-indol-6-yl]-5,5-dimethylimidazolidine-2,4-dione prepared as described for example 136
M+H+measured=494
LC/MS retention time [min]=1.01

EXAMPLE 189

1-(2-Aminopyrimidin-4-ylmethyl)-3-[1-(2-azetidin-1-ylacetyl)-3,3-dimethyl-2,3-dihydro-1H-indol-6-yl]-5,5-dimethylimidazolidine-2,4-dione prepared as described for example 136
M+H+measured=478
LC/MS retention time [min]=1.01

EXAMPLE 190

1-(2-Aminopyrimidin-4-ylmethyl)-3-[1-(2-cyclopropylaminoacetyl)-3,3-dimethyl-2,3-dihydro-1H-indol-6-yl]-5,5-dimethylimidazolidine-2,4-dione prepared as described for example 136
M+H+measured=478
LC/MS retention time [min]=0.96

EXAMPLE 191

1-(2-Aminopyrimidin-4-ylmethyl)-3-[1-(2-cyclopentylaminoacetyl)-3,3-dimethyl-2,3-dihydro-1H-indol-6-yl]-5,5-dimethylimidazolidine-2,4-dione prepared as described for example 136
M+H+measured=506
LC/MS retention time [min]=1.05

EXAMPLE 192

1-(2-Aminopyrimidin-4-ylmethyl)-3-[3,3-dimethyl-1-(pyridine-2-carbonyl)-2,3-dihydro-1H-indol-6-yl]-5,5-dimethylimidazolidine-2,4-dione prepared as described for example 167
M+H+measured=486
LC/MS retention time [min]=1.23

EXAMPLE 193

1-(2-Aminopyrimidin-4-ylmethyl)-3-[1-(2-azetidin-1-yl-2-phenylacetyl)-3,3-dimethyl-2,3-dihydro-1H-indol-6-yl]-5,5-dimethylimidazolidine-2,4-dione prepared as described for example 136 c) by use of chlorophenylacetyl chloride in 1,2-dichloroethane as a solvent.
M+H+measured=554
LC/MS retention time [min]=1.15

EXAMPLE 194

1-(2-Aminopyrimidin-4-ylmethyl)-3-[3,3-dimethyl-1-(pyridine-3-carbonyl)-2,3-dihydro-1H-indol-6-yl]-5,5-dimethylimidazolidine-2,4-dione prepared as described for example 167
M+H+measured=486
LC/MS retention time [min]=1.07

EXAMPLE 195

1-(2-Aminopyrimidin-4-ylmethyl)-3-[3,3-dimethyl-1-((S)-piperidine-2-carbonyl)-2,3-dihydro-1H-indol-6-yl]-5,5-dimethylimidazolidine-2,4-dione prepared as described for example 120
M+H+measured=492
LC/MS retention time [min]=1.05

EXAMPLE 196

1-(2-Aminopyrimidin-4-ylmethyl)-3-[3,3-dimethyl-1-((R)-piperidine-2-carbonyl)-2,3-dihydro-1H-indol-6-yl]-5,5-dimethylimidazolidine-2,4-dione prepared as described for example 120
M+H+measured=492
LC/MS retention time [min]=1.01

EXAMPLE 197

1-(2-Aminopyrimidin-4-ylmethyl)-3-[3,3-dimethyl-1-((R)-1,2,3,4-tetrahydroisoquinoline-1-carbonyl)-2,3-dihydro-1H-indol-6-yl]-5,5-dimethylimidazolidine-2,4-dione prepared as described for example 120
M+H+measured=540
LC/MS retention time [min]=1.16

EXAMPLE 198

1-(2-Aminopyrimidin-4-ylmethyl)-3-[3,3-dimethyl-1-((S)-1,2,3,4-tetrahydroisoquinoline-1-carbonyl)-2,3-dihydro-1H-indol-6-yl]-5,5-dimethylimidazolidine-2,4-dione prepared as described for example 120
M+H+measured=540
LC/MS retention time [min]=1.23

EXAMPLE 199

3-[1-(2-Dimethylamino-acetyl)-3,3-dimethyl-2,3-dihydro-1H-indol-6-yl]-5,5-dimethyl-1-quinolin-4-ylmethyl-imidazolidine-2,4-dione To a solution of 50 mg 3-(3,3-dimethyl-2,3-dihydro-1H-indol-6-yl)-5,5-dimethyl-1-quinolin-4-ylmethyl-imidazolidine-2,4-dione in 1 ml 1,2-dichloroethane 0.04 ml ethyl-diisopropyl-amine and 13.7 mg chloroacetylchloride were added at 0° C. After stirring for 1 hour at 0° C. 5.5 mg dimethyl-amine were added and the reaction mixture was stirred for 2 days at room temperature. After removing of the solvent under reduced pressure the residue was purified by preparative HPLC (C18 reverse phase column, elution with a water/acetonitrile gradient with 0.1% trifluoroacetic acid). After lyophilization of the solution the resulting crude product was purified in addition by flash chromatography on silica gel with a dichloro-methane/methanol gradient. The fractions containing the product were evaporated to yield a white solid.
Yield: 3 mg
M+H+measured=500
1H-NMR (500 MHz, DMSO/TMS): d=8.98 (d, 1H); 8.25 (d, 1H); 8.12 (s, 1H); 8.08 (d, 1H); 7.83 (t, 1H); 7.70 (t, 1H); 7.60 (d, 1H); 7.43 (d, 1H); 7.19 (d, 1H); 5.15 (s, 2H); 3.93 (s, 2H); 2.65 (m, 2H); 2.60-2.40 (s, 6H); 1.44 (s, 6H); 1.35 (s, 6H)

EXAMPLE 200

3-{3,3-Dimethyl-1-[2-(2,2,2-trifluoro-ethylamino)-acetyl]-2,3-dihydro-1H-indol-6-yl}-5,5-dimethyl-1-quinolin-4-ylmethyl-imidazolidine-2,4-dione To a solution of 100 mg 3-(3,3-dimethyl-2,3-dihydro-1H-indol-6-yl)-5,5-dimethyl-1-quinolin-4-ylmethyl-imidazolidine-2,4-dione in 2 ml 1,2-dichloroethane in a process vial 0.08 ml ethyl-diisopropyl-amine and 27.2 mg chloroacetyl-chloride were added at 0° C. After stirring for 1 hour at 0° C. 119.4 mg 2,2,2-trifluoro-ethylamine were added. The resulting mixture was stirred for 1 hour at room temperature and then further 119.4 mg 2,2,2-trifluoro-ethylamine were added. The vial was sealed with a teflon septum and placed in the microwave cavity. The reaction mixture was stirred for 15 minutes at 100° C. by microwave-assisted heating (Emrys Optimizer, Personal Chemistry). After further 15 minutes stirring at 150° C. the solution was heated for 1 hour at 150° C. The solvent was removed under reduced pressure and the residue purified by preparative HPLC (C18 reverse phase column, elution with a water/acetonitrile gradient with 0.1% trifluoracetic acid). Lyophilization of the solution yielded a white solid.
Yield: 39 mg
M+H+measured=554
1H-NMR (500 MHz, DMSO/TMS): d=8.96 (d, 1H); 8.33 (d, 1H); 8.14 (m, 2H); 7.90 (t, 1H); 7.75 (m, 2H); 7.42 (d, 1H); 7.16 (d, 1H); 5.21 (s, 2H); 3.88 (s, 2H); 3.80 (s, 2H); 3.55 (m, 2H); 1.46 (s, 6H); 1.35 (s, 6H)

EXAMPLE 201

3-{3,3-Dimethyl-1-[2-(4-methyl-piperazin-1-yl)-acetyl]-2,3-dihydro-1H-indol-6-yl}-5,5-dimethyl-1-quinolin-4-ylmethyl-imidazolidine-2,4-dione To a solution of 70 mg 3-(3,3-dimethyl-2,3-dihydro-1H-indol-6-yl)-5,5-dimethyl-1-quinolin-4-ylmethyl-imidazolidine-2,4-dione in 2 ml 1,2-dichloroethane in a process vial 0.06 ml ethyl-diisopropyl-amine and 13.5 mg chloroacetyl-chloride were added at 0° C. After stirring for 1 hour at 0° C. 33.9 mg 1-methyl-piperazine were added. The resulting mixture was stirred for 2 hours at room temperature. The solvent was removed under reduced pressure and the residue purified by preparative HPLC (C18 reverse phase column, elution with a water/acetonitrile gradient with 0.1% trifluoroacetic acid). Lyophilization of the solution yielded a white solid.

Yield: 65 mg
M+H+measured=555
1H-NMR (500 MHz, DMSO/TMS): d=8.90 (d, 1H); 8.28 (d, 1H); 8.11 (m, 2H); 7.85 (t, 1H); 7.73 (t, 1H); 7.65 (d, 1H); 7.41 (d, 1H); 7.16 (dd, 1H); 5.17 (s, 2H); 3.94 (s, 2H); 3.90-3.30 (m, 4H); 3.10 (m, 4H); 2.79 (s, 3H); 2.68 (m, 2H); 1.44 (s, 6H); 1.35 (s, 6H)

EXAMPLE 202

3-[1-(2-Cyclopentylamino-acetyl)-3,3-dimethyl-2,3-dihydro-1H-indol-6-yl]-5,5-dimethyl-1-quinolin-4-ylmethyl-imidazolidine-2,4-dione The following compounds were prepared in analogy to example 201 by using the corresponding amines instead of 1-methyl-piperazine. Further 0.1 ml of the corresponding amines were added and the reaction mixtures were stirred for 15 minutes at 100° C. by microwave-assisted heating (Emrys Optimizer, Personal Chemistry).

The product was obtained as its trifluoroacetic salt.
Yield: 45 mg
M+H+measured=540
1H-NMR (500 MHz, DMSO/TMS): d=8.95 (m, 2H); 8.90 (d, 1H); 8.28 (d, 1H); 8.13 (d, 1H); 8.10 (d, 1H); 7.85 (t, 1H); 7.72 (t, 1H); 7.63 (d, 1H); 7.48 (d, 1H); 7.25 (dd, 1H); 5.17 (s, 2H); 4.20 (t, 2H); 3.97 (s, 2H); 2.00 (m, 2H); 1.70 (m, 4H); 1.55 (m, 2H); 1.44 (s, 6H); 1.38 (s, 6H)

EXAMPLE 203

3-[1-(2-Isopropylamino-acetyl)-3,3-dimethyl-2,3-dihydro-1H-indol-6-yl]-5,5-dimethyl-1-quinolin-4-ylmethyl-imidazolidine-2,4-dione The product was obtained as its trifluoroacetic salt.
Yield: 43 mg
M+H+measured=
1H-NMR (500 MHz, DMSO/TMS): d=8.90 (d, 1H); 8.79 (m, 2H); 8.28 (d, 1H); 8.13 (d, 1H); 8.10 (d, 1H); 7.85 (t, 1H); 7.72 (t, 1H); 7.63 (d, 1H); 7.48 (d, 1H); 7.25 (dd, 1H); 5.17 (s, 2H); 4.19 (t, 2H); 4.00 (s, 2H); 3.37 (m, 1H); 1.45 (s, 6H); 1.38 (s, 6H); 1.28 (d, 6H)

EXAMPLE 204

3-{3,3-Dimethyl-1-[2-(pyrrolidin-3-ylamino)-acetyl]-2,3-dihydro-1H-indol-6-yl}-5,5-dimethyl-1-quinolin-4-ylmethyl-imidazolidine-2,4-dione In addition the reaction mixture was stirred for further 15 minutes at 100° C. by microwave-assisted heating (Emrys Optimizer, Personal Chemistry). After lyophilization the residue was dissolved in 2 ml of a 8 N solution of hydrochloric acid in methanol and stirred for 1 hour at room temperature. After removal of the solvent under reduced pressure the residue was dissolved in a mixture of 2 ml water and 1 ml acetonitrile. Lyophilization of the resulting mixture yielded a white foam. The product was obtained as its hydrochloric salt.

Yield: 19 mg
M+H+measured=541
1H-NMR (500 MHz, DMSO/TMS): d=9.90-9.25(m, 4H); 8.98 (d, 1H); 8.35 (d, 1H); 8.19 (d, 1H); 8.13 (s, 1H); 7.95 (d, 1H); 7.80 (m, 2H); 7.48 (d, 1H); 7.25 (d, 1H); 5.13 (s, 2H); 4.29 (m, 2H); 3.96 (m, 3H); 3.70-3.30 (m, 2H); 3.25 (m, 2H); 2.35 (m, 1H); 2.25 (m, 1H); 1.46 (s, 6H); 1.39 (s, 6H)

EXAMPLE 205

3-{1-[2-(2-Dimethylamino-ethylamino)-acetyl]-3,3-dimethyl-2,3-dihydro-1H-indol-6-yl}-5,5-dimethyl-1-quinolin-4-ylmethyl-imidazolidine-2,4-dione After lyophilization the crude product was partitioned between 5 ml ethyl acetate and 5 ml of a saturated aqueous solution of sodium hydrogen carbonate. The organic layer was dried over sodium sulphate. After removing of the solvent under reduced pressure the residue was purified in addition by flash chromatography on silica gel with a dichloromethane/methanol/water/triethylamine gradient. The fractions containing the product were evaporated to yield a white solid.

Yield: 9.5 mg
M+H+measured=543
1H-NMR (500 MHz, DMSO/TMS): d=8.89 (d, 1H); 8.25 (d, 1H); 8.12 (s, 1H); 8.08 (d, 1H); 7.82 (t, 1H); 7.70 (t, 1H); 7.60 (d, 1H); 7.40 (d, 1H); 7.13 (d, 1H), 5.13 (s, 2H); 3.89 (s, 2H); 3.52 (d, 2H); 2.65 (t, 2H); 2.36 (t, 2H); 2.17 (s, 6H); 1.43 (s, 6H); 1.33 (s, 6H)

EXAMPLE 206

3-{3,3-Dimethyl-1-[2-(1-methyl-piperidin-4-ylamino)-acetyl]-2,3-dihydro-1H-indol-6-yl}-5,5-dimethyl-1-quinolin-4-ylmethyl-imidazolidine-2,4-dione After lyophilization the crude product was purified in addition by flash chromatography on silica gel with a dichloromethane/methanol/water/triethylamine gradient. The fractions containing the product were evaporated to yield a white solid.

Yield: 2 mg
M+H+measured=569
1H-NMR (500 MHz, DMSO/TMS): d=8.89 (d, 1H); 8.25 (d, 1H); 8.12 (s, 1H); 8.08 (d, 1H); 7.82 (t, 1H); 7.70 (t, 1H); 7.60 (d, 1H); 7.40 (d, 1H); 7.15 (d, 1H), 5.14 (s, 2H); 3.93 (s, 2H); 3.60 (m, 2H); 3.52 (s, 1H); 3.32 (s, 3H); 2.85 (m, 2H); 2.28 (m, 2H); 1.84 (m, 2H); 1.43 (s, 6H); 1.34 (s, 6H)

EXAMPLE 207a 3,3-Dimethyl-6-nitro-2,3-dihydro-1H-indole 2 g 1-(3,3-dimethyl-6-nitro-2,3-dihydro-indol-1-yl)-ethanone were dissolved in a mixture of 6 ml dioxane and 6 ml of an aqueous 2 N solution of hydrochloric acid in a process vial. The vial was sealed with a teflon septum and placed in the microwave cavity. The reaction mixture was stirred for 15 minutes at 120° C. by microwave-assisted heating (Emrys Optimizer, Personal Chemistry). After removal of the solvent under reduced pressure the residue was treated with an aqueous saturated solution of sodium carbonate and extracted with ethyl acetate. The organic layer was dried over anhydrous sodium sulfate. Filtration and concentration of the solvent under reduced pressure yielded a white solid.
Yield: 1.7 g
M+H+measured=193
1H-NMR (400 MHz, DMSO/TMS): d=7.43 (dd, 1H); 7.19 (m, 2H); 6.15 (s, 1H); 3.35-3.25 (s, 2H); 1.25 (s, 6H)

EXAMPLE 207b 4-(3,3-Dimethyl-6-nitro-2,3-dihydro-indol-1-ylmethyl)-piperidine-1-carboxylic acid tert-butyl ester A process vial with a suspension of 1 g 3,3-dimethyl-6-nitro-2,3-dihydro-1H-indole, 1.59 g 4-bromomethyl-piperidine-1-carboxylic acid tert-butyl ester and 1.17 g potassium tert-butoxide in 10 ml N,N-dimethylformamide was sealed with a teflon septum and placed in the microwave cavity. The reaction mixture was stirred for 15 minutes at 100° C. by microwave-assisted heating (Emrys Optimizer, Personal Chemistry). After removal of the solvent under reduced pressure the residue was purified by flash chromatography on silica gel with a n-heptane/ethylacetate gradient. The fractions containing the product were combined and evaporated to yield a white solid.
Yield: 0.24 g
M+H+measured=388
1H-NMR (400 MHz, DMSO/TMS): d=7.44 (m, 1H); 7.19 (m, 2H); 3.95 (m, 2H); 3.27 (s, 2H); 3.05 (d, 2H); 2.70 (m, 2H); 1.83 (m, 1H); 1.65 (m, 2H); 1.40 (s, 9H); 1.28 (s, 6H); 1.10 (m, 2H)

EXAMPLE 207c 4-(6-Amino-3,3-dimethyl-2,3-dihydro-indol-1-ylmethyl)-piperidine-1-carboxylic acid tert-butyl ester A mixture of 240 mg 4-(3,3-dimethyl-6-nitro-2,3-dihydro-indol-1-ylmethyl)-piperidine-1-carboxylic acid tert-butyl ester, 20 mg of 10% palladium on carbon and 5 ml ethanol was stirred for 3 hours under hydrogen atmosphere. The mixture was filtered through a chem elut cartridge and the compound was eluted with ethanol. After concentration under reduced pressure the residue was directly subjected to the subsequent reaction without further purification.
Yield: 216 mg
M+H+measured=360
1H-NMR (400 MHz, DMSO/TMS): d=6.59 (d, 1H); 5.80 (d, 1H); 5.73 (s, 1H); 4.61 (s, 2H); 3.95 (m, 2H); 3.00 (s, 2H); 2.79 (d, 2H); 2.70 (m, 2H); 1.72 (m, 3H); 1.39 (s, 9H); 1.15 (s, 6H); 1.05 (m, 2H)

EXAMPLE 207d

4-[6-(4,4-Dimethyl-2,5-dioxo-3-quinolin-4-ylmethyl-imidazolidin-1-yl)-3,3-dimethyl-2,3-dihydro-indol-1-ylmethyl]-piperidine-1-carboxylic acid tert-butyl ester To a solution of 50 mg 4-(6-amino-3,3-dimethyl-2,3-dihydro-indol-1-ylmethyl)-piperidine-1-carboxylic acid tert-butyl ester in 5 ml tetrahydrofuran 0.05 ml ethyl-diisopropylamine and 28 mg 4-nitrophenyl chloroformate were added and the mixture was stirred for 2 hours at room temperature. Afterwards 36 mg 2-methyl-2-[(quinolin-4-ylmethyl)-amino]-propionic acid methyl ester were added to the reaction mixture. After 16 hours stirring at room temperature the solvent was removed under reduced pressure and the residue was purified by preparative HPLC (C18 reverse phase column, elution with a water/acetonitrile gradient with 0.1% trifluoroacetic acid). Lyophilization of the solution yielded a white solid.
Yield: 25 mg
M+H+measured=612
1H-NMR (250 MHz, DMSO/TMS): d=8.97 (d, 1H); 8.35 (d, 1H); 8.13 (d, 1H); 7.91 (t, 1H); 7.79 (t, 1H); 7.70 (d, 1H); 7.08 (d, 1H); 6.60 (d, 1H); 6.51 (s, 1H); 5.19 (s, 2H); 4.20-3.80 (m, 2H); 3.17 (s, 2H); 2.93 (d, 2H); 2.75 (m, 2H); 1.73 (m, 3H); 1.43 (s, 6H); 1.38 (s, 9H); 1.26 (s, 6H); 1.07 (m, 2H)

EXAMPLE 208

3-(3,3-Dimethyl-1-piperidin-4-ylmethyl-2,3-dihydro-1H-indol-6-yl)-5,5-dimethyl-1-quinolin-4-ylmethyl-imidazolidine-2,4-dione A solution of 25 mg 4-[6-(4,4-dimethyl-2,5-dioxo-3-quinolin-4-ylmethyl-imidazolidin-1-yl)-3,3-dimethyl-2,3-dihydro-indol-1-ylmethyl]-piperidine-1-carboxylic acid tert-butyl ester in 2 ml of a 8 N solution of hydrochloric acid in methanol was stirred for 1 hour at room temperature. After removal of the solvent under reduced pressure the residue was purified by preparative HPLC (C18 reverse phase column, elution with a water/acetonitrile gradient with 0.1% trifluoroacetic acid). Lyophilization of the combined fractions containing the product yielded a white solid, that was partitioned between 2 ml of a satured aqueous solution of sodium hydrogen carbonate and 2 ml ethyl acetate. The organic layer was dried over sodium sulfate. After filtration the solvent was removed under reduced pressure. The residue was dissolved in a mixture of 1 ml acetonitrile and 2 ml water. After addition of 0.01 ml of a 1 N solution of hydrochloric acid the resulting solution was lyophilized to yield a white foam. The product was obtained as its hydrochloric salt.
Yield: 15 mg
M+H+measured=512
1H-NMR (500 MHz, DMSO/TMS): d=8.95 (d, 1H); 8.73 (m, 1H); 8.50 (m, 1H); 8.33 (d, 1H); 8.15 (d, 1H); 7.90 (t, 1H); 7.76 (t, 1H); 7.68 (m, 1H); 7.10 (d, 1H); 6.63 (dd, 1H); 6.55 (d, 1H); 5.19 (s, 2H); 3.30 (m, 2H); 3.17 (s, 2H); 2.95 (d, 2H); 2.88 (m, 2H); 1.90 (m, 3H); 1.50-1.35 (m, 8H); 1.27 (s, 6H)

General Procedure for the Preparation of the Following Compounds (Example 209 to 221)

The following compounds were prepared in analogy to example 201 by using 100 mg 3-(3,3-dimethyl-2,3-dihydro-1H-indol-6-yl)-5,5-dimethyl-1-quinolin-4-ylmethyl-imidazolidine-2,4-dione as starting material and 3 equivalents of the corresponding amines instead of 1-methyl-piperazine. The reaction mixture was stirred for 1 hour at 100° C. by microwave-assisted heating (Emrys Optimizer, Personal Chemistry). After purification the residue was partitioned between 5 ml of a saturated aqueous solution of sodium hydrogen carbonate and 5 ml ethyl acetate. The organic layer was dried over sodium sulfate. After filtration the solvent was removed under reduced pressure. The residue was dissolved in a mixture of 1 ml acetonitrile and 2 ml water and lyophilized.

EXAMPLE 209 cis/trans-3-{1-[2-(3,5-Dimethyl-piperazin-1-yl)-acetyl]-3,3-dimethyl-2,3-dihydro-1H-indol-6-yl}-5,5-dimethyl-1-quinolin-4-ylmethyl-imidazolidine-2,4-dione This title compound was purified in addition by flash chromatography on silica gel with a dichloro-methane/methanol/water/triethylamine gradient. The fractions containing the product were combined and evaporated to yield a white solid.
Yield: 35.5 mg
M+H+measured=569
1H-NMR (500 MHz, DMSO/TMS): d=8.88 (d, 1H); 8.25 (d, 1H); 8.08 (m, 2H); 7.82 (t, 1H); 7.69 (t, 1H); 7.60 (d, 1H); 7.39 (d, 1H); 7.13 (dd, 1H); 5.15 (s, 2H); 4.05 (s, 2H); 3.23 (s, 2H); 2.73 (m, 4H); 1.67 (t, 2H); 1.44 (s, 6H); 1.33 (s, 6H); 0.91 (d, 6H)

EXAMPLE 210

3-[1-(2-Diethylamino-acetyl)-3,3-dimethyl-2,3-dihydro-1H-indol-6-yl]-5,5-dimethyl-1-quinolin-4-ylmethyl-imidazolidine-2,4-dione Yield: 50 mg
M+H+measured=528
1H-NMR (500 MHz, DMSO/TMS): d=8.88 (d, 1H); 8.25 (d, 1H); 8.08 (m, 2H); 7.82 (t, 1H); 7.69 (t, 1H); 7.60 (d, 1H); 7.39 (d, 1H); 7.12 (dd, 1H); 5.15 (s, 2H); 4.05 (s, 2H); 3.36 (s, 2H); 2.60 (q, 4H); 1.44 (s, 6H); 1.33 (S, 6H); 1.01 (t, 6H)

EXAMPLE 211

3-[3,3-Dimethyl-1-(2-pyrrolidin-1-yl-acetyl)-2,3-dihydro-1H-indol-6-yl]-5,5-dimethyl-1-quinolin-4-ylmethyl-imidazolidine-2,4-dione Yield: 19.5 mg
M+H+measured=526
1H-NMR (500 MHz, DMSO/TMS): d=8.88 (d, 1H); 8.25 (d, 1H); 8.08 (m, 2H); 7.82 (t, 1H); 7.69 (t, 1H); 7.60 (d, 1H); 7.39 (d, 1H); 7.12 (dd, 1H); 5.15 (s, 2H); 3.98 (s, 2H); 3.43 (s, 2H); 2.60 (m, 4H); 1.72 (m, 4H); 1.44 (s, 6H); 1.34 (s, 6H)

EXAMPLE 212

(S)-3-(1-{2-[(1-Ethyl-pyrrolidin-2-ylmethyl)-amino]-acetyl}-3,3-dimethyl-2,3-dihydro-1H-indol-6-yl)-5,5-dimethyl-1-quinolin-4-ylmethyl-imidazolidine-2,4-dione The title compound was purified in addition by flash chromatography on silica gel with a dichloro-methane/methanol/water/triethylamine gradient. The fractions containing the product were evaporated to yield a white solid.
Yield: 30.5 mg
M+H+measured=583
1H-NMR (500 MHz, DMSO/TMS): d=8.88 (d, 1H); 8.25 (d, 1H); 8.13 (S, 1H); 8.08 (d, 1H); 7.82 (t, 1H); 7.69 (t, 1H); 7.60 (d, 1H); 7.39 (d, 1H); 7.13 (dd, 1H); 5.15 (s, 2H); 3.90 (s, 2H); 3.50 (q, 2H); 3.05 (m, 1H); 2.83 (m, 1H); 2.40 (m, 1H); 2.14 (m, 1H); 2.05 (m, 1H); 1.82 (m, 1H); 1.64 (m, 3H); 1.46 (s, 6H); 1.35 (s, 6H); 1.24 (m, 2H); 1.04 (t, 3H); 0.86 (m, 1H)

EXAMPLE 213

3-[1-(2-Cyclopropylamino-acetyl)-3,3-dimethyl-2,3-dihydro-1H-indol-6-yl]-5,5-dimethyl-1-quinolin-4-ylmethyl-imidazolidine-2,4-dione Yield: 46 mg
M+H+measured=512
1H-NMR (500 MHz, DMSO/TMS): d=8.88 (d, 1H); 8.25 (d, 1H); 8.13 (s, 1H); 8.09 (d, 1H); 7.82 (t, 1H); 7.69 (t, 1H); 7.60 (d, 1H); 7.39 (d, 1H); 7.13 (dd, 1H); 5.15 (s, 2H); 3.91 (s, 2H); 3.53 (s, 2H); 2.25 (m, 1H); 1.45 (s, 6H); 1.35 (s, 6H); 0.37 (m, 2H); 0.26 (m, 2H)

EXAMPLE 214

3-[1-(2-Cyclobutylamino-acetyl)-3,3-dimethyl-2,3-dihydro-1H-indol-6-yl]-5,5-dimethyl-1-quinolin-4-ylmethyl-imidazolidine-2,4-dione Yield: 18.8 mg
M+H+measured=526
1H-NMR (500 MHz, DMSO/TMS): d=8.88 (d, 1H); 8.25 (d, 1H); 8.08 (m, 2H); 7.82 (t, 1H); 7.70 (t, 1H); 7.60 (s, 1H); 7.38 (d, 1H); 7.14 (d, 1H); 5.15 (s, 2H); 3.92. (s, 2H); 3.44 (s, 2H); 3.25 (m, 1H); 2.08 (m, 2H); 1.72 (m, 2H); 1.64 (m, 1H); 1.55 (m, 1H); 1.43 (s, 6H); 1.34 (s, 6H)

EXAMPLE 215

3-[1-(2-Cyclohexylamino-acetyl)-3,3-dimethyl-2,3-dihydro-1H-indol-6-yl]-5,5-dimethyl-1-quinolin-4-ylmethyl-imidazolidine-2,4-dione Yield: 50.8 mg
M+H+measured=554
1H-NMR (500 MHz, DMSO/TMS): d=8.88 (d, 1H); 8.25 (d, 1H); 8.12 (s, 1H); 8.08 (d, 1H); 7.82 (t, 1H); 7.70 (t, 1H); 7.60 (s, 1H); 7.38 (d, 1H); 7.12 (d, 1H); 5.14 (s, 2H); 3.92 (s, 2H); 3.50 (s, 2H); 2.37 (m, 1H); 1.83 (m, 2H); 1.68 (m, 2H); 1.55 (m, 1H); 1.43 (s, 6H); 1.34 (s, 6H); 1.19 (m, 4H); 1.05 (m, 2H)

EXAMPLE 216

(R)-3-{1-[2-(3-Dimethylamino-pyrrolidin-1-yl)-acetyl]-3,3-dimethyl-2,3-dihydro-1H-indol-6-yl}-5,5-dimethyl-1-quinolin-4-ylmethyl-imidazolidine-2,4-dione The title compound was purified in addition by flash chromatography on silica gel with a dichloro-methane/methanol/water/triethylamine gradient. The fractions containing the product were combined and evaporated to yield a white solid.
Yield: 33.7 mg
M+H+measured=569
1H-NMR (500 MHz, DMSO/TMS): d=8.88 (d, 1H); 8.25 (d, 1H); 8.08 (m, 2H); 7.82 (t, 1H); 7.70 (t, 1H); 7.60 (d, 1H); 7.39 (d, 1H); 7.12 (dd, 1H); 5.14 (s, 2H); 3.97 (s, 2H); 3.35-3.30 (s, 2H); 2.73 (m, 3H); 2.60 (m, 1H); 2.10 (s, 6H); 1.84 (m, 1H); 1.60 (m, 1H); 1.43 (s, 6H); 1.32 (s, 6H); 0.85 (m, 1H)

EXAMPLE 217

3-{1-[2-(4-Isopropyl-piperazin-1-yl)-acetyl]-3,3-dimethyl-2,3-dihydro-1H-indol-6-yl}-5,5-dimethyl-1-quinolin-4-ylmethyl-imidazolidine-2,4-dione Yield: 40.4 mg
M+H+measured=583
1H-NMR (500 MHz, DMSO/TMS): d=8.88 (d, 1H); 8.25 (d, 1H); 8.08 (m, 2H); 7.82 (t, 1H); 7.70 (t, 1H); 7.60 (d, 1H); 7.39 (d, 1H); 7.12 (dd, 1H); 5.14 (s, 2H); 4.03 (s, 2H); 3.25 (s, 2H); 2.60-2.40 (m, 9H); 1.43 (s, 6H); 1.32 (s, 6H); 0.95 (d, 6H)

EXAMPLE 218

3-{3,3-Dimethyl-1-[2-(4-methyl-[1,4]diazepan-1-yl)-acetyl]-2,3-dihydro-1H-indol-6-yl}-5,5-dimethyl-1-quinolin-4-ylmethyl-imidazolidine-2,4-dione The title compound was purified in addition by flash chromatography on silica gel with a dichloro-methane/methanol/water/triethylamine gradient. The fractions containing the product were combined and evaporated to yield a white solid.
Yield: 16.5 mg
M+H+measured=569
1H-NMR (500 MHz, DMSO/TMS): d=8.88 (d, 1H); 8.25 (d, 1H); 8.08 (m, 2H); 7.82 (t, 1H); 7.70 (t, 1H); 7.60 (d, 1H); 7.39 (d, 1H); 7.12 (d, 1H); 5.14 (s, 2H); 4.02 (s, 2H); 3.45 (s, 2H); 2.78 (m, 4H); 2.24 (s, 3H); 1.75 (m, 2H); 1.45 (s, 6H); 1.30 (m, 10H)

EXAMPLE 219

3-{1-[2-(3-Dimethylamino-2,2-dimethyl-propylamino)-acetyl]-3,3-dimethyl-2,3-dihydro-1H-indol-6-yl}-5,5-dimethyl-1-quinolin-4-ylmethyl-imidazolidine-2,4-dione The title compound was purified in addition by flash chromatography on silica gel with a dichloro-methane/methanol/water/triethylamine gradient. The fractions containing the product were combined and evaporated to yield a white solid.
Yield: 30.8 mg
M+H+measured=585
1H-NMR (500 MHz, DMSO/TMS): d=8.88 (d, 1H); 8.25 (d, 1H); 8.12 (s, 1H); 8.08 (d, 1H); 7.80 (t, 1H); 7.70 (t, 1H); 7.60 (d, 1H); 7.40 (d, 1H); 7.12 (d, 1H); 5.14 (s, 2H); 3.92 (s, 2H); 3.48 (s, 2H); 2.39 (d, 2H); 2.21 (s, 6H); 2.12 (s, 2H); 1.89 (m, 1H); 1.43 (s, 6H); 1.33 (s, 6H); 0.85 (s, 6H)

EXAMPLE 220

(R)-3-(1-{2-[(1-Ethyl-pyrrolidin-2-ylmethyl)-amino]-acetyl}-3,3-dimethyl-2,3-dihydro-1H-indol-6-yl)-5,5-dimethyl-1-quinolin-4-ylmethyl-imidazolidine-2,4-dione The title compound was purified in addition by flash chromatography on silica gel with a dichloro-methane/methanol/water/triethylamine gradient. The fractions containing the product were combined and evaporated to yield a white solid.
Yield: 9 mg
M+H+measured=583
1H-NMR (500 MHz, DMSO/TMS): d=8.88 (d, 1H); 8.25 (d, 1H); 8.13 (s, 1H); 8.08 (d, 1H); 7.82 (t, 1H); 7.69 (t, 1H); 7.60 (d, 1H); 7.39 (d, 1H); 7.13 (dd, 1H); 5.15 (s, 2H); 3.90 (s, 2H); 3.50 (q, 2H); 3.05 (m, 1H); 2.83 (m, 1H); 2.40 (m, 1H); 2.14 (m, 1H); 2.05 (m, 1H); 1.82 (m, 1H); 1.64 (m, 3H); 1.46 (s, 6H); 1.35 (s, 6H); 1.24 (m, 2H); 1.04 (t, 3H); 0.86 (m, 1H)

EXAMPLE 221

3-{1-[2-(4,4-Difluoro-piperidin-1-yl)-acetyl]-3,3-dimethyl-2,3-dihydro-1H-indol-6-yl}-5,5-dimethyl-1-quinolin-4-ylmethyl-imidazolidine-2,4-dione The following compound was prepared in analogy to example A003440050 by using 4,4-difluoro-piperidine instead of 2,6 dimethylpiperazine.

The reaction mixture was stirred for 15 minutes at 100° C. by microwave-assisted heating (Emrys Optimizer, Personal Chemistry).

Yield: 55 mg
M+H+measured=576
1H-NMR (500 MHz, DMSO/TMS): d=8.88 (d, 1H); 8.25 (d, 1H); 8.08 (m, 2H); 7.82 (t, 1H); 7.69 (t, 1H); 7.60 (d, 1H); 7.39 (d, 1H); 7.13 (dd, 1H); 5.15 (s, 2H); 3.98 (s, 2H); 3.44 (s, 2H); 2.72 (m, 4H); 1.97 (m, 4H); 1.45 (s, 6H); 1.35 (s, 6H)

EXAMPLE 222

Pharmaceutical Composition

Tablets corresponding to the following formula were prepared:

| | |
|---|---|
| Product of Example 9 | 0.2 g |
| Excipient for a finished tablet weighing | 1 g |
| (details of the excipient: lactose, talc, starch, magnesium stearate). | |

EXAMPLE 223

Pharmaceutical Composition

Tablets corresponding to the following formula were prepared:

| | |
|---|---|
| Product of Example 32 | 0.2 g |
| Excipient for a finished tablet weighing | 1 g |
| (details of the excipient: lactose, talc, starch, magnesium stearate). | |

The examples of pharmaceutical compositions 222 and 223 above illustrate the present invention, it being understood that the same preparations may be made with other preferred products of the present invention and form part of the present invention.

What is claimed is:

1. A compound of formula (I):

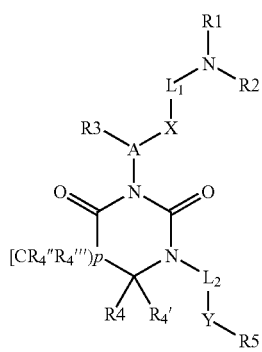

in which:
- p represents the integer 0;
- A represents aryl, heteroaryl or a monocyclic or bicyclic fused carbocyclic or heterocyclic 5- to 11-membered radical, all these radicals optionally being substituted with one or more substituents, which may be identical or different, chosen from the values of R3;
- X represents a single bond or the following divalent radicals: —N(R6)-; —NH-alk-; alkylene; —O—; —C(O)—; —S(O)n-; —N(R6)-C(O)—; NH—CO-alk-, —N(R6)-C(O)—N(R6')—; —N(R6)-C(S)—N(R6')—; —N(R6)-C(O)O—; —N(R6)-SO2—; —N(R6)-SO2—N(R6')—; —C(O)—N(R6)-; —SO2—N(R6)-; and —C(O)O—;
- $L_1$ represents a single bond or the following divalent radicals: alkylene, alkenylene, alkynylene and cycloalkylene, all optionally substituted with one or more substituents, which may be identical or different, chosen from the values of R7; or $L_1$ represents phenylene and heteroarylene, these last two radicals optionally substituted with one or more substituents chosen from the values of R8;
- the radical NR1R2 is such that:
- either R1 and R2, which may be identical or different, are such that:
- R1 represents a hydrogen atom; alkyl, alkenyl, alkynyl and cycloalkyl, all optionally substituted with one or more substituents, which may be identical or different, chosen from the values of R7; aryl, heteroaryl, arylalkyl and heteroarylalkyl in which each of the aromatic rings may optionally be substituted with one or more substituents, which may be identical or different, chosen from the values of R8; —SO2R9; —C(O)R9; —C(O)OR9; —C(O)NR10R11, —C(S)NR10R11 and —SO2NR10R11;
- and R2 represents a hydrogen atom; alkyl, alkenyl, alkynyl and cycloalkyl, all optionally substituted with one or more substituents, which may be identical or different, chosen from the values of R7;
- or R1 and R2 form, together with the nitrogen atom to which they are attached, a 4- to 10-membered heterocycle optionally containing one or more other hetero atoms, which may be identical or different, chosen from O, N, NR12 and S, and optionally substituted with one or more substituents, which may be identical or different, chosen from the values of R7;
- or NR1 with $L_1$ or NR2 with $L_1$ together form a 4- to 10-membered heterocycle—optionally containing one or more other hetero atoms, which may be identical or different, chosen from O, N, NR12 and S, and optionally substituted with one or more substituents, which may be identical or different, chosen from the values of R7;
- R3 represents a hydrogen atom; a halogen atom; hydroxyl; alkyl, alkenyl, alkynyl, cycloalkyl, alkoxy and alkylenedioxy, all optionally substituted with one or more substituents, which may be identical or different, chosen from the values of R7; or R3 represents —NR13R14; —C(O)R13; —S(O)$_n$R13; —C(O)OR13; —C(O)NR15R16; —S(O)$_n$NR15R16; SF5; nitro; cyano; 4- to 7-membered heterocycloalkyl optionally substituted with one or more radicals, which may be identical or different, chosen from halogen atoms and alkyl, alkoxy or oxo radicals; or R3 represents aryl and heteroaryl, these last two radicals optionally substituted with one or more substituents, which may be identical or different, chosen from the values of R8;
- provided that when A represents a mono or bicyclic fused 11-membered radical, R3 represents one or more oxo;
- R4, R4', $R_4$", and $R_4$''', which may be identical or different, are chosen from the values defined below for R4;
- R4 represents a hydrogen atom; a halogen atom; an alkyl, alkenyl, alkynyl or cycloalkyl radical, all optionally substituted with one or more substituents, which may be identical or different, chosen from the values of R7; or R4 represents aryl and heteroaryl, these last two radicals optionally substituted with one or more substituents, which may be identical or different, chosen from the values of R8; or R4 represents oxo;
- $L_2$ is chosen from a single bond; an alkylene; alkenylene; alkynylene; cycloalkylene; —O—; —NR17—; —C(O)— and SO2 radical;
- Y represents a saturated, partially saturated or unsaturated N-heterocycle optionally containing one or more hetero atoms, which may be identical or different, chosen from O, S, N and NR12 and optionally substituted with one or more substituents, which may be identical or different, chosen from the values of R5;
- R5 represents a hydrogen atom; a halogen atom; an alkyl, alkenyl, alkynyl or cycloalkyl radical, all optionally substituted with one or more substituents, which may be identical or different, chosen from the values of R7; or R5 represents aryl, arylalkyl, heteroaryl and heteroarylalkyl, in which the aromatic rings are optionally substituted with one or more substituents, which may be identical or different, chosen from the values of R8; or R5 represents —OR18; —NR19R20; —NR19COR20; —NR19CONR19'R20; —NR19—S(O)2—R20; —NR19-S(O)2—NR19'R20; —COR18; COOR21; —CONR22R23; —S(O)nR18; —SO2NR22R23; cyano; or nitro;
- R6 is such that:
- either R6 represents a hydrogen atom; an alkyl, alkenyl, alkynyl, acyl or cycloalkyl radical, all optionally substituted with one or more substituents, which may be identical or different, chosen from the values of R7; R6 represents aryl and heteroaryl, these last two radicals optionally substituted with one or more substituents, which may be identical or different, chosen from the values of R8;
- or R6 with NR1R2 together form a 4- to 8-membered heterocycle optionally containing one or more hetero atoms, which may be identical or different, chosen from O, S, N and NR12 and optionally substituted with one or more substituents, which may be identical or different, chosen from the values of R7;

or R6 with L$_1$ together form a 4- to 8-membered heterocycle optionally containing one or more hetero atoms, which may be identical or different, chosen from O, S, N and NR12 and optionally substituted with one or more substituents, which may be identical or different, chosen from the values of R7;

R6', which may be identical to or different from R6, is chosen from the values of R6;

R7 represents a halogen atom; alkyl; cycloalkyl; cycloalkylalkyl; hydroxyl; alkoxy; cycloalkoxy; cyano; —CF3; —NR24R25; —NR26COR27; —NR26CONR26'R27; —NR26—S(O)2—R27; —NR26—S(O)2—NR26'R27; —COOR26; —COR26; —CO(NR24R25); S(O)nR26; —S(O)2NR24R25; 4- to 7-membered heterocycle optionally substituted with one or more substituents, which may be identical or different, chosen from OH and NH2 radicals, halogen atoms, and alkyl, alkoxy or oxo radicals; or R7 represents aryl optionally substituted with one or more substituents, which may be identical or different, chosen from halogen atoms and alkyl and alkoxy radicals; or R7 represents heteroaryl, optionally substituted with one or more substituents, which may be identical or different, chosen from halogen atoms and NH2, alkyl and alkoxy radicals; or R7 represents phenoxy, optionally substituted with one or more substituents, which may be identical or different, chosen from halogen atoms and alkyl and alkoxy radicals;

R8, which may be identical to or different from R7, represents the same values as R7; nitro; —OCF3; alkylenedioxy; difluoromethylenedioxy; or benzyl optionally substituted with one or more substituents, which may be identical or different, chosen from halogen atoms and alkyl and alkoxy radicals;

R9, which may be identical to or different from R6, represents the same values as R6;

R10 and R11, which may be identical to or different from each other and also which may be identical to or different from R6, are chosen from the same values as R6 and may optionally form, with the nitrogen atom to which they are attached, a 4- to 10-membered heterocycle optionally containing one or more hetero atoms, which may be identical or different, chosen from O, S, N and NR12 and optionally substituted with one or more substituents, which may be identical or different, chosen from the values of R7;

R12 represents a hydrogen atom; an alkyl, alkenyl, alkynyl, cycloalkyl, alkylCO or alkylSO$_2$ radical, all optionally substituted with one or more substituents, which may be identical or different, chosen from halogen atoms, OH, alkoxy and dialkylamino radicals; or R12 represents aryl and heteroaryl, these last two radicals optionally substituted with one or more substituents, which may be identical or different, chosen from halogen atoms and alkyl and alkoxy radicals;

R13, which may be identical to or different from R6, represents the same values as R6;

R14, which may be identical to or different from R13, represents the same values as R13 and also represents C(O)R28; C(O)N28R29; SO2R28 and SO2NR28R29;

R13 and R14 may optionally form, together with the nitrogen atom to which they are attached, a 4- to 10-membered heterocycle optionally containing one or more hetero atoms, which may be identical or different, chosen from O, S, N and NR12 and optionally substituted with one or more substituents, which may be identical or different, chosen from the values of R7;

R15 and R16, which may be identical to or different from each other and also which may be identical to or different from R13, are chosen from the same values as R13 and may optionally form, with the nitrogen atom to which they are attached, a 4- to 10-membered heterocycle optionally containing one or more hetero atoms, which may be identical or different, chosen from O, S, N and NR12 and optionally substituted with one or more substituents, which may be identical or different, chosen from the values of R7;

R17 represents a hydrogen atom, alkyl or cycloalkyl;

R18, which may be identical to or different from R6, represents the same values as R6;

R19 and R20, which may be identical to or different from each other and also which may be identical to or different from R6, are chosen from the same values as R6 and may optionally form, with the nitrogen atom to which they are attached, a 4- to 10-membered heterocycle optionally containing one or more hetero atoms, which may be identical or different, chosen from O, S, N and NR12 and optionally substituted with one or more substituents, which may be identical or different, chosen from the values of R7;

R21, which may be identical to or different from R13, represents the same values as R13 or hydrogen;

R22 and R23, which may be identical to or different from each other and also which may be identical to or different from R6, are chosen from the same values as R6 and may optionally form, with the nitrogen atom to which they are attached, a 4- to 10-membered heterocycle optionally containing one or more hetero atoms, which may be identical or different, chosen from O, S, N and NR12 and optionally substituted with one or more substituents, which may be identical or different, chosen from the values of R7;

R24 and R25, which may be identical or different, represent a hydrogen atom or an alkyl, alkenyl or alkynyl radical optionally substituted with one or more substituents, which may be identical or different, chosen from halogen atoms and OH and alkoxy radicals, or alternatively R24 and R25 may optionally form, with the nitrogen atom to which they are attached, a 4- to 7-membered heterocycle optionally containing one or more hetero atoms, which may be identical or different, chosen from O, S, N, N-alkyl and N—C(O)alkyl, and optionally substituted with one or more substituents, which may be identical or different, chosen from halogen atoms and OH, alkyl, alkoxy and oxo radicals;

R26 represents a hydrogen atom or an alkyl, alkenyl or alkynyl radical optionally substituted with one or more substituents, which may be identical or different, chosen from halogen atoms and OH and alkoxy radicals;

R26', which may be identical to or different from R26, represents the same values as R26;

R27, which may be identical to or different from R26, represents the same values as R26;

R26 and R27 may also optionally form, with the nitrogen atom to which they are attached, a 4- to 7-membered heterocycle optionally containing one or more hetero atoms, which may be identical or different, chosen from O, S, N, N-alkyl and N—C(O)alkyl, and optionally substituted with one or more substituents, which may be identical or different, chosen from halogen atoms and OH, alkyl, alkoxy and oxo radicals;

R28, which may be identical to or different from R26, represents the same values as R26;

R29, which may be identical to or different from R26, represents the same values as R26;

R30, which may be identical to or different from R26, represents the same values as R26; and n represents the integers 0, 1 and 2; or a racemate, enantiomer, diastereoisomer of such compound or mixture thereof, or an addition salt of such compound, racemate, enantiomer, diastereomer or mixture with a mineral acid or organic acid or with a mineral base or organic base.

2. A compound according to claim 1 in which p represents the integer 0;

A represents aryl, heteroaryl or a monocyclic or bicyclic fused carbocyclic or heterocyclic 5- to 11-membered radical, all these radicals optionally being substituted with one or more substituents, which may be identical or different, chosen from the values of R3;

X represents a single bond or the following divalent radicals: —N(R6)-; —O—; —C(O)—; —S(O)n—; —N(R6)-C(O)—; —N(R6)-C(O)—N(R6')-; —N(R6)-C(S)—N(R6')-; —N(R6)-C(O)O—; —N(R6)-SO2—; —N(R6)-SO2—N(R6')-; —C(O)—N(R6)-; —SO2—N(R6)-; and —C(O)O—;

$L_1$ represents a divalent radical selected from alkylene, alkenylene, alkynylene and cycloalkylene, all optionally substituted with one or more substituents, which may be identical or different, chosen from the values of R7; or L1 represents phenylene and heteroarylene, these last two radicals optionally substituted with one or more substituents chosen from the values of R8;

the radical NR1R2 is such that:

either R1 and R2, which may be identical or different, are such that:

R1 represents a hydrogen atom; alkyl, alkenyl, alkynyl and cycloalkyl, all optionally substituted with one or more substituents, which may be identical or different, chosen from the values of R7; R1 represents aryl, heteroaryl, arylalkyl and heteroarylalkyl in which each of the aromatic rings may optionally be substituted with one or more substituents, which may be identical or different, chosen from the values of R8; R1 represents —SO2R9; —C(O)R9; —C(O)OR9; —C(O)NR10R11, —C(S)NR10R11 and —SO2NR10R11;

and R2 represents a hydrogen atom; alkyl, alkenyl, alkynyl and cycloalkyl, all optionally substituted with one or more substituents, which may be identical or different, chosen from the values of R7;

or R1 and R2 form, together with the nitrogen atom to which they are attached, a 4- to 10-membered heterocycle optionally containing one or more other hetero atoms, which may be identical or different, chosen from O, N, NR12 and S, and optionally substituted with one or more substituents, which may be identical or different, chosen from the values of R7;

or NR1 with $L_1$ or NR2 with $L_1$ together form a 4- to 8-membered heterocycle, optionally containing one or more other hetero atoms, which may be identical or different, chosen from O, N, NR12 and S, and optionally substituted with one or more substituents, which may be identical or different, chosen from the values of R7;

R3 represents a hydrogen atom, a halogen atom, hydroxyl, alkyl, alkenyl, alkynyl, cycloalkyl, alkoxy or alkylenedioxy, all optionally substituted with one or more substituents, which may be identical or different, chosen from the values of R7; or R3 represents —NR13R14, —C(O)R13, —S(O)$_n$R13, —C(O)OR13, —C(O)NR15R16, —S(O)$_n$NR15R16, SF$_5$, nitro, cyano, 4- to 7-membered heterocycloalkyl optionally substituted with one or more radicals, which may be identical or different, chosen from halogen atoms and alkyl, alkoxy or oxo radicals; or R3 represents aryl and heteroaryl, these last two radicals optionally substituted with one or more substituents, which may be identical or different, chosen from the values of R8;

provided that when A represents a mono or bicyclic fused 11-membered radical, R3 represents one or more oxo;

R4, R4', R4" and R4'", which may be identical or different, are chosen from the values defined below for R4;

R4 represents a hydrogen atom a halogen atom, an alkyl, alkenyl, alkynyl or cycloalkyl radical, all optionally substituted with one or more substituents, which may be identical or different, chosen from the values of R7; or R4 represents aryl and heteroaryl, these last two radicals optionally substituted with one or more substituents, which may be identical or different, chosen from the values of R8; or R4 represents oxo;

$L_2$ is chosen from a single bond; an alkylene; alkenylene; alkynylene; cycloalkylene, —O—, —NR17—, —C(O)— and SO2 radical;

Y represents a saturated, partially saturated or unsaturated N-heterocycle optionally containing one or more hetero atoms, which may be identical or different, chosen from O, S, N and NR12 and optionally substituted with one or more substituents, which may be identical or different, chosen from the values of R5;

R5 represents a hydrogen atom, a halogen atom; an alkyl, alkenyl, alkynyl or cycloalkyl radical, all optionally substituted with one or more substituents, which may be identical or different, chosen from the values of R7; or R5 represents aryl, arylalkyl, heteroaryl or heteroarylalkyl, in which the aromatic rings are optionally substituted with one or more substituents, which may be identical or different, chosen from the values of R8; or R5 represents —OR18, —NR19R20, —NR19COR20, —NR19CONR19'R20, —NR19—S(O)2-R20, —NR19—S(O)2-NR19R20, —COR18, COOR21, —CONR22R23, —S(O)nR18, —SO2NR22R23, cyano, or nitro;

R6 is such that:

either R6 represents a hydrogen atom, an alkyl, alkenyl, alkynyl or cycloalkyl radical, all optionally substituted with one or more substituents, which may be identical or different, chosen from the values of R7; R6 represents aryl and heteroaryl, these last two radicals optionally substituted with one or more substituents, which may be identical or different, chosen from the values of R8;

or R6 with NR1R2 together form a 4- to 8-membered heterocycle optionally containing one or more hetero atoms, which may be identical or different, chosen from O, S, N and NR12 and optionally substituted with one or more substituents, which may be identical or different, chosen from the values of R7;

or R6 with $L_1$ together form a 4- to 8-membered heterocycle optionally containing one or more hetero atoms, which may be identical or different, chosen from O, S, N and NR12 and optionally substituted with one or more substituents, which may be identical or different, chosen from the values of R7;

R6', which may be identical to or different from R6, is chosen from the values of R6;

R7 represents a halogen atom, alkyl, cycloalkyl, Cycloalkylalkyl, hydroxyl, alkoxy, cycloalkoxy, cyano, —CF3, —N24R25, —NR26COR27, —NR26CONR26'R27, —NR26—S(O)2—R27, —NR26—

S(O)2—NR26'R27, —COOR26, —COR26, —CO(NR24R25), S(O)nR26, —S(O)2NR24R25, or 4- to 7-membered heterocycle optionally substituted with one or more substituents, which may be identical or different, chosen from OH and NH2 radicals, halogen atoms, and alkyl, alkoxy and oxo radicals; or R7 represents aryl optionally substituted with one or more substituents, which may be identical or different, chosen from halogen atoms and alkyl and alkoxy radicals; or R7 represents heteroaryl, optionally substituted with one or more substituents, which may be identical or different, chosen from halogen atoms and NH2, alkyl and alkoxy radicals; or R7 represents phenoxy, optionally substituted with one or more substituents, which may be identical or different, chosen from halogen atoms and alkyl and alkoxy radicals;

R8, which may be identical to or different from R7, represents the same values as R7 and in addition represents a halogen atom, nitro, —OCF3, alkylenedioxy, difluoromethylenedioxy, benzyl optionally substituted with one or more substituents, which may be identical or different, chosen from halogen atoms and alkyl and alkoxy radicals;

R9, which may be identical to or different from R6, represents the same values as R6;

R10 and R11, which may be identical to or different from each other and also which may be identical to or different from R6, are chosen from the same values as R6 and may optionally form, with the nitrogen atom to which they are attached, a 4- to 10-membered heterocycle optionally containing one or more, hetero atoms, which may be identical or different, chosen from O, S, N and NR12 and optionally substituted with one or more substituents, which may be identical or different, chosen from the values of R7;

R12 represents a hydrogen atom; an alkyl, alkenyl, alkynyl, cycloalkyl, alkylCO or alkylSO$_2$ radical, all optionally substituted with one or more substituents, which may be identical or different, chosen from halogen atoms, OH, alkoxy and dialkylamino radicals; or R12 represents aryl and heteroaryl, these last two radicals optionally substituted with one or more substituents, which may be identical or different, chosen from halogen atoms and alkyl and alkoxy radicals;

R13, which may be identical to or different from R6, represents the same values as R6;

R14, which may be identical to or different from R13, represents the same values as R13 and also represents C(O)R28; C(O)N28R29; SO2R28 and SO2NR28R29;

R13 and R14 may optionally form, together with the nitrogen atom to which they are attached, a 4- to 10-membered heterocycle optionally containing one or more hetero, atoms, which may be identical or different, chosen from O, S, N and NR12 and optionally substituted with one or more substituents, which may be identical or different, chosen from the values of R7;

R15 and R16, which may be identical to or different from each other and also which may be identical to or different from R13, are chosen from the same values as R13 and may optionally form, with the nitrogen atom to which they are attached, a 4- to 10-membered heterocycle optionally containing one or more hetero atoms, which may be identical or different, chosen from O, S, N and NR12 and optionally substituted with one or more substituents, which may be identical or different, chosen from the values of R7;

R17 represents a hydrogen atom, alkyl or cycloalkyl;

R18, which may be identical to or different from R6, represents the same values as R6;

R19 and R20, which may be identical to or different from each other and also which may be identical to or different from R6, are chosen from the same values as R6 and may optionally form, with the nitrogen atom to which they are attached, a 4- to 10-membered heterocycle optionally containing one or more hetero atoms, which may be identical or different, chosen from O, S, N and NR12 and optionally substituted with one or more substituents, which may be identical or different, chosen from the values of R7;

R21, which may be identical to or different from R13, represents the same values as R13 and also represents hydrogen;

R22 and R23, which may be identical to or different from each other and also which may be identical to or different from R6, are chosen from the same values as R6 and may optionally form, with the nitrogen atom to which they are attached, a 4- to 10-membered heterocycle optionally containing one or more hetero atoms, which may be identical or different, chosen from O, S, N and NR12 and optionally substituted with one or more substituents, which may be identical or different, chosen from the values of R7;

R24 and R25, which may be identical or different, represent an alkyl, alkenyl or alkynyl radical optionally substituted with one or more substituents, which may be identical or different, chosen from halogen atoms and OH and alkoxy radicals, or alternatively R24 and R25 may optionally form, with the nitrogen atom to which they are attached, a 4- to 7-membered heterocycle optionally containing one or more hetero atoms, which may be identical or different, chosen from O, S, N,N-alkyl and N—C(O)alkyl, and optionally substituted with one or more substituents, which may be identical or different, chosen from halogen atoms and OH, alkyl, alkoxy and oxo radicals;

R26 represents a hydrogen atom or an alkyl, alkenyl or alkynyl radical optionally substituted with one or more substituents, which may be identical or different, chosen from halogen atoms and OH and alkoxy radicals;

R26', which may be identical to or different from R26, represents the same values as R26;

R27, which may be identical to or different from R26, represents the same values as R26;

R26 and R27 may also optionally form, with the nitrogen atom to which they are attached, a 4- to 7-membered heterocycle optionally containing one or more hetero atoms, which may be identical or different, chosen from O, S, N , N-alkyl and N—C(O)alkyl, and optionally substituted with one or more substituents, which may be identical or different, chosen from halogen atoms and OH, alkyl, alkoxy and oxo radicals;

R28, which may be identical to or different from R26, represents the same values as R26;

R29, which may be identical to or different from R26, represents the same values as R26;

R30, which may be identical to or different from R26, represents the same values as R26; and n represents the integers 0, 1 and 2; or a racemate, enantiomer, diastereoisomer of such compound or mixture thereof, or an addition salt of such compound, racemate, enantiomer, diastereomer or mixture with a mineral acid or organic acid or with a mineral base or organic base.

3. A compound according to claim 1 corresponding to formula (Ia):

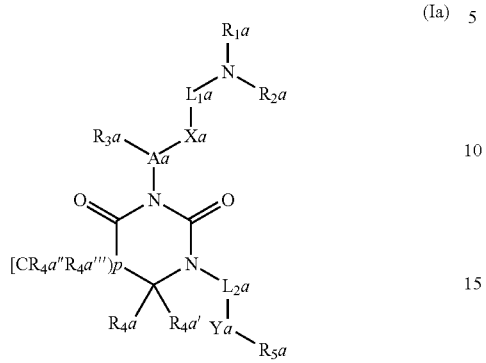

in which:
p represents the integer 0,
Aa represents phenyl, heteroaryl and a monocyclic or bicyclic fused carbocyclic or heterocyclic 5- to 11-membered radical, optionally substituted with one or more substituents, which may be identical or different, chosen from the values of $R_3a$;
Xa represents a single bond or a divalent radical selected from —N(R6a)—, —O—, —C(O)—, —S(O)n—, —N(R6a)—C(O)—, —N(R6a)—C(O)—N(R6'a)—, —N(R6a)—SO2—, —C(O)—N(R6a)—, and —SO2—NR6a—;
$L_1a$ represents an alkylene radical containing 1 to 4 carbon atoms and optionally substituted with one or more substituents chosen from the values of R7a;
the radical $NR_1aR_2a$ is such that:
either $R_1a$ and $R_2a$, which may be identical or different, are such that:
$R_1a$ represents a hydrogen atom; alkyl and cycloalkyl, these last two radicals being optionally substituted with one or more substituents, which may be identical or different, chosen from the values of R7a; $R_1a$ represents aryl, heteroaryl, arylalkyl and heteroarylalkyl in which each of the aromatic rings may be optionally substituted with one or more substituents, which may be identical or different, chosen from the values of R8a;
and $R_2a$ represents a hydrogen atom, alkyl and cycloalkyl, these last two radicals being optionally substituted with one or more substituents, which may be identical or different, chosen from the values of R7a;
or $R_1a$ and $R_2a$ form, together with the nitrogen atom to which they are attached, a 4- to 10-membered heterocycle optionally containing one or more other hetero atoms, which may be identical or different, chosen from O, N, NR12a and S and optionally substituted with one or more substituents, which may be identical or different, chosen from the values of R7a;
or $NR_1a$ with $L_1a$ or $NR_2a$ with $L_1a$ together form a 4- to 8-membered heterocycle optionally substituted with one or more substituents, which may be identical or different, chosen from the values of R7a;
$R_3a$ represents a hydrogen atom, a halogen atom; an alkyl, cycloalkyl, alkoxy or alkylenedioxy radical, all optionally substituted with one or more substituents, which may be identical or different, chosen from the values of R7a; —NR13aR14a; —C(O)R13a; —S(O)$_n$R13a; —C(O)NR15aR16a; —S(O)NR15aR16a; aryl and heteroaryl, these last two radicals being optionally substituted with one or more substituents, which may be identical or different, chosen from the values of R8a;
$R_4a$, $R_4a'$, $R_4a''$ and $R_4a'''$, which may be identical or different, are chosen from the values defined below for $R_4a$;
$R_4a$ represents a hydrogen atom, a halogen atom, an alkyl or cycloalkyl radical, all optionally substituted with one or more substituents, which may be identical or different, chosen from the values of R7a;
$L_2a$ is chosen from a single bond, alkylene, cycloalkylene, —O— and —NR17a-,
Ya represents an N-heterocycle optionally containing one or more hetero atoms, which may be identical or different, chosen from O, S and N and optionally substituted with one or more substituents, which may be identical or different, chosen from the values of $R_5a$;
$R_5a$ represents a hydrogen atom, a halogen atom, an alkyl or cycloalkyl radical, optionally substituted with one or more substituents, which may be identical or different, chosen from the values of R7a; or $R_5a$ represents aryl, arylalkyl, heteroaryl or heteroarylalkyl, in which the aromatic rings are optionally substituted with one or more substituents, which may be identical or different, chosen from the values of R8a; or $R_5a$ represents —OR18a, —NR19a R20a, —NR19a COR20a, —NR19a CONR19'aR20a, —NR19a —S(O)2-R20a, —NR19a —S(O)2—NR19a'R20a, —COR18a, COOR21a, —CONR22aR23a, —S(O)nR18a, —SO2NR22a R23a, or cyano;
R6a is such that:
either R6a represents a hydrogen atom or an alkyl or cycloalkyl radical, all optionally substituted with one or more substituents, which may be identical or different, chosen from the values of R7a;
or R6a with $NR_1aR_2a$ together form a 5- to 7-membered heterocycle optionally substituted with one or more substituents, which may be identical or different, chosen from the values of R7a;
or R6a with $L_1a$ together form a 5- to 7-membered heterocycle optionally substituted with one or more substituents, which may be identical or different, chosen from the values of R7a;
R6a', which may be identical to or different from R6a, is chosen from the values of R6a;
R7a represents a halogen atom, an alkyl, hydroxyl, alkoxy, cycloalkoxy, or cyano radical, —CF3, —N24aR25a, —NR26a COR27a, —NR26a CONR26a'R27a, —NR26a —S(O)2-R27a, —NR26a — S(O)2—NR26a'R27a, —COOR26a, —COR26a, —CO(NR24aR25a ), S(O)nR26a, —S(O)2NR24aR25a, a 4- to 7-membered heterocycle optionally substituted with one or more substituents, which may be identical or different, chosen from OH and NH2 radicals, halogen atoms, and alkyl, alkoxy or oxo radicals; or R7a represents aryl optionally substituted with one or more substituents, which may be identical or different, chosen from halogen atoms and alkyl and alkoxy radicals; or R7a represents heteroaryl, optionally substituted with one or more substituents, which may be identical or different, chosen from halogen atoms and NH2, alkyl and alkoxy radicals; or R7a represents phenoxy, optionally substituted with one or more substituents, which may be identical or different, chosen from halogen atoms and alkyl and alkoxy radicals;

R8a, which may be identical to or different from R7a, represents the same values as R7a and also represents halogen atoms and —OCF3, alkylenedioxy and difluoromethylenedioxy radicals;

R12a represents a hydrogen atom or an alkyl, cycloalkyl, alkylCO or alkylSO$_2$ radical, all optionally substituted with one or more substituents, which may be identical or different, chosen from halogen atoms and alkoxy radicals;

R13a represents an alkyl or cycloalkyl radical optionally substituted with one or more substituents, which may be identical or different, chosen from the values of R7a; or R13 represents a phenyl radical optionally substituted with one or more substituents, which may be identical or different, chosen from halogen atoms and alkyl and alkoxy radicals; or R13a 5- or 6-membered heteroaryl radical optionally substituted with one or more substituents, which may be identical or different, chosen from halogen atoms and alkyl and alkoxy radicals;

R14a represents an alkyl or cycloalkyl radical optionally substituted with one or more substituents, which may be identical or different, chosen from the values of R7a; or R14a represents C(O)R28a;

R13a and R14a may optionally form, together with the nitrogen atom to which they are attached, a 4- to 7-membered heterocycle optionally containing one or more hetero atoms, which may be identical or different, chosen from O, S, N and N-alkyl and optionally substituted with one or more substituents, which may be identical or different, chosen from the values of R7a;

R15a and R16a, which may be identical to or different from each other and also identical to or different from R13a, are chosen from the same values as R13a and may optionally form, with the nitrogen atom to which they are attached, a 4- to 7-membered heterocycle optionally containing one or more hetero atoms which may be identical or different, chosen from O, S, N and NR12A and optionally substituted with one or more substituents, which may be identical or different, chosen from the values of R7a;

R17a represents a hydrogen atom or an alkyl or cycloalkyl radical;

R18a, which may be identical to or different from R6a, represents the same values as R6a;

R19a represents a hydrogen atom or an alkyl or cycloalkyl radical;

R20a represents a hydrogen atom or an alkyl or cycloalkyl radical optionally substituted with one or more substituents, which may be identical or different, chosen from the values of R7a;

or R20 a represents aryl and heteroaryl, optionally substituted with one or more substituents, which may be identical or different, chosen from the values of R8a;

R19a and R20a, which may be identical to or different from each other, may also form, with the nitrogen atom to which they are attached, a 4- to 7-membered heterocycle optionally containing one or more hetero atoms, which may be identical or different, chosen from O, S, N and NR12a and optionally substituted with one or more substituents, which may be identical or different, chosen from the values of R7a;

R21a, which may be identical to or different from R13a, is chosen from the values of R13a and also represents a hydrogen atom;

R22a and R23a, which may be identical to or different from each other and identical to or different from R6a, are chosen from the values of R6a and may also form, with the nitrogen atom to which they are attached, a 4- to 7-membered heterocycle optionally containing one or more hetero atoms, which may be identical or different, chosen from O, S, N and NR12a and optionally substituted with one or more substituents, which may be identical or different, chosen from the values of R7a;

R24a and R25a, which may be identical or different, represent an alkyl radical optionally substituted with one or more substituents, which may be identical or different, chosen from halogen atoms (F) and OH and alkoxy radicals, or alternatively R24a and R25a may optionally form, with the nitrogen atom to which they are attached, a 4- to 7-membered heterocycle optionally containing one or more hetero atoms, which may be identical or different, chosen from O, S, N , N-alkyl and N—C(O) alkyl, and optionally substituted with one or more substituents, which may be identical or different, chosen from halogen atoms and OH, alkyl, alkoxy or oxo radicals;

R26a represents a hydrogen atom or an alkyl radical optionally substituted with one or more substituents, which may be identical or different, chosen from halogen atoms (F) and OH and alkoxy radicals;

R26a', which may be identical to or different from R26a, is chosed from the values of R26a R27a, which may be identical to or different from R26a, is chosen from the values of R26a;

R26a and R27a, may also optionally form, with the nitrogen atom to which they are attached, a 4- to 7-membered heterocycle optionally containing one or more hetero atoms, which may be identical or different, chosen from O, S, N,N-alkyl and N—C(O)alkyl, and optionally substituted with one or more substituents, which may be identical or different, chosen from halogen atoms and OH, alkyl, alkoxy or oxo radicals;

R28a, which may be identical to or different from R26a, is chosen from the values of R26a;

R29a, which may be identical to or different from R26a, is chosen from the values of R26a;

R30a, which may be identical to or different from R26a, is chosen from the values of R26a; and n represents the integers 0, 1 and 2; or a racemate, enantiomer, diastereoisomer of such compound or mixture thereof, or an addition salt of such compound, racemate, enantiomer, diastereomer or mixture with a mineral acid or organic acid or with a mineral base or organic base.

4. A compound according to claim 1 of formula (Ib):

(Ib)

in which Ab represents phenyl, heteroaryl or a monocyclic or bicyclic fused carbocyclic or heterocyclic 7- to 11-membered cyclic radical, optionally substituted with one or more substituents, which may be identical or different, chosen from the values of R$_3$b;

Xb represents a single bond or a divalent radical selected from —N(R6b)—, —O—, —C(O)—, —S(O)n—, —N(R6b)—C(O)— and —N(R6b)—SO2—;

L₁b represents an alkylene radical containing 1 to 4 carbon atoms and optionally substituted with one or more substituents, which may be identical or different, chosen from halogen atoms and OH and alkoxy radicals;

the radical NR₁bR₂b is such that:

either R₁b and R₂b, which may be identical or different, are such that:

R₁b represents a hydrogen atom or an alkyl or cycloalkyl radical, these last two radicals being optionally substituted with one or more substituents, which may be identical or different, chosen from the values of R7b; R₁b represents aryl and heteroaryl, both optionally substituted with one or more substituents, which may be identical or different, chosen from the values of R8b;

and R₂b represents a hydrogen atom or an alkyl or cycloalkyl radical, these last two radicals being optionally substituted with one or more substituents, which may be identical or different, chosen from the values of R7b;

or R₁b and R₂b form, together with the nitrogen atom to which they are attached, a 4- to 10-membered heterocycle optionally containing one or more other hetero atoms, which may be identical or different, chosen from O, N,N-alkyl and S and optionally substituted with one or more substituents, which may be identical or different, chosen from the values of R7b;

or NR₁b with L₁b or NR₂b with L₁b together form a 4- to 8-membered heterocycle optionally substituted with one or more substituents, which may be identical or different, chosen from the values of R7b;

R₃b represents a hydrogen atom, an alkyl, alkoxy or cycloalkyl radical, optionally substituted with one or more substituents, which may be identical or different, chosen from F; OCF3; S(O)ₙ-alkyl radicals, the alkyl residue containing 1 to 4 carbon atoms and being optionally substituted with one or more F; alkylamino, optionally substituted with one or more F; dialkylamino, in which the two alkyl residues may optionally form, with the nitrogen atom to which they are attached, a 4- to 10-membered heterocyclic radical optionally containing one or more other hetero atoms, which may be identical or different, chosen from O, N,N-alkyl and S and optionally substituted with one or more substituents, which may be identical or different, chosen from F and alkyl and alkoxy radicals;

R₄b and R₄'b, which may be identical or different, represent a hydrogen atom, a halogen atom F and an alkyl or cycloalkyl radical, optionally substituted with one or more F;

L₂b is chosen from a single bond and methylene;

Yb represents a monocyclic or bicyclic heteroaryl radical chosen from pyridyl, pyrimidinyl, pyridazine, pyrazine, azaindolyl, quinolyl, isoquinolyl, cinnolinyl, quinazolinyl, thiazolyl, imidazolyl, oxazolyl, pyrazolyl, isoxazolyl, 1H-pyrrolo[2,3-b]pyridyl, furazanyl, morpholinyl, pyrrolidinyl, 3H-imidazo-(4,5b)-pyridine, 1H-pyrazolo-(3,4b)-pyridine, 1H-pyrazolo-(3,4d)-pyrimidine, piperidyl, thienyl, indolyl, pyrrolyl, purinyl, benzoxazinyl, and benzimidazolyl, these radicals being optionally substituted with one or more radicals chosen from the values of R₅b;

R₅b represents a hydrogen atom, a halogen atom, alkyl, cycloalkyl, —NHR20b, —NHCOR20b, —NHCONR19bR20b, or —NH—S(O)2-R20b;

R6b represents a hydrogen atom or an alkyl radical containing from 1 to 4 carbon atoms;

R6b and NR₁bR₂b may optionally together form a 5- to 7-membered heterocycle optionally substituted with one or more radicals, which may be identical or different, chosen from the values of R7b;

R7b represents a halogen atom, hydroxyl, cyano, COOH, —CF3, alkyl, alkoxy, alkylamino, dialkylamino, —NHCO-alkyl, —CO(NH-alkyl) or CO(Ndialkyl) in which the alkyl residues are optionally substituted with one or more substituents, which may be identical or different, chosen from halogen atoms, OH and methoxy; or R7b represents an aryl radical optionally substituted with one or more substituents, which may be identical or different, chosen from halogen atoms and alkyl and alkoxy radicals; or R7b represents a 4- to 7-membered heterocycle; or heteroaryl, optionally substituted with one or more substituents, which may be identical or different, chosen from halogen atoms and NH2, alkyl and alkoxy radicals;

R8b, which may be identical to or different from R7b, is chosen from the values of R7b and in addition represents a halogen atom, —OCF3, alkylenedioxy or difluoromethylenedioxy radicals;

R19b represents a hydrogen atom or an alkyl or cycloalkyl radical;

R20b represents a hydrogen atom or an alkyl or cycloalkyl radical optionally substituted with one or more substituents, which may be identical or different, chosen from the values of R7b; aryl and heteroaryl, optionally substituted with one or more substituents, which may be identical or different, chosen from the values of R8b;

R19b and R20b, which may be identical to or different from each other, may also form, with the nitrogen atom to which they are attached, a 4- to 7-membered heterocycle optionally containing one or more hetero atoms, which may be identical or different, chosen from O, S, N and Nalkyl and optionally substituted with one or more substituents, which may be identical or different, chosen from the values of R7b; and n represents the integers 0, 1 and 2; or a racemate, enantiomer, diastereoisomer of such compound or mixture thereof, or an addition salt of such compound, racemate, enantiomer, diastereomer or mixture with a mineral acid or organic acid or with a mineral base or organic base.

5. A compound of formula (Ic):

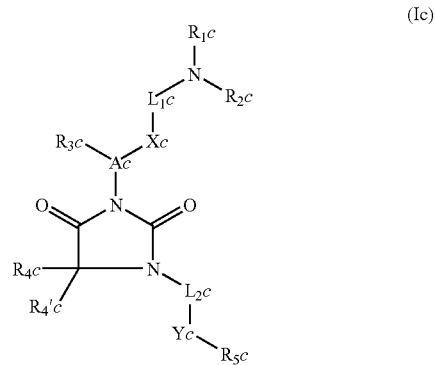

(Ic)

in which

A represents a phenyl, a 5 to 6-membered heteroaryl or a condensed heterocyclic ring system selected from the group consisting of 1,2,3,4-tetrahydro-quinolin, 1,2,3,4-tetrahydro-isoquinolin, indolyl, 2,3-dihydro-1H-indolyl, 2,3-dihydro-1H-isoindolyl, 2,3-dihydro-benzothiazole, tetrahydroquinoline and tetrahydroisoquinoline, all these radicals being optionally substituted with one or more substituents, which may be identical or different, chosen from alkyl, alkoxy, cycloalkyl, alkylamino and dialkylamino radicals, each alkyl radical being optionally substituted with one or more substituents, which may be identical or different, chosen from F, —OCF3, SCF3 and SO2CF3 radicals;

Xc represents a single bond or a divalent radicals selected from —N(R6c)—; —O—; —C(O)—; and —N(R6c)—C(O)—;

$L_1c$ represents an alkylene radical containing 1 to 4 carbon atoms, optionally substituted with a hydroxyl radical;

either $R_1c$ and $R_2c$, which may be identical or different, are such that:

$R_1c$ represents an alkyl or cycloalkyl radical optionally substituted with one or more substituents, which may be identical or different, chosen from halogen atoms; hydroxyl; alkoxy; cyano, free or esterified carboxyl, phenyl, 3- to 7-membered cycloalkyl, alkylamino, dialkylamino, —NHCO-alkyl, —CO(NH-alkyl), CO(Ndialkyl) and saturated, partially saturated or unsaturated 5-, 6- or 7-membered heteroaryl radicals containing one or more hetero atoms, which may be identical or different, chosen from O, S, N, NH and N-alkyl and optionally substituted with one or more substituents, which may be identical or different, chosen from halogen atoms and alkyl, NH2 and alkoxy radicals; or alternatively $R_1c$ represents a phenyl radical or a saturated, partially saturated or unsaturated 4- to 7-membered heterocyclic radical, itself containing one or more hetero atoms chosen from O, S, N, NH and N-alkyl, and optionally substituted with one or more radicals chosen from halogen atoms and alkyl, NH2 and alkoxy radicals;

and $R_2c$ represents a hydrogen atom or an alkyl or cycloalkyl radical optionally substituted with one or more halogen atoms;

or $R_1c$ and $R_2c$ form, together with the nitrogen atom to which they are attached, a 4- to 7-membered heterocycle optionally containing one or more other hetero atoms, which may be identical or different, chosen from O, N, NH, N-alkyl and S and optionally substituted with one or more substituents, which may be identical or different, chosen from halogen atoms and alkyl, alkoxy, CF3 and free or esterified carboxyl radicals;

or $NR_1c$ with $L_1c$ or $NR_2c$ with $L_1C$ together form a 4- to 7-membered heterocycle optionally substituted with one or more substituents, which may be identical or different, chosen from halogen atoms, and alkyl, alkoxy and free or esterified carboxyl radicals;

$R_3c$ represents a hydrogen atom, an alkyl, alkoxy or cycloalkyl radical, optionally substituted with one or more substituents, which may be identical or different, chosen from F; OCF3; $S(O)_n$-alkyl radicals, the alkyl residue containing 1 to 4 carbon atoms and being optionally substituted with one or more F; alkylamino, optionally substituted with one or more F; dialkylamino, in which the two alkyl residues may optionally form, with the nitrogen atom to which they are attached, a 4- to 10-membered heterocyclic radical optionally containing one or more other hetero atoms, which may be identical or different, chosen from O, N,N-alkyl and S and optionally substituted with one or more substituents, which may be identical or different, chosen from F and alkyl and alkoxy radicals;

$L_2c$ is chosen from a single bond and methylene;

$R_4c$ and $R_4'c$, which may be identical or different, represent a hydrogen atom, an alkyl or cycloalkyl radical optionally substituted with one or more halogen atoms;

Yc represents a heteroaryl radical chosen from pyrid-4-yl, pyrimidin-4-yl, quinolin-4-yl, isoquinolin-5-yl; azaindol-4-yl and quinazolin-4-yl, these radicals being optionally substituted with one or more substituents, which may be identical or different, chosen from the values of $R_5c$;

$R_5c$ represents a hydrogen atom, a halogen atom; an alkyl, cycloalkyl, NH2, —NH-cycloalkyl, —NHCO-alkyl, —NHCO-cycloalkyl, —NHCONH-alkyl or —NHCON(dialkyl) radical, the alkyl and cycloalkyl residues being optionally substituted with one or more radicals, which may be identical or different, chosen from halogen atoms and alkoxy, morpholinyl, piperidyl, piperazinyl, N-methyl-piperazinyl and COOH radicals; or $R_5c$ represents NH-aryl, NH-heteroaryl, —NHCO-aryl and —NHCO-heteroaryl in which the aromatic residues are optionally substituted with one or more radicals chosen from halogen atoms and alkyl, alkoxy and COOH radicals;

R6c represents a hydrogen atom or an alkyl radical containing from 1 to 4 carbon atoms;

R6c and $NR_1cR_{2c}$ may optionally together form a 5- to 7-membered heterocycle optionally substituted with one or more radicals, which may be identical or different, chosen from halogen atoms and alkyl and alkoxy radicals; or a racemate, enantiomer, diastereoisomer of such compound or mixture thereof, or an addition salt of such compound, racemate, enantiomer, diastereomer or mixture with a mineral acid or organic acid or with a mineral base or organic base.

6. A compound or formula (I):

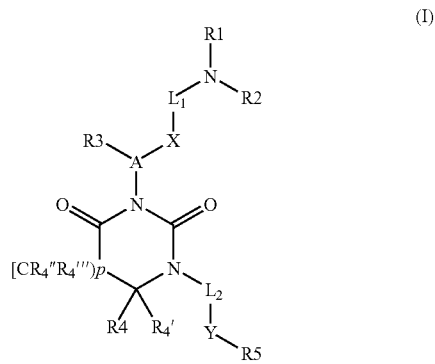

wherein:

p represents the integer 0;

A represents a phenyl, 2,3-dihydro-1H-indolyl, or indolyl radical optionally substituted with one or more radicals chosen from the values of R3;

X represents a single bond, —NH-alk-, alkylene, —O—, Nalk-CO—, NH—CO, NH—CO-alk-, NH—CO—NH—, —CO—NH—, —SO2, —NR6d or —CO—;

$L_1$ represents a single bond, an alkylene radical containing 1 to 5 carbon atoms optionally substituted with a hydroxyl radical, a cycloalkylalkyl radical, or a phenyl radical;

R1 and R2, which may be identical or different, are such that:

either R1 represents a hydrogen atom, an alkyl radical optionally substituted with one or more radicals chosen from halogen atoms and hydroxyl, alkoxy, NH2, NH(alk), N(alk)2, cyano, free or esterified carboxyl, phenyl and 3- to 7-membered cycloalkyl radicals and a saturated, partially saturated or unsaturated 4- to 7-membered heterocyclic radical, itself optionally substituted with one or more alkyl radicals and containing one or more hetero atoms, which may be identical or different, chosen from O, S, N, NH and N-alkyl, or R1 represents a 3- to 7-membered cycloalkyl radical, a phenyl radical or a saturated, partially saturated or unsaturated 4- to 7-membered heterocyclic radical, itself optionally substituted with one or more alkyl radicals and containing one or more hetero atoms chosen from O, S, N, NH and N-alkyl, and R2 represents a hydrogen atom or an alkyl radical;

or R1 and R2 form, with the nitrogen atom to which they are attached, a saturated or unsaturated 4- to 7-membered heterocyclic radical optionally containing one or more other hetero atoms chosen from O, S, N, NH and N-alkyl, this radical formed by R1 and R2 with N being itself optionally substituted with one or more radicals chosen from alkyl, halogen, NH2, NH(alk), N(alk)2, CF3 and free or esterified carboxyl radicals, all the above alkyl and alkoxy radicals being linear or branched and containing up to 6 carbon atoms;

or NR1R2 forms with $L_1$ a saturated or unsaturated 4- to 10-membered heterocycle containing at least one nitrogen atom and optionally containing one or more other hetero atoms chosen from O, S, N, NH and N-alkyl, this radical formed by NR1R2 with $L_1$ being itself optionally substituted with one or more radicals chosen from alkyl, cycloalkyl and free or esterified carboxyl radicals;

R3 represents one or more substituents of the ring A, which may be identical or different, chosen from a hydrogen atom and an alkyl or alkoxy radical containing up to 4 carbon atoms, optionally substituted with one or more F; alkyl-S(O)n optionally substituted by F; OCF3; SO2CF2; or SCF3; with n representing 0 or 2;

R4 and $R_4'$, which may be identical or different, are chosen from a hydrogen atom and an alkyl radical containing up to 4 carbon atoms;

R5 represents a hydrogen atom, a halogen atom; an alkyl, cycloalkyl, NH2, —NH-cycloalkyl, —NHCO-alkyl, —NHCO-cycloalkyl, —NHCONH-alkyl or —NHCON (dialkyl) radical, the alkyl and cycloalkyl residues being optionally substituted with one or more radicals, which may be identical or different, chosen from halogen atoms and alkoxy, morpholinyl, piperidyl, piperazinyl, N-methyl-piperazinyl and COOH radicals; or R5 represents NH-aryl, NH-heteroaryl, —NHCO-aryl and —NHCO-heteroaryl in which the aromatic residues are optionally substituted with one or more radicals chosen from halogen atoms and alkyl, alkoxy and COOH radicals;

R6d represents a hydrogen atom, an acyl radical optionally substituted with one or more F or an alkyl radical containing from 1 to 4 carbon atoms, $L_2$ represents an alkylene radical; and Y represents a quinolyl, pyridyl or pyrimidinyl radical, optionally substituted by NH2; or a racemate, enantiomer, diastereoisomer of such compound or mixture thereof, or an addition salt of such compound, racemate, enantiomer, diastereomer or mixture with a mineral acid or organic acid or with a mineral base or organic base.

7. A compound of formula (Id):

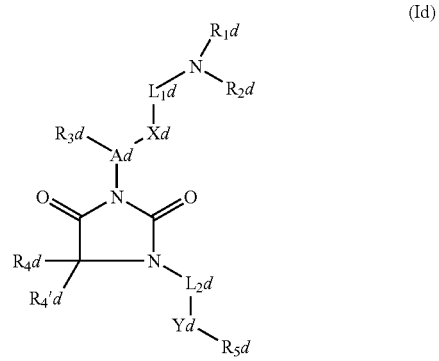

(Id)

wherein:

Ad represents a phenyl or indolyl radical optionally substituted with one or more radicals chosen from the values of R3d;

Xd represents —O—, NH—CO, —NR6d or —CO—, $L_1$d represents an alkylene radical containing 1 to 3 carbon atoms optionally substituted with a hydroxyl radical;

$R_1$d and $R_2$d, which may be identical or different, are such that:

either $R_1$d represents an alkyl radical optionally substituted with one or more radicals chosen from halogen atoms and hydroxyl, alkoxy, cyano, free or esterified carboxyl, phenyl and 3- to 7-membered cycloalkyl radicals and a saturated, partially saturated or unsaturated 4- to 7-membered heterocyclic radical, itself optionally substituted with one or more alkyl radicals and containing one or more hetero atoms, which may be identical or different, chosen from O, S, N, NH and N-alkyl, or $R_1$d represents a 3- to 7-membered cycloalkyl radical, a phenyl radical or a saturated, partially saturated or unsaturated 4- to 7-membered heterocyclic radical, itself optionally substituted with one or more alkyl radicals and containing one or more hetero atoms chosen from O, S, N, NH and N-alkyl, and $R_2$d represents a hydrogen atom or an alkyl radical;

or $R_1$d and $R_2$d form, with the nitrogen atom to which they are attached, a saturated or unsaturated 4- to 7-membered heterocyclic radical optionally containing one or more other hetero atoms chosen from O, S, N, NH and N-alkyl, this radical formed by $R_1$d and $R_2$d with N being itself optionally substituted with one or more radicals chosen from alkyl, CF3 and free or esterified carboxyl radicals, all the above alkyl and alkoxy radicals being linear or branched and containing up to 6 carbon atoms;

or $NR_1dR_2d$ forms with $L_1$d a saturated or unsaturated 4- to 8-membered heterocycle containing at least one nitrogen atom and optionally containing one or more other hetero atoms chosen from O, S, N, NH and N-alkyl, this radical formed by $NR_1R_2$d with $L_1$d being itself optionally substituted with one or more radicals chosen from alkyl and free or esterified carboxyl radicals;

$R_3$d represents one or more substituents of the ring Ad, which may be identical or different, chosen from a hydrogen atom and an alkyl or alkoxy radical containing up to 4 carbon atoms, optionally substituted with one or more F; alkyl-S(O)n optionally substituted by F; OCF3; SO2CF2; or SCF3; with n representing 0 or 2;

R₄d and R₄'d, which may be identical or different, are chosen from a hydrogen atom and an alkyl radical containing up to 4 carbon atoms;

R₅d represents a hydrogen atom, a halogen atom; an alkyl, cycloalkyl, NH2, —NH-cycloalkyl, —NHCO-alkyl, —NHCO-cycloalkyl, —NHCONH-alkyl or —NHCON (dialkyl) radical, the alkyl and cycloalkyl residues being optionally substituted with one or more radicals, which may be identical or different, chosen from halogen atoms and alkoxy, morpholinyl, piperidyl, piperazinyl, N-methyl-piperazinyl and COOH radicals; or R₅d represents NH-aryl, NH-heteroaryl, —NHCO-aryl and —NHCO-heteroaryl in which the aromatic residues are optionally substituted with one or more radicals chosen from halogen atoms and alkyl, alkoxy and COOH radicals;

L₂d represents an alkylene radical; and

Yd represents a quinolyl, pyridyl or pyrimidinyl radical; or a racemate, enantiomer, diastereoisomer of such compound or mixture thereof, or an addition salt of such compound, racemate, enantiomer, diastereomer or mixture with a mineral acid or organic acid or with a mineral base or organic base.

8. A compound which is

N-[5-(4,4-Dimethyl-2,5-dioxo-3-pyridin-4-ylmethyl-imidazolidin-1-yl)-2-trifluoromethoxy-phenyl]-2-morpholin-4-yl-acetamide;

N-[5-(4,4-Dimethyl-2,5-dioxo-3-pyridin-4-ylmethyl-imidazolidin-1-yl)-2-trifluoromethoxy-phenyl]-2-(dimethyl-morpholin-4-yl)-acetamide;

2-Cyclopentylamino-N-[5-(4,4-dimethyl-2,5-dioxo-3-pyridin-4-ylmethyl-imidazolidin-1-yl)-2-trifluoromethoxy-phenyl]-acetamide;

N-[5-(4,4-Dimethyl-2,5-dioxo-3-pyridin-4-ylmethyl-imidazolidin-1-yl)-2-trifluoromethoxy-phenyl]-2-(2,2,2-trifluoro-ethylamino)-acetamide;

2-Diethylamino-N-[5-(4,4-dimethyl-2,5-dioxo-3-pyridin-4-ylmethyl-imidazolidin-1-yl)-2-trifluoromethoxy-phenyl]-acetamide;

N-[5-(4,4-Dimethyl-2,5-dioxo-3-pyridin-4-ylmethyl-imidazolidin-1-yl)-2-trifluoromethoxy-phenyl]-2-thiomorpholin-4-yl-acetamide;

N-[5-(4,4-Dimethyl-2,5-dioxo-3-pyridin-4-ylmethyl-imidazolidin-1-yl)-2-trifluoromethoxy-phenyl]-2-pyrrolidin-1-yl-acetamide;

N-[5-(4,4-Dimethyl-2,5-dioxo-3-pyridin-4-ylmethyl-imidazolidin-1-yl)-2-trifluoromethoxy-phenyl]-2-(4-methyl-piperazin-1-yl)-acetamide;

N-[5-(4,4-Dimethyl-2,5-dioxo-3-pyridin-4-ylmethyl-imidazolidin-1-yl)-2-trifluoromethoxy-phenyl]-2-piperidin-1-yl-acetamide;

N-[5-(4,4-Dimethyl-2,5-dioxo-3-pyridin-4-ylmethyl-imidazolidin-1-yl)-2-trifluoromethoxy-phenyl]-2-[(pyridin-2-ylmethyl)-amino]-acetamide;

N-[5-(4,4-Dimethyl-2,5-dioxo-3-pyridin-4-ylmethyl-imidazolidin-1-yl)-2-trifluoromethoxy-phenyl]-2-[(pyridin-3-ylmethyl)-amino]-acetamide;

N-[5-(4,4-Dimethyl-2,5-dioxo-3-pyridin-4-ylmethyl-imidazolidin-1-yl)-2-trifluoromethoxy-phenyl]-2-[(pyridin-4-ylmethyl)-amino]-acetamide;

N-[5-(4,4-Dimethyl-2,5-dioxo-3-pyridin-4-ylmethyl-imidazolidin-1-yl)-2-trifluoromethoxy-phenyl]-2-(2-hydroxy-ethylamino)-acetamide;

N-[5-(4,4-Dimethyl-2,5-dioxo-3-pyridin-4-ylmethyl-imidazolidin-1-yl)-2-trifluoromethoxy-phenyl]-2-(2-methoxy-ethylamino)-acetamide;

2-Dimethylamino-N-[5-(4,4-dimethyl-2,5-dioxo-3-pyridin-4-ylmethyl-imidazolidin-1-yl)-2-trifluoromethoxy-phenyl]-acetamide;

2-(Cyanomethyl-amino)-N-[5-(4,4-dimethyl-2,5-dioxo-3-pyridin-4-ylmethyl-imidazolidin-1-yl)-2-trifluoromethoxy-phenyl]-acetamide;

N-[5-(4,4-Dimethyl-2,5-dioxo-3-pyridin-4-ylmethyl-imidazolidin-1-yl)-2-trifluoromethoxy-phenyl]-2-(4-methyl-piperidin-1-yl)-acetamide;

N-[5-(4,4-Dimethyl-2,5-dioxo-3-pyridin-4-ylmethyl-imidazolidin-1-yl)-2-trifluoromethoxy-phenyl]-2-(4-methyl-[1,4]diazepan-1-yl)-acetamide;

2-tert-Butylamino-N-[5-(4,4-dimethyl-2,5-dioxo-3-pyridin-4-ylmethyl-imidazolidin-1-yl)-2-trifluoromethoxy-phenyl]-acetamide;

N-[5-(4,4-Dimethyl-2,5-dioxo-3-pyridin-4-ylmethyl-imidazolidin-1-yl)-2-trifluoromethoxy-phenyl]-2-(1,2,2-trimethyl-propylamino)-acetamide;

{[5-(4,4-Dimethyl-2,5-dioxo-3-pyridin-4-ylmethyl-imidazolidin-1-yl)-2-trifluoromethoxy-phenylcarbamoyl]-methyl)-amino}-acetic acid methyl ester;

2-(2,2-Difluoro-ethylamino)-N-[5-(4,4-dimethyl-2,5-dioxo-3-pyridin-4-ylmethyl-imidazolidin-1-yl)-2-trifluoromethoxy-phenyl]-acetamide;

N-[5-(4,4-Dimethyl-2,5-dioxo-3-pyridin-4-ylmethyl-imidazolidin-1-yl)-2-trifluoromethoxy-phenyl]-2-(4,4-dimethyl-piperidin-1-yl)-acetamide;

N-[5-(4,4-Dimethyl-2,5-dioxo-3-pyridin-4-ylmethyl-imidazolidin-1-yl)-2-trifluoromethoxy-phenyl]-2-(4-trifluoromethyl-piperidin-1-yl)-acetamide;

N-[5-(4,4-Dimethyl-2,5-dioxo-3-pyridin-4-ylmethyl-imidazolidin-1-yl)-2-trifluoromethoxy-phenyl]-2-[1,4]oxazepan-4-yl-acetamide;

1-{[5-(4,4-Dimethyl-2,5-dioxo-3-pyridin-4-ylmethyl-imidazolidin-1-yl)-2-trifluoromethoxy-phenylcarbamoyl]-methyl}-pyrrolidine-3-carboxylic acid methyl ester;

2-Azetidin-1-yl-N-[5-(4,4-dimethyl-2,5-dioxo-3-pyridin-4-ylmethyl-imidazolidin-1-yl)-2-trifluoromethoxy-phenyl]-acetamide;

N-[5-(4,4-Dimethyl-2,5-dioxo-3-pyridin-4-ylmethyl-imidazolidin-1-yl)-2-trifluoromethoxy-phenyl]-2-(2-fluoro-ethylamino)-acetamide;

N-[5-(4,4-Dimethyl-2,5-dioxo-3-pyridin-4-ylmethyl-imidazolidin-1-yl)-2-trifluoromethoxy-phenyl]-2-[(2-methoxy-ethyl)-methyl-amino]-acetamide;

({[5-(4,4-Dimethyl-2,5-dioxo-3-pyridin-4-ylmethyl-imidazolidin-1-yl)-2-trifluoromethoxy-phenylcarbamoyl]-methyl)-amino}-acetic acid;

2-Cyclohexylamino-N-[5-(4,4-dimethyl-2,5-dioxo-3-pyridin-4-ylmethyl-imidazolidin-1-yl)-2-trifluoromethoxy-phenyl]-acetamide;

2-Cyclopropylamino-N-[5-(4,4-dimethyl-2,5-dioxo-3-pyridin-4-ylmethyl-imidazolidin-1-yl)-2-trifluoromethoxy-phenyl]-acetamide;

N-[5-(4,4-Dimethyl-2,5-dioxo-3-pyridin-4-ylmethyl-imidazolidin-1-yl)-2-trifluoromethoxy-phenyl]-3-morpholin-4-yl-propionamide;

N-[5-(4,4-Dimethyl-2,5-dioxo-3-pyridin-4-ylmethyl-imidazolidin-1-yl)-2-trifluoromethoxy-phenyl]-3-(dimethyl-morpholin-4-yl)-propionamide;

N-[5-(4,4-Dimethyl-2,5-dioxo-3-pyridin-4-ylmethyl-imidazolidin-1-yl)-2-trifluoromethoxy-phenyl]-3-(4-methyl-piperazin-1-yl)-propionamide;

N-[5-(4,4-Dimethyl-2,5-dioxo-3-pyridin-4-ylmethyl-imidazolidin-1-yl)-2-trifluoromethoxy-phenyl]-3-piperidin-1-yl-propionamide;

N-[5-(4,4-Dimethyl-2,5-dioxo-3-pyridin-4-ylmethyl-imidazolidin-1-yl)-2-trifluoromethoxy-phenyl]-3-thiomorpholin-4-yl-propionamide;

N-[5-(4,4-Dimethyl-2,5-dioxo-3-pyridin-4-ylmethyl-imidazolidin-1-yl)-2-trifluoromethoxy-phenyl]-3-pyrrolidin-1-yl-propionamide;

3-Cyclopentylamino-N-[5-(4,4-dimethyl-2,5-dioxo-3-pyridin-4-ylmethyl-imidazolidin-1-yl)-2-trifluoromethoxy-phenyl]-propionamide;

N-[5-(4,4-Dimethyl-2,5-dioxo-3-pyridin-4-ylmethyl-imidazolidin-1-yl)-2-trifluoromethoxy-phenyl]-3-(2,2,2-trifluoro-ethylamino)-propionamide;

3-Diethylamino-N-[5-(4,4-dimethyl-2,5-dioxo-3-pyridin-4-ylmethyl-imidazolidin-1-yl)-2-trifluoromethoxy-phenyl]-propionamide;

N-[5-(4,4-Dimethyl-2,5-dioxo-3-pyridin-4-ylmethyl-imidazolidin-1-yl)-2-isopropyl-phenyl]-2-morpholin-4-yl-acetamide;

N-[5-(4,4-Dimethyl-2,5-dioxo-3-pyridin-4-ylmethyl-imidazolidin-1-yl)-2-isopropyl-phenyl]-2-piperidin-1-yl-acetamide;

N-[5-(4,4-Dimethyl-2,5-dioxo-3-pyridin-4-ylmethyl-imidazolidin-1-yl)-2-isopropyl-phenyl]-2-(4-methyl-piperazin-1-yl)-acetamide;

2-Dimethylamino-N-[5-(4,4-dimethyl-2,5-dioxo-3-pyridin-4-ylmethyl-imidazolidin-1-yl)-2-isopropyl-phenyl]-acetamide;

2-Diethylamino-N-[5-(4,4-dimethyl-2,5-dioxo-3-pyridin-4-ylmethyl-imidazolidin-1-yl)-2-isopropyl-phenyl]-acetamide;

2-tert-Butylamino-N-[5-(4,4-dimethyl-2,5-dioxo-3-pyridin-4-ylmethyl-imidazolidin-1-yl)-2-isopropyl-phenyl]-acetamide;

2-Cyclopentylamino-N-[5-(4,4-dimethyl-2,5-dioxo-3-pyridin-4-ylmethyl-imidazolidin-1-yl)-2-isopropyl-phenyl]-acetamide;

1-Methyl-piperidine-4-carboxylic acid [5-(4,4-dimethyl-2,5-dioxo-3-pyridin-4-ylmethyl-imidazolidin-1-yl)-2-trifluoromethoxy-phenyl]-amide;

3-[3-(2-Cyclopentylamino-ethoxy)-4-methoxy-phenyl]-5,5-dimethyl-1-quinolin-4-ylmethyl-imidazolidine-2,4-dione;

3-(3-{2-[(Furan-2-ylmethyl)-amino]-ethoxy}-4-methoxy-phenyl)-5,5-dimethyl-1-quinolin-4-ylmethyl-imidazolidine-2,4-dione;

3-{3-[2-(2-Hydroxy-1-phenyl-ethylamino)-ethoxy]-4-methoxy-phenyl}-5,5-dimethyl-1-quinolin-4-ylmethyl-imidazolidine-2,4-dione;

3-[3,3-Dimethyl-1-(2-morpholin-4-yl-acetyl)-2,3-dihydro-1H-indol-6-yl]-5,5-dimethyl-1-quinolin-4-ylmethyl-imidazolidine-2,4-dione;

3-[3,3-Dimethyl-1-(2-thiomorpholin-4-yl-acetyl)-2,3-dihydro-1H-indol-6-yl]-5,5-dimethyl-1-quinolin-4-ylmethyl-imidazolidine-2,4-dione;

3-{4-Methoxy-3-[2-(2-morpholin-4-yl-ethylamino)-ethoxy]-phenyl}-5,5-dimethyl-1-quinolin-4-ylmethyl-imidazolidine-2,4-dione;

3-[4-Methoxy-3-(2-pyrrolidin-1-yl-ethoxy)-phenyl]-5,5-dimethyl-1-quinolin-4-ylmethyl-imidazolidine-2,4-dione;

3-(4-Methoxy-3-{2-[(pyridin-2-ylmethyl)-amino]-ethoxy}-phenyl)-5,5-dimethyl-1-quinolin-4-ylmethyl-imidazolidine-2,4-dione;

3-(4-Methoxy-3-[2-(tetrahydro-pyran-4-ylamino)-ethoxy]-phenyl}-5,5-dimethyl-1-quinolin-4-ylmethyl-imidazolidine-2,4-dione;

3-{4-Methoxy-3-[2-(1-methyl-piperidin-4-ylamino)-ethoxy]-phenyl}-5,5-dimethyl-1-quinolin-4-ylmethyl-imidazolidine-2,4-dione;

3-{3-[2-Hydroxy-3-(tetrahydro-pyran-4-ylamino)-propoxy]-4-methoxy-phenyl}-5,5-dimethyl-1-quinolin-4-ylmethyl-imidazolidine-2,4-dione;

3-{3-[2-Hydroxy-3-(pyridin-4-ylamino)-propoxy]-4-methoxy-phenyl}-5,5-dimethyl-1-quinolin-4-ylmethyl-imidazolidine-2,4-dione; or 3-{3-[2-Hydroxy-3-(1-methyl-piperidin-4-ylamino)-propoxy]-4-methoxy-phenyl}-5,5-dimethyl-1-quinolin-4-ylmethyl-imidazolidine-2,4-dione; or a racemate, enantiomer, diastereoisomer of such compound or mixture thereof, or an addition salt of such compound, racemate, enantiomer, diastereomer or mixture with a mineral acid or organic acid or with a mineral base or organic base.

9. A compound which is:

N-[5-(4,4-Dimethyl-2,5-dioxo-3-pyridin-4-ylmethyl-imidazolidin-1-yl)-2-trifluoromethoxy-phenyl]-2-morpholin-4-yl-acetamide;

N-[5-(4,4-Dimethyl-2,5-dioxo-3-pyridin-4-ylmethyl-imidazolidin-1-yl)-2-trifluoromethoxy-phenyl]-2-(dimethyl-morpholin-4-yl)-acetamide;

2-Cyclopentylamino-N-[5-(4,4-dimethyl-2,5-dioxo-3-pyridin-4-ylmethyl-imidazolidin-1-yl)-2-trifluoromethoxy-phenyl]-acetamide;

N-[5-(4,4-Dimethyl-2,5-dioxo-3-pyridin-4-ylmethyl-imidazolidin-1-yl)-2-trifluoromethoxy-phenyl]-2-(2,2,2-trifluoro-ethylamino)-acetamide;

2-Diethylamino-N-[5-(4,4-dimethyl-2,5-dioxo-3-pyridin-4-ylmethyl-imidazolidin-1-yl)-2-trifluoromethoxy-phenyl]-acetamide;

N-[5-(4,4-Dimethyl-2,5-dioxo-3-pyridin-4-ylmethyl-imidazolidin-1-yl)-2-trifluoromethoxy-phenyl]-2-thiomorpholin-4-yl-acetamide;

N-[5-(4,4-Dimethyl-2,5-dioxo-3-pyridin-4-ylmethyl-imidazolidin-1-yl)-2-trifluoromethoxy-phenyl]-2-pyrrolidin-1-yl-acetamide trifluoroacetate;

N-[5-(4,4-Dimethyl-2,5-dioxo-3-pyridin-4-ylmethyl-imidazolidin-1-yl)-2-trifluoromethoxy-phenyl]-2-(4-methyl-piperazin-1-yl)-acetamide;

N-[5-(4,4-Dimethyl-2,5-dioxo-3-pyridin-4-ylmethyl-imidazolidin-1-yl)-2-trifluoromethoxy-phenyl]-2-piperidin-1-yl-acetamide;

N-[5-(4,4-Dimethyl-2,5-dioxo-3-pyridin-4-ylmethyl-imidazolidin-1-yl)-2-trifluoromethoxy-phenyl]-2-[(pyridin-2-ylmethyl)-amino]-acetamide;

N-[5-(4,4-Dimethyl-2,5-dioxo-3-pyridin-4-ylmethyl-imidazolid in-1-yl)-2-trifluoromethoxy-phenyl]-2-[(pyridin-3-ylmethyl)-amino]-acetamide;

N-[5-(4,4-Dimethyl-2,5-dioxo-3-pyridin-4-ylmethyl-imidazolidin-1-yl)-2-trifluoromethoxy-phenyl]-2-[(pyridin-4-ylmethyl)-amino]-acetamide;

N-[5-(4,4-Dimethyl-2,5-dioxo-3-pyridin-4-ylmethyl-imidazolidin-1-yl)-2-trifluoromethoxy-phenyl]-2-(2-hydroxy-ethylamino)-acetamide;

N-[5-(4,4-Dimethyl-2,5-dioxo-3-pyridin-4-ylmethyl-imidazolidin-1-yl)-2-trifluoromethoxy-phenyl]-2-(2-methoxy-ethylamino)-acetamide;

2-Dimethylamino-N-[5-(4,4-dimethyl-2,5-dioxo-3-pyridin-4-ylmethyl-imidazolidin-1-yl)-2-trifluoromethoxy-phenyl]-acetamide;

2-(Cyanomethyl-amino)-N-[5-(4,4-dimethyl-2,5-dioxo-3-pyridin-4-ylmethyl-imidazolidin-1-yl)-2-trifluoromethoxy-phenyl-]acetamide;

N-[5-(4,4-Dimethyl-2,5-dioxo-3-pyridin-4-ylmethyl-imidazolidin-1-yl)-2-trifluoromethoxy-phenyl]-2-(4-methyl-piperidin-1-yl)-acetamide;
N-[5-(4,4-Dimethyl-2,5-dioxo-3-pyridin-4-ylmethyl-imidazolidin-1-yl)-2-trifluoromethoxy-phenyl]-2-(4-methyl-[1,4]diazepan-1-yl)-acetamide;
2-tert-Butylamino-N-[5-(4,4-dimethyl-2,5-dioxo-3-pyridin-4-ylmethyl-imidazolidin-1-yl)-2-trifluoromethoxy-phenyl]-acetamide;
N-[5-(4,4-Dimethyl-2,5-dioxo-3-pyridin-4-ylmethyl-imidazolidin-1-yl)-2-trifluoromethoxy-phenyl]-2-(1,2,2-trimethyl-propylamino)-acetamide;
({[5-(4,4-Dimethyl-2,5-dioxo-3-pyridin-4-ylmethyl-imidazolidin-1-yl)-2-trifluoromethoxy-phenylcarbamoyl]-methyl}-amino)-acetic acid methyl ester;
2-(2,2-Difluoro-ethylamino)-N-[5-(4,4-dimethyl-2,5-dioxo-3-pyridin-4-ylmethyl-imidazolidin-1-yl)-2-trifluoromethoxy-phenyl]-acetamide;
N-[5-(4,4-Dimethyl-2,5-dioxo-3-pyridin-4-ylmethyl-imidazolidin-1-yl)-2-trifluoromethoxy-phenyl]-2-(4,4-dimethyl-piperidin-1-yl)-acetamide;
N-[5-(4,4-Dimethyl-2,5-dioxo-3-pyridin-4-ylmethyl-imidazolidin-1-yl)-2-trifluoromethoxy-phenyl]-2-(4-trifluoromethyl-piperidin-1-yl)-acetamide;
N-[5-(4,4-Dimethyl-2,5-dioxo-3-pyridin-4-ylmethyl-imidazolidin-1-yl)-2-trifluoromethoxy-phenyl]-2-[1,4]oxazepan-4-yl-acetamide;
1-{[5-(4,4-Dimethyl-2,5-dioxo-3-pyridin-4-ylmethyl-imidazolidin-1-yl)-2-trifluoromethoxy-phenylcarbamoyl]-methyl}-pyrrolidine-3-carboxylic acid methyl ester;
2-Azetidin-1-yl-N-[5-(4,4-dimethyl-2,5-dioxo-3-pyridin-4-ylmethyl-imidazolidin-1-yl)-2-trifluoromethoxy-phenyl]-acetamide;
N-[5-(4,4-Dimethyl-2,5-dioxo-3-pyridin-4-ylmethyl-imidazolidin-1-yl)-2-trifluoromethoxy-phenyl]-2-(2-fluoro-ethylamino)-acetamide;
N-[5-(4,4-Dimethyl-2,5-dioxo-3-pyridin-4-ylmethyl-imidazolidin-1-yl)-2-trifluoromethoxy-phenyl]-2-[(2-methoxy-ethyl)-methyl-amino]-acetamide;
({[5-(4,4-Dimethyl-2,5-dioxo-3-pyridin-4-ylmethyl-imidazolidin-1-yl)-2-trifluoromethoxy-phenylcarbamoyl]-methyl)-amino}-acetic acid;
2-Cyclohexylamino-N-[5-(4,4-dimethyl-2,5-dioxo-3-pyridin-4-ylmethyl-imidazolidin-1-yl)-2-trifluoromethoxy-phenyl]-acetamide;
2-Cyclopropylamino-N-[5-(4,4-dimethyl-2,5-dioxo-3-pyridin-4-ylmethyl-imidazolidin-1-yl)-2-trifluoromethoxy-phenyl]-acetamide;
N-[5-(4,4-Dimethyl-2,5-dioxo-3-pyridin-4-ylmethyl-imidazolidin-1-yl)-2-trifluoromethoxy-phenyl]-3-morpholin-4-yl-propionamide;
N-[5-(4,4-Dimethyl-2,5-dioxo-3-pyridin-4-ylmethyl-imidazolidin-1-yl)-2-trifluoromethoxy-phenyl]-3-(dimethyl-morpholin-4-yl)-propionamide;
N-[5-(4,4-Dimethyl-2,5-dioxo-3-pyridin-4-ylmethyl-imidazolidin-1-yl)-2-trifluoromethoxy-phenyl]-3-(4-methyl-piperazin-1-yl)-propionamide;
N-[5-(4,4-Dimethyl-2,5-dioxo-3-pyridin-4-ylmethyl-imidazolidin-1-yl)-2-trifluoromethoxy-phenyl]-3-piperidin-1-yl-propionamide;
N-[5-(4,4-Dimethyl-2,5-dioxo-3-pyrididazolidin-1-yl)-2-trifluoromethoxy-phenyl]-3-thiomorpholin-4-yl-propionamide;
N-[5-(4,4-Dimethyl-2,5-dioxo-3-pyridin-4-ylmethyl-imidazolidin-1-yl)-2-trifluoromethoxy-phenyl]-3-pyrrolidin-1-yl-propionamide;
3-Cyclopentylamino-N-[5-(4,4-dimethyl-2,5-dioxo-3-pyridin-4-ylmethyl-imidazolidin-1-yl)-2-trifluoromethoxy-phenyl]-propionamide;
N-[5-(4,4-Dimethyl-2,5-dioxo-3-pyridin-4-ylmethyl-imidazolidin-1-yl)-2-trifluoromethoxy-phenyl]-3-(2,2,2-trifluoro-ethylamino)-propionamide;
3-Diethylamino-N-[5-(4,4-dimethyl-2,5-dioxo-3-pyridin-4-ylmethyl-imidazolidin-1-yl)-2-trifluoromethoxy-phenyl]-propionamide;
N-[5-(4,4-Dimethyl-2,5-dioxo-3-pyridin-4-ylmethyl-imidazolidin-1-yl)-2-isopropyl-phenyl]-2-morpholin-4-yl-acetamide;
N-[5-(4,4-Dimethyl-2,5-dioxo-3-pyridin-4-ylmethyl-imidazolidin-1-yl)-2-isopropyl-phenyl]-2-piperidin-1-yl-acetamide;
N-[5-(4,4-Dimethyl-2,5-dioxo-3-pyridin-4-ylmethyl-imidazolidin-1-yl)-2-isopropyl-phenyl]-2-(4-methyl-piperazin-1-yl)-acetamide trifluoroacetate;
2-Dimethylamino-N-[5-(4,4-dimethyl-2,5-dioxo-3-pyridin-4-ylmethyl-imidazolidin-1-yl)-2-isopropyl-phenyl]-acetamide trifluoroacetate;
2-Diethylamino-N-[5-(4,4-dimethyl-2,5-dioxo-3-pyridin-4-ylmethyl-imidazolidin-1-yl)-2-isopropyl-phenyl]-acetamide;
2-tert-Butylamino-N-[5-(4,4-dimethyl-2,5-dioxo-3-pyridin-4-ylmethyl-imidazolidin-1-yl)-2-isopropyl-phenyl]-acetamide;
2-Cyclopentylamino-N-[5-(4,4-dimethyl-2,5-dioxo-3-pyridin-4-ylmethyl-imidazolidin-1-yl)-2-isopropyl-phenyl]-acetamide;
1-Methyl-piperidine-4-carboxylic acid [5-(4,4-dimethyl-2,5-dioxo-3-pyridin-4-ylmethyl-imidazolidin-1-yl)-2-trifluoromethoxy-phenyl]-amide;
3-[3-(2-Cyclopentylamino-ethoxy)-4-methoxy-phenyl)-5,5-dimethyl-1-quinolin-4-ylmethyl-imidazolidine-2,4-dione;
3-(3-{2-[(Furan-2-ylmethyl)-amino]-ethoxy}-4-methoxy-phenyl)-5,5-dimethyl-1-quinolin-4-ylmethyl-imidazolidine-2,4-dione;
3-{3-[2-(2-Hydroxy-1-phenyl-ethylamino)-ethoxy]-4-methoxy-phenyl}-5,5-dimethyl-1-quinolin-4-ylmethyl-imidazolidine-2,4-dione;
3-[3,3-Dimethyl-1-(2-morpholin-4-yl-acetyl)-2,3-dihydro-1H-indol-6-yl]-5,5-dimethyl-1-quinolin-4-ylmethyl-imidazolidine-2,4-dione; or
3-[3,3-Dimethyl-1-(2-thiomorpholin-4-yl-acetyl)-2,3-dihydro-1H-indol-6-yl]-5,5-dimethyl-1-quinolin-4-ylmethyl-imidazolidine-2,4-dione; or
a racemate, enantiomer, diastereoisomer of such compound or mixture thereof, or an addition salt of such compound, racemate, enantiomer, diastereomer or mixture with a mineral acid or organic acid or with a mineral base or organic base.

10. A compound according to claim 1 wherein, when A represents a phenyl radical, then X represents —O—, —NR6, or —NH—CO.

11. A compound according to claim 5 wherein, when Ac represents a phenyl radical, then Xc represents —O—, —NR6c, or —NH—CO.

12. A compound according to claim 6 wherein, when A represents a phenyl radical, then X represents —O—, —NR6d, or —NH—CO.

13. A compound according to claim 7 wherein, when Ad represents a phenyl radical, then Xd represents —O—, —NR6d, or —NH—CO.

14. A compound according to claim 2 wherein, when A represents a phenyl radical, then X represents —O—, —NR6, or —NH—CO.

15. A compound according to claim 3 wherein, when Aa represents a phenyl radical, then Xa represents —O—, —NR6a, or —NH—CO.

16. A compound according to claim 4 wherein, when A represents a phenyl radical, then Xb represents —O—, —NR6b, or —NH—CO.

17. A pharmaceutical composition comprising a compound according to claim 1, or a pharmaceutically acceptable salt thereof, and a pharmaceutically acceptable excipient.

18. A compound of formula (I):

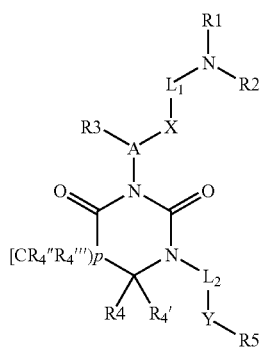

(I)

in which:
p represents the integer 0;
A represents aryl, heteroaryl or a monocyclic or bicyclic fused carbocyclic or heterocyclic 5- to 11-membered radical, all these radicals optionally being substituted with one or more substituents, which may be identical or different, chosen from the values of R3;
X represents a single bond or the following divalent radicals: —N(R6)-; —NH-alk-; alkylene; —O-; —C(O)—; —S(O)n—; —N(R6)-C(O)—; NH—CO-alk-, —N(R6)-C(O)—N(R6')-; —N(R6)-C(S)—N(R6')-; —N(R6)-C(O)O-; —N(R6)-SO2—; —N(R6)-SO2—N(R6')-; —C(O)—N(R6)-; —SO2—N(R6)-; and —C(O)O—;
$L_1$ represents a single bond or the following divalent radicals: alkylene, alkenylene, alkynylene and cycloalkylene, all optionally substituted with one or more substituents, which may be identical or different, chosen from the values of R7; or $L_1$ represents phenylene and heteroarylene, these last two radicals optionally substituted with one or more substituents chosen from the values of R8;
the radical NR1R2 is such that:
either R1 and R2, which may be identical or different, are such that:
R1 represents a hydrogen atom; alkyl, alkenyl, alkynyl and cycloalkyl, all optionally substituted with one or more substituents, which may be identical or different, chosen from the values of R7; aryl, heteroaryl, arylalkyl and heteroarylalkyl in which each of the aromatic rings may optionally be substituted with one or more substituents, which may be identical or different, chosen from the values of R8; —SO2R9; —C(O)R9; —C(O)OR9; —C(O)NR10R11; —C(S)NR10R11 and —SO2NR10R11;
and R2 represents a hydrogen atom; alkyl, alkenyl, alkynyl and cycloalkyl, all optionally substituted with one or more substituents, which may be identical or different, chosen from the values of R7;
or R1 and R2 form, together with the nitrogen atom to which they are attached, a 4- to 10-membered heterocycle optionally containing one or more other hetero atoms, which may be identical or different, chosen from O, N, NR12 and S, and optionally substituted with one or more substituents, which may be identical or different, chosen from the values of R7;
or NR1 with $L_1$ or NR2 with $L_1$ together form a 4- to 10-membered heterocycle - optionally containing one or more
other hetero atoms, which may be identical or different, chosen from O, N, NR12 and S, and optionally substituted with one or more substituents, which may be identical or different, chosen from the values of R7;
R3 represents a hydrogen atom; a halogen atom; hydroxyl; alkyl, alkenyl, alkynyl, cycloalkyl, alkoxy and alkylenedioxy, all optionally substituted with one or more substituents, which may be identical or different, chosen from the values of R7; or R3 represents —NR13R14; —C(O)R13; —S(O)$_n$R13; —C(O)OR13; —C(O)NR15R16; —S(O)$_n$NR15R16; SF5; nitro; cyano; 4- to 7-membered heterocycloalkyl optionally substituted with one or more radicals, which may be identical or different, chosen from halogen atoms and alkyl, alkoxy or oxo radicals; or R3 represents aryl and heteroaryl, these last two radicals optionally substituted with one or more substituents, which may be identical or different, chosen from the values of R8;
provided that when A represents a mono or bicyclic fused 11-membered radical, R3 represents one or more oxo;
R4, R4', R4" and R4''', which may be identical or different, are chosen from the values defined below for R4;
R4 represents a hydrogen atom; a halogen atom; an alkyl, alkenyl, alkynyl or cycloalkyl radical, all optionally substituted with one or more substituents, which may be identical or different, chosen from the values of R7; or R4 represents aryl and heteroaryl, these last two radicals optionally substituted with one or more substituents, which may be identical or different, chosen from the values of R8; or R4 represents oxo;
$L_2$ is chosen from a single bond; an alkylene; alkenylene; alkynylene; cycloalkylene; —O—; —NR17—; —C(O)— and SO2 radical;
Y represents a saturated, partially saturated or unsaturated N-heterocycle optionally containing one or more hetero atoms, which may be identical or different, chosen from O, S, N and NR12 and optionally substituted with one or more substituents, which may be identical or different, chosen from the values of R5;
R5 represents a hydrogen atom; a halogen atom; an alkyl, alkenyl, alkynyl or cycloalkyl radical, all optionally substituted with one or more substituents, which may be identical or different, chosen from the values of R7; or R5 represents aryl, arylalkyl, heteroaryl and heteroarylalkyl, in which the aromatic rings are optionally substituted with one or more substituents, which may be identical or different, chosen from the values of R8; or R5 represents —OR18; —NR19R20; —NR19COR20; —NR19CONR19'R20; —NR19—S(O)2—R20; —NR19—S(O)2—NR19'R20; —COR18; COOR21; —CONR22R23; —S(O)nR18; —SO2NR22R23; cyano; or nitro;
R6 is such that:
either R6 represents a hydrogen atom; an alkyl, alkenyl, alkynyl, acyl or cycloalkyl radical, all optionally substituted with one or more substituents, which may be identical or different, chosen from the values of R7; R6 represents aryl and heteroaryl, these last two radicals optionally substituted with one or more substituents, which may be identical or different, chosen from the values of R8;

or R6 with NR1R2 together form a 4- to 8-membered heterocycle optionally containing one or more hetero atoms, which may be identical or different, chosen, from O, S, N and NR12 and optionally substituted with one or more substituents, which may be identical or different, chosen from the values of R7;

or R6 with $L_1$ together form a 4- to 8-membered heterocycle optionally containing one or more hetero atoms, which may be identical or different, chosen from O, S, N and NR12 and optionally substituted with one or more substituents, which may be identical or different, chosen from the values of R7;

R6', which may be identical to or different from R6, is chosen from the values of R6;

R7 represents a halogen atom; alkyl; cycloalkyl; cycloalkylalkyl; hydroxyl; alkoxy; cycloalkoxy; cyano; —CF3; —NR24R25; —NR26COR27; —NR26CONR26'R27; —NR26—S(O)2-R27; —NR26—S(O)2-NR26'R27; —COOR26; —COR26; —CO(NR24R25); S(O)nR26; —S(O)2NR24R25; 4- to 7-membered heterocycle optionally substituted with one or more substituents, which may be identical or different, chosen from OH and NH2 radicals, halogen atoms, and alkyl, alkoxy or oxo radicals; or R7 represents aryl optionally substituted with one or more substituents, which may be identical or different, chosen from halogen atoms and alkyl and alkoxy radicals; or R7 represents heteroaryl, optionally substituted with one or more substituents, which may be identical or different, chosen from halogen atoms and NH2, alkyl and alkoxy radicals; or R7 represents phenoxy, optionally substituted with one or more substituents, which may be identical or different, chosen from halogen atoms and alkyl and alkoxy radicals;

R8, which may be identical to or different from R7, represents the same values as R7; nitro; —OCF3; alkylenedioxy; difluoromethylenedioxy; or benzyl optionally substituted with one or more substituents, which may be identical or different, chosen from halogen atoms and alkyl and alkoxy radicals;

R9, which may be identical to or different from R6, represents the same values as R6;

R10 and R11, which may be identical to or different from each other and also which may be identical to or different from R6, are chosen from the same values as R6 and may optionally form, with the nitrogen atom to which they are attached, a 4- to 10-membered heterocycle optionally containing one or more hetero atoms, which may be identical or different, chosen from O, S, N and NR12 and optionally substituted with one or more substituents, which may be identical or different, chosen from the values of R7;

R12 represents a hydrogen atom; an alkyl, alkenyl, alkynyl, cycloalkyl, alkylCO or alkylSO$_2$ radical, all optionally substituted with one or more substituents, which may be identical or different, chosen from halogen atoms, OH, alkoxy and dialkylamino radicals; or R12 represents aryl and heteroaryl, these last two radicals optionally substituted with one or more substituents, which may be identical or different, chosen from halogen atoms and alkyl and alkoxy radicals;

R13, which may be identical to or different from R6, represents the same values as R6;

R14, which may be identical to or different from R13, represents the same values as R13 and also represents C(O)R28; C(O)N28R29; SO2R28 and SO2NR28R29;

R13 and R14 may optionally form, together with the nitrogen atom to which they are attached, a 4- to 10-membered heterocycle optionally containing one or more hetero atoms, which may be identical or different, chosen from O, S, N and NR12 and optionally substituted with one or more substituents, which may be identical or different, chosen from the values of R7;

R15 and R16, which may be identical to or different from each other and also which may be identical to or different from R13, are chosen from the same values as R13 and may optionally form, with the nitrogen atom to which they are attached, a 4- to 10-membered heterocycle optionally containing one or more hetero atoms, which may be identical or different, chosen from O, S, N and NR12 and optionally substituted with one or more substituents, which may be identical or different, chosen from the values of R7;

R17 represents a hydrogen atom, alkyl or cycloalkyl;

R18, which may be identical to or different from R6, represents the same values as R6;

R19 and R20, which may be identical to or different from each other and also which may be identical to or different from R6, are chosen from the same values as R6 and may optionally form, with the nitrogen atom to which they are attached, a 4- to 10-membered heterocycle optionally containing one or more hetero atoms, which may be identical or different, chosen from O, S, N and NR12 and optionally substituted with one or more substituents, which may be identical or different, chosen from the values of R7;

R21, which may be identical to or different from R13, represents the same values as R13 or hydrogen;

R22 and R23, which may be identical to or different from each other and also which may be identical to or different from R6, are chosen from the same values as R6 and may optionally form, with the nitrogen atom to which they are attached, a 4- to 10-membered heterocycle optionally containing one or more hetero atoms, which may be identical or different, chosen from O, S, N and NR12 and optionally substituted with one or more substituents, which may be identical or different, chosen from the values of R7;

R24 and R25, which may be identical or different, represent a hydrogen atom or an alkyl, alkenyl or alkynyl radical optionally substituted with one or more substituents, which may be identical or different, chosen from halogen atoms and OH and alkoxy radicals, or alternatively R24 and R25 may optionally form, with the nitrogen atom to which they are attached, a 4- to 7-membered heterocycle optionally containing one or more hetero atoms, which may be identical or different, chosen from O, S, N,N-alkyl and N—C(O)alkyl, and optionally substituted with one or more substituents, which may be identical or different, chosen from halogen atoms and OH, alkyl, alkoxy and oxo radicals;

R26 represents a hydrogen atom or an alkyl, alkenyl or alkynyl radical optionally substituted with one or more substituents, which may be identical or different, chosen from halogen atoms and OH and alkoxy radicals;

R26', which may be identical to or different from R26, represents the same values as R26;

R27, which may be identical to or different from R26, represents the same values as R26;

R26 and R27 may also optionally form, with the nitrogen atom to which they are attached, a 4- to 7-membered heterocycle optionally containing one or more hetero atoms, which may be identical or different, chosen from O, S, N , N-alkyl and N—C(O)alkyl, and optionally substituted with one or more substituents, which may be identical or different, chosen from halogen atoms and OH, alkyl, alkoxy and oxo radicals;

R28, which may be identical to or different from R26, represents the same values as R26;

R29, which may be identical to or different from R26, represents the same values as R26;

R30, which may be identical to or different from R26, represents the same values as R26; and n represents the integers 0, 1 and 2; or a racemate, enantiomer, diastereoisomer of such compound or mixture thereof, or an addition salt of such compound, racemate, enantiomer, diastereomer or mixture with a pharmaceutically acceptable mineral acid or pharmaceutically acceptable organic acid or with a pharmaceutically acceptable mineral base or pharmaceutically acceptable organic base.

* * * * *

UNITED STATES PATENT AND TRADEMARK OFFICE
CERTIFICATE OF CORRECTION

| | | |
|---|---|---|
| PATENT NO. | : 7,759,379 B2 | Page 1 of 5 |
| APPLICATION NO. | : 11/627518 | |
| DATED | : July 20, 2010 | |
| INVENTOR(S) | : Hartmut Strobel et al. | |

It is certified that error appears in the above-identified patent and that said Letters Patent is hereby corrected as shown below:

On the Title Page, Item (57), in "Abstract", line 5, delete "adminstration" an insert -- administration --, therefor.

In column 2, line 7, delete "over" and insert -- over- --, therefor.

In column 5, line 47, delete "1-" and insert -- 11- --, therefor.

In column 10, line 12, delete "cycloalkyle;" and insert -- cycloalkyl --, therefor.

In column 10, line 13, delete "cycloalkylalkyle" and insert -- cycloalkylalkyl --, therefor.

In column 14, line 13, delete "pyrindolinyl" and insert -- pyridolinyl --, therefor.

In column 20, line 58, delete "alcoxy" and insert -- alkoxy --, therefor.

In column 23, line 33, delete "oner" and insert -- one --, therefor.

In column 25, line 53, delete "or6-" and insert -- or 6- --, therefor.

In column 27, line 26, after "particularly," delete "5".

In column 30, line 5, delete "or7-" and insert -- or 7- --, therefor.

Signed and Sealed this
Thirty-first Day of May, 2011

David J. Kappos
*Director of the United States Patent and Trademark Office*

CERTIFICATE OF CORRECTION (continued)
U.S. Pat. No. 7,759,379 B2

In column 31, line 49-64, delete " 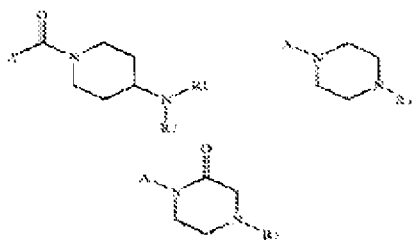 " and insert -- 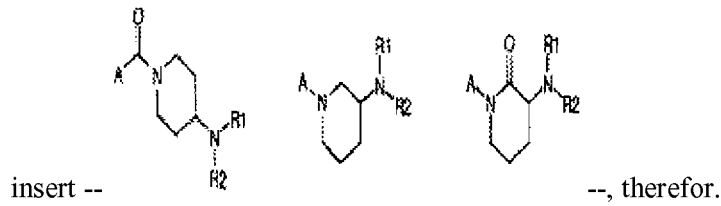 --, therefor.

In column 34, line 61, delete "chose" and insert -- chosen --, therefor.

In column 61, line 21-22, delete "antitumour" and insert -- antitumor --, therefor.

In column 61, line 26, delete "olomucine" and insert -- olomoucine --, therefor.

In column 61, line 31-32, delete "antioestrogens" and insert -- antiestrogens --, therefor.

In column 61, line 39, delete "biphosphonates" and insert -- bisphosphonates --, therefor.

In column 62, line 13, delete "chromoatography" and insert -- chromatography --, therefor.

In column 62, line 15, delete "methylenchoride" and insert -- methylenchlorid --, therefor.

In column 62, line 53, delete "chromoatography" and insert -- chromatography --, therefor.

In column 63, line 2-3, delete "chloroacetylchlorid" and insert -- chloroacetylchloride --, therefor.

In column 63, line 4, delete "hydrochlric" and insert -- hydrochloric --, therefor.

In column 63, line 19, delete "owere" and insert -- were --, therefor.

In column 63, line 23-24, delete "chromoatography" and insert -- chromatography --, therefor.

In column 63, line 39, delete "trifluoracetic" and insert -- trifluoroacetic --, therefor.

In column 67, line 9, delete "glycimethylester" and insert -- glycinemethylester --, therefor.

In column 67, line 51, delete "trifluormethyl" and insert -- trifluoromethyl --, therefor.

In column 67, line 63, delete "hydrochlorid" and insert -- hydrochloride --, therefor.

In column 68, line 33, delete "hydrochlorid" and insert -- hydrochloride --, therefor.

In column 68, line 64, delete "trifluoracetic" and insert -- trifluoroacetic --, therefor.

In column 69, line 27-28, delete "cyclopropylamin" and insert -- cyclopropylamine --, therefor.

In column 69, line 45, delete "evapoarted" and insert -- evaporated --, therefor.

In column 69, line 62, delete "by by" and insert -- by --, therefor.

In column 69, line 62, delete "reversedd" and insert -- reversed --, therefor.

In column 69, line 63, delete "trifluoracetic" and insert -- trifluoroacetic --, therefor.

In column 71, line 13, delete "trifluorethylamine." and insert -- trifluoroethylamine. --, therefor.

In column 71, line 64, delete "trifluoracetic" and insert -- trifluoroacetic --, therefor.

In column 72, line 50, delete "trifluoracetic" and insert -- trifluoroacetic --, therefor.

In column 72, line 65, delete "amterial" and insert -- material --, therefor.

In column 73, line 1, delete "trifluoracetic" and insert -- trifluoroacetic --, therefor.

In column 73, line 18, delete "trifluoracetic" and insert -- trifluoroacetic --, therefor.

In column 73, line 35, delete "trifluoracetic" and insert -- trifluoroacetic --, therefor.

In column 73, line 52, delete "trifluoracetic" and insert -- trifluoroacetic --, therefor.

In column 74, line 2, delete "trifluoracetic" and insert -- trifluoroacetic --, therefor.

In column 74, line 19, delete "trifluoracetic" and insert -- trifluoroacetic --, therefor.

In column 74, line 33, delete "choride" and insert -- chloride --, therefor.

In column 74, line 42, delete "was was" and insert -- was --, therefor.

In column 74, line 44, delete "trifluoracetic" and insert -- trifluoroacetic --, therefor.

In column 74, line 58, delete "follwoed" and insert -- followed --, therefor.

CERTIFICATE OF CORRECTION (continued)
U.S. Pat. No. 7,759,379 B2

In column 75, line 1, delete "was was" and insert -- was --, therefor.

In column 75, line 2, delete "trifluoracetic" and insert -- trifluoroacetic --, therefor.

In column 75, line 39, delete "contration" and insert -- contraction --, therefor.

In column 93, line 57, delete "ethaolic" and insert -- ethanolic --, therefor.

In column 107, line 38, delete "CH2Cl1:CH3OH" and insert -- CH2Cl1:CH3OH --, therefor.

In column 108, line 25, delete "cyanatoborohydride" and insert -- cyanoborohydride --, therefor.

In column 112, line 51, delete "trifluoracetic" and insert -- trifluoroacetic --, therefor.

In column 113, line 8, delete "trifluoracetic" and insert -- trifluoroacetic --, therefor.

In column 116, line 32, delete "satured" and insert -- saturated --, therefor.

In column 117, line 32, delete "S," and insert -- s, --, therefor.

In column 117, line 62, delete "S," and insert -- s, --, therefor.

In column 121, line 29, in claim 1, delete "NH—CO-" and insert -- —NH—CO- --, therefor.

In column 126, line 39, in claim 2, delete "—NR19—S(O)2-NR19R20," and insert -- —NR19—S(O)2—NR19'R20, --, therefor.

In column 130, line 27, in claim 3, delete "—NR19a R20a," and insert -- —NR19aR20a, --, therefor.

In column 130, line 27-29, in claim 3, delete "—NR19a COR20a, —NR19a CONR19'aR20a, —NR19a —S(O)2- R20a, —NR19a —S(O)2—NR19a'R20a," and insert -- —NR19aCOR20a, —NR19aCONR19'aR20a, —NR19a—S(O)2—R20a, —NR19a—S(O)2—NR19a'R20a, --, therefor.

In column 130, line 31, in claim 3, delete "—SO2NR22a R23a," and insert -- —SO2NR22aR23a, --, therefor.

In column 130, line 51-52, in claim 3, delete "—NR26a COR27a, —NR26a CONR26a'R27a, —NR26a —S(O)2- R27a, —NR26a —S(O)2 — NR26a'R27a," and insert -- —NR26aCOR27a, —NR26aCONR26a'R27a, —NR26a—S(O)2—R27a, —NR26a—S(O)2—NR26a'R27a, --, therefor.

In column 136, line 56-57, in claim 6, delete "Nalk—CO—, NH—CO, NH—CO—alk—, NH—CO—NH—," and insert -- —Nalk—CO—, —NH—CO, —NH—CO—alk—, —NH—CO—NH—, --, therefor.

CERTIFICATE OF CORRECTION (continued)
U.S. Pat. No. 7,759,379 B2

In column 138, line 59, in claim 7, delete "$NR_1R_2d$" and insert -- $NR_1dR_2d$ --, therefor.

In column 142, line 50-51, in claim 9, delete "imidazolid in" and insert -- imidazolidin --, therefor.

In column 145, line 40, in claim 18, delete "NH—CO-alk-," and insert -- —NH—CO—alk—, --, therefor.